United States Patent
Okamoto et al.

(10) Patent No.: US 6,969,712 B2
(45) Date of Patent: Nov. 29, 2005

(54) BENZIMIDAZOLE DERIVATIVES

(75) Inventors: Osamu Okamoto, Tsukuba (JP); Hiroshi Kawamoto, Tsukuba (JP); Kensuke Kobayashi, Tsukuba (JP); Satoru Itoh, Tsubuka (JP); Tetsuya Kato, Tsukuba (JP); Izumi Yamamoto, Tsukuba (JP); Yoshikazu Iwasawa, Tsukuba (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 4 days.

(21) Appl. No.: 10/416,790

(22) PCT Filed: Nov. 14, 2001

(86) PCT No.: PCT/JP01/09956
§ 371 (c)(1),
(2), (4) Date: May 15, 2003

(87) PCT Pub. No.: WO02/40019
PCT Pub. Date: May 23, 2002

(65) Prior Publication Data
US 2004/0044056 A1 Mar. 4, 2004

(30) Foreign Application Priority Data
Nov. 15, 2000 (JP) ......... 2000-348064

(51) Int. Cl.[7] .......... C07D 403/14; C07D 487/08; A61K 31/496; A61K 31/551
(52) U.S. Cl. ......... 514/218; 514/253.04; 514/254.06; 514/249; 514/303; 514/395; 540/575; 544/350; 544/362; 546/118; 548/306.1
(58) Field of Search .......... 514/218, 253.04, 514/254.06, 249, 303, 395; 540/575; 544/350, 362; 546/118; 548/306.1

(56) References Cited

U.S. PATENT DOCUMENTS

| | | | |
|---|---|---|---|
| 5,554,631 A | * | 9/1996 | Kim et al. .......... 514/338 |
| 6,051,570 A | | 4/2000 | Lohray et al. ......... 514/217.04 |

FOREIGN PATENT DOCUMENTS

| | | |
|---|---|---|
| EP | 0 963 987 | 12/1999 |
| EP | 1 072 263 | 1/2001 |
| JP | 63-91385 | 4/1988 |
| JP | 2-306916 | 12/1990 |
| JP | 2001-58991 | 3/2001 |
| WO | 99/36421 | 7/1999 |
| WO | 99/59997 | 11/1999 |
| WO | 00/27815 | 5/2000 |
| WO | 00/08013 | 2/2002 |

OTHER PUBLICATIONS

Zaveri N., Life Sci. Jun. 27, 2003;73(6):663–78.*
Calo' G, Guerrini R, Rizzi A, Salvadori S, Regoli D., Br J Pharmacol. Apr. 2000;129(7):1261–83.*
Paquette, Leo A., Principles of Modern Heterocyclic Chemistry, W.A. Benjamin, New York, 1968, p. 241.*
N. Murphy et al., Neuroscience, vol. 75(1), pp. 1–4 (1996).
J. Mogil, Neuroscience, vol. 75(2), pp. 333–337 (1996).
D. Kapusta et al., "Life Science", vol. 60(1), pp. PL15–PL–22 (1997).
B. Gumusel et al., "Life Science", vol. 60(8), pp. PL141–PL145 (1997).
H. Ueda et al., Neuroscience Letters, vol. 237, pp. 136–138 (1997).
T. Manabe et al., "Nature", vol. 394, pp. 577–581 (1998).
Meunier et al., "Nature", vol. 377, pp. 532–535 (1995).
A. Levine, "Society for Neuroscience", vol. 22, p. 455 (1996).
R. Stratford et al., "NeuroReport", vol. 8(2), p. 423–426 (1997).
J. Sandin et al., "European Journal of Neuroscience", vol. 9, pp. 194–197 (1997).

* cited by examiner

Primary Examiner—Thomas C. McKenzie
(74) Attorney, Agent, or Firm—Wenderoth, Lind & Ponack, L.L.P.

(57) ABSTRACT

This invention relates to the compounds represented by a general formula [I]:

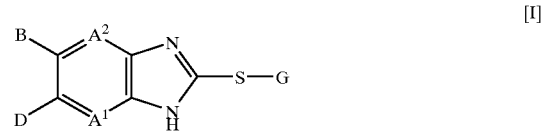

[in which $A^1$ and $A^2$ represent optionally fluorine-substituted methine or the like; B represents halogen, cyano, lower alkyl or the like; D represents optionally substituted heterocyclic group or the like; and G represents $C_3$–$C_{20}$ aliphatic group such as alicyclic group]. These compounds inhibit nociceptin activities due to their high affinity to nociceptin receptor, and are useful as analgesic, antiobestic, corebral function improver, drugs for treatment of alzheimer's disease and dementia, remedies for schizophrenia and neurodegenerative diseases, antidepressant, remedies for diabetes insipidus, polyuria, hypotension and so on.

13 Claims, No Drawings

BENZIMIDAZOLE DERIVATIVES

TECHNICAL FIELD

This invention relates to benzimidazole derivatives which are useful in the field of pharmaceuticals. These benzimidazole derivatives exhibit an action of inhibiting binding of nociceptin to nociseptin receptor ORL1 (Opioid receptor like-1 receptor) and are useful as an analgesic, a reliever against tolerance to narcotic analgesic represented by morphine, a reliever against dependence on narcotic analgesic represented by morphine, an analgesic enhancer, an antiobestic, a drug for ameliorating brain function, a drug for treating Alzheimer's disease, an anti-dementia drug, a remedy for schizophrenia, a drug for treating regressive neurodegenerative diseases represented by Parkinsonism and chorea, an antidepressant, a remedy for diabetes insipidus, a remedy for polyuria, or a remedy for hypotension.

BACKGROUND ART

Nociceptin (the same substance as orphanin FQ) is a peptide comprising 17 amino acids and having a similar structure to that of opioid peptide. Nociceptin has an augmenting activity on reaction against nociceptive stimulation, an appetite stimulating activity, an activity for reducing a space learning ability, an antagonism against an analgesic action of classic opiate agonists, a dopamine release inhibitory action, a water diuresis action, a vasodilative action and a systemic blood pressure-lowering action, and it is considered to take part in controlling pain, appetite and memory learning through a nociceptin receptor ORL1 [refer to *Nature*, vol. 377, p. 532 (1995); *Society for Neuroscience*, vol. 22, p. 455 (1996); *NeuroReport*, vol. 8, p. 423 (1997); *Eur. J. Neuroscience*, vol. 9, p. 194 (1997); *Neuroscience*, vol. 75, pp. 1 and 333 (1996); and *Life Science*, vol. 60, pp. PL15 and PL141 (1997)]. Further, it is known that morphine tolerance is reduced or memory and learning ability are improved in knockout mice in which expression of nociceptin receptor ORL1 is inhibited [*Neuroscience Letters*, vol. 237, p. 136 (1997)]; *Nature*, vol. 394, p. 577 (1998)].

Therefore, substances which specifically inhibit binding of nociceptin to nociceptin receptor ORL1 are useful as an analgesic against diseases accompanied with pain such as cancerous pain, postoperative pain, migraine, gout, chronic rheumatism, chronic pain and neuralgia; a reliever against tolerance to narcotic analgesic represented by morphine, a reliever against dependence on narcotic analgesic represented by morphine, an analgesic enhancer, an antiobestic, a drug for ameliorating brain function, a prophylactic for Alzheimer's disease, a drug for treating Alzheimer's disease, a prophylactic for dementia, an anti-dementia drug, a remedy for schizophrenia, a drug for treating regressive neurodegenerative diseases represented by Parkinsonism and chorea, an antidepressant, a remedy for diabetes insipidus, a remedy for polyuria or a remedy for hypotension.

Substances which specifically inhibit binding of nociceptin to nociceptin receptor ORL1 are described, for example, in International Publications WO00/27815A, WO99/59997A, WO99/48492A and WO99/36421A or EPO Publication EP963987A2. None of those is a compound having a skeletal structure of benzimidazole, and it was entirely unknown that those benzimidazole derivatives of the present invention can be such substances which specifically inhibit binding of nociceptin to nociceptin receptor ORL1.

On the other hand, compounds having structures analogous to those of the benzimidazole derivatives of the invention are described, for example, in JP-A-Sho 63(1988)-91385 or JP-A-Hei 2(1990)-306916. However, those compounds which have a specific aliphatic group on 2-position of benzimidazole skeletal structure, bound through or not through a hetero atom, have a specific substituent group on 5-position and furthermore have an aliphatic, nitrogen-containing heterocyclic group on 6-position, which are characteristic of the compounds of the invention, are not specifically disclosed in above-cited references, and they are compounds not hitherto disclosed in literature.

For example, in those benzimidazole derivatives disclosed in JP-A-Sho 63(1988)-91385, the part of substituent G corresponding to the structure of the present invention is methylene group having an aromatic group as the substituent, and they are different from the compounds of this invention. JP-A-Hei 2(1990)-306916 shows a structure analogous to that of the compounds of the present invention, but contains no disclosure on such specific structure of benzimidazole skeleton having a specific aliphatic group at its 2-position, a specific substituent group at 5-position and further an aliphatic, nitrogen-containing heterocyclic group at 6-position, the characteristic of the compounds of the present invention. Furthermore, the benzimidazole derivatives described in JP-A-Sho 63-91385 have use as anti-ulcer drug, while the benzimidazole derivatives described in JP-A-Hei 2-306916 are used for a platelet adhesion-inhibiting agent. Neither of them have antagonism to nociceptin receptor of the present invention.

DISCLOSURE OF THE INVENTION

The object of the present invention is to provide a novel analgesic, a reliever against tolerance to narcotic analgesic represented by morphine, a reliever against dependence on narcotic analgesic represented by morphine, an analgesic enhancer, an antiobestic, a drug for ameliorating brain function, a prophylactic for Alzheimer's disease, a drug for treating Alzheimer's disease, a prophylactic for dementia, an anti-dementia drug, a remedy for schizophrenia, a drug for treating regressive neurodegenerative diseases represented by Parkinsonism and chorea, an antidepressant, a remedy for diabetes insipidus, a remedy for polyuria or a remedy for hypotension, which have an action to inhibit binding of nociceptin to nociceptin receptor ORL1.

We have concentratively investigated for compounds which inhibit binding of nociceptin to nociceptin receptor ORL1, to discover that benzimidazole derivatives, which are characterized by having an aliphatic, nitrogen-containing heterocyclic group at 6-position, a specific substituent group at 5-position, and furthermore a specific aliphatic group at 2-position via sulfur atom, of benzimidazole skeletal structure, are novel substances not disclosed in prior art literature and inhibit binding of nociceptin to nociceptin receptor ORL1. In the course of subsequent investigations we also discovered that not only said novel substances but also those derivatives analogous in their structure inhibit binding of nociceptin to nociceptin receptor ORL1 and that these benzimidazole derivatives are effective as pharmaceuticals for diseases associated with the nociceptin receptor. The present invention has come to be completed based on these knowledges.

Namely, the present invention relates to:

(1) benzimidazole derivatives represented by the following general formula [I] or pharmaceutically acceptable salts thereof:

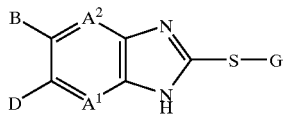
[I]

[in which $A^1$ and $A^2$ are same or different, and represent optionally fluorine-substituted methine group or nitrogen atom, B represents a group selected from a group consisting of halogen, cyano, lower alkylcarbonyl, lower alkylsulfonyl, mono-lower alkylsulfamoyl, di-lower alkylsulfamoyl, optionally fluorine-substituted lower alkyl and optionally fluorine-substituted lower alkyloxy.

D is an aliphatic, nitrogen-containing heterocyclic group which is selected from a group consisting of those of a formula [D-1], formula [D-2] and formula [D-3]

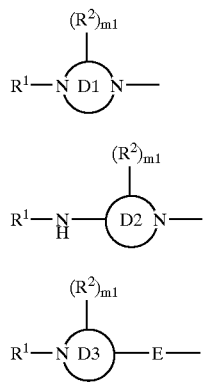

(in which $R^1$ represents hydrogen atom or lower alkyl, and said lower alkyl may be substituted with a substituent selected from a group consisting of halogen, hydroxyl, amino, lower alkyloxy, lower alkylsulfonylamino, aminocarbonylamino, mono-lower alkylcarbamoyl, acetamido, lower cycloalkyl, aromatic heterocyclic group and aromatic carbocyclic group.

$R^2$ binds to an optional carbon atom or atoms on the aliphatic, nitrogen-containing heterocyclic ring, and represents carboxyl, lower alkyloxycarbonyl, carbamoyl, mono-lower alkylcarbamoyl, di-lower alkylcarbamoyl or lower alkyl, said lower alkyl being optionally substituted with a substituent selected from a group consisting of halogen, hydroxyl, optionally fluorine-substituted lower alkyloxy, lower alkylcarbonyl, carboxyl, lower alkyl, lower alkyloxycarbonyl, carbamoyl, mono-lower alkylcarbamoyl and di-lower alkylcarbamoyl, or two $R^2$'s together form an oxo group;

m1 stands for 0 or an integer of 1–2, where m1=2, two $R^2$'s, which may be same or different, bind to same or different optional carbon atom(s) on the aliphatic nitrogen-containing heterocyclic ring;

E stands for a single bond, NR or O, R standing for hydrogen atom, methyl or ethyl;

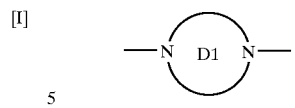

(hereinafter referred to as "D1 ring") stands for a 5–10 membered mono- or di-cyclic aliphatic, nitrogen-containing heterocyclic group which has two nitrogen atoms;

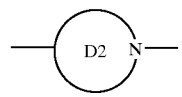

(hereinafter referred to as "D2 ring") stands for a 3–10 membered mono- or di-cyclic aliphatic, nitrogen-containing heterocyclic group which has one nitrogen atom;

(hereinafter referred to as "D3 ring") stands for a 3–10 membered mono- or di-cyclic aliphatic, nitrogen-containing heterocyclic group which has one nitrogen atom.);

G is a $C_3$–$C_{20}$ aliphatic group represented by a formula [G-1]

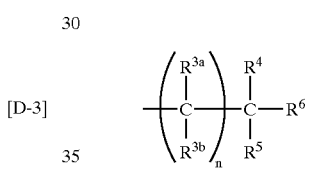

(in which $R^{3a}$ and $R^{3b}$ are same or different and stand for hydrogen atom, methyl or ethyl, $R^4$ stands for hydrogen atom or optionally substituted lower alkyl, and $R^5$ and $R^6$ are same or different and have the same meaning with $R^4$, or $R^5$ and $R^6$ together form an aliphatic cyclic group, in combination with the carbon atom to which they bind, and n is 0 or an integer of 1–4)]:

(2) benzimidazole derivatives represented by the following general formula [I-1] or their pharmaceutically acceptable salts,

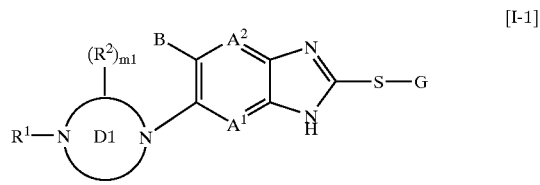

[in which $A^1$, $A^2$, B, G, $R^1$, $R^2$, m1 and D1 ring are same as above-defined]:

(3) compounds which are described in (1) or (2), wherein $A^1$ and $A^2$ are methine groups, or $A^1$ is fluorinated methine group and $A^2$ is methine group:

(4) compounds which are described in (1) or (2), wherein B is fluorine atom, chlorine atom, cyano group or methyl group:

(5) compounds which are described in (1) or (2), wherein optionally substituted lower alkyl groups represented by $R^4$ are lower alkyl groups optionally having substituents selected from the following group α:

[group α]

halogen, hydroxyl, amino, mono-lower alkylamino, di-lower alkylamino, optionally fluorine-substituted lower alkyloxy, lower alkyloxycarbonyl, (lower alkyloxycarbonyl)amino, (lower alkyloxycarbonyl)lower alkylamino, carboxyl, lower alkylcarbonyl, lower alkylcarbonyloxy, (lower alkylcarbonyl)amino, (lower alkylcarbonyl)lower alkylamino, carbamoyl, mono-lower alkylcarbamoyl, di-lower alkylcarbamoyl, carbamoylamino, mono-lower alkylcarbamoylamino, di-lower alkylcarbamoylamino, (mono-lower alkylcarbamoyl)lower alkylamino, (di-lower alkylcarbamoyl)lower alkylamino, carbamoyloxy, mono-lower alkylcarbamoyloxy, di-lower alkylcarbamoyloxy, lower alkylsulfonyl, lower alkylsulfonylamino, sulfamoyl, mono-lower alkylsulfamoyl, di-lower alkylsulfamoyl, sulfamoylamino, (mono-lower alkylsulfamoyl)amino, (di-lower alkylsulfamoyl)amino, (mono-lower alkylsulfamoyl)lower alkylamino, and (di-lower alkylsulfamoyl) lower alkylamino:

(6) compounds which are described in (1) or (2), wherein D is a group selected from the group consisting of piperazin-1-yl, 4-methylpiperazin-1-yl, 4-ethylpiperazin-1-yl, 4-isopropylpiperazin-1-yl, 4-(cyclopropylmethyl)piperazin-1-yl, 4-(2-fluoroethyl)piperazin-1-yl, 4-(2-methoxyethyl) piperazin-1-yl, 4-ethyl-2-methylpiperazin-1-yl, 4-(2-fluoroethyl)-2-methylpiperazin-1-yl, 4-(2-methoxyethyl)-2-methylpiperazin-1-yl, 4-(2-hydroxyethyl)-2-methylpiperazin-1-yl, 4-(2-hydroxyethyl)piperazin-1-yl, 4-[2-(acetamido)ethyl]piperazin-1-yl, 4-(2,6-dimethoxybenzyl)piperzin-1-yl, 2,5-diazabicyclo[2.2.1]heptan-2-yl, 5-(2-hydroxyethyl)-2,5-diazabicyclo[2.2.1]heptan-2-yl, 1,4-diazepan-1-yl, 4-(2-hydroxyethyl)-1,4-diazepan-1-yl, 1-ethylpyrrolidin-3-yl, 1-(2-methoxyethyl)pyrrolidin-3-yl, [1-(2-methoxyethyl)pyrrolidin-3-yl](methyl)amino and [1-(2-methoxyethyl)pyrrolidin-3-yl]oxy:

(7) compounds which are described in (1) or (2), wherein G is a group selected from the group consisting of 2-methoxy-1-(methoxymethyl)ethyl, 2-ethoxy-1-(ethoxymethyl)ethyl, 2-dimethylamino-1,1-dimethylethyl, 2-dimethylamino-1-methylethyl, 2-(acetamido)ethyl, 2-hydroxy-1-(hydroxymethyl)ethyl, 1-(methoxycarbonyl)propyl, 1-ethylpropyl, tert-butyl, 1,1-dimethylpropyl, 1,1-dimethylbutyl, 1,3,3-trimethylbutyl, 3-methoxy-1,3-dimethylbutyl, 3-hydroxy-1,3-dimethylbutyl, 1-ethyl-3-methyl-3-hydroxybutyl, 3-acetoxy-1,1-dimethylbutyl, 3-hydroxy-1,1-dimethylbutyl, cyclobutyl, 1-methylcyclobutyl, cyclopentyl, 1-methylcyclopentyl, cyclohexyl, 1-methylcyclohexyl, 4-(methoxycarbonyl)cyclohexyl, 4-oxocyclohexyl, 4-(ethoxycarbonylamino)cyclohexyl, 4-methoxycarbonylamino-1-methylcyclohexyl, 4-ethoxycarbonylamino-1-methylcyclohexyl, 4-hydroxycyclohexyl, 4-hydroxy-4-methylcyclohexyl, 4-(ethoxycarbonylamino)cyclohexyl, 1-methylpiperidin-4-yl, 1-(methoxycarbonyl)piperidin-4-yl, 1-(ethoxycarbonyl)piperidin-4-yl, 1-methoxycarbonyl-4-methylpiperidin-4-yl, 1-ethoxycarbonyl-4-methylpiperidin-4-yl, 1-methylpyrrolidin-3-yl, 1-methylpiperidin-3-yl, 1-(methoxycarbonyl)pyrrolidin-3-yl, 1-(methoxycarbonyl)piperidin-3-yl, 1-(allyloxycarbonyl)piperidin-4-yl, 1-(ethylsulfonyl)piperidin-4-yl, 1-acetylpiperidin-4-yl, tetrahydrofuran-3-yl, tetrahydro-2H-pyran-4-yl, 4-methyl-tetrahydro-2H-pyran-4-yl, 4-ethyl-tetrahydro-2H-pyran-4-yl, 1,4-dihydroxyoctahydro-2-pentalenyl, 1,4-dioxaspiro[4,5]decan-8-yl, 8-oxabicyclo[3.2.1]octan-3-yl and 8-oxabicyclo[3.2.1]octan-3-yl:

(8) compounds which are described in (1) or (2), in which G is represented by a formula [G-2], $$-C(R_X)(R_Y)(R_Z)$$ [G-2]

[in which $R_X$ stands for lower alkyl which may have a substituent selected from the group α, $R_Y$ and $R_Z$ may be same or different lower alkyl which may have a substituent selected from the group α, or $R_Y$ and $R_Z$ together form a 3–10 membered aliphatic carbocyclic ring concurrently with the carbon atom to which they bind]:

(9) compounds which are described in (8), in which G is a group selected from the group consisting of 1-methylcyclobutyl, 1-methylcyclopentyl, 1-methylcyclohexyl, tert-butyl, 1,1-dimethylpropyl, 1,1-dimethylbutyl, 3-methyltetrahydrofuran-3-yl and 4-methyltetrahydro-2H-pyran-4-yl:

(10) compounds which are described in (1), in which the benzimidazole derivatives represented by the general formula [1] are 5-chloro-6-[4-(2-hydroxyethyl)piperazin-1-yl]-2-[1-(methylcyclobutyl)sulfanyl]benzimidazole, 5-chloro-7-fluoro-6-[4-(2-hydroxyethyl)piperazin-1-yl]-2-[(1-methylcyclopentyl)sulfanyl]benzimidazole, 6-[4-ethyl-2-methylpiperazin-1-yl]-2-[(1,1-dimethylethyl)sulfanyl]-5-methylbenzimidazole, 5-chloro-2-[(1-ethylpropyl)sulfanyl]-6-[1-(2-hydroxyethyl)piperidin-4-yl]benzimidazole, 5-chloro-6-[1,4-diazabicyclo[3.2.1]octan-4-yl]-2-[(1,1-dimethylpropyl)sulfanyl]benzimidazole, 5-chloro-2-[4-[(ethoxycarbonyl)amino]-1-methylcyclohexyl]-sulfanyl]-6-[4-(2-fluoroethyl)piperazin-1-yl]benzimidazole, 5-chloro-2-[(1,1-dimethylpropyl)sulfanyl]-6-[4-(2-hydroxyethyl)piperazin-1-yl]benzimidazole, 5-cyano-2-[(1,1-dimethylethyl)sulfanyl]-7-fluoro-6-[4-(2-fluoroethyl)-2-methylpiperazin-1-yl]benzimidazole, or 5-chloro-2-[(1-ethylpropyl)sulfanyl]-6-[5-(2-hydroxyethyl)-2,5-diazabicyclo[2.2.1]hept-2-yl]benzimidazole:

(11) pharmaceutical compositions containing the compounds which are described in (1) to (10):

(12) nociceptin receptor antagonists which contain the compounds represented by a general formula [I']

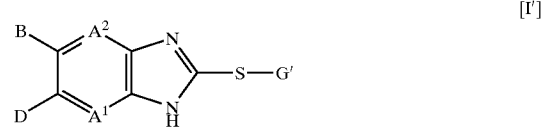

[I']

[wherein $A^1$, $A^2$, B and D are same as above-defined, and G' stands for an optionally substituted $C_3$–$C_{20}$ aliphatic group] as the active ingredient:

(13) nociceptin receptor antagonist of (12), in which G' is represented by a formula [G-1]

[G-1]

[in which $R^{3a}$, $R^{3b}$, $R^4$, $R^5$, $R^6$ and n are same as above-defined]:

(14) nociceptin receptor antagonist of (12), in which $A^1$ and $A^2$ are methine groups, or $A^1$ is fluorinated methine group and $A^2$ is methine group.

(15) nociceptin receptor antagonist of (12), in which B is fluorine atom, chlorine atom, cyano group or methyl group:

(16) nociceptin receptor antagonist of (12), in which D is one represented by the formula [D-1]:

(17) nociceptin receptor antagonist of (12), in which D is a group selected from the group consisting of piperazin-1-yl, 4-methylpiperazin-1-yl, 4-ethylpiperazin-1-yl, 4-isopropylpiperazin-1-yl, 4-(cyclopropylmethyl)piperazin-1-yl, 4-(2-fluoroethyl)piperazin-1-yl, 4-(2-methoxyethyl)piperazin-1-yl, 4-ethyl-2-methylpiperazin-1-yl, 4-(2-fluoroethyl)-2-methylpiperazin-1-yl, 4-(2-methoxyethyl)-2-methylpiperazin-1-yl, 4-(2-hydroxyethyl)-2-methylpiperazin-1-yl, 4-(2-hydroxyethyl)piperazin-1-yl, 4-[2-(acetamido)ethyl]piperazin-1-yl, 4-(2,6-dimethoxybenzyl)piperazin-1-yl, 2,5-diazabicyclo[2.2.1]heptan-2-yl, 5-(2-hydroxyethyl)-2,5-diazabcyclo[2.2.1]heptan-2-yl, 1,4-diazepan-1-yl, 4-(2-hydroxyethyl)-1,4-diazepan-1-yl, 1-ethylpyrrolidin-3-yl, 1-(2-methoxyethyl)pyrrolidin-3-yl, [1-(2-methoxyethyl)pyrrolidin-3-yl](methyl)amino and [1-(2-methoxyethyl)pyrrolidin-3-yl]oxy:

(18) nociceptin receptor antagonist of (12), in which G' is represented by a formula [G-2]

$$—C(R_X)(R_Y)(R_Z) \qquad [G-2]$$

[in which $R_X$ stands for lower alkyl which may have a substituent selected from the group α, $R_Y$ and $R_Z$ may be same or different lower alkyl which may have a substituent selected from the group α, or $R_Y$ and $R_Z$ together form a 3–10 membered aliphatic carbocyclic ring in combination with the carbon atom to which they bind]:

(19) nociceptin receptor antagonist of (18), in which G' is a group selected from the group consisting of 1-methylcyclobutyl, 1-methylcyclopentyl, 1-methylcyclohexyl, tert-butyl, 1,1-dimethylpropyl, 1,1-dimethylbutyl, 3-methyltetrahydrofuran-3-yl and 4-methyltetrahydro-2H-pyran-4-yl:

(20) an analgesic, a reliever against tolerance to narcotic analgesic, a reliever against dependence on narcotic analgesic, an analgesic enhancer, an antiobestic, a drug for ameliorating brain function, an agent for treating Alzheimer's disease, an anti-dementia drug, a remedy for schizophrenia, a remedy for Parkinsonism, a remedy for chorea, an antidepressant, a remedy for diabetes insipidus, a remedy for polyuria, or a remedy for hypotension, which contain the nociceptin receptor antagonists that are descrbed in (12)–(19) as the active ingredient:

(20') an analgesic, a reliever against tolerance to narcotic analgesic, a reliever against dependence on narcotic analgesic, an analgesic enhancer, an antiobestic, a drug for ameliorating brain function, an agent for treating Alzheimer's disease, an anti-dementia drug, a remedy for schizophrenia, a remedy for Parkinsonism, a remedy for chorea, an antidepressant, a remedy for diabetes insipidus, a remedy for polyuria, or a remedy for hypotension, which contain the compounds which are described in (1)–(10) as the active ingredient:

(21) a method for producing a compound represented by the general formula [I-1]

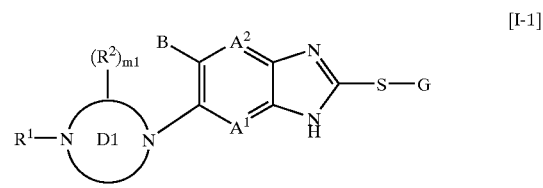

[in which $A^1$, $A^2$, B, G, $R^1$, $R^2$, m1 and D1 ring are same as above-defined] which comprises 1) a step of reacting a compound represented by a general formula [II]

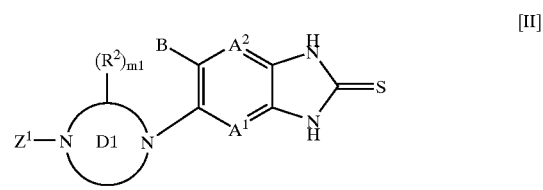

[in which $Z^1$ stands for $R^1$ or P, P stands for an amino-protective group, and $A^1$, $A^2$, B, $R^1$, $R^2$, m1 and D1 ring are same as above-defined] with a compound of a general formula [III]

$$G\text{-}L \qquad [III]$$

[in which G is same as above-defined, and L stands for a leaving group selected from the group consisting of halogen, lower alkylsulfonyloxy, arylsulfonyloxy, imidazolinyl and 0-isourea] in a reaction solvent in the presence or absence of a basic compound, whereby obtaining a compound represented by a general formula [IV]

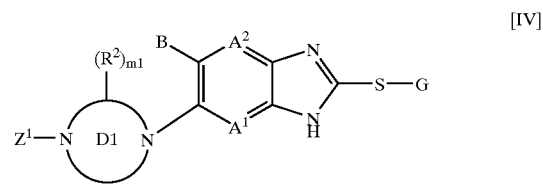

[in which $A^1$, $A^2$, B, G, $R^2$, $Z^1$, m1 and $D^1$ ring are same as above-defined], 2) a step of eliminating the protective group P in the compound represented by the general formula [IV], where $Z^1$ is P, and 3) where necessary, a step of condensing the compound obtained in above step 2) with a compound represented by a general formula [V]

$$R^{1a}—CHO \qquad [V]$$

[in which $R^{1a}$ stands for a group of $R^1$ from whose α-position side methylene group is removed] in a reaction solvent, in the presence of a reducing agent:

(22) a method for producing a compound represented by a general formula [I-2]

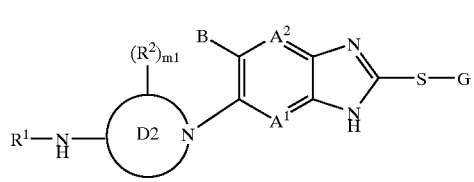

[1-2]

[in which $A^1$, $A^2$, B, G, $R^1$, $R^2$, m1 and D2 ring are same as above-defined] which comprises 1) a step for reacting a compound represented by a general formula [VI]

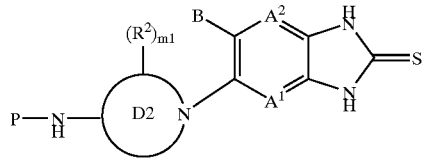

[VI]

[in which $A^1$, $A^2$, B, $R^2$, P, m1 and D2 ring are same as above-defined] with a compound represented by the general formula [III]

G-L   [III]

[in which G and L are same as above-defined] in a reaction solvent in the presence or absence of a basic compound, to obtain a compound represented by a formula [VII]

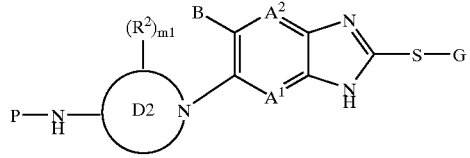

[VII]

[in which $A^1$, $A^2$, B, G, $R^2$, P, m1 and D2 ring are same as above-defined], 2) a step for eliminating the protective group P in the compound of the general formula [VII] which is obtained in the above step 1), and 3) where necessary, a step of condensing the compound obtained in above step 2) with a compound represented by the general formula [V]

$R^{1a}$—CHO   [V]

[in which $R^{1a}$ is same as earlier defined] in a reaction solvent in the presence of a reducing agent: and

(23) a method for producing a compound represented by a general formula [X-1]

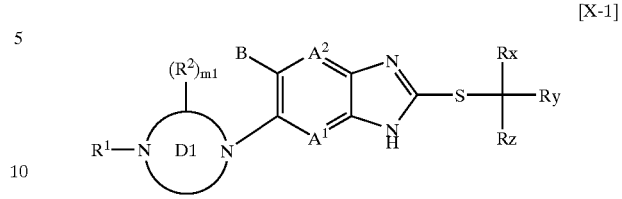

[X-1]

[in which $A^1$, $A^2$, B, $R^1$, $R^2$, $R_X$, $R_Y$, $R_Z$, m1 and $D^1$ ring are same as above-defined] which comprises a step of reacting a compound represented by a general formula [6']

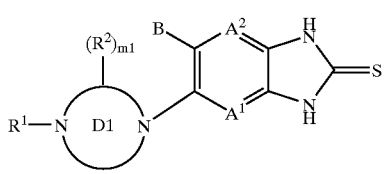

[6']

[in which $A^1$, $A^2$, B, $R^1$, $R^2$, m1 and D1 ring are same as above-defined] with a compound represented by a general formula [XI]

$R_X$—C($R_Y$)($R_Z$)—OH   [XI]

[in which $R_X$, $R_Y$ and $R_Z$ are same as above-defined] in the presence of an acid catalyst.

The invention, furthermore, relates to

(24) benzimidazole derivatives represented by a general formula [K]

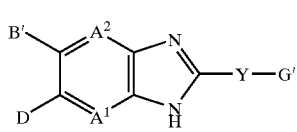

[K]

[in which Y stands for a single bond, NH or O; B' stands for a group selected from the group consisting of halogen, cyano, lower alkylcarbonyl, lower alkylsulfonyl, mono-lower alkylsulfamoyl, di-lower alkylsulfamoyl and optionally fluorine-substituted lower alkyloxy; $A^1$, $A^2$, D and G' are same as above-defined] and pharmaceutically acceptable salts thereof:

(25) the compound as described in (24), in which $A^1$ and $A^2$ are methine groups, or $A^1$ is fluorinated methine group and $A^2$ is methine group:

(26) the compounds as described in (24), in which D is a group selected from the group consisting of piperazin-1-yl, 4-methylpiperazin-1-yl, 4-ethylpiperazin-1-yl, 4-isopropylpiperazin-1-yl, 4-(cyclopropylmethyl)piperazin-1-yl, 4-(2-fluoroethyl)piperazin-1-yl, 4-(2-methoxyethyl) piperazin-1-yl, 4-ethyl-2-methylpiperazin-1-yl, 4-(2-fluoroethyl)-2-methylpiperazin-1-yl, 4-(2-methoxyethyl)-2-methylpiperazin-1-yl, 4-(2-hydroxyethyl)-2-methylpiperazin-1-yl, 4-(2-hydroxyethyl)piperazin-1-yl, 4-[2-(acetamido)ethyl]piperazin-1-yl, 4-(2,6-dimethoxybenzyl)piperzin-1-yl, 2,5-diazabicyclo[2.2.1] heptan-2-yl, 5-(2-hydroxyethyl)-2,5-diazabicyclo[2.2.1] heptan-2-yl, 1,4-diazepan-1-yl, 4-(2-hydroxyethyl)-1,4-diazepan-1-yl, 1-ethylpyrrolidin-3-yl, 1-(2-methoxyethyl)

pyrrolidin-3-yl, [1-(2-methoxyethyl)pyrrolidin-3-yl] (methyl)amino and [1-(2-methoxyethyl)pyrrolidin-3-yl]oxy:

(27) the compounds as described in (24), in which G' is a group selected from the group consisting of 2-methoxy-1-(methoxymethyl)ethyl, 2-ethoxy-1-(ethoxymethyl)ethyl, 2-dimethylamino-1,1-dimethylethyl, 2-dimethylamino-1-methylethyl, 2-(acetamido)ethyl, 2-hydroxy-1-(hydroxymethyl)ethyl, 1-(methoxycarbonyl)propyl, 1-ethylpropyl, tert-butyl, 1,1-dimethylpropyl, 1,1-dimethylbutyl, 1,3,3-trimethylbutyl, 3-methoxy-1,3-dimethylbutyl, 3-hydroxy-1,3-dimethylbutyl, 1-ethyl-3-methyl-3-hydroxybutyl, 3-acetoxy-1,1-dimethylbutyl, 3-hydroxy-1,1-dimethylbutyl, cyclobutyl, 1-methylcyclobutyl, cyclopentyl, 1-methylcyclopentyl, cyclohexyl, 1-methylcyclohexyl, 4-(methoxycarbonyl) cyclohexyl, 4-oxocyclohexyl, 4-(ethoxycarbonylamino) cyclohexyl, 4-methoxycarbonylamino-1-methylcyclohexyl, 4-ethoxycarbonylamino-1-methylcyclohexyl, 4-hydroxycyclohexyl, 4-hydroxy-4-methylcyclohexyl, 4-(ethoxycarbonylamino)cyclohexyl, 1-methylpiperidin-4-yl, 1-(methoxycarbonyl)piperidin-4-yl, 1-(ethoxycarbonyl) piperidin-4-yl, 1-methoxycarbonyl-4-methylpiperidin-4-yl, 1-ethoxycarbonyl-4-methylpiperidin-4-yl, 1-methylpyrrolidin-3-yl, 1-methylpiperidin-3-yl, 1-(methoxycarbonyl)pyrrolidin-3-yl, 1-(methoxycarbonyl) piperidin-3-yl, 1-(allyloxycarbonyl)piperidin-4-yl, 1-(ethylsulfonyl)piperidin-4-yl, 1-acetylpiperidin-4-yl, tetrahydrofuran-3-yl, tetrahydro-2H-pyran-4-yl, 4-methyl-tetrahydro-2H-pyran-4-yl, 4-ethyl-tetrahydro-2H-pyran-4-yl, 1,4-dihydroxyoctahydro-2-pentalenyl, 1,4-dioxaspiro[4,5]decan-8-yl, 8-oxabicyclo[3.2.1]octan-3-yl and 8-oxobicyclo[3.2.1]octan-3-yl:

(28) nociceptin receptor antagonists which contain the compounds of (24)–(27) as the active ingredient: and

(29) an analgesic, a reliever against tolerance to narcotic analgesic, a reliever against dependence on narcotic analgesic, an analgesic enhancer, an antiobestic, a drug for ameliorating brain function, an agent for treating Alzheimer's disease, an anti-dementia drug, a remedy for schizophrenia, a remedy for Parkinsonism, a remedy for chorea, antidepressant, a remedy for diabetes insipidus, a remedy for polyuria, or a remedy for hypotension, which contain the compounds that are described in (24)–(27).

Hereinafter the signs and terms used in the present specification are explained.

As substituents which are selected from the group α, the following are shown as examples:
[group α]
halogen, hydroxyl, amino, mono-lower alkylamino, di-lower alkylamino, optionally fluorine-substituted lower alkyloxy, lower alkyloxycarbonyl, (lower alkyloxycarbonyl)amino, (lower alkyloxycarbonyl)lower alkylamino, carboxyl, lower alkylcarbonyl, lower alkylcarbonyloxy, (lower alkylcarbonyl)amino, (lower alkylcarbonyl)lower alkylamino, carbamoyl, mono-lower alkylcarbamoyl, di-lower alkylcarbamoyl, carbamoylamino, mono-lower alkylcarbamoylamino, di-lower alkylcarbamoylamino, (mono-lower alkylcarbamoyl)lower alkylamino, (di-lower alkylcarbamoyl)lower alkylamino, carbamoyloxy, mono-lower alkylcarbamoyloxy, di-lower alkylcarbamoyloxy, lower alkylsulfonyl, lower alkylsulfonylamino, sulfamoyl, mono-lower alkylsulfamoyl, di-lower alkylsulfamoyl, sulfamoylamino, (mono-lower alkylsulfamoyl)amino, (di-lower alkylsulfamoyl)amino, (mono-lower alkylsulfamoyl)lower alkylamino, and (di-lower alkylsulfamoyl) lower alkylamino, As "halogen", fluorine, chlorine, bromine or iodine atom can be exemplified.

As "lower alkyl", $C_1$–$C_6$ alkyl groups can be exemplified, specific examples including $C_1$–$C_6$ linear or $C_3$–$C_6$ branched alkyl groups such as methyl, ethyl, propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-metylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl or 1-ethyl-1-methylpropyl and the like groups.

"Oxo group" signifies a group wherein two substituent groups, in combination with the carbon atom to which they bind, form a carbonyl group. For example, taking the case of $R^8$, two $R^8$'s and the carbon atom to which they bind together form a carbonyl group.

As "optionally fluorine-substituted lower alkyl", those lower alkyl groups as above-named, in which 1, 2 or more optional hydrogen atoms are substituted with fluorine atom(s) can be exemplified. Besides said lower alkyl groups, fluoromethyl, difluoromethyl, trifluoromethyl, 2-fluoroethyl, 2,2-difluoroethyl, 2,2,2-trifluoroethyl and the like can also be named as examples.

As "lower alkylamino", amino groups which are mono-substituted with above lower alkyl groups can be exemplified, specific examples including methylamino, ethylamino, propylamino, isopropylamino, butylamino, sec-butylamino and tert-butylamino groups and the like.

As "di-lower alkylamino", amino groups which are di-substituted with above lower alkyl groups can be exemplified, specific examples including dimethylamino, diethylamino, ethylmethylamino, dipropylamino, methylpropylamino and diisopropylamino groups and the like.

As "optionally fluorine-substituted lower alkyloxy", oxygen atom which is substituted with above lower alkyl or fluorine-substituted lower alkyl can be exemplified, specific examples including, as lower alkyloxy, methoxy, ethoxy, propoxy, isopropoxy, butoxy, tert-butoxy and pentyloxy groups, and as fluorine-substituted lower alkyloxy, fluoromethoxy, difluoromethoxy, trifluoromethoxy, 1,2-difluoroethoxy and the like groups.

As "lower alkyloxycarbonyl", those in which carbonyl is substituted with above lower alkyloxy, i.e., $C_1$–$C_6$ alkyloxycarbonyl groups can be exemplified, specific examples including methoxycarbonyl, ethoxycarbonyl, propyloxycarbonyl, isopropyloxycarbonyl, butoxycarbonyl, isobutoxycarbonyl, tert-butoxycarbonyl, pentyloxycarbonyl and the like groups.

As "(lower alkyloxycarbonyl)amino", those in which amino group is substituted with above lower alkyloxycarbonyl group, i.e., $C_1$–$C_6$ alkyloxycarbonylamino groups can be exemplified, specific examples including methoxycarbonylamino, ethoxycarbonylamino, propyloxycarbonylamino, isopropyloxycarbonylamino, butoxycarbonylamino, isobutoxycarbonylamino, tert-butoxycarbonylamino, pentyloxycarbonylamino and the like groups.

As "(lower alkyloxycarbonyl)lower alkylamino", those mono-lower alkylamino groups which are substituted with above lower alkyloxycarbonyl can be exemplified, specific examples including (methoxycarbonyl)methylamino, (ethoxycarbonyl)methylamino, (n-propyloxycarbonyl) methylamino and the like groups.

As "lower alkylcarbonyl", carbonyl group substituted with said lower alkyl groups i.e., $C_1$–$C_6$ alkylcarbonyl can be exemplified, specific examples including acetyl, propionyl, butyryl, isobutyryl, valeryl, isovaleryl, pivaloyl and the like groups.

As "lower alkylcarbonylamino", amino group which is mono-substituted with above lower alkylcarbonyl can be exemplified, specific examples including acetamido, propionylamino, isobutyrylamino, valerylamino, isovalerylamino, pivaloylamino and the like groups.

As "(lower alkylcarbonyl)lower alkylamino", mono-lower alkylamino groups substituted with above lower alkylcarbonyl can be exemplified, specific examples including (methylcarbonyl)methylamino, (ethylcarbonyl)methylamino, (n-propylcarbonyl)methylamino and the like groups.

As "lower alkylcarbonyloxy", oxygen atom which is substituted with above lower alkylcarbonyl can be exemplified, specific examples including acetoxy, propionyloxy, valeryloxy, isovaleryloxy, pivaloyloxy and the like groups.

As "lower alkenyl", $C_2$–$C_6$ linear or branched alkenyl groups can be exemplified, specific examples including vinyl, 1-propenyl, 2-propenyl, isopropenyl, 3-butenyl, 2-butenyl, 1-butenyl, 1-methyl-2-propenyl, 1-methyl-1-propenyl, 1-ethyl-1-ethenyl, 2-methyl-2-propenyl, 2-methyl-1-propenyl, 3-methyl-2-butenyl, 4-pentenyl and the like groups.

As "lower alkenyloxycarbonyl", above lower alkenyl groups substituted with oxycarbonyl can be exemplified, specific examples including vinyloxycarbonyl, allyloxycarbonyl, 1-butyleneoxycarbonyl and the like groups.

As "lower cycloalkyl", $C_3$–$C_6$ cycloalkyl groups can be exemplified, specific examples including cyclopropyl, cyclobutyl, cyclopentyl, cyclohexyl and the like groups.

As "mono-lower alkylcarbamoyl", carbamoyl which is mono-substituted with lower alkyl can be exemplified, specific examples including methylcarbamoyl, ethylcarbamoyl, propylcarbamoyl, isopropylcarbamoyl, butylcarbamoyl, sec-butylcarbamoyl, tert-butylcarbamoyl and the like groups.

As "di-lower alkylcarbamoyl", carbamoyl which is di-substituted with said lower alkyl can be exemplified, specific examples including dimethylcarbamoyl, diethylcarbamoyl, ethylmethylcarbamoyl, dipropylcarbamoyl, methylpropylcarbamoyl, diisopropylcarbamoyl and the like groups.

As "mono-lower alkylcarbamoylamino", amino which is substituted with said mono-lower alkylcarbamoyl can be exemplified, specific examples including methylcarbamoylamino, ethylcarbamoylamino, propylcarbamoylamino, isopropylcarbamoylamino, butylcarbamoylamino, sec-butylcarbamoylamino, tert-butylcarbamoylamino and the like groups.

As "di-lower alkylcarbamoylamino", amino which is substituted with said di-lower alkylcarbamoyl can be exemplified, specific examples including dimethylcarbamoylamino, diethylcarbamoylamino, dipropylcarbamoylamino, diisopropylcarbamoylamino, dibutylcarbamoylamino, di-sec-butylcarbamoylamino, di-tert-butylcarbamoylamino and the like groups.

As "(mono-lower alkylcarbamoyl)lower alkylamino", mono-lower alkylamino substituted with said mono-lower alkylcarbamoyl can be exemplified, specific examples including (monomethylcarbamoyl)methylamino, (monoethylcarbamoyl)methylamino, [mono-(n-propyl)carbamoyl]methylamino and the like groups.

As "(di-lower alkylcarbamoyl) lower alkylamino", mono-lower alkylamino substituted with said di-lower alkylcarbamoyl can be exemplified, specific examples including (dimethylcarbamoyl)methylamino, (diethylcarbamoyl)methylamino, (di-n-propylcarbamoyl)methylamino and the like groups.

As "mono-lower alkylcarbamoyloxy", oxygen atom which is substituted with said lower alkylcarbamoyl can be exemplified, specific examples including methylcarbamoyloxy, ethylcarbamoyloxy, propylcarbamoyloxy, isopropylcarbamoyloxy, butylcarbamoyloxy, sec-butylcarbamoyloxy, tert-butylcarbamoyloxy and the like group.

As "di-lower alkylcarbamoyloxy", oxygen atom which is substituted with said di-lower alkylcarbamoyl can be exemplified, specific examples including dimethylcarbamoyloxy, diethylcarbamoyloxy, ethylmethylcarbamoyloxy, dipropylcarbamoyloxy, methylpropylcarbamoyloxy, diisopropylcarbamoyloxy and the like groups.

As "lower alkylsulfonyl", sulfonyl which is substituted with said lower alkyl can be exemplified, specific examples including methylsulfonyl, ethylsulfonyl, propylsulfonyl, isopropylsulfonyl, butylsulfonyl, sec-butylsulfonyl, tert-butylsulfonyl and the like groups.

As "lower alkylsulfonylamino", amino which is mono-substituted with said lower alkylsulfonyl can be exemplified, specific examples including methylsulfonylamino, ethylsulfonylamino, propylsulfonylamino, isopropylsulfonylamino, butylsulfonylamino, sec-butylsulfonylamino, tert-butylsulfonylamino and the like groups.

As "mono-lower alkylsulfamoyl", sulfamoyl which is mono-substituted with said lower alkyl can be exemplified, specific examples including monomethylsulfamoyl, monoethylsulfamoyl, monopropylsulfamoyl, monoisopropylsulfamoyl, monobutylsulfamoyl, mono-(sec-butyl)sulfamoyl, mono-(tert-butyl)sulfamoyl and the like groups.

As "di-lower alkylsulfamoyl", sulfamoyl which is di-substituted with said di-lower alkyl can be exemplified, specific examples including dimethylsulfamoyl, diethylsulfamoyl, dipropylsulfamoyl, diisopropylsulfamoyl, dibutylsulfamoyl, di-sec-butylsulfamoyl, di-tert-butylsulfamoyl and the like groups.

As "(mono-lower alkylsulfamoyl)amino", amino which is mono-substituted with said mono-lower alkylsulfamoyl can be exemplified, specific examples including (monomethylsulfamoyl)amino, (monoethylsulfamoyl)amino, (monopropylsulfamoyl)amino, (monoisopropylsulfamoyl)amino, (monobutylsulfamoyl)amino, mono-(sec-butyl)sulfamoylamino, (tert-butyl)sulfamoylamino and the like groups.

As "di-(lower alkylsulfamoyl)amino", amino which is mono-substituted with said di-lower alkylsulfamoyl can be exemplified, specific examples of which including (dimethylsulfamoyl)amino, (diethylsulfamoyl)amino, (ethylmethylsulfamoyl)amino, (dipropylsulfamoyl)amino, (methylpropylsulfamoyl)amino, (diisopropylsulfamoyl)amino and the like groups.

As "(mono-lower alkylsulfamoyl)lower alkylamino", "mono-lower alkylamino" which is substituted with said mono-lower alkylsulfamoyl can be exemplified, specific examples including (monomethylsulfamoyl)methylamino, (monoethylsulfamoyl)methylamino, [mono-(n-propyl)sulfamoyl]methylamino and the like groups.

As "(di-lower alkylsulfamoyl)lower alkylamino", "mono-lower alkylamino" which is substituted with said di-lower alkylsulfamoyl can be exemplified, specific examples including (dimethylsulfamoyl)methylamino, (diethylsulfamoyl)methylamino, [di-(n-propyl)sulfamoyl] methylamino and the like groups.

As "aliphatic, nitrogen-containing heterocyclic groups", mono- or di-cyclic aliphatic heterocyclic groups can be exemplified, specific examples including, as 3- to 10-membered aliphatic heterocyclic groups containing one nitrogen atom, azetizin-1-yl, azetidin-2-yl, azetidin-3-yl, pyrrolidin-1-yl, pyrrolidin-2-yl, pyrrolidin-3-yl, piperidin-1-yl, piperidin-2-yl, piperidin-3-yl, piperidin-4-yl, hexamethyleneimin-1-yl,heptamethyleneimin-1-yl and the like groups; and as 5- to 10-membered aliphatic heterocyclic groups having two nitrogen atoms, piperazin-1-yl, 2,5-diazabicyclo[2.2.1]heptan-2-yl, 1,4-diazepan-1-yl, 2,5-diazabicyclo[2.2.2]octan-2-yl, 1,4-diazabicyclo[3.2.1]octan-4-yl, 3,4,5,6-tetrahydropyrrolo-[3,4-C]pyrrolo-2-(1H)-yl, decahydro[1,6]naphthylidin-6-yl and the like groups.

As "aliphatic cyclic groups", 3- to 10-membered mono- to tri-cyclic aliphatic carbocyclic groups and 3- to 10-membered, monoto tri-cyclic aliphatic heterocyclic groups containing 1 to 3 hetero atoms which may be same or different and which are selected from a group consisting of oxygen, sulfur and nitrogen (preferably oxygen and/or nitrogen) can be exemplified, specific examples including: as 3- to 10-membered mono- to tri-cyclic aliphatic carbocyclic groups, cyclopropyl, cyclobutyl, cyclopentyl, cyclohexyl, cycloheptyl, cyclooctyl, cyclononyl, cyclodecyl, cyclohexenyl, cyclohexadienyl, cycloheptenyl, cycloheptadienyl, cyclooctenyl, cyclooctadienyl, cyclononenyl, cyclononadienyl, cyclodecenyl, cyclodecadienyl, bicyclo[2.2.1]heptan-2-yl, bicyclo[2.2.1]hept-2-en-2-yl, bicyclo[3.1.1]heptan-3-yl, bicyclo[3.1.1]hept-2-en-3-yl, bicyclo[2.2.2]octan-2-yl, bicyclo[3.2.1]octan-1-yl, bicyclo[3.2.1]octan-2-yl, bicyclo[3.2.1]octan-3-yl, bicyclo[3.2.1]octan-6-yl, bicyclo[3.2.1]octan-8-yl, bicyclo[3.2.2]nonan-2-yl, bicyclo[3.2.2]nonan-3-yl, bicyclo[3.3.1]nonan-2-yl, bicyclo[3.3.1]nonan-3-yl, bicyclo[3.3.1]nonan-9-yl, bicyclo[4.2.1]nonan-2-yl, bicyclo[4.2.1]nonan-3-yl, bicyclo[4.3.0]nonan-2-yl, bicyclo[4.3.0]nonan-3-yl, bicyclo[3.3.2]decan-2-yl, bicyclo[3.3.2]decan-3-yl, bicyclo[4.2.2]decan-2-yl, bicyclo[4.2.2]decan-3-yl, bicyclo[4.3.1]decan-2-yl, bicyclo[4.3.1]decan-3-yl, bicyclo[4.4.0]decan-1-yl, bicyclo[4.4.0]decan-2-yl, bicyclo[4.4.0]decan-3-yl, tricyclo[3.2.1.1$^{3,7}$]nonan-1-yl, tricyclo[3.3.1.1$^{3,7}$]decan-1-yl, tricyclo[3.3.1.1$^{3,7}$]decan-2-yl, spiro[2.4]heptan-4-yl, spiro[2.5]octan-4-yl, spiro[3.4]octan-5-yl, spiro[3.5]nonan-5-yl, spiro[4.4]nonan-6-yl, spiro[4.5]decan-1-yl, spiro[4.5]decan-6-yl, spiro[4.5]decan-7-yl, spiro[4.5]decan-8-yl, spiro[bicyclo[2.2.1]heptan-2,1'-cyclopropan]-3-yl, spiro[bicyclo[2.2.1]heptan-2,1'-cyclobutan]-3-yl, spiro[bicyclo[2.2.1]heptan-2,1'-cyclopentan]-3-yl and the like groups; and as the mono- to tri-cyclic aliphatic heterocyclic groups containing 1 to 3 hetero atoms which may be same of different and which are selected from the group consisting of oxygen, sulfur and nitrogen (preferably oxygen and/or nitrogen), 1) as those containing one nitrogen atom, pyrrolidin-1-yl, pyrrolidin-2-yl, pyrrolidin-3-yl, piperidin-1-yl, piperidin-2-yl, piperidin-3-yl, and piperidin-4-yl;
2) as those containing two nitrogen atoms, piperazin-1-yl, 2,5-diazabicyclo[2.2.1]heptan-2-yl, 1,4-diazepan-1-yl, 1,4-diazabicyclo[3.2.1]octan-4-yl and 3,4,5,6-tetrahydropyrrolo-[3,4-C]pyrrol-2(1H)-yl;
3) as those containing one each of nitrogen and oxygen atoms, 2-morpholinyl, 3-morpholinyl, 4-morpholinyl (morpholino);
4) as those containing one each of nitrogen and sulfur atoms, 2-thiomorpholinyl, 3-thiomorpholinyl, 4-thiomorpholinyl (thiomorpholino), thiazolidin-2-yl, thiazolidin-4-yl and thiazolidin-5-yl;
5) as those containing one oxygen atom, tetrahydrofuran-2-yl, tetrahydrofuran-3-yl, tetrahydropyran-2-yl, tetrahydropyran-3-yl, tetrahydropyran-4-yl, 1,4-dihydroxyoctahydro-2-pentalenyl, 1,4-dioxaspiro[4,5]decan-8-yl, 8-oxabicyclo[3.2.1]octan-3-yl, 3-oxabicyclo[3,2,1]octan-8-yl, 3-oxabicyclo[3,3,1]nonan-9-yl, 8-oxabicyclo[3,2,1]octan-3-yl, 9-oxabicyclo[3,3,1]nonan-3-yl and the like groups; and
6) as those containing one sulfur atom, tetrahydrothiophen-2-yl, tetrahydrothiophen-3-yl, tetrahydro-2H-thiopyran-2-yl, tetrahydro-2H-thiopyran-3-yl, tetrahydro-2H-thiopyran-4-yl and the like groups.

As "aromatic heterocyclic groups", 5- or 6-membered monocyclic aromatic heterocyclic groups containing 1,2 or more, preferably 1–3, hetero atoms which may be same or different and are selected from a group consisting of oxygen, nitrogen and sulfur atoms; or condensed ring aromatic heterocyclic groups formed by condensation of said monocyclic aromatic heterocyclic groups with aromatic carbocyclic groups such as phenyl, naphthyl, anthryl or the like, or mutual condensation of same or different monocyclic aromatic heterocyclic groups as aforesaid can be exemplified, said aromatic hetrocyclic groups optionally having substituent group(s). Specific examples include pyrrolyl, furyl, thienyl, imidazolyl, pyrazolyl, thiazolyl, isothiazolyl, oxazolyl, isooxazolyl, triazolyl, tetrazolyl, oxadiazolyl, thiadiazolyl, pyridyl, pyrazinyl, pyrimidinyl, pyridazinyl, indolyl, benzofuranyl, benzothienyl, benzimidazolyl, benzoxazolyl, benzisoxazolyl, benzothiazolyl, benzisothiazolyl, quinolyl, isoquinolyl, naphthilidinyl, quinoxalinyl, quinazolinyl and the like groups. As the substituent(s) which may be present on the aromatic heterocyclic groups, one, two or more substituents which may be same or different can be exemplified, specific examples including those selected from the group α, or lower alkyl which may have substituent(s) selected from the group α.

As "aromatic carbocyclic group", phenyl, naphthyl, anthryl and the like groups are exemplified, and as the substituent thereon, those selected from the group α or lower alkyl optionally having a substituent selected from the group α can be exemplified.

As "$C_3$–$C_{20}$ aliphatic groups", optionally substituted $C_3$–$C_{10}$ alkyl, optionally substituted $C_3$–$C_{10}$ alkenyl, optionally substituted $C_3$–$C_{10}$ alkynyl, optionally substituted 3- to 10-membered aliphatic cyclic groups which may contain 1–3 hetero atoms selected from a group consisting of oxygen, sulfur and nitrogen atoms, and $C_1$–$C_{10}$ alkyl having, as a substituent, 3- to 10-membered aliphatic cyclic group optionally containing 1–3 hetero atoms selected from a group consisting of oxygen, sulfur and nitrogen atoms are exemplified. As substituents which these groups may have, substituent groups selected from the group α can be exemplified.

"Pharmaceutically acceptable salts" of the compounds represented by the general formula [I] or the general formula [K] signify customary ones which are acceptable for medical use, for example, where the compounds have carboxyl group, base addition salts at the carboxyl group, or when they have amino group or basic hetero ring, acid addition salts at the amino group or the basic hetero ring.

As said base addition salts, alkali metal salts such as sodium salt and potassium salt; alkaline earth metal salts such as calcium salt and magnesium salt; ammonium salt, organic amine salts such as trimethylamine salt, triethylamine salt, dicyclohexylamine salt, ethanolamine salt, diethanolamine salt, triethanolamine salt, procaine salt and N,N'-dibenzylethylenediamine salt can be exemplified.

As said acid addition salts, inorganic acid salts such as hydrochloride, sulfate, nitrate, phosphate and perchlorate; organic acid salts such as maleate, fumarate, tartarate, citrate, ascorbate and trifluoroacetate; and sulfonates such as methanesulfonate, isethionate, benzenesulfonate and p-toluenesulfonate can be exemplified.

Compounds which are Represented by the General Formula [I] or those Represented by the General Formula [K]

For still concrete disclosure on the compounds represented by the general formula [I] or those represented by the general formula [K], various symbols are explained, citing their preferred specific examples. In the following, examples of the substituents on the compounds represented by the general formula [I] or [K] are same, unless otherwise specified. Preferred scopes also are in common.

The numbers assigned to the positions of the benzimidazole skeletal structure of the compounds of the present invention are as below, the following explanations referring thereto.

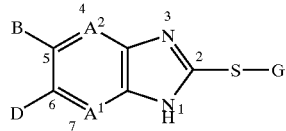

Those benzimidazole derivatives of the present invention can also exist as those represented by the formula [b] having an equilibrium relationship, which compounds also being encompassed by the present invention.

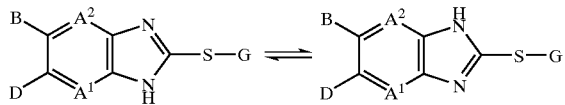

In the compounds of this invention, recommendable combinations of $A^1$ and $A^2$ are, for example:

$A^1$ is methine and $A^2$ is methine,
$A^1$ is methine and $A^2$ is —CF—,
$A^1$ is methine and $A^2$ is nitrogen,
$A^1$ is —CF— and $A^2$ is methine,
$A^1$ is —CF— and $A^2$ is —CF—,
$A^1$ is —CF— and $A^2$ is nitrogen,
$A^1$ is nitrogen and $A^2$ is methine,
$A^1$ is nitrogen and $A^2$ is —CF—, and
$A^1$ is nitrogen and $A^2$ is nitrogen, among which those preferred are:
$A^1$ is methine and $A^2$ is methine,
$A^1$ is —CF— and $A^2$ is methine,
$A^1$ is nitrogen and $A^2$ is methine.
Even more preferred are
$A^1$ is methine and $A^2$ is methine, and
$A^1$ is —CF— and $A^2$ is methine.

In the compounds of the present invention, as B, specifically halogen, cyano, $C_1$–$C_6$ lower alkylcarbonyl, $C_1$–$C_6$ lower alkylsulfonyl, mono-$C_1$–$C_6$ lower alkylsulfamoyl, di-$C_1$–$C_6$ lower alkylsulfamoyl, optionally fluorine-substituted $C_1$–$C_6$ lower alkyl or optionally fluorine-substituted $C_1$–$C_6$ lower alkyloxy are exemplified.

Also as B', halogen, cyano, $C_1$–$C_6$ lower alkylcarbonyl, $C_1$–$C_6$ lower alkylsulfonyl, mono-$C_1$–$C_6$ lower alkylsulfamoyl, di-$C_1$–$C_6$ lower alkylsulfamoyl or optionally fluorine-substituted $C_1$–$C_6$ lower alkyloxy are exemplified.

As more specific B or B', as examples of halogen, fluorine, bromine, chlorine and iodine are exemplified; as $C_1$–$C_6$ lower alkylcarbonyl, acetyl, ethylcarbonyl, n-propylcarbonyl, isopropylcarbonyl and n-butylcarbonyl; as $C_1$–$C_6$ lower alkylsulfonyl, methanesulfonyl, ethanesulfonyl, n-propanesulfonyl, isopropylsulfonyl and n-butanesulfonyl; as mono-$C_1$–$C_6$ lower alkylsulfamoyl, methylsulfamoyl, ethylsulfamoyl and n-propylsulfamoyl; as di-$C_1$–$C_6$ lower alkylsulfamoyl, dimethylsulfamoyl, diethylsulfamoyl, di(n-propyl)sulfamoyl and methylethylsulfamoyl; as optionally fluorine-substituted $C_1$–$C_6$ lower alkyl (applicable to B only), methyl, ethyl, n-propyl, isopropyl, monofluoromethyl, difluoromethyl, trifluoromethyl and 2,2,2-trifluoroethyl; and as optionally fluorine-substituted $C_1$–$C_6$ lower alkyloxy, methoxy, ethoxy, n-propyloxy, isopropyloxy, monofluoromethoxy, difluoromethoxy, trifluoromethoxy and 2,2,2-trifluoroethoxy are exemplified.

Of those, from the viewpoint of nociceptin receptor inhibiting action, fluorine, chlorine, cyano, acetyl and methyl (applicable to B only) are preferred, in particular, fluorine, chlorine, cyano or methyl (applicable to B only) are recommended.

In the substituent D, as specific 5- to 10-membered, mono- or di-cyclic aliphatic, nitrogen-containing heterocyclic ring (D1 ring) of the formula [D-1], 1,4-piperazin-1-yl, 2,5-diazabicyclo[2.2.1]heptan-2-yl, 1,4-diazepan-1-yl, 1,4-diazabicyclo[3.2.1]octan-1-yl, 2,5-diazabicyclo[2.2.2]octan-2-yl, decahydro[1,6]naphthyridin-6-yl and 3,4,5,6-tetrahydropyrrolo-[3,4-C]pyrrolo-2(1H)-yl are exemplified.

As specific 3- to 10-membered, mono- or di-cyclic aliphatic nitrogen-containing heterocyclic ring (D2 ring) of the formula [D-2], azetidin-1-yl, piperidin-1-yl, pyrrolidin-1-yl, hexamethyleneimin-1-yl, heptamethyleneimin-1-yl, octamethyleneimin-1-yl and nonamethyleneimin-1-yl are exemplified.

As specific 3- to 10-membered, mono- or di-cyclic aliphatic nitrogen-containing heterocyclic ring (D3 ring) of the formula [D-3], azetidin-2-yl, azetidin-3-yl, pyrrolidin-2-yl, pyrrolidin-3-yl, piperidin-2-yl, piperidin-3-yl, piperidin-4-yl, hexamethyleneimin-2-yl and heptamethyleneimin-2-yl are exemplified.

Of the above D1 ring, D2 ring and D3 ring, recommended D1 ring are piperazin-1-yl, 1,4-diazepan-1-yl or 2,5-diazabicyclo[2.2.1]heptan-2-yl; recommended D2 ring are piperidin-1-yl or pyrrolidin-1-yl, and recommended D3 ring is piperidin-4-yl.

As $R^1$ in the substituent D, specifically, besides hydrogen, $C_1$–$C_6$ lower alkyl such as methyl, ethyl, n-propyl, isopropyl, n-butyl, isobutyl and tert-butyl, in particular, $C_1$–$C_3$ lower alkyl; halogen-containing lower alkyl such as monofluoromethyl, difluoromethyl, trifluoromethyl, 2-fluoroethyl, 3-fluoropropyl, 2,2-difluoroethyl and 2,2,2-trifluoroethyl; hydroxyl-containing lower alkyl such as hydroxymethyl and hydroxyethyl, amino-containing lower alkyl, lower alkyloxy-containing lower alkyl such as methoxymethyl, 2-methoxyethyl and 3-methoxypropyl; alkylsulfonylamino-containing lower alkyl; aminocarbonylamino-containing lower alkyl; lower alkyl having lower alkylcarbamoyl such as methylcarbamoyl, ethylcarbamoyl, dimethylcarbamoyl and diethylcarbamoyl; lower alkyl having acetamido; lower alkyl having lower cycloalkyl such as cyclopropyl, cyclobutyl, cyclopentyl and cyclohexyl; lower alkyl having aromatic heterocyclic group such as 1,3-thiazol-2-yl, 1H-imidazol-1-yl, 1H-imidazol-2-yl and 1H-pyrazol-3-yl; and lower alkyl having aromatic carbocyclic group such as phenyl, p-chlorophenyl, p-tolyl, p-methoxyphenyl, 2,6-dimethoxyphenyl, 2-methoxyphenyl, 3-methoxyphenyl, 4-methoxyphenyl, 2-methylphenyl, 2-cyanophenyl, 2-trifluoromethylphenyl, 2-chlorophenyl and 2,6-dichlorophenyl are exemplified. Lower alkyl groups having these substituents may have two or more same or different substituents.

Inter alia, as $R^1$ hydrogen, methyl, ethyl, isopropyl, 2-fluoroethyl, 3-fluoropropyl, hydroxymethyl, 2-hydroxyethyl, 3-hydroxypropyl, 2-methoxyethyl, 3-methoxypropyl, acetamidomethyl, acetamidoethyl, cyclopropylmethyl, 2,2-dimethyl-2-hydroxyethyl, 2-hydroxy-1-(hydroxymethyl)ethyl, 1,3-thiazol-2-ylmethyl, 1H-imidazol-1-ylmethyl, 1H-imidazol-2-ylmethyl, 1H-pyrazol-3-ylmethyl, benzyl, 2,6-dimethoxybenzyl, cyclopropylethyl, 1,3-thiazol-2-ylethyl, 1H-imidazol-1-ylethyl, 1H-imidazol-2-ylethyl, 1H-pyrazol-3-ylethyl, phenylethyl, 2,6-dimethoxyphenylethyl, 2-methoxybenzyl, 3-methoxybenzyl, 4-methoxybenzyl, 2-methylbenzyl, 2-cyanobenzyl, 2-trifluoromethylbenzyl, 2-chlorobenzyl and 2,6-dichlorobenzyl are recommended.

As $R^2$ in the substituent D, specifically carboxyl; lower alkyloxy carbonyl such as methoxycarbonyl, ethoxycarbonyl, n-propyloxycarbonyl and isopropyloxycarbonyl; carbamoyl; mono-(lower alkyl)carbamoyl such as methylcarbamoyl, ethylcarbamoyl, n-propylcarbamoyl and isopropylcarbamoyl; di-(lower alkyl)carbamoyl such as dimethylcarbamoyl, diethylcarbamoyl, di-(n-propyl)carbamoyl, di-isopropylcarbamoyl and (methyl)(ethyl)carbamoyl; lower alkyl such as methyl, ethyl, n-propyl, isopropyl and n-butyl; lower alkyl having halogen, e.g., fluorine, chlorine, bromine and the like, such as chloromethyl, dichloromethyl and trichloromethyl; hydroxyl-containing lower alkyl such as hydroxymethyl and hydroxyethyl; lower alkyl having optionally fluorine-substituted lower alkyloxy such as methoxy, ethoxy, n-propyloxy, isopropyloxy, monofluoromethoxy, difluoromethoxy, trifluoromethoxy, tetrafluoroethyloxy, pentafluoroethyloxy and 2,2,2-trifluoroethoxy; lower alkyl having lower alkylcarbonyl such as methylcarbonyl, ethylcarbonyl, n-butylcarbonyl and isobutylcarbonyl; carboxyl-containing lower alkyl; lower alkyl having lower alkyl such as methyl, ethyl, n-propyl and isopropyl; lower alkyl having lower alkyloxycarbonyl such as methoxycarbonyl, ethoxycarbonyl, n-propyloxycarbonyl, isopropyloxycarbonyl and t-butyloxycarbonyl; lower alkyl having carbamoyl; lower alkyl having lower alkylcarbamoyl such as methylcarbamoyl and ethyl carbamoyl; and lower alkyl having di-lower alkylcarbamoyl such as dimethylcarbamoyl, diethylcarbamoyl and (methyl)(ethyl) carbamoyl are exemplified. Furthermore, oxo group formed by two $R^2$'s as combined (here "oxo group" refers to the two $R^2$'s which are bound onto a same carbon and together form a carbonyl group with said carbon) is exemplified.

As preferred $R^2$, in particular, methyl, ethyl, hydroxymethyl, hydroxyethyl, carboxyl and methoxycarbonyl are exemplified, inter alia, methyl, ethyl and hydroxyethyl.

m1 Stands for 0 or an integer of 1–2, signifying, when m1 is 0, that hydrogen atom binds to the carbon atom on the aliphatic nitrogen-containing heterocyclic ring, instead of $R^2$. When m1 is 2, furthermore, two $R^2$'s bind to same or different, optional carbon atom(s) on the aliphatic nitrogen-containing carbocyclic ring. The two $R^2$'s may be same or different.

Examples of preferred combinations of $R^2$ and m1 are:
m1=0
m1=1, $R^2$=methyl, ethyl, hydroxyethyl
m1=2, $R^2$=methyl and methyl, and
m1=2, $R^2$=ethyl and methyl.

$R^2$ may bind to optional carbon atom(s) on D1 ring, D2 ring and D3 ring, and the binding site(s) is(are) not limited.

Whereas, the substituent E in the formula [D-3] stands for single bond, NR or O, and R stands for hydrogen, methyl or ethyl, preferably hydrogen or methyl.

As the groups represented by the formula [D-1], more specifically, 1,4-piperazin-1-yl (hereafter referred to as "piperazin-1-yl"), 4-methylpiperazin-1-yl, 4-ethylpiperazin-1-yl, 4-isopropylpiperazin-1-yl, 4-(cyclopropylmethyl)piperazin-1-yl, 4-(2-hydroxyethyl)piperazin-1-yl, 4-(3-hydroxypropyl)piperazin-1-yl, 4-(2-fluoroethyl)piperazin-1-yl, 4-(2-methoxyethyl)piperazin-1-yl, 4-[2-(acetamido)ethyl]piperazin-1-yl, 4-(2-methyl-2-hydroxypropyl)piperazin-1-yl, 4-[2-hydroxy-1-(hydroxymethyl)ethyl]piperazin-1-yl, 4-benzylpiperazin-1-yl, 4-methyl-3-(hydroxymethyl)piperazin-1-yl, 4-(1,3-thiazol-2-ylmethyl)piperazin-1-yl, 4-(1H-imidazol-2-ylmethyl)piperazin-1-yl, 4-(1H-imidazol-5-ylmethyl)piperazin-1-yl, 4-(1H-pyrazol-3-ylmethyl)piperazin-1-yl, 4-(2,6-dimethoxybenzyl)piperazin-1-yl, 3-methylpiperazin-1-yl, 4-methyl-3-methylpiperazin-1-yl, 4-ethyl-3-methylpiperazin-1-yl, 4-isopropyl-3-methylpiperazin-1-yl, 4-cyclopropylmethyl-3-methylpiperazin-1-yl, 4-ethyl-2-methylpiperazin-1-yl, 4-(2-fluoroethyl)-2-methylpiperazin-1-yl, 4-(2-methoxyethyl)-2-methylpiperazin-1-yl, 4-(2-hydroxyethyl)-2-methylpiperazin-1-yl, 4-(2-hydroxyethyl)-3-methylpiperazin-1-yl, 4-(3-hydroxypropyl)-3-methylpiperazin-1-yl, 4-[2-(acetamido)ethyl]-3-methylpiperazin-1-yl, 4-(2-methyl-2-hydroxypropyl)-3-methylpiperazin-1-yl, 4-[2-hydroxy-1-(hydroxymethyl)ethyl]-3-methylpiperazin-1-yl, 4-benzyl-3-methylpiperazin-1-yl, 4-methyl-5-(hydroxymethyl)-3-methylpiperazin-1-yl, 4-(1,3-thiazol-2-ylmethyl)-3-methylpiperazin-1-yl, 4-(1H-imidazol-2-ylmethyl)-3-methylpiperazin-1-yl, 4-(1H-imidazol-5-ylmethyl)-3-methylpiperazin-1-yl, 4-(1H-pyrazol-3-ylmethyl)-3-methylpiperazin-1-yl, 4-(2,6-dimethoxybenzyl)-3-methylpiperazin-1-yl, 3-carboxypiperazin-1-yl, 3-(methoxyearbonyl)piperazin-1-yl, 3-(hydroxymethyl)piperazin-1-yl, 3,5-dimethylpiperazin-1-yl, 1,4-diazepan-1-yl, 4-methyl-1,4-diazepan-1-yl, 4-ethyl-1,4-diazepan-1-yl, 4-isopropyl-1,4-diazepan-1-yl, 4-cyclopropylmethyl-1,4-diazepan-1-yl, 4-(2-hydroxyethyl)-1,4-diazepan-1-yl, 4-(3-hydroxypropyl)-1,4-diazepan-1-yl, 4-[2-(acetamido)ethyl]-1,4-diazepan-1-yl, 4-(2-methyl-2-hydroxypropyl)-1,4-diazepan-1-yl, 4-[2-hydroxy-1-(hydroxymethyl)ethyl]-1,4-diazepan-1-yl, 4-benzyl-1,4-diazepan-1-yl, 2,5-diazabicyclo[2.2.1]heptan-2-yl, 5-(2-hydroxyethyl)-2,5-diazabicyclo[2.2.1]heptan-2-yl, 1,4-diazabicyclo[3.2.1]octan-4-yl and 3,4,5,6-tetrahydropyrrolo-[3,4-C]pyrrol-2(1H)-yl are exemplified.

Preferred examples are piperazin-1-yl, 3-methylpiperazin-1-yl, 4-methylpiperazin-1-yl, 4-ethylpiperazin-1-yl, 4-isopropylpiperazin-1-yl, 4-(cyclopropylmethyl)piperazin-1-yl, 4-(2-hydroxyethyl)piperazin-1-yl, 4-(3-hydroxypropyl)piperazin-1-yl, 4-(2-fluoroethyl)piperazin-1-yl, 4-(2-methoxyethyl)piperazin-1-yl, 4-[2-(acetamido)ethyl]piperazin-1-yl, 4-(2-methyl-2- hydroxypropyl)piperazin-1-yl, 4-ethyl-2-methylpiperazin-1-yl, 4-(2-fluoroethyl)-2-methylpiperazin-1-yl, 4-(2-methoxyethyl)-2-methylpiperazin-1-yl, 4-(2-hydroxyethyl)-2-methylpiperazin-1-yl, 4-[2-hydroxy-1-hydroxymethyl]ethyl]piperazin-1-yl, 4-benzylpiperazin-1-yl, 4-methyl-3-(hydroxymethyl)piperazin-1-yl, 4-(1,3-thiazol-2-ylmethyl)piperazin-1-yl, 4-(1H-imidazol-2-ylmethyl)piperazin-1-yl, 4-(1H-imidazol-5-ylmethyl)piperazin-1-yl, 4-(1H-pyrazol-3-ylmethyl)piperazin-1-yl, 4-(2,6-dimethoxybenzyl)piperazin-1-yl, 3-carboxypiperazin-1-yl, 3-(methoxycarbonyl)piperazin-1-yl, 3-(hydroxymethyl)piperazin-1-yl, 3,5-dimethylpiperazin-1-yl, 2,5-diazabicyclo[2.2.1]heptan-2-yl, 5-(2-hydroxyethyl)-2,5-diazabicyclo[2.2.1]heptan-2-yl, 1,4-diazepan-1-yl, 4-methyl-1,4-diazepan-1-yl, 4-ethyl-1,4-diazepan-1-yl, 4-(2-hydroxyethyl)-1,4-diazepan-1-yl, 1,4-diazabicyclo[3.2.1]octan-4-yl and 3,4,5,6-tetrahydropyrrolo[3,4-C]pyrrol-2(1H)-yl are exemplified.

Inter alia, piperazin-1-yl, 4-methylpiperazin-1-yl, 4-ethylpiperazin-1-yl, 4-isopropylpiperazin-1-yl, 4-(cyclopropylmethyl)piperazin-1-yl, 4-(2-fluoroethyl)piperazin-1-yl, 4-(2-methoxyethyl)piperazin-1-yl, 4-ethyl-2-methylpiperazin-1-yl, 4-(2-fluoroethyl)-2-methylpiperazin-1-yl, 4-(2-methoxyethyl)-2-methylpiperazin-1-yl, 4-(2-hydroxyethyl)-2-methylpiperazin-1-yl, 4-(2-hydroxyethyl)piperazin-1-yl, 4-(2,6-dimethoxybenzyl)piperazin-1-yl, 4-(acetamidoethyl)piperazin-1-yl, 2,5-diazabicyclo[2.2.1]heptan-2-yl, 5-(2-hydroxyethyl)-2,5-diazabicyclo[2.2.1]heptan-2-yl, 1,4-diazepan-1-yl and 4-(2-hydroxyethyl)-1,4-diazepan-1-yl are recommended.

As the groups represented by the formula [D-2], specifically 3-amino-azetidin-1-yl, 3-amino-hexamethyleneimin-1-yl, 4-amino-hexamethyleneimin-1-yl, 4-(methylamino)piperidin-1 yl, 4-(ethylamino)piperidin-1-yl, 4-(isopropylamino)piperidin-1-yl, 4-(cyclohexylmethylamino)piperidin-1-yl, 4-((2-hydroxyethyl)amino)piperidin-1-yl, 3-(methylamino)piperidin-1-yl, 3-(ethylamino)piperidin-1-yl, 3-(isopropylamino)piperidin-1-yl, 3-(cyclohexylmethylamino)piperidin-1-yl, 3-((2-hydroxyethyl)amino)piperidin-1-yl, 3-(methylamino)pyrrolidin-1-yl, 3-(ethylamino)pyrrolidin-1-yl, 3-(isopropylamino)pyrrolidin-1-yl, 3-(cyclohexylmethylamino)pyrrolidin-1-yl and 3-((2-hydroxyethyl)amino)pyrrolidin-1-yl are exemplified.

Preferably, 4-aminopiperidin-1-yl, 3-aminopiperidin-1-yl and 3-aminopyrrolidin-1-yl are recommended.

As the groups represented by the formula [D-3], specifically pyrrolidin-2-yl, pyrrolidin-3-yl, piperidin-2-yl, piperidin-3-yl, piperidin-4-yl (which may hereinafter be referred to as "4-piperidinyl"), 1-ethylpiperidin-4-yl, 1-isopropylpiperidin-4-yl, 1-(cyclopropylmethyl)piperidin-4-yl, 1-(2-hydroxyethyl)piperidin-4-yl, 1-(3-hydroxypropyl)piperidin-4-yl, 1-(2-methyl-2-hydroxypropyl)piperidin-4-yl, 1-[2-hydroxy-1-(hydroxymethyl)ethyl]piperidin-4-yl, 1-benzylpiperidin-4-yl, 1-(1H-imidazol-2-ylmethyl)piperidin-4-yl, 1-(1H-imidazol-5-ylmethyl)piperidin-4-yl, 1-1H-pyrazol-3-ylmethyl)piperidin-4-yl, 1-ethylpyrrolidin-3-yl, 1-(2-methoxyethyl)pyrrolidin-3-yl, [1-(2-methoxyethyl)pyrrolidin-3-yl](methyl)amino, [1-(2-methoxyethyl)pyrrolidin-3-yl]oxy, 1-methylpiperidin-4-yl, 1-(acetamido)ethyl)piperidin-4-yl and 1-(2,6-dimethoxybenzyl)piperidin-4-yl are exemplified.

As those which are preferred, 1-ethyl-pyrrolidin-3-yl, 1-(2-methoxyethyl)pyrrolidin-3-yl, piperidin-4-yl, 1-ethylpiperidin-4-yl, 1-isopropylpiperidin-4-yl, 1-(cyclopropylmethyl)piperidin-4-yl, 1-(2-hydroxyethyl)piperidin-4-yl, [1-(2-methoxyethyl)pyrrolidin-3-yl](methyl)amino, [1-(2-methoxyethyl)pyrrolidin-3-yl]oxy, 1-methylpiperidin-4-yl, 1-(1-acetamidoethyl)piperidin-4-yl and 1-(2,6-dimethoxybenzyl)piperidin-4-yl are exemplified.

As those still more favorable, 1-ethylpyrrolidin-3-yl, 1-(2-methoxyethyl)pyrrolidin-3-yl, piperidin-4-yl, 1-ethylpiperidin-4-yl, 1-isopropylpiperidin-4-yl, 1-(cyclopropylmethyl)piperidin-4-yl, 1-(2-hydroxyethyl)piperidin-4-yl, [1-(2-methoxyethyl)pyrrolidin-3-yl](methyl)amino and [1-(2-methoxyethyl)pyrrolidin-3-yl]oxy are recommended.

As those particularly favored D, piperazin-1-yl, 4-methylpiperazin-1-yl, 4-ethylpiperazin-1-yl, 4-isopropylpiperazin-1-yl, 4-(cyclopropylmethyl)piperazin-1-yl, 4-(2-fluoroethyl)piperazin-1-yl, 4-(2-methoxyethyl)piperazin-1-yl, 4-ethyl-2-methylpiperazin-1-yl, 4-(2-fuoroethyl)-2-methylpiperazin-1-yl, 4-(2-methoxyethyl)-2-methylpiperazin-1-yl, 4-(2-hydroxyethyl)-2-methylpiperazin-1-yl, 4-(2-hydroxyethyl)piperazin-1-yl, 4-[2-(acetamido)ethyl]piperazin-1-yl, 4-(2,6-dimethoxybenzyl)piperazin-1-yl, 2,5-diazabicyclo[2.2.1]heptan-2-yl, 5-(2-hydroxyethyl)-2,5-diazabicyclo[2.2.1]heptan-2-yl, 1,4-diazepan-1-yl, 4-(2-hydroxyethyl)-1,4-diazepan-1-yl, 1-ethylpyrrolidin-3-yl, 1-(2-methoxyethyl)pyrrolidin-3-yl, [1-(2-methoxyethyl)pyrrolidin-3-yl](methyl)amino, [1-(2-methoxyethyl)pyrrolidin-3-yl]oxy, 4-aminopiperidin-1-yl, 3-aminopiperidin-1-yl, 3-aminopyrrolidin-1-yl, piperidin-4-yl, 1-ethylpiperidin-4-yl, 1-isopropylpiperidin-4-yl, 1-(cyclopropyl)piperidin-4-yl and 1-(2-hydroxyethyl)piperidin-4-yl are exemplified.

Preferably, one selected from a group consisting of piperazin-1-yl, 4-methylpiperazin-1-yl, 4-ethylpiperazin-1-yl, 4-isopropylpiperazin-1-yl, 4-(cyclopropylmethyl)piperazin-1-yl, 4-(2-fluoroethylpiperazin-1-yl, 4-(2-methoxyethyl)piperazin-1-yl, 4-ethyl-2-methylpiperazin-1-yl, 4-(2-fluoroethyl)-2-methylpiperazin-1-yl, 4-(2-methoxyethyl)-2-methylpiperazin-1-yl, 4-(2-hydroxyethyl)-2-methylpiperazin-1-yl, 4-(2-hydroxyethyl)piperazin-1-yl, 4-[2-(acetamido)ethyl]piperazin-1-yl, 4-(2,6-dimethoxybenzyl)piperazin-1-yl, 2,5-diazabicyclo[2.2.1]heptan-2-yl, 5-(2-hydroxyethyl)-2,5-diazabicyclo[2.2.1]heptan-2-yl, 1,4-diazepan-1-yl, 4-(2-hydroxyethyl)-1,4-diazepan-1-yl, 1-ethylpyrrolidin-3-yl, 1-(2-methoxyethyl)pyrrolidin-3-yl, [1-(2-methoxyethyl)pyrrolidin-3-yl](methyl)amino and [1-(2-methoxyethyl)pyrrolidin-3-yl]oxy is recommended.

In the compounds of the present invention, G' stands for an aliphatic group having a total carbon number of 3–20, which may have substituent group(s).

As specific G', aliphatic groups having a total carbon number of 3–20, which are:
1) optionally substituted $C_3$–$C_{10}$ alkyl,
2) optionally substituted $C_3$–$C_{10}$ alkenyl
3) optionally substituted $C_3$–$C_{10}$ alkynyl,
4) optionally substituted 3- to 10-membered aliphatic carbocyclic group,
5) optionally substituted 3- to 10-membered aliphatic heterocyclic group which contains 1–3 hetero atoms selected from the group consisting of oxygen, sulfur and nitrogen,
6) $C_1$–$C_{10}$ alkyl having as the substituent 3- to 10-membered aliphatic carbocyclic groups,
7) $C_1$–$C_{10}$ alkyl having as the substituent a 3- to 10-membered aliphatic heterocyclic group containing 1–3 hetero atoms selected from the group consisting of oxygen, sulfur and nitrogen and the like are exemplified.

Here referring to a $C_{10}$ alkyl group, for example, it can be an aliphatic group of a carbon number up to 20, combining those of the $C_{10}$ alkyl and the total carbon number of the substituent(s) on said alkyl group.

As specific $C_3-C_{10}$ alkyl, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl, 1-ethyl-1-methylpropyl, n-heptyl, isoheptyl, n-octyl, isooctyl, 2-ethylhexyl, n-nonyl, isononyl, 3,5,5-trimethylhexyl, n-decyl, isodecyl and the like groups are exemplified.

As $C_3-C_{10}$ alkenyl, allyl, 1-propenyl, isopropenyl, 2-butenyl, isobutenyl, 2-pentenyl, 2-hexenyl, 2-heptenyl, 2-octenyl and the like groups are exemplified.

As $C_3-C_{10}$ alkynyl, 1-propinyl, 1-butenyl, 1-pentenyl, 1-hexinyl, 1-heptinyl, 1-octinyl and the like groups are exemplified.

As substituents which may be on above alkyl, alkenyl, cycloalkyl or aliphatic cyclic groups, those selected from the group α, or oxo (limited to the aliphatic cyclic groups only) are exemplified. These alkyl, alkenyl, cycloalkyl or aliphatic cyclic groups may have two or more substituents which may be same or different.

As preferred substituent G', those represented by the formula [G-1], one type of the substituent G,

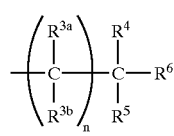

[G-1]

[in which $R^{3a}$ and $R^{3b}$ are same or different, and stand for hydrogen, methyl or ethyl. $R^4$ stands for hydrogen or optionally substituted lower alkyl, $R^5$ and $R^6$ are same or different and have the same signification as that of $R^4$, or $R^5$ and $R^6$ together form an aliphatic cyclic group, with the carbon atom to which they bind, and n stands for 0 or an integer of 1–4] are exemplified.

As specific $R^4$, hydrogen or lower alkyl optionally having a substituent selected from the group α are exemplified, and n stands for 0 or an integer of 1–4.

Whereas, as those in which $R^5$ and $R^6$ in the formula G-1 together form an aliphatic cyclic group with the carbon atom to which they bind, those represented by the following formulae [CY-b], [CY-c] and [CY-d] are exemplified.

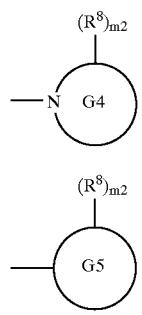

[CY-a]

[CY-b]

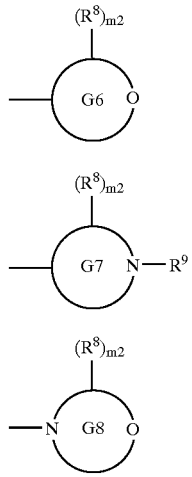

[CY-c]

[CY-d]

[CY-e]

In the above formulae, $R^8$ bind(s) to any optional carbon atom(s) on the aliphatic ring, and either stand(s) for a substituent(s) selected from the group α or lower alkyl which may have a substituent selected from the group α, or two $R^8$'s together form an oxo group; and m2 stands for 0 or an integer of 1–3. Where m2 is 2 or 3, two or three $R^8$'s bind to optional, different carbon atoms or a same carbon atom. The two or three $R^8$'s may be same or different:

$R^9$ binds onto a nitrogen atom, and stands for hydrogen, lower alkyloxycarbonyl, lower alkenyloxycarbonyl, lower alkylcarbonyl, mono-lower alkylcarbamoyl, di-lower alkylcarbamoyl, lower alkylsulfonyl, mono-lower alkylsulfamoyl, di-lower alkylsulfamoyl, or lower alkyl which may have a substituent selected from the group α:

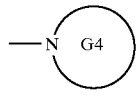

(which may hereinafter be referred to as "G4 ring") stands for a 3- to 10-membered mono- to tri-cyclic aliphatic, nitrogen-containing heterocyclic group having one nitrogen atom:

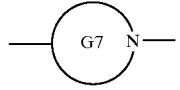

(which may hereinafter be referred to as "G7 ring") stands for a 3- to 10-membered mono- to tri-cyclic aliphatic, nitrogen-containing heterocyclic group having one nitrogen atom:

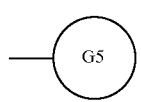

(which may hereinafter be referred to as "G5 ring") stands for a 3- to 10-membered mono- to tri-cyclic aliphatic carbocyclic group.

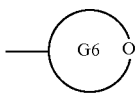

(which may hereinafter be referred to as "G6 ring") stands for a 3- to 10-membered mono- to tri-cyclic aliphatic, oxygen-containing heterocyclic group having one oxygen atom: and

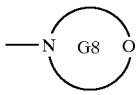

(which may hereinafter be referred to as "G8 ring") stands for a 5- to 10-membered mono- to tri-cyclic aliphatic heterocyclic group having one each of nitrogen atom and oxygen atom.

In the above formulae, furthermore, the compounds represented by [CY-a] or [CY-e] also possess nociceptin receptor antagonism and belong to the present invention. In that case, those represented by the following formula [G-3] or [G-4], instead of the formula [G-1], are adequate:

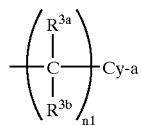
[G-3]

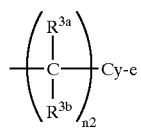
[G-4]

[in which n1 or n2 have the same signification as n. $R^{3a}$, $R^{3b}$, CY-a or CY-b are same to the above].

In the above formula, $R^{3a}$ and $R^{3b}$ are same or different and stand for hydrogen, methyl or ethyl, and n stands for 0 or an integer of 1–4, preferably 0, 1 or 2.

Also as preferred $R^4$, $R^5$ and $R^6$, hydrogen; hydroxyl; amino; mono-lower alkylamino such as methylamino, ethylamino, n-propylamino and isopropylamino; di-lower alkylamino such as dimethylamino, diethylamino, di(n-propyl)amino, and diisopropylamino; optionally fluorine-substituted lower alkyloxy such as methoxy, ethoxy, n-propyloxy, isopropyloxy, monofluoromethoxy, difluoromethoxy, trifluoromethoxy, 2,2,2-trifluoroethyloxy, 1-ethylpropyloxy, 3-methoxy-3-methylbutoxy and 3-methoxy-1,3-dimethylbutoxy; lower alkyloxycarbonyl such as methoxycarbonyl, ethoxycarbonyl, n-propyloxycarbonyl, isobutyloxycarbonyl, n-butyloxycarbonyl, isobutyloxycarbonyl and tert-butyloxycarbonyl; lower alkylcarbonyl such as methylcarbonyl, ethylcarbonyl, n-propylcarbonyl and tert-butylcarbonyl; lower alkylcarbonyloxy such as methylcarbonyloxy, ethylcarbonyloxy, n-propylcarbonyloxy and isopropylcarbonyloxy; (lower alkylcarbonyl)amino such as methylcarbonylamino, ethylcarbonylamino, n-propylcarbonylamino and isopropylcarbonylamino; carbamoyl; mono-(lower alkylcarbamoyl) such as methylcarbamoyl, ethylcarbamoyl and tert-butylcarbamoyl; di-lower alkylcarbamoyl such as dimethylcarbamoyl, diethylcarbamoyl and methylethylcarbamoyl; and $C_1$–$C_6$ lower alkyl groups such as methyl, ethyl, n-propyl, isopropyl, n-butyl, isobutyl and tert-butyl are exemplified.

As G4 ring, 3- to 10-membered mono- to tri-cyclic, preferably 5- to 6-membered mono- or di-cyclic, aliphatic nitrogen-containing heterocyclic groups are exemplified. Specifically, azetidin-1-yl, piperidin-1-yl, pyrrolidin-1-yl, hexamethyleneimin-1-yl, heptamethyleneimin-1-yl and the like groups are exemplified and preferably pyrrolidin-1-yl and piperidin-1-yl are recommended.

As G5 ring, 3- to 10-membered mono- to tri-cyclic, preferably 4- to 6-membered mono- or di-cyclic, aliphatic carbocyclic groups are exemplified. Specifically, cyclopropyl, cyclobutyl, cyclopentyl, cyclohexyl, cycloheptyl, cyclooctyl, 1,4-dioxaspiro[4,5]decan-8-yl, tricyclo[3.2.1.1$^{3,7}$]nonan-1-yl, tricyclo[3.3.1.1$^{3,7}$]decan-1-yl, tricyclo[3.3.1.1$^{3,7}$]decan-2-yl and the like groups are exemplified, and preferably cyclobutyl, cyclopentyl and cyclohexyl are recommended.

As G6 ring, 3- to 10-membered mono- to tri-cyclic, preferably 5- to 6-membered mono- or di-cyclic aliphatic oxygen-containing heterocyclic groups are exemplified. Specifically, tetrahydrofuran-3-yl, tetrahydro-2H-pyran-4-yl, 2,2-dimethyltetrahydro-2H-pyran-4-yl, 1,4-dihydroxyoctahydro-2-pentalenyl, 8-oxabicyclo[3.2.1] octan-3-yl and the like groups are exemplified. Preferably tetrahydrofuran-3-yl and tetrahydro-2H-pyran-4-yl are recommended.

As G7 ring, 3- to 10-membered mono- to tri-cyclic, preferably 5- or 6-membered mono- or di-cyclic aliphatic nitrogen-containing heterocyclic groups are exemplified. Specificlly, azetidin-2-yl, piperidin-2-yl, piperidin-3-yl, piperidin-4-yl, pyrrolidin-3-yl, pyrrolidin-2-yl and the like groups are exemplified. Preferably, pyrrolidin-3-yl and piperidin-4-yl are recommended.

As G8 ring, 5- to 10-membered mono- to tri-cyclic, preferably 6-membered monocyclic, aliphatic heterocyclic groups are exemplified, and specifically morpholino group is exemplified.

As specific $R^8$, preferably methyl, ethyl, hydroxyl, oxo, methoxycarbonyl, ethoxycarbonyl, methoxycarbonylamino, ethoxycarbonylamino, fluoromethyl, 2-fluoroethyl and 2,2-difluoroethyl are recommended.

As m2, preferably 0 or an integer of 1–2 are exemplified. Where m2 is 0, it signifies that a hydrogen atom, instead of $R^8$, is bound to the carbon atom on the aliphatic ring.

As preferred combinations of $R^8$ and m2,
m2=0,
m2=1, $R^8$=hydroxyl,
m2=1, $R^8$=methyl,
m2=1, $R^8$=ethoxycarbonylamino,
m2=2, $R^8$=oxo,
m2=2, $R^8$=methyl×2
m2=2, $R^8$=methyl and hydroxyl are exemplified.

$R^8$ may bind to any optional carbon atom(s) on the aliphatic ring. Where two or three $R^8$ are present, they may be on each different carbon atoms, and two $R^8$'s may bind onto a same carbon atom.

As specific $R^9$, preferably methyl, ethyl, acetyl, pivaloyl, methylcarbamoyl, dimethylcarbamoyl, ethylcarbamoyl, diethylcarbamoyl, methanesulfonyl, ethylsulfonyl, methoxycarbonyl and ethoxycarbonyl are recommended.

Of those represented by the formula [G-1], for antagonism to nociceptin receptor, particularly those groups represented by a formula [G-2], $$—C(R_x)(R_y)(R_z) \qquad [G\text{-}2]$$

[in which $R_x$ stands for lower alkyl which may have a substituent selected from the group α, and $R_y$ and $R_z$ are same or different, either standing for lower alkyl which optionally have substituent(s) selected from the group α, or $R_y$ and $R_z$ together forming a 3- to 10-membered aliphatic carbocyclic ring] are recommended. Here, as the aliphatic carbocyclic group, those represented by the formula [CY-b] are recommended.

As G, i.e., as those represented by the formula [G-1], specifically 1-methylethyl, 2-dimethylamino-1,1-dimethylethyl, 2-dimethylamino-2-methylethyl, 2-dimethylamino-1-methylethyl, 2-dimethylamino-2,2-dimethylethyl, 2-(diisopropylamino)ethyl, 2,2-dimethyl-2-hydroxyethyl, 2-hydroxy-1-(hydroxymethyl)ethyl, 2-ethoxy-1-(ethoxymethyl)ethyl, 2-methoxy-1-(methoxymethyl)ethyl, 1-ethylpropyl, 1-(methoxycarbonyl) propyl, 2-methoxy-2-methylpropyl, 1-acetyl-2-oxopropyl, 1-[(tert-butylamino)carbonyl]propyl, tert-butyl, 1,1-dimethylpropyl, 1,1-dimethylbutyl, 2-ethylbutyl, 3-amino-3-methylbutyl, 3-methoxy-3-methylbutyl, 3-methoxy-1,3-dimethylbutyl, 3-methoxybutyl, 1,3,3-trimethylbutyl, 3-hydroxy-2,3-dimethylbutyl, 3,3-dimethyl-2-oxobutyl, 1-ethyl-3-methyl-3-hydroxybutyl, 2-ethyl-2-hydroxybutyl, 2-ethyl-3-hydroxy-3-methylbutyl, 3-acetoxy-1,1-dimethylbutyl, 3-hydroxy-1,1-dimethylbutyl, 3-hydroxy-1,3-dimethylbutyl, 3-hydroxy-3-methylbutyl, 3-hydroxy-1-methylbutyl, 2,4-dimethyl-4-methoxypentyl, 5-methylhexyl and the like groups are exemplified.

Also as those where $R^5$ and $R^6$ together form an aliphatic cyclic group with the carbon atom to which they bind,
1) cyclobutyl, 1-methylcyclobutyl, cyclopentyl, 1-methylcyclopentyl, cyclopentylmethyl, 2-cyclopentylethyl, 2-(1-hydroxycyclopentyl)ethyl, 3-ethyl-3-hydroxypentyl, cyclohexyl, 1-methylcyclohexyl, cyclohexylmethyl, cyclohexylethyl, 4-oxocyclohexyl, 4-(methoxycarbonyl)cyclohexyl, 2-(1-hydroxycyclohexyl)ethyl, 4-(ethoxycarbonylamino) cyclohexyl, 4-hydroxycyclohexyl, 4-hydroxy-4-methylcyclohexyl, 4-(methoxycarbonylamino) cyclohexyl, 4-(isopropoxycarbonylamino)cyclohexyl, 4-(acetamino)cyclohexyl, 4-(methanesulfonylamino) cyclohexyl, 1,4-oxaspiro[4,5]decan-8-yl, 4-methoxycarbonylamino-1-methylcyclohexyl and 4-ethoxycarbonylamino-1-methylcylohexyl,
2) 1-methylpyrrolidin-3-yl, 1-(methoxycarbonyl)pyrrolidin-3-yl, 1-methylpiperidin-4-yl, 1-(ethoxycarbonyl) piperidin-4-yl, 1-(methoxycarbonyl)piperidin-4-yl, 1-(allyloxycarbonyl)piperidin-4-yl, 1-(methylsulfonyl) piperidin-4-yl, 1-(ethylsulfonyl)piperidin-4-yl, 1-acetylpiperidin-4-yl, 1-(ethoxycarbonyl)piperidin-4-yl, 1-pivaloylpiperidin-4-yl, 1-(diethylcarbamoyl)piperidin-4-yl, 1-methylpiperidin-3-yl, 1-(methoxycarbonyl) piperidin-3-yl, 1-methoxycarbonyl-4-methylpiperidin-4-yl and 1-ethoxycarbonyl-4-methylpiperidin-4-yl, and
3) tetrahydro-2H-pyran-4-yl, tetrahydro-2H-pyran-4-ylmethyl, 4-methyl-tetrahydro-2H-pyran-4-yl and 4-ethyl-tetrahydro-2H-pyran-4-yl are exemplified.

Also as those represented by the formula [G-3] or [G-4],
1) 1,1-dimethyl-2-(piperidin-1-yl)ethyl and 1,1-dimethyl-2-(pyrrolidin-1-yl)ethyl,
2) 2-methyl-2-(morpholino)ethyl, 1-methyl-2-(morpholino) ethyl, 2,2-dimethyl-2-(morpholino)ethyl and 1-(morpholinocarbonyl)propyl are exemplified.

Of those above-named [G-1], in particular, 2-methoxy-1-(methoxymethyl)ethyl, 2-ethoxy-1-(ethoxymethyl)ethyl, 2-dimethylamino-1,1-dimethylethyl, 2-dimetylamino-1-methylethyl, 2-(acetamido)ethyl, 2-hydroxy-1-(hydroxymethyl)ethyl, 1-(methoxycarbonyl)propyl, 1-ethylpropyl, tert-butyl, 1,1-dimethylpropyl, 1,1-dimethylbutyl, 1,3,3-trimethylbutyl, 3-methoxy-1,3-dimethylbutyl, 3-hydroxy-1,3-dimethylbutyl, 1-ethyl-3-methyl-3-hydroxybutyl, 3-acetoxy-1,1-dimethylbutyl, 3-hydroxy-1,1-dimethylbutyl, cyclobutyl, 1-methylcyclobutyl, cyclopentyl, 1-methylcyclopentyl, cyclohexyl, 1-methylcyclohexyl, 4-(methoxycarbonyl) cyclohexyl, 4-oxocyclohexyl, 4-(ethoxycarbonylamino) cyclohexyl, 4-methoxycarbonylamino-1-methylcyclohexyl, 4-ethoxycarbonylamino-1-methylcyclohexyl, 4-hydroxycylohexyl, 4-hydroxy-4-methylcyclohexyl, 4-(ethoxycarbonylamino)cyclohexyl, 1-methylpiperidin-4-yl, 1-(methoxycarbonyl)piperidin-4-yl, 1-(ethoxycarbonyl) piperidin-4-yl, 1-methoxycarbonyl-4-methylpiperidin-4-yl, 1-ethoxycarbonyl-4-methylpiperidin-4-yl, 1-methylpyrrolidin-3-yl, 1-methylpiperidin-3-yl, 1-(methoxycarbonyl)pyrrolidin-3-yl, 1-(methoxycarbonyl) piperidin-3-yl, 1-(allyloxycarbonyl)piperidin-4-yl, 1-(ethylsulfonyl)piperidin-4-yl, 1-acetylpiperidin-4-yl, tetrahydrofuran-3-yl, tetrahydro-2H-pyran-4-yl, 4-methyl-tetrahydro-2H-pyran-4-yl, 4-ethyl-tetrahydro-2H-pyran-4-yl, 1,4-dihydroxyoctahydro-2-pentalenyl, 1,4-dioxaspiro[4,5]decan-8-yl, 8-oxabicyclo[3.2.1]octan-3-yl and 8-oxabicyclo[3.2.1]octan-3-yl are recommended.

Also of those represented by the formula [G-2], preferably 1-methylcyclobutyl, 1-methylcyclopentyl, 1-methylcyclohexyl, tert-butyl, 1,1-dimethylpropyl, 1,1-dimethylbutyl, 3-methyltetrahydrofuran-3-yl or 4-methyltetrahydro-2H-pyran-4-yl are recommended.

Hence, as the preferred compound groups which are represented by the general formula [I], the following are exemplified:

a) compounds represented by the general formula [I-1]

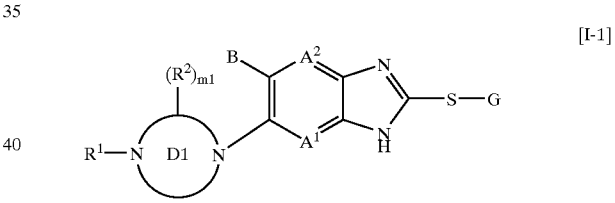

b) compounds represented by the general formula [I-2]

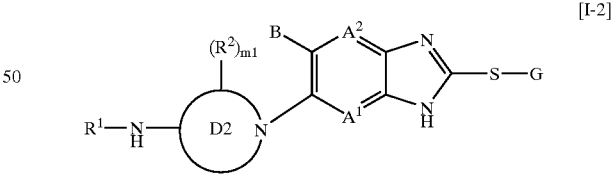

c) compounds represented by the general formula [I-3]

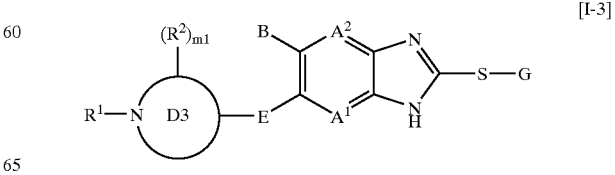

d) Furthermore, among those compounds represented by the general formulae [I-1] to [1-3], compounds in which G falls within the scope of the formula [G-2],

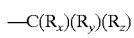 [G-2]

[in which $R_x$ stands for lower alkyl, and $R_y$ and $R_z$ either may be same or different and stand for lower alkyl, or, $R_y$ and $R_z$ together stand for a $C_3$–$C_{10}$ aliphatic carbocyclic ring] also are recommended. Here, as the aliphatic carbocyclic ring, those represented by the formula [CY-b] are recommended.

Also as the compounds represented by the general formula [K], preferably those in which e) Y is NH

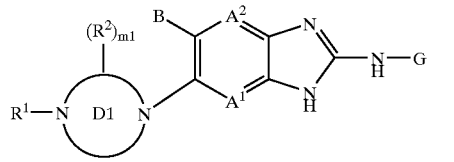 [K-a1]

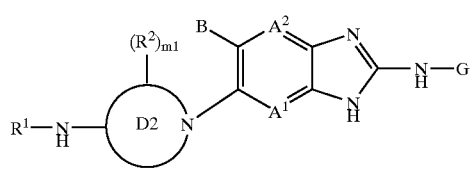 [K-a2]

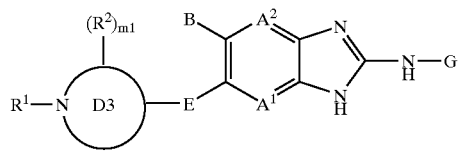 [K-a3]

f) Y is O

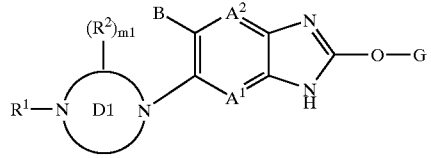 [K-b1]

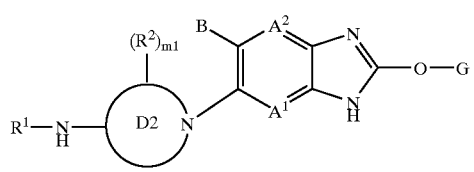 [K-b2]

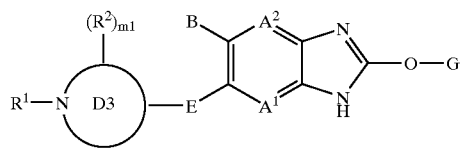 [K-b3]

g) Y is single bond

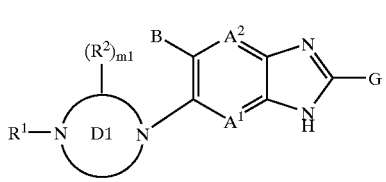 [K-c1]

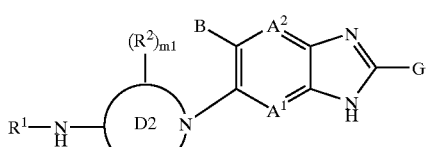 [K-c2]

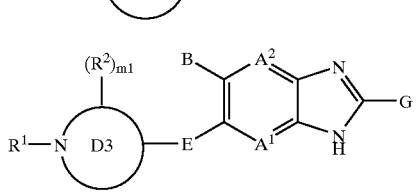 [K-c3]

are recommended.

As specific benzimidazole derivatives represented by the general formula [I], preferably the following can be named:

5-chloro-6-[4-(2-hydroxyethyl)piperazin-1-yl]-2-[(1-methylcyclobutyl)sulfanyl]-benzimidazole, 5-chloro-7-fluoro-6-[4-(2-hydroxyethyl)piperazin-1-yl]-2-[(1-methylcyclopentyl)sulfanyl]-benzimidazole, 5-cyano-2-[(1,1-dimethylethyl)sulfanyl]-7-fluoro-6-[4-(2-fluoroethyl)-2-methylpiperazin-1-yl]-benzimidazole, 5-chloro-2-[(1,1-dimethylethyl)sulfanyl]-6-[1-(2-methoxyethyl)pyrrolidin-3-yl](methyl)amino-benzimidazole, 5-cyano-2-[(1,1-dimethylpropyl)sulfanyl]-6-(1-ethylpyrrolidin-3-yl)oxy-benzimidazole, 6-[4-ethyl-2-methylpiperazin-1-yl]-2-[(1,1-dimethylethyl)sulfanyl]-5-methyl-benzimidazole, 6-[4-ethyl-2-methylpiperazin-1-yl]-2-[(1,1-dimethylpropyl)sulfanyl]-5-trifluoromethyl-benzimidazole, 5-chloro-2-[(cyclohexylmethyl)sulfanyl]-6-[4-(cyclopropylmethyl)piperazin-1-yl]-benzimidazole, 5-chloro-2-[(1-ethylpropyl)sulfanyl-6-piperazin-1-yl]-benzimidazole, 5-chloro-2-[(1-ethylpropyl)sulfanyl]-6-[4-(2-hydroxyethyl)piperazin-1-yl]-benzimidazole, 5-chloro-2-[(1-ethylpropyl)sulfanyl]-6-[1-(2-hydroxyethyl)piperidin-4-yl]-benzimidazole, 5-chloro-2-[(1-ethyl-3-methyl-3-hydroxybutyl)sulfanyl]-6-(piperazin-1-yl)-benzimidazole, 5-chloro-2-[(1-ethyl-3-methyl-3-hydroxybutyl)sulfanyl]-6-[1-(2-hydroxyethyl)piperazine-4-yl]-benzimidazole, 5-chloro-6-(1,4-diazepan-1-yl)-2-[(1-ethylpropyl)sulfanyl]-benzimidazole, 5-chloro-2-[((1-ethoxycarbonyl)piperidin-4-yl)sulfanyl]-6-(piperazin-1-yl)-benzimidazole, 5-chloro-6-(4-ethyl-1,4-diazepan-1-yl)-2-[(1-ethylpropyl)sulfanyl]-benzimidazole, 5-chloro-2-[[4-[(ethoxycarbonyl)amino]cyclohexyl]sulfanyl]-6-[4-(2-hydroxyethyl)piperazin-1-yl]-benzimidazole, 5-chloro-2-[(1-ethylpropyl)sulfanyl)]-6-(3-methylpiperazin-1-yl)-benzimidazole, 5-chloro-2-[(1,1-dimethylethyl)sulfanyl]-6-[4-(2-hydroxyethyl)piperazin-1-yl]-benzimidazole, 5-chloro-2-[(1-ethylpropyl)sulfanyl]-6-[5-(2-hydroxyethyl)-2,5-diazabicyclo[2.2.1]hept-2-yl-benzimidazole, 5-chloro-2-[(1,1-dimethylpropyl)sulfanyl]-6-[4-(2-hydroxyethyl)piperazin-1-yl]-benzimidazole, 2-[(cyclohexylmethyl)sulfanyl]-5-fluoro-6-(piperazin-1-yl)-benzimidazole, 6-chloro-2-[(1-ethylpropyl)sulfanyl]-5-(piperazin-1-yl)-imidazo-[4,5-b]pyridin, 5-chloro-6-[1,4-diazabicyclo[3.2.1]octan-4-yl]-2-[(1,1-dimethylpropyl)sulfanyl]-benzimidazole, or 5-chloro-2-[4-[(ethoxycarbonyl)amino]-1-methylcyclohexyl]sulfanyl]-6-[4-(2-fluoroethyl)piperazine-1-yl]-benzimidazole, and the like.

Of those, 5-chloro-6-[4-(2-hydroxyethyl)piperazin-1-yl]-2-[(1-methylcyclobutyl)sulfanyl]-benzimidazole, 5-chloro-7-fluoro-6-[4-(2-hydroxyethyl)piperazin-1-yl]-2-[(1-methylcyclopentyl)sulfanyl]-benzimidazole, 6-[(4-ethyl-2-methylpiperazin-1-yl]-2-[(1,1-dimethylethyl)sulfanyl]-5-methyl-benzimidazole, 5-chloro-2-[(1-ethylpropyl)sulfanyl]-6-[1-(2-hydroxyethyl)piperidin-4-yl]-benzimidazole, 5-chloro-6-[1,4-diazabicyclo[3.2.1]octan-4-yl]-2-[(1,1-dimethylpropyl)sulfanyl]-benzimidazole, 5-chloro-2-[4-[(ethoxycarbonyl)amino]-1-methylcyclohexyl]sulfanyl]-6-[4-(2-fluoroethyl)piperazin-1-yl]-benzimidazole, 5-chloro-2-[(1,1-dimethylpropyl)sulfanyl]-6-[4-(2-hydroxyethyl)piperazin-1-yl]-benzimidazole, 5-cyano-2-[(1,1-dimethylethyl)sulfanyl]-7-fluoro-6-[4-(2-fluoroethyl)-2-methylpiperazin-1-yl]-benzimidazole, and 5-chloro-2-[(1-ethylpropyl)sulfanyl]-6-[5-(2-hydroxyethyl)-2,5-diazabicyclo[2.2.1]hept-2-yl]-benzimidazole are recommended.

As the preferred specific examples of the benzimidazole derivatives represented by the general formula [K], 5-chloro-2-[(2-ethylbutyl)oxy]-6-(piperazin-1-yl)-benzimidazole, 5-chloro-2-(3-ethylpentyl)-6-(piperazin-1-yl)-benzimidazole and 5-chloro-2-(2,2-dimethylpropanoyl)-6-[(4-ethyl-2-methylpiperazin-1-yl]-benzimidazole can be named.

In occasions there may be present stereoisomers such as optical isomers, diastereoisomers and geometrical isomers of the compounds of the present invention, depending on the mode of substituent groups thereon. The compounds of the invention encompass all of these stereoisomers and mixtures thereof.

Also those various crystals, hydrates and solvates of the compounds of the present invention belong to the scope of the present invention. Again pro-drugs of the compounds of the invention also belong to the scope of the present invention.

Production Processes of the Compounds Represented by the General Formula [I] or the General Formula [K]

The compounds of the present invention are prepared, for example, by the following processes.

Production Process 1

This process is useful when the D in the general formula [I] is represented by the formula [D-1].

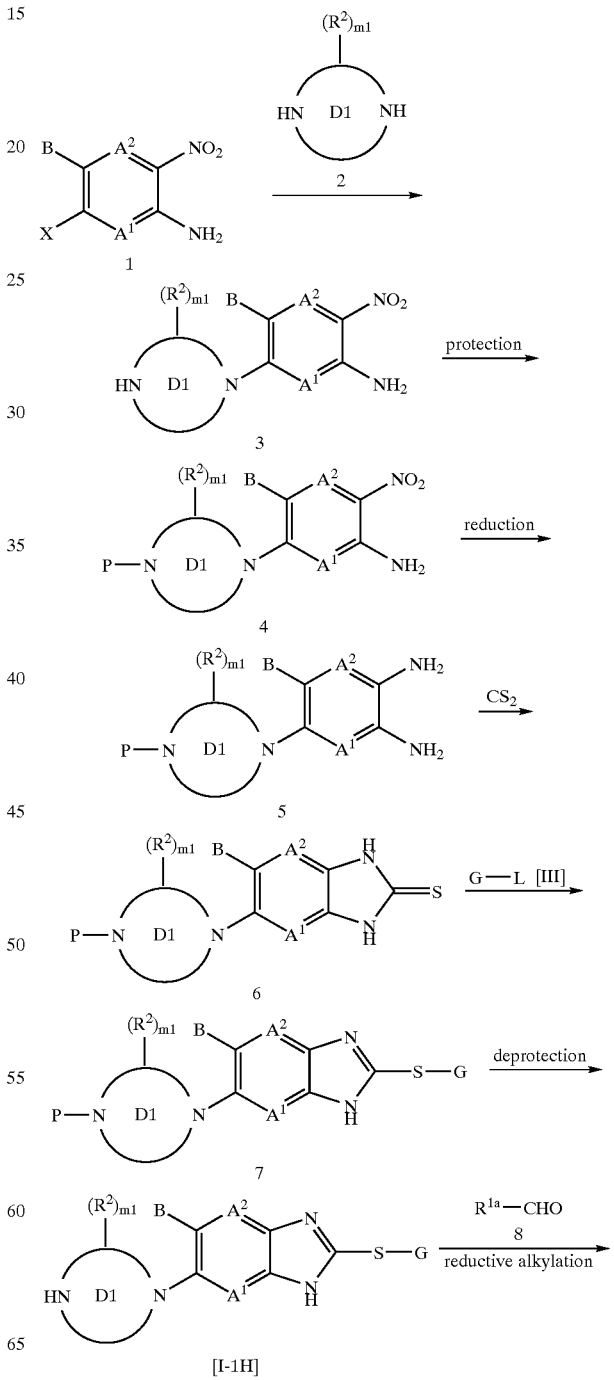

-continued

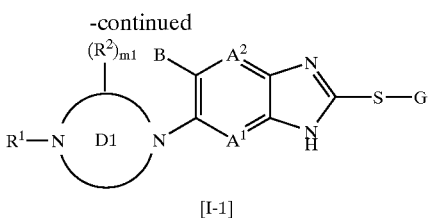

[I-1]

In the above scheme, $A^1, A^2, B, G, R^1, R^2$, m1 and D1 ring are same to those earlier defined. P stands for amino-protective group. X stands for halogen. L stands for leaving group, e.g., halogen such as chlorine, bromine or iodine; lower alkylsulfonyloxy such as methanesulfonyloxy or trifluoromethanesulfonyloxy; arylsulfonyloxy such as p-toluenesulfonyloxy; 1-imidazolyl or 0-isourea and the like. $R^{1a}$ is $R^1$ (where $R^1$ is not hydrogen) from which methylene is removed from the α-position side, to serve as $R^1$ as a $R^{1a}$—$CH_2$—.

Step 1-1: Reaction from Compound 1 to Compound 3

Starting from compound 1 which is reacted with compound 2 which is a diamine, to be converted to compound 3. This reaction is conducted in a reaction solvent, in the presence or absence of a basic compound (preferably in the presence of a basic compound). As the reaction solvent, halogenated carbons such as methylene chloride, chloroform, dichloroethane, carbon tetrachloride and the like; aliphatic hydrocarbons such as n-heptane, n-hexane and the like; aromatic hydrocarbons such as benzene, toluene, xylene and the like; alcohols such as methanol, ethanol, isopropyl alcohol, cyclohexanol and the like; ethers such as diethyl ether, tetrahydrofuran, 1,4-dioxane, ethylene glycol dimethyl ether and the like; esters such as methyl acetate, ethyl acetate and the like; and aprotic solvents such as N,N-dimetylformamide, dimethylsulfoxide and the like are exemplified. As the basic compound, potassium carbonate, sodium carbonate, lithium carbonate and the like are exemplified.

Use ratio of compound 1 to compound 2 is, per mole of compound 1, 0.9–20 moles, preferably 0.95–1.5 moles, of the basic compound.

When a basic compound is used, the use ratio is, per mole of compound 1, 0.9–20 moles, preferably 0.95–1.5 moles, of the basic compound.

As the reaction temperature, 0–200° C., preferably 60–180° C., are recommended, and the reaction terminates usually in about 2–20 hours.

After termination of the reaction, the reaction liquid is dissolved in an organic solvent such as ethyl acetate, chloroform, methylene chloride or the like, after optional condensation, and thereafter the organic solvent is washed with saturated brine. The organic layer after the washing is dried over anhydrous sodium sulfate, and the solvent is distilled off. Thus obtained residue is subjected to purification where necessary, by such means as washing with organic solvent, recrystallization, reprecipitation, chromatography, or the like, and supplied to the next step reaction. (In the reactions at each step of the following production processes 1 to 9, similar operations are conducted, unless specifically described otherwise.)

Moreover, when the substituent $R^2$ in compound 2 contains oxo, hydroxyl or carboxyl which do not participate in the reaction, said oxo, hydroxyl or carboxyl are preferably protected with suitable oxo-protective, hydroxyl-protective or carboxyl-protective groups and thereafter the reaction is conducted, which protective group(s) being removed after the final step (in this reaction, step 1-8).

As the protective group for oxo, for example, acetal, ketal or the like, such as ethylene ketal, trimethylene ketal and dimethyl ketal can be named.

As the protective group for hydroxyl, for example, substituted silyl such as trimethylsilyl, tert-butyldimethylsilyl and tert-butyldiphenylsilyl; lower alkoxymethyl such as methoxymethyl, 2-methoxyethoxymethyl and trimethylsilylethoxymethyl, tetrahydropyranyl; aralkyl such as benzyl, p-methoxybenzyl, 2,3-dimethoxybenzyl, o-nitrobenzyl, p-nitrobenzyl and trityl; and acyl such as formyl and acetyl can be named. In particular, methoxymethyl, tetrahydropyranyl, trityl, trimethylsilylethoxymethyl, tert-butyldimetylsilyl and acetyl are preferred.

As the protective group for carboxyl, lower alkyl such as methyl, ethyl, propyl, isopropyl and tert-butyl; lower alkenyl such as 2-propenyl; and aralkyl such as benzyl, p-methoxybenzyl, p-nitrobenzyl and benzhydryl can be named. In particular, methyl, ethyl, tert-butyl, 2-propenyl, benzyl, p-methoxybenzyl and benzhydryl are preferred. Among such protective groups, those which are not affected under the reaction conditions of each step in the production process 1 can be suitably selected and used.

As methods for introduction of protective group/deprotection, for example, those described in *Protective Groups in Organic Synthesis*, T. W. Greene, John Wiley & Sons (1981) can be adopted.

Step 1-2: Reaction from Compound 3 to Compound 4

Then the amino group in the resulting compound 3 is protected with a protective group P [here it is tert-butyloxycarbonyl (hereinafter abbreviated as "Boc group")]. In the reaction, compound 3 is reacted with a butyloxycarbonylating reagent [e.g., di-tert-butylcarbonate, 2-(tert-butoxycarbonyloxyimino)-2-phenylacetonitrile or the like] in a reaction solvent, in the presence or absence of a basic compound.

As the reaction solvent, halogenated hydrocarbons such as methylene chloride, chloroform, dichloroethane and carbon tetrachloride; alcohols such as methanol, ethanol, isopropyl alcohol and cyclohexanol; hydrocarbons such as n-heptane and n-hexane; aromatic hydrocarbons such as benzene, toluene and xylene; ethers such as diethyl ether, tetrahydrofuran and 1,4-dioxane; esters such as methyl acetate and ethyl acetate; and aprotic solvents such as N,N-dimethylformamide and dimethylsulfoxide and the like can be exemplified.

As the basic compound, triethylamine, potassium carbonate, sodium carbonate, lithium carbonate, sodium hydroxide, potassium hydroxide and the like are exemplified, and their use ratio is, per mole of compound 3, for example, 1–2 moles of the basic compound is used. Also as the use ratio between compound 3 and butyloxycarbonylating reagent, 1.05–1.5 moles, preferably 1.05–1.2 moles, of butyloxycarbonylating reagent is used per mole of compound 3.

As the reaction temperature, 0–100° C., preferably 0–60° C., are recommended, and the reaction usually terminates in 0.5–4 hours.

Moreover, in this reaction protective groups for amino other than Boc groups can be used, examples of which include aralkyl such as benzyl, p-methoxybenzyl, 3,4-dimethoxybenzyl, benzhydryl and trityl; lower alkanoyl such as formyl, acetyl, propionyl, butyryl and privaloyl; arylalkanoyl such as benzoyl; lower alkoxycarbonyl such as methoxycarbonyl, ethoxycarbonyl and propyloxycarbonyl; lower alkenyloxycarbonyl such as allyloxycarbonyl; aralkyloxycarbonyl such as benzyloxycarbonyl, p-nitrobenzyloxycarbonyl and phenethyloxycarbonyl; lower alkylsilyl such as trimethylsilyl and tert-butyldimethylsilyl; and aralkylidene such as benzylidene, p-chlorobenzylidene and o-nitrobenzylidene and the like. In particular, acetyl, allyloxycarbonyl and p-nitrobenzyloxycarbonyl are recommended.

While these protective groups can be introduced by a method similar to that of Boc groups, the introduction can also be conducted by such methods as described in *Protective Groups in Organic Synthesis*, T. W. Greene, John Wiley & Sons (1981) or those known methods following them.

Step 1-3: Reaction from Compound 4 to Compound 5

The nitro group in compound 4 is reduced to form compound 5 having amino group. Method for the reduction is subject to no specific limitation so long as it does not affect the substituent B. For example, reduction by combination of transition metal such as iron, tin and the like with hydrochloric acid or ammonium chloride, catalytic reduction, reduction with hydrazine hydrate-Raney nickel, or reduction using such reducing agent as sodium hydrosulfite, ammonium sulfide or the like, may be exemplified.

In the reduction by a combination of transition metal such as iron or tin with hydrochloric acid or ammonium chloride, 3–20 moles, preferably 10–15 moles, of the transition metal is used per mole of compound 4; and 2–10 moles, preferably 2.5–7 moles, of hydrochloric acid or ammonium chloride is used per mole of compound 4.

As the reaction solvent, inert solvents, e.g. alcohols such as methanol, ethanol or isopropyl alcohol; ethers such as dimethyl ether, ethyl ether, diisopropyl ether, dibutyl ether, dimethoxyethane, dioxane, tetrahydrofuran or diglyme; aliphatic hydrocarbons such as pentane, hexane, heptane or cyclohexane; or aromatic hydrocarbons such as benzene or toluene; and mixed solvents of these solvents with water can be used.

As the reaction temperature, for example, 0–150° C., preferably 60–130° C. are exemplified, and the reaction usually terminates in 30 minutes to 5 hours.

Where compound 4 is converted to compound 5 by means of catalytic reduction, as useful catalyst palladium-on-carbon, palladium-on-alumina, platinum oxide, ruthenium, rhodium, Raney nickel and the like are exemplified. As the amount of the catalyst, 0.1–2 parts by weight, preferably 0.1–0.5 part by weight, of the catalyst is used per 100 parts by weight of compound 4.

As the hydrogen pressure, 1–6 atmospheres are exemplified, 1–4 atmospheres being recommended. As the reaction solvent, furthermore, those earlier exemplified can be used.

As the reaction temperature in case of the catalytic reduction, 0–100° C., preferably 10–40° C., are exemplified, and usually the reaction terminates in 1–8 hours.

Where compound 4 is converted to compound 5 using a reducing agent, the use amount of the reducing agent is about 1–20 moles, preferably about 1–10 moles, per mole of compound 4.

As the reaction solvent, those earlier exemplified can be used, as the reaction temperature 0–150° C., preferably 20–120° C. are exemplified, and the reaction terminates usually in 1–24 hours.

Step 1-4: Reaction from Compound 5 to Compound 6

Through reaction of compound 5 with carbon disulfide, thiocarbonyldiimidazole, thiophosgene or thiourea in a reaction solvent and in the presence of an aqueous solution of a basic compound, compound 6 is obtained.

As the reaction solvent, inert solvents, e.g., alcoholic solvents such as methanol, ethanol, n-propanol and isopropanol; ethers such as dimethyl ether, ethyl ether, diisopropyl ether, dibutyl ether, dimethoxyethane, dioxane, tetrahydrofuran or diglyme; aliphatic hydrocarbons such as pentane, hexane, heptane or cyclohexane; or aromatic hydrocarbons such as benzene or toluene; and mixed solvents of these solvents with water can be used.

As the basic compound, sodium hydroxide, potassium hydroxide and the like are exemplified, and its use amount is 0.1–5 moles, preferably 0.5–3 moles, per mole of compound 5.

The use amount of carbon disulfide, thiocarbonyldiimidazole, thiophosgene or thiourea, 1–5 moles, preferably 1–1.5 moles, of carbon disulfide or thiourea is used per mole of compound 5. As the reaction temperature, 0–100° C., preferably 20–80° C., are exemplified, and the reaction terminates usually in 1–8 hours.

Step 1-5: Reaction from Compound 6 to Compound 7

Through reaction of compound 6 with a compound represented by a general formula [III]

$$G-L \qquad [III]$$

[in which G is same as that given in the general formula [I]. L stands for a leaving group, e.g., halogen such as chlorine, bromine or iodine; lower alkylsulfonyloxy such as methanesulfonyloxy or trifluoromethanesulfonyloxy; arylsulfonyloxy such as p-toluenesulfonyloxy; 1-imidazolyl or 0-isourea and the like] in a reaction solvent, in the presence or absence of a basic compound (preferably in the presence of a basic compound), compound 7, is obtained.

In said reaction, as the reaction solvent, halogenated carbons such as methylene chloride, chloroform, dichloroethane and carbon tetrachloride; hydrocarbon solvents such as n-heptane and n-hexane; aromatic hydrocarbons such as benzene, toluene, xylene; ether-type solvents such as diethyl ether, tetrahydrofuran and 1,4-dioxane; ester-type solvents such as methyl acetate and ethyl acetate; and aprotic solvents such as N,N-dimethylformamide and dimethylsulfoxide are exemplified.

As the basic catalyst, potassium carbonate, sodium carbonate, sodium hydroxide, potassium hydroxide and the like are exemplified, preferably potassium carbonate and sodium carbonate being recommended.

As the use ratio of compound 6 and the compound represented by the formula [III], 0.9–1.5 moles, preferably 1.05–1.2 moles, of the compound of formula [III] is used per mole of compound 6.

Also as the use amount of the basic compound, 0.1–5 moles, preferably 0.1–2 moles, of the basic compound is used per mole of compound 6.

As the reaction temperature, 0–150° C., preferably 40–90° C., are exemplified, and the reaction terminates usually in 1–24 hours.

When the substituent G on the compound represented by the formula [III] contains amino, oxo, hydroxyl, carboxyl or the like which do not participate in the reaction, said amino, oxo, hydroxyl or carboxyl are preferably protected with suitable amino-protective, oxo-protective, hydroxyl-protective or carboxyl-protective groups and thereafter the reaction is conducted, which protective group(s) being removed after the final step (in this reaction, after step 1-8).

As the protective groups for amino, for example, aralkyl such as benzyl, p-methoxybenzyl, 3,4-dimethoxybenzyl, benzhydryl and trityl; lower alkanoyl such as formyl and acetyl; arylalkanoyl such as benzoyl; lower alkoxycarbonyl such as methoxycarbonyl, ethoxycarbonyl and propyloxycarbonyl; lower alkenyloxycarbonyl such as allyloxycarbonyl; aralkyloxycarbonyl such as benzyloxycarbonyl and p-nitrobenzyloxycarbonyl; lower alkylsilyl such as trimethylsilyl and tert-butyldimethylsilyl; and aralkylidene such as benzylidene, p-chlorobenzylidene and o-nitrobenzylidene can be named. In particular, acetyl, allyloxycarbonyl, p-nitrobenzyloxycarbonyl and tert-butoxycarbonyl are preferred.

As the protective group for oxo, for example, acetal, ketal or the like, such as ethylene ketal, trimethylene ketal and dimethyl ketal can be named.

As the protective group for hydroxyl, for example, substituted silyl such as trimethylsilyl, tert-butyldimethylsilyl and tert-butyldiphenylsilyl; lower alkoxymethyl such as methoxymethyl, 2-methoxyethoxymethyl and trimethylsilylethoxymethyl; tetrahydropyranyl, aralkyl such as benzyl, p-methoxybenzyl, 2,3-dimethoxybenzyl and trityl; and acyl such as formyl and acetyl can be named. In particular, methoxymethyl, tetrahydropyranyl, trityl, trimethylsilylethoxymethyl, tert-butyldimetylsilyl and acetyl are preferred.

As the protective group for carboxyl, lower alkyl such as methyl, ethyl, propyl, isopropyl and tert-butyl; lower alkenyl such as 2-propenyl; and aralkyl such as benzyl, p-methoxybenzyl, p-nitrobenzyl and benzhydryl can be named. In particular, methyl, ethyl, tert-butyl, 2-propenyl, benzyl, p-methoxybenzyl and benzhydryl are preferred.

It is furthermore preferred that the protective group P used in the step 1-2 is the one which is removable by a mechanism differing from that used for removing protective groups for the amino, oxo, hydroxyl or carboxyl group not participating in the reaction, which are in the substituent G on the compound represented by the formula [III]. That is, for example where tert-butyloxycarbonyl group is used as P, protective group(s) used for the substituent G is(are) recommendably such protective group(s) which are inert under the conditions used in the step 1-6 (e.g., a 10% hydrogen chloride in methanol treatment).

As methods for introduction/deprotection of the protective group, for example, those described in *Protective Groups in Organic Synthesis*, T. W. Greene, John Wiley & Sons (1981) can be adopted.

Step 1-6: Reaction from Compound 7 to a Compound Represented the General Formula [I-1H]

By removing the protective group P (deprotection) of compound 7, a compound represented by the general formula [I-1H] is obtained.

As methods for removing the protective group P, heretofore known methods such as those described in *Protective Groups in Organic Synthesis*, T. W. Greene, John Wiley & Sons (1981) can be used. Specifically, where a Boc group is adopted as the protective group P, deprotection can be effected by dissolving 100 parts by weight of the compound 7 in 100–1,000 wt parts, preferably 100–500 wt parts, of 10% hydrogen chloride in methanol solution and stirring it at reaction temperature of 0–60° C., preferably 0–40° C., usually for 0.1–24 hours, preferably around 0.1–15 hours.

Step 1-7: Reaction from a Compound of General Formula [I-1H] to a Compound of General Formula [I-1]

Through reaction of a compound of general formula [I-1H] with compound 8 in the presence or absence of a reducing agent [preferably in the presence of a reducing agent (hereinafter the reaction in the presence of a reducing agent may be referred to as "reductive alkylation")] and, where necessary, deprotection of protected group(s), the former can be converted to the intended compound of the formula [I-1].

$R^{1a}$ in compound 8 has the same signification as before, which is converted to $R^1$ by hydrogenating and reducing, either after or during formation of C=N bond through the reaction of the aldehyde group in compound 8 with the nitrogen atom in compound 1, the double bond and further deprotecting the protected group where necessary.

As specific $R^{1a}$, hydrogen, methyl, ethyl, n-propyl, cyclopropyl, tert-butyloxymethyl, tert-butyldimethylsilyloxymethyl, phenyl, thiazol-2-yl, imidazol-2-yl, imidazol-4-yl, pyrazol-3-yl, 2,6-dimethoxyphenyl and the like can be exemplified.

The reaction between a compound of general formula [I-1H] and compound 8 is conducted by mixing them in a reaction solvent.

As the reaction solvent, alcohols such as methanol, ethanol, propanol and 2-propanol; ethers such as ethyl ether, tetrahydrofuran and dioxane; halogenated hydrocarbons such as methylene chloride, chloroform and 1,2-dichloroethane; aromatic hydrocarbons such as benzene, toluene, chlorobenzene and xylene; aprotic polar solvents such as dimethylformamide, ethyl acetate, acetonitrile and hexamethylphosphoramide; or mixed solvents of the foregoing can be named.

As the use ratio of the compound of general formula [I-1H] and compound 8, 1–5 moles, preferably 1–3 moles, of compound 8 is used per mole of the compound of general formula [I-1H].

The reducing agent is subject to no particular limitation so long as it does not affect the substituent B, and for example lithium borohydride, sodium borohydride, sodium cyanoborohydride, zinc cyanoborohydride, sodium triacetoxyborohydride, lithium aluminium hydride and the like may be exemplified. In particular, sodium cyanoborohydride, zinc cyanoborohydride and sodium triacetoxyborohydride are recommended.

As the use rate of the reducing agent, 1–10 moles, preferably 1–5 moles, of the reducing agent is used per mole of the compound of general formula [I-1H].

As the reaction temperature, 0–150° C., preferably 20–100° C., are exemplified. The reaction normally terminates in 5 minutes–48 hours, preferably 10 minutes–24 hours.

Whereas, it is also possible to react the compound of general formula [I-1H] with compound 8 in the absence of a reducing agent. In that case, after isolation of the formed product, it can be converted to the compound of general formula [I-1] by hydrogenation reduction using said reducing agent or by catalytic reduction in which hydrogenation is conducted in the presence of a metal catalyst.

In the catalytic reduction reaction conducting hydrogenation in the presence of a metal catalyst, palladium-on-carbon catalyst, Raney-nickel catalyst, rhodium catalyst, ruthenium catalyst, platinum oxide and the like can be used as the metal catalyst.

Hydrogen pressure in the catalytic reduction reaction normally ranges 1–6 atmospheres. Preferably 1–4 atmospheres is recommended. The use rate of the catalyst is 0.01–100 wt parts, preferably 0.01–10 wt parts, of the catalyst per 100 wt parts of the compound of general formula [I-1H].

As the reaction temperature, −20–100° C., preferably 0–30° C., are exemplified, and normally the reaction terminates in 5 minutes–7 days, preferably 1–6 hours.

As the reaction solvent, any of those solvents which are inert to the reducing agent can be used, examples of which including alcohols such as methanol and ethanol; ethers such as dimethyl ether, ethyl ether, diisopropyl ether, dibutyl ether, dimethoxyethane, dioxane, tetrahydrofuran and diglyme; halogenated hydrocarbons such as methylene chloride, chloroform and dichloroethane; aliphatic hydrocarbons such as pentane, hexane, heptane and cyclohexane; aromatic hydrocarbons such as benzene and toluene; or their mixed solvents.

It is also possible to use compound 2' in place of compound 2, in the production process 1. In that case, by conducting the steps 1-1, 1-3 and 1-4 using compound 2' as the starting material, compound 6' is obtained. The steps are illustrated by the following formulae. Where the substituents $R^1$ and $R^2$ on compound 2' contain oxo, hydroxyl, carboxyl or amino which do not participate in the reaction, they are preferably protected adequately with protective groups of oxo, hydroxyl, carboxyl or amino, respectively.

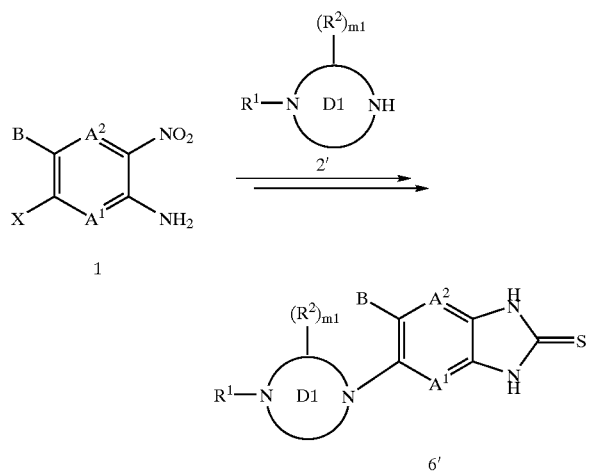

Upon conducting the step 1-5 using compound 6', a compound of general formula [I-1] can be obtained.

Those compound 6 and compound 6' may hereafter be collectively referred to as compounds of general formula [II].

Furthermore, when the compound obtained after the steps 1-8 contains, among its substituents, ($R^1$, $R^2$) in which protective groups of oxo, hydroxyl or carboxyl which do not participate in the reaction are substituted, the protective groups can be removed by a heretofore known method (for example, the method described in said *Protective Groups in Organic Synthesis*). For instance, where compound 8 has tert-butyldimethylsilyl group, it can be removed with tetrabutylammonium fluoride.

In this production process 1, as compound 1, compounds on the market or those known from literature (as clearly identified in Examples), such as 4,5-dichloro-2-nitroaniline, 4,5-difluoro-2-nitroaniline, 5-fluoro-4-acetyl-2-nitroaniline, 5-fluoro-4-cyano-2-nitroaniline and the like are exemplified.

As compound 2, those on the market or known from literature (as clearly identified in Examples), such as piperazine, 2-methylpiperazine, 2,6-dimethylpiperazine, cis-2,6-dimethylpiperazine, 2,2-dimethylpiperazine, 2-piperidinecarboxylic acid, 2-piperidine methanol, 1,4-diazepane, 2,5-diazabicyclo[2.2.1]heptane, 3,4,5,6-tetrahydropyrrolo[3,4-c]pyrrole, 1,2,3,4,5,6-hexahydropyrrolo[3,4-c]pyrrole, octahydropyrrolo[3,4-c]pyrrole, 2,5-diazabicyclo[2,2,2]octane, decahydro[1,6]naphthyridine, 2,5-diazabicyclo[3.2.1]octane and the like are exemplified.

As compound 2', those on the market or known from literature (as clearly identified in Examples), such as 1-methylpiperazine, 1-ethylpiperazine, 1-piperazine ethanol, 1-(cyclopropylmethyl)piperazine, 1-benzylpiperazine, 2,2,6,6-tetramethylpiperazine, tetrahydro-2(1H)-pyrazinone, 1,4-diazabicyclo[3.2.1]octane, octahydropyrazino[2,1-c][1,4]oxazine and the like are exemplified.

As those compounds which are represented by the general formula [III], where L is chlorine atom, 2-chloro-4-hydroxy-4-methylpentane, 3-chloro-2,4-pentanedione and the like are exemplified; where L is bromine atom, bromomethylcyclohexane, 3-bromopentane, cyclopentyl bromide, 1-bromopinacolone, methyl 2-bromobutyrate, 2-bromo-N-(tert-butyl)butanamide, 2-bromo-1-morpholino-1-butanone, 2-bromopropane and the like are exemplified; where L is methanesulfonyloxy group, 3-methoxy-3-methylbutyl methanesulfonate, 5-methylhexyl methanesulfonate, 1,3,3-trimethylbutyl methanesulfonate, 3-methoxy-1,3-dimethylbutyl methanesulfonate, 2-methoxy-2-methylpropyl methanesulfonate, 3-methoxybutyl methanesulfonate, tetrahydro-4H-pyran-4-yl methanesulfonate, 3-methoxypropyl methanesulfonate, 3-azido-3-methylbutyl methanesulfonate, 3-hydroxy-2,3-dimetylbutyl methanesulfonate, 1-ethyl-3-hydroxy-3-methylbutyl methanesulfonate, 2-ethyl-2-hydroxybutyl methanesulfonate, tetrahydro-4H-pyran-4-ylmethyl methanesulfonate, 3-tetrahydro-4H-pyran-4-ylpropyl methanesulfonate, 2-(diisopropylamino)ethyl methanesulfonate, 2-(1-hydroxycyclohexyl)ethyl methanesulfonate, 2-(1-hydroxycyclopentyl)ethyl methanesulfonate, tetrahydro-3-furanylmethyl methanesulfonate, 2,2-dimethyltetrahydro-4H-pyran-4-yl methanesulfonate, 2-ethyl-3-hydroxy-3-methyl methanesulfonate, 1,4-dioxaspiro[4,5]decan-8-yl methanesulfonate, 1-methylpyrrolidin-3-yl methanesulfonate, 3-ethyl-3-hydroxypentyl methanesulfonate, 3-hydroxy-1-methylbutyl methanesulfonate, 1-(methoxymethyl)propyl methanesulfonate, 8-oxabicyclo[3.2.1]octan-3-yl methanesulfonate, 4-{(ethoxycarbonyl)amino}cyclohexyl methanesulfonate, methyl 3-{(methylsulfonyl)oxy}tetrahydro-1(2H)-pyridinecarboxylate and the like are exemplified; where L is p-toluenesulfonyloxy group, 3-hydroxy-3-methylbutyl 4-methylbenzenesulfonate and the like are exemplified; and where L is O-isourea group, N,N'-di-diisopropyl-0-tert-butylisourea, N,N'-di-diisopropyl-0-tert-amylisourea and the like are exemplified. Preferably, 3-bromopentane, 1,3,3-trimethylbutyl methanesulfonate, 3-methoxy-1,3-dimethylbutyl methanesulfonate, tetrahydro-4H-pyran-4-yl methanesulfonate, 3-hydroxy-2,3-dimethylbutyl methanesulfonate, 1-ethyl-3-hydroxy-3-methylbutyl methanesulfonate and 3-hydroxy-1-methylbutyl methanesulfonate are recommended. As these compounds, commercially available compounds can be used. Besides, they can be readily prepared by condensing corresponding alcohols with methanesulfonyl chloride or toluenesulfonyl chloride by a heretofore known method.

As compound 8, those on the market or known from literature (as clearly identified in Examples), such as cyclopropanecarboxyaldehyde, formaline, acetaldehyde, tert-butyloxyacetaldehyde, tert-butyldimethylsilyloxyacetaldehyde, benzaldehyde, 2-formylthiazole, 2-formylimidazole, 4-formylimidazole, pyrazole-3-carbaldehyde, 2,6-dimethoxybenzaldehyde and the like are exemplified. Preferably, cyclopropanecarboxyaldehyde, formaline, acetaldehyde, tert-butyloxyacetaldehyde, tert-butyldimethylsilyloxyacetaldehyde and 2,6-dimethoxybenzaldehyde are recommended.

It is also possible, furthermore, to obtain the compounds represented by general formula [I-1], by using ketones such as acetone, methyl ethyl ketone, diethyl ketone and the like, in place of compound 8.

Production Process 2

This is an effective production process when D is one represented by the formula [D-2].

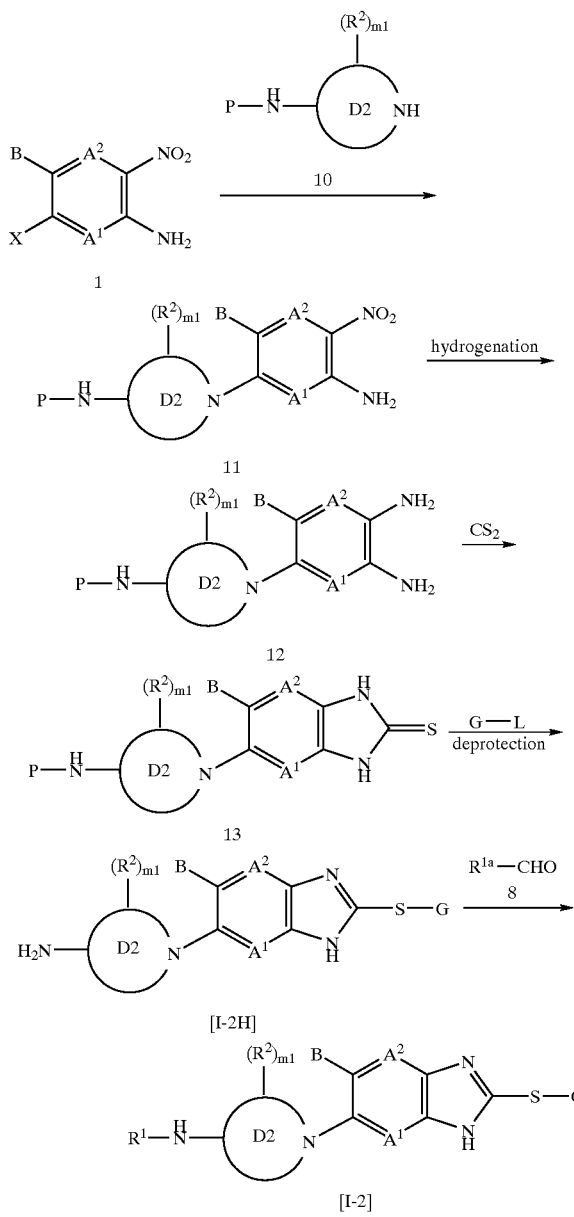

[in the above formulae, $A^1$, $A^2$, B, G, $R^1$, $R^2$, P, L, X, m1 and D2 ring are same to those as earlier defined].

Step 2-1: Reaction from Compound 1 to Compound 11

Condensing compound 1 with compound 10 following the method described in the step 1-1, compound 11 is formed. Similar reaction conditions and molar ratios in the reaction to those as described in the step 1-1 are applicable.

Step 2-2: Reaction from Compound 11 to Compound 12

The nitro group in compound 11 is hydrogenated and reduced following the method as described in the step 1-3, to convert the compound to diamine 12. Similar reaction conditions and molar ratios in the reaction to those as described in the step 1-3 are applicable.

Step 2-3: Reaction from Compound 12 to Compound 13

Ring-closing the diamine of compound 12 using carbon disulfide following the step 1-4, compound 13 is obtained. Similar reaction conditions and molar ratios in the reaction to those as described in the step 1-4 are applicable. This compound 13 shall be referred to as the compound represented by general formula [VI].

Step 2-4: Reaction from Compound 13 to Compound Represented by General Formula [I-2H]

Successively reacting compound 13 with a compound of general formula [III] following the method as described in the step 1-5 and removing the amino-protecting group P (deprotection) following the method as described in the step 1-6, the intended compound of general formula [I-2H] is formed. Similar reaction conditions and molar ratios in the reaction to those as described in the steps 1-5 or 1-6 are applicable.

Step 2-5: Reaction from the Compound Represented by General Formula [I-2H] to the Compound Represented by General Formula [I-2]

The compound represented by general formula [I-2H] as obtained in the above step can be converted to one represented by general formula [I-2] where necessary, by reductive alkylation using compound 8 following the step 1-7.

Here, as compound 10, those on the market or known from literature (as clearly identified in Examples), such as 4-(tert-butoxycarbonylamino)piperidine, 3-(tert-butoxycarbonylamino)-pyrrolidine, 3-(tert-butoxycarbonylamino)piperidine and the like are exemplified.

Production Process 3

This is an effective production process when D is one represented by the formula [D-3] and E is single bond. Moreover, both $A^1$ and $A^2$ preferably are optionally fluorine-substituted methine groups.

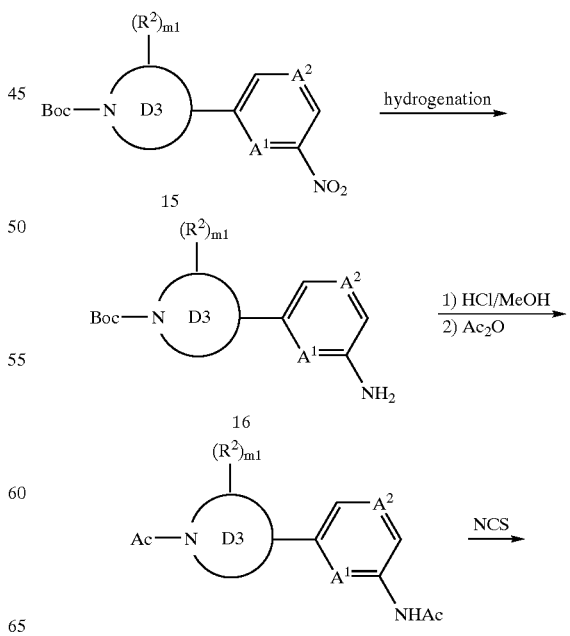

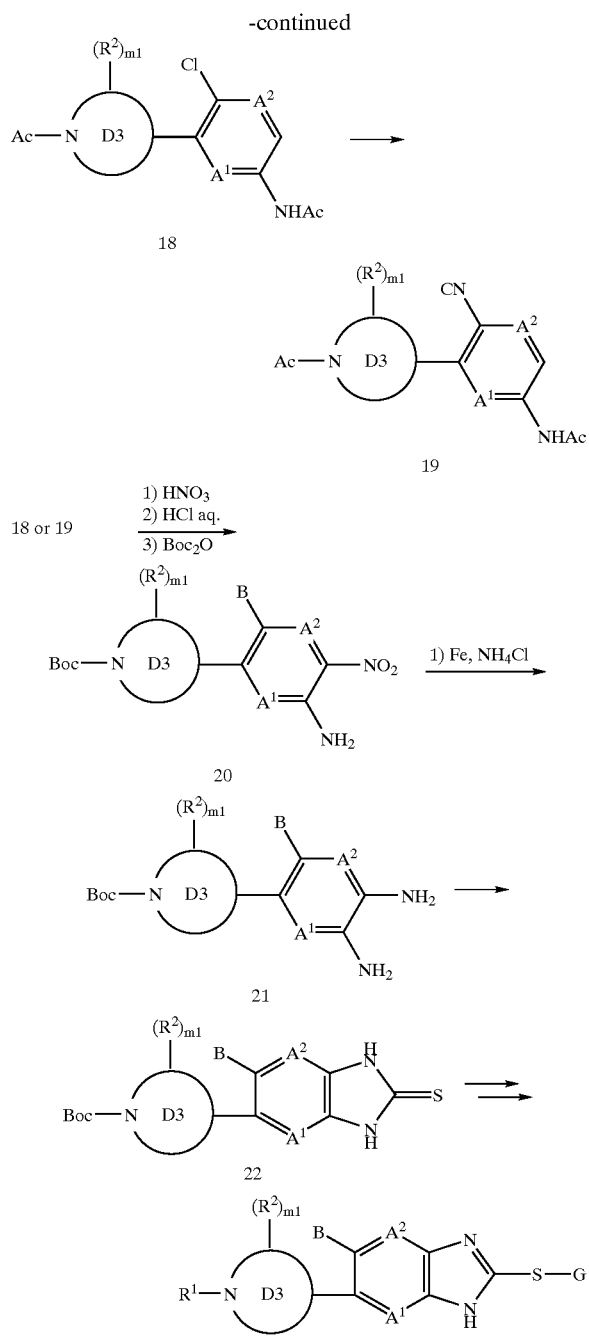

[in which A¹, A², B, G, R¹, R², m1 and D3 ring are same to those as earlier defined, and Ac stands for acetyl group].

Step 3-1: Reaction from Compound 15 to Compound 16

Through hydrogenation reduction of the nitro group in compound 15, compound 16 is formed. Here the hydrogenation reduction is conducted by catalytic reduction using metal catalyst, and as the catalyst, palladium-on-carbon, Raney-nickel, platinum, rhodium-alumina catalysts and the like are exemplified. As the amount of such a catalyst, 5–50 wt parts, preferably 10–20 wt parts, of the catalyst is used per 100 wt parts of compound 15. As the hydrogen pressure, 1–6 atmospheres is exemplified. Preferably, 1–4 atmospheres is recommended.

As the reaction solvent, inert solvents, e.g., alcohols such as methanol, ethanol, isopropyl alcohol and the like; ethers such as dimethyl ether, ethyl ether, diisopropyl ether, dibutyl ether, dimethoxyethane, dioxane, tetrahydrofuran, diglyme and the like; and aliphatic hydrocarbons such as pentane, hexane, heptane, cyclohexane and the like; or mixed solvents of these solvents with water can be used.

As the reaction temperature, 0–80° C., preferably 10–50° C., are exemplified, and the reaction terminates normally within 1 to 6 hours.

Step 3-2: Reaction from Compound 16 to Compound 17

Removing the Boc group in compound 16 for deprotection and acetylating the resulting amine, compound 17 is formed. As the deprotecting method, for example, step 1-6 can be followed.

Successively, the obtained amine is acetylated using an acetylation agent to form compound 17. For the acetylation, heretofore known acetylation agents are useful. For example, acetyl chloride, acetyl bromide, acetic anhydride and the like are exemplified.

Where acetic anhydride is used, for example, 100 wt parts of the amine is dissolved in 50–500 wt parts of acetic anhydride and 50–3,000 wt parts of pyridine, preferably 100–300 wt parts of acetic anhydride and 100–1,000 wt parts of pyridine, and the reaction is conducted at temperatures ranging 0–100° C., preferably 10–40° C., under stirring. The reaction time normally is 1–8 hours.

Step 3-3: Reaction from Compound 17 to Compound 18

Reacting compound 17 with N-chlorosuccinimide (NCS) in a reaction solvent, compound 18 is formed.

As the useful reaction solvent, halogenated carbons such as methylene chloride, chloroform, dichloroethane, carbon tetrachloride and the like; alcohols such as methanol, ethanol, isopropyl alcohol and the like; hydrocarbon solvents such as n-heptane, n-hexane and the like; ether solvents such as diethyl ether, tetrahydrofuran, 1,4-dioxane and the like; and aprotic solvents such as N,N-dimethylformamide, dimethylsulfoxide and the like are exemplified.

As the use rates of compound 17 and NCS, 1.0–5.0 moles, preferably 1.1–2.0 moles, of NCS is used per mole of compound 17. As the reaction temperature, 50–200° C., preferably 70–120° C., are exemplified. The reaction normally terminates in 0.5–2 hours.

Where N-bromosuccinimide is used in place of NCS, compound of general formula [I] in which B is bromine atom is obtained. For example, when N-fluorobenzenesulfonimide is used, the compound in which B is fluorine atom is obtained.

Further reacting compound 18 with sodium cyanide, potassium cyanide, copper cyanide or the like, compound 19 is obtained.

Step 3-4: Reaction from Compound 18 (or 19) to Compound 20

Compound 18 (or 19) is converted to compound 20, by nitration thereof with a nitrating agent, hydrolyzing the acetyl group in the resulting compound and then butyloxycarboxylating the same. In respect of the reactivity, use of compound 18 as the starting material is preferred.

Nitration of compound 18 (or 19) can be effected using heretofore known nitrating agent, and as such a nitrating agent, fuming nitric acid can be named. The solvent to be used for the nitration reaction is preferably optionally selected according to individual nitrating agent used, acetic acid, acetic anhydride, trifluoroacetic acid, sulfuric acid, dichloroethane, chloroform, carbon tetrachloride and the like being exemplified.

Use rates of compound 18 (or 19) and fuming nitric acid are: 5.0–15.0 moles, preferably 3.0–8.0 moles, of fuming nitric acid per mole of compound 18 (or 19). As the reaction temperature, 0–150° C., preferably 0–50° C., are exemplified. The reaction normally terminates in 1–2 hours.

Hydrolysis of the acetyl group in the resulting compound is successively conducted by heretofore known hydrolyzing method. In this reaction, preferably hydrolysis using an acid is recommended, while that using a base is also possible. As useful base, for example, lithium hydroxide, sodium hydroxide, potassium hydroxide, sodium carbonate, potassium carbonate, sodium methoxide, sodium ethoxide and the like may be named. Also as useful acid, hydrochloric acid, hydrobromic acid, sulfuric acid and the like can be named.

The solvent to be used in hydrolysis of this reaction preferably is selected according to the hydrolyzing method, for example, from water, methanol, ethanol, propanol, tetrahydrofuran, dioxane, benzene, toluene, xylene, chlorobenzene, N,N-dimethylformamide, dimethylsulfoxide, formic acid, acetic acid, and mixed solvents of the foregoing.

As reaction temperature in the occasion of the hydrolysis, 0–150° C., preferably 50–130° C., are exemplified,and the reaction terminates normally in 2–24 hours.

Successively the deacetylated amine is butyloxycarboxylated following, for example, the step 1-2, with a butyloxycarboxylating agent, to provide compound 20.

Step 3-5: Reaction from Compound 20 to Compound 22

Compound 20 is hydrogenated and reduced following the step 1-3 to be converted to compound 21. Reaction conditions as described in the step 1-3 can be applied as they are. Further, the resulting compound 21 is reacted following the step 1-4 to be converted to compound 22.

Further introducing substituent group G into compound 22 following the step 1-5 and subsequently introducing substituent group $R^1$ following the steps 1-6 to 1-8, a compound represented by general formula [I-3] can be obtained.

In the production process 3, amino-protective groups other than Boc groups can be used. As such protective groups, those named in the step 1-2 (protective group P) can be used, and in that case compounds represented by general formula [VIII] are obtained instead of compound 22.

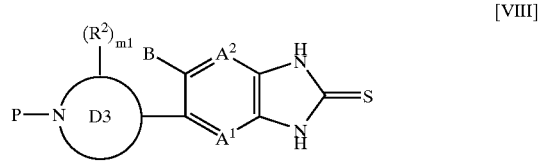

[VIII]

Also in the production process 3, as an example of compound 15, tert-butyl-1,2,3,4-tetrahydro-4-(3-nitrophenyl)pyridinecarboxylate can be named, which compound can be prepared, for example, by the method as described in *Synthesis*, 1991, 993–995.

Production Process 4

Compounds of general formula [K] in which Y=N and D is represented by formula [D-1] can be prepared by the following process. While the following shows a synthesis method of the compounds having substituent groups G, those compounds having G' instead of G can also be synthesized by the similar method. (This applies also to other production processes.)

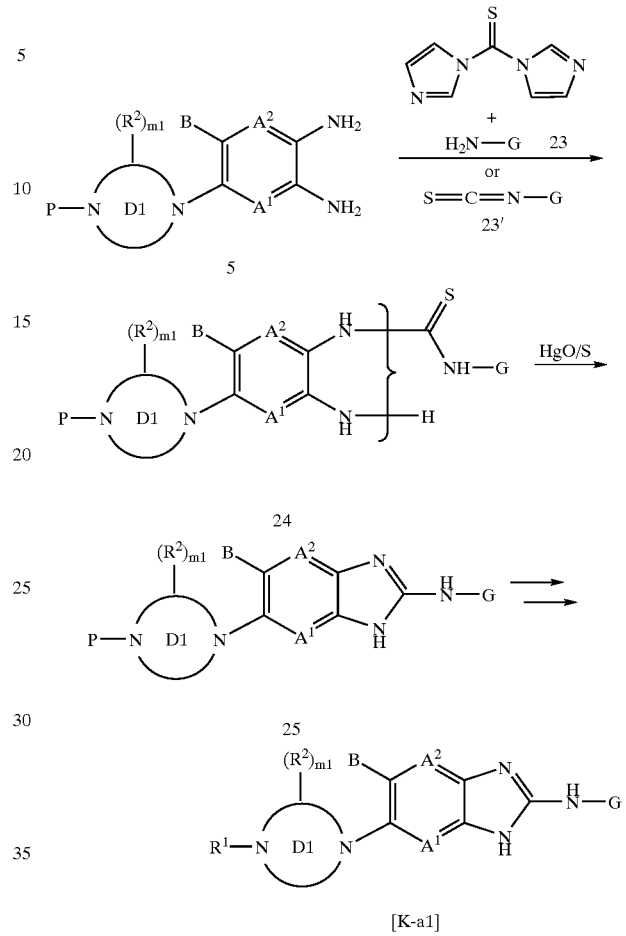

[K-a1]

[in which $A^1$, $A^2$, B, G, $R^1$, $R^2$, m1, D and D1 ring are same to those as earlier defined].

Step 4-1: Reaction from Compound 5 to Compound 24

Stirring thiocarbonyldiimidazole and compound 23 in a solvent, then adding compound 5 to the reaction liquid formed and further continuing stirring, compound 24 is obtained. Or by stirring isothiocyanate 23' and compound 5 in a reaction solvent, compound 24 is obtained.

In said reaction, as the use rates of compound 5 and thiocarbonyldiimidazole, 0.5–2.0 moles, preferably 0.5–1.0 mole, of thiocarbonyldiimidazole is used per mole of compound 5. Also as the use rates of compound 5 and compound 23, 0.5–2.0 moles, preferably 0.5–1.0 mole, of compound 23 is used per mole of compound 5.

As the reaction solvent, halogenated carbons such as methylene chloride, chloroform, dichloroethane, carbon tetrachloride and the like; aliphatic hydrocarbons such as n-heptane, n-hexane and the like; aromatic hydrocarbons such as benzene, toluene, xylene and the like; ethers such as diethyl ether, tetrahydrofuran, 1,4-dioxane, ethylene glycol dimethyl ether and the like; and aprotic solvents such as N,N-dimethylformamide, dimethylsulfoxide, acetonitrile and the like are exemplified.

As the reaction temperature, 0–100° C., preferably 0–60° C., are exemplified, and the reaction norally terminates in 12 hours–3 days.

Whereas, in the reaction between isothiocyanate 23' and compound 5, as the use rates of compound 5 and compound 23, 0.95–2.0 moles, preferably 1.0–1.05 moles, of compound 23' is used per mole of compound 5. Also as the solvent and reaction conditions, those as above-described are applicable.

Step 4-2: Reaction from Compound 24 to Compound 25

Compound 25 is obtained by reaction of compound 24 with HgO in a reaction solvent and in the presence of sulfur.

As the use rates of compound 24 and HgO, 1–5 moles, preferably 2–3 moles, of HgO is used per mole of compound 24, and as the use rate of sulfur, 0.01–0.1 wt part, preferably 0.02–0.05 wt part, of sulfur is used per 100 wt parts of compound 24.

As the reaction solvent, halogenated carbons such as methylene chloride, chloroform, dichloroethane, carbon tetrachloride and the like; aliphatic hydrocarbons such as n-heptane, n-hexane and the like; aromatic hydrocarbons such as benzene, toluene, xylene and the like; alcohols such as methanol, ethanol, isopropyl alcohol, cyclohexanol and the like; ethers such as diethyl ether, tetrahydrofuran, 1,4-dioxane and the like; esters such as methyl acetate, ethyl acetate and the like; aprotic solvents such as N,N-dimethylformamide, dimethylsulfoxide and the like, or mixed solvents of the foregoing are exemplified.

As the reaction temperature, 0–150° C., preferably 50–100° C., are exemplified, and the reaction normally terminates in 0.5–10 hours.

Thus obtained compound 25 can be converted to the compound represented by general formula [K-a1], through the reactions for introducing $R^1$ following the steps 1-6, 1-7 and 1-8.

Where compound 12 or compound 22 is used in place of compound 5 in the production process 4, compounds represented by a general formula [K-a2]

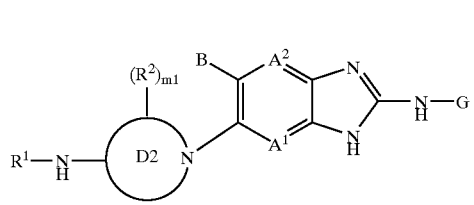

[K-a2]

[in which $A^1$, $A^2$, B, G, $R^1$, $R^2$, m1 and D2 ring are same as earlier defined] or a general formula [K-a3]

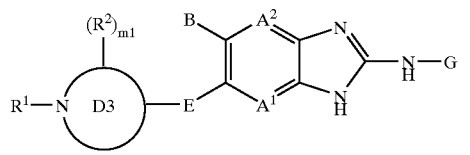

[K-a3]

[in which $A^1$, $A^2$, B, G, $R^1$, $R^2$, m1 and D3 ring are same as earlier defined] are obtained.

Compound 23 which is used in the production process 4 is an amine in which an amino group is bonded to substituent G, specific examples including
2-amino-4-hydroxy-4-methylpentane, 3-amino-2,4-pentanedione, aminomethylcyclohexane, 3-aminopentane, cyclopentylamine, 1-aminopinacolone, methyl 2-aminobutyrate, 2-amino-N-(tert-butyl)butanamide, 2-amino-1-morpholino-1-butanone, 2-aminopropane, 3-methoxy-3-methylbutylamine, 5-methylhexylamine, 1,3,3-trimethylbutylamine, 3-methoxy-1,3-dimethylbutylamine, 2-methoxy-2-methylpropylamine, 3-methoxybutylamine, tetrahydro-4H-pyran-4-ylamine, 3-methoxypropylamine, 3-hydroxy-2,3-dimethylbutylamine, 1-ethyl-3-hydroxy-3-methylbutylamine, 2-ethyl-2-hydroxybutylamine, tetrahydro-4H-pyran-4-ylmethylamine, 3-tetrahydro-4H-pyran-4-ylpropylamine, 2-(diisopropylamino)ethylamine, 2-(1-hydroxycyclohexyl)ethylamine, 2-(1-hydroxycyclopentyl)ethylamine, tetrahydrofuran-3-ylmethylamine, 2,2-dimethyltetrahydro-4H-pyran-4-ylamine, 2-ethyl-3-hydroxy-3-methylbutylamine, 1,4-dioxaspiro[4,5]decan-8-ylamine, 1-methyl-3-aminopyrrolidine, 3-ethyl-3-hydroxypentylamine, 3-hydroxy-1-methylbutylamine, 1-(methoxymethyl)propylamine, 8-oxabicyclo[3.2.1]octan-3-ylamine, 4-{(ethoxycarbonyl)amino}cyclohexylamine, methyl 3-amino-tetrahydro-1(2H)-pyridinecarboxylate, 3-hydroxy-3-methylbutylamine, tert-butylamine, tert-amylamine and the like.

As compound 23, those on the market can be used. Besides, it can be readily prepared by such known methods as, for example, reacting a compound of general formula [III] with sodium azide and reducing the resulting azide; or by reacting a compound of general formula [III] with potassium phthalimide and decomposing the resulting compound with hydrazine.

Compound 23' is a compound in which an isothiocyanate group is bonded to substituent G, and which is commercially available. Besides, it can be readily prepared from compound 23 and thiophosgene by heretofore known methods.

Production Process 5

This is an effective production process where Y=O in the general formula [K].

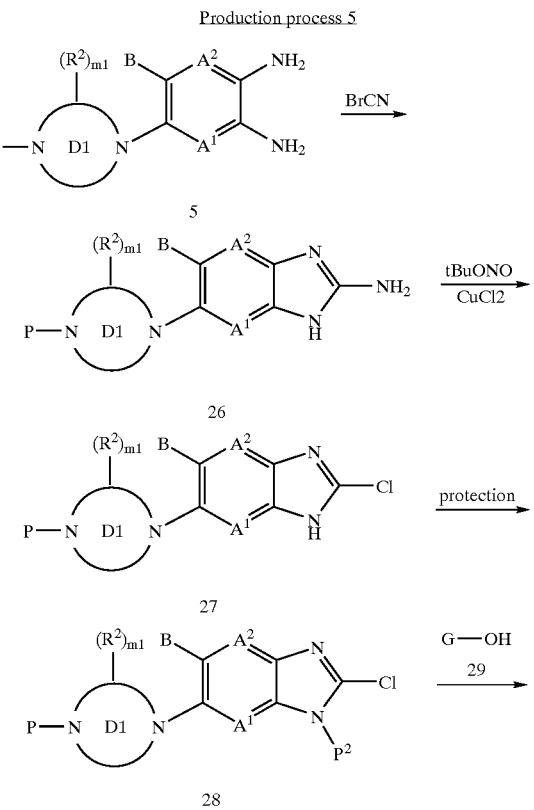

Production process 5

-continued

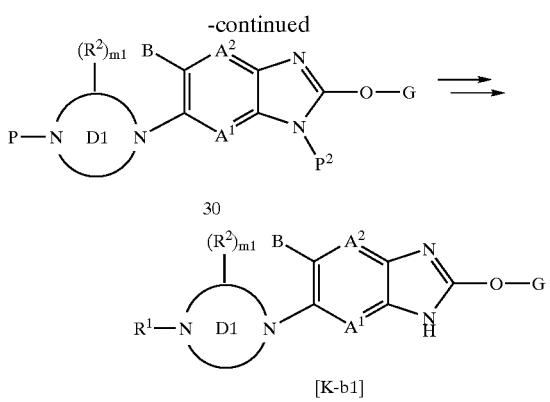

[K-b1]

[in which $A^1$, $A^2$, B, G, $R^1$, $R^2$, m1, P and D1 ring are same to those as earlier defined; $P^2$ stands for an imidazole-protecting group].

Step 5-1: Reaction from Compound 5 to Compound 26

Using compound 5 as the starting material, compound 26 is obtained by reacting the starting material with cyanogen bromide, cyanamide or guanidine.

As the use rates of compound 5 and cyanogen bromide, cyanamide or guanidine, per mole of compound 5, 1.0–2.0 moles, preferably 1.0–1.2 moles, of cyanogen bromide, cyanamide or guanidine is used.

As the reaction solvent, halogenated carbons such as methylene chloride, chloroform, dichloroethane and carbon tetrachloride; aliphatic hydrocarbons such as n-heptane and n-hexane; aromatic hydrocarbons such as benzene, toluene and xylene; alcohols such as methanol and ethanol; ethers such as diethyl ether, tetrahydrofuran, 1,4-dioxane and ethylene glycol dimethyl ether; esters such as methyl acetate and ethyl acetate; and aprotic solvents such as N,N-dimethylformamide, dimethylsulfoxide and acetonitrile are exemplified.

As the reaction temperature, 0–100° C., preferably 0–30° C., are exemplified, and the reaction terminates usually in 1–24 hours, preferably 1–4 hours.

Step 5-2: Reaction from Compound 26 to Compound 27

Compound 27 is obtained by reacting compound 26 with copper chloride in a reaction solvent, in the presence of t-butyl nitrite or sodium nitrite.

As the use rates of compound 26 and t-butyl nitrite or sodium nitrite, 1–5 moles, preferably 1–3 moles, of t-butyl nitrite or sodium nitrite is used per mole of compound 26. Also as the use rates of compound 26 and copper chloride, 1–2 moles of copper chloride is used per mole of compound 26.

As the reaction solvent, halogenated carbons such as methylene chloride, chloroform, dichloroethane and carbon tetrachloride; aliphatic hydrocarbons such as n-heptane and n-hexane; aromatic hydrocarbons such as benzene, toluene and xylene; alcohols such as methanol, ethanol, isopropyl alcohol and cyclohexanol; ketones such as acetone and methyl ethyl ketone; ethers such as diethyl ether, tetrahydrofuran, 1,4-dioxane and ethylene glycol dimethyl ether; esters such as methyl acetate and ethyl acetate; and aprotic solvents such as N,N-dimethylformamide and dimethylsulfoxide are exemplified.

As the reaction temperature, 0–100° C., preferably 30–60° C., are exemplified, and the reaction terminates usually in 30 minutes–3 hours, preferably 30 minutes–an hour.

Step 5-3: Reaction from Compound 27 to Compound 28

Compound 28 is formed by protecting the imidazole group in compound 27 with a protective group $P^2$. As $P^2$, for example, methoxymethyl (MOM), tetrahydropyranyl (THP), tert-butyloxycarbonyl (Boc), benzyl, p-methoxybenzyl and 2,3-dimethoxybenzyl are exemplified. These protective groups can be introduced by the methods as described in *Protective Groups in Organic Synthesis*, T. W. Greene, John Wiley & Sons (1981).

For example, introduction of tetrahydropyranyl as the imidazole-protective group can be effected by reacting compound 27 with 3,4-dihydro-2H-pyrane in a reaction solvent and in the presence of an acidic catalyst. As the acidic catalyst, camphor-sulfonic acid, p-toluene-sulfonic acid, hydrochloric acid and the like can be exemplified.

As the use rates of compound 27 and 3,4-dihydro-2H-pyrane, 1–20 moles, preferably 3–10 moles, of 3,4-dihydro-2H-pyrane is used per mole of compound 27, and as the use ratio of compound 27 and the acidic catalyst, 0.05–0.5 wt part of the acidic catalyst is used per 100 wt parts of compound 27.

As the reaction solvent, halogenated carbon such as methylene chloride, chloroform, dichloroethane and carbon tetrachloride; aliphatic hydrocarbons such as n-heptane and n-hexane, aromatic hydrocarbons such as benzene, toluene and xylene; ethers such as diethyl ether, tetrahydrofuran, 1,4-dioxane and ethylene glycol dimethyl ether; esters such as methyl acetate and ethyl acetate; aprotic solvents such as N,N-dimethylformamide and dimethylsulfoxide; or mixed solvents of the foregoing can be exemplified.

As the reaction temperature, 20–100° C., preferably 20–60° C., are exemplified. The reaction normally terminates in 1–24 hours, preferably 8–24 hours.

Step 5-4: Reaction from Compound 28 to Compound 30

Compound 30 is obtained by contacting compound 29 with a basic compound in a reaction solvent, and adding compound 28 to the resulting mixed solution to react compound 28 with compound 29.

As the basic compound, sodium hydride, potassium hydride, calcium hydride and the like are exemplified, sodium hydride being recommended.

As the use rates of compound 29 and the basic compound, 1–2 moles, preferably 1–1.5 moles, of the basic compound is used per mole of compound 29. Also as the use rates of compound 28 and compound 29, per mole of compound 28, 1–2 moles, preferably 1–1.5 moles of compound 29 is used.

As the reaction solvent, aliphatic hydrocarbons such as n-heptane and n-hexane, aromatic hydrocarbons such as benzene, toluene and xylene; ethers such as diethyl ether, tetrahydrofuran, 1,4-dioxane and ethylene glycol dimethyl ether; and aprotic solvents such as N,N-dimethylformamide and dimethylsulfoxide are exemplified.

Specifically, compound 29 and the basic compound are contacted in a reaction solvent at reaction temperatures ranging 0–60° C., preferably 0–20° C., for about 5 minutes–an hour, preferably 10–30 minutes, and then compound 28 is added to this reaction mixture and reacted at reaction temperatures ranging 20–100° C., preferably 50–80° C., for about 4–24 hours, preferably 8–16 hours to form compound 30.

Using compound 30 as the starting material, the substituent $R^1$ is introduced following the steps 1-6 and 1-7, and where necessary the protective group is removed to provide a compound represented by the general formula [K-b1].

It is possible to remove the protective group $P^2$ before the reaction of step 1-6, or after the reaction of step 1-7. Furthermore, depending on the kind of protective group used, it may be removed during the reaction of step 1-6. For example, where tetrahydropyranyl is used as the protective group $P^2$, the deprotection can be effected by stirring the obtained compound in 10% hydrogen chloride in methanol solution (the operation of step 1-6).

By conducting the reactions of production process 5 using compound 12 or 22 in place of compound 5, those compounds represented by a general formula [K-b2]

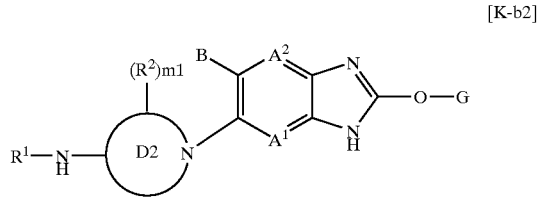

[K-b2]

[in which $A^1$, $A^2$, B, G, $R^1$, $R^2$, m1 and D2 ring are same to those as earlier defined], or those represented by a formula [K-b3]

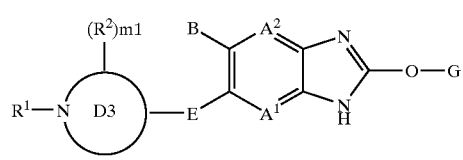

[K-b3]

[in which $A^1$, $A^2$, B, G, $R^1$, $R^2$, E, m1 and D3 ring are same to those as earlier defined] can be obtained respectively.

Compound 29 used in production process 5 is an alcohol in which a hydroxyl group binds to the substituent G. Specifically, as those commercially available or known from literature (as clearly identified in Examples), cyclohexyl methanol, 3-hydroxypentane, cyclopentanol, isopropanol, 3-methoxy-3-methyl-1-butanol, 5-methyl-1-hexanol, 1,3,3-trimethyl-1-butanol, 3-methoxy-1,3-dimethyl-1-butanol, 2-methoxy-2-methyl-1-propanol, 3-methoxy-1-butanol, tetrahydro-4H-pyran-4-ol, 3-methoxy-1-propanol, 3-azido-3-methyl-1-butanol, 3-hydroxy-2,3-dimethyl-1-butanol, 1-ethyl-3-hydroxy-3-methyl-1-butanol, 2-ethyl-2-hydroxy-1-butanol, tetrahydro-4H-pyran-4-ylmethanol, 3-tetrahydro-2H-pyran-4-yl-1-propanol, 2-(diisopropylamino)-1-ethanol, 2-(1-hydroxycyclohexyl)-1-ethanol, 2-(1-hydroxycyclopentyl)-1-ethanol, tetrahydro-3-furanylmethanol, 2,2-dimethyltetrahydro-4H-pyran-4-ol, 2-ethyl-3-hydroxy-3-methyl-1-butanol, 1,4-dioxaspiro[4,5]decan-8-ol, 1-methyl-3-hydroxypyrrolidine, 3-ethyl-3-hydroxy-1-pentanol, 1-(methoxymethyl)-1-propanol, 8-oxabicyclo[3.2.1]octan-3-ol, 4-[(ethoxycarbonyl)amino]cyclohexanol, methyl 3-hydroxy-tetrahydro-1(2H)-pyridinecarboxylate, tert-butyl alcohol, tert-amyl alcohol and the like are exemplified.

Production Process 6

This is an effective production process where Y in the general formula [K] is a single bond.

Production Process 6

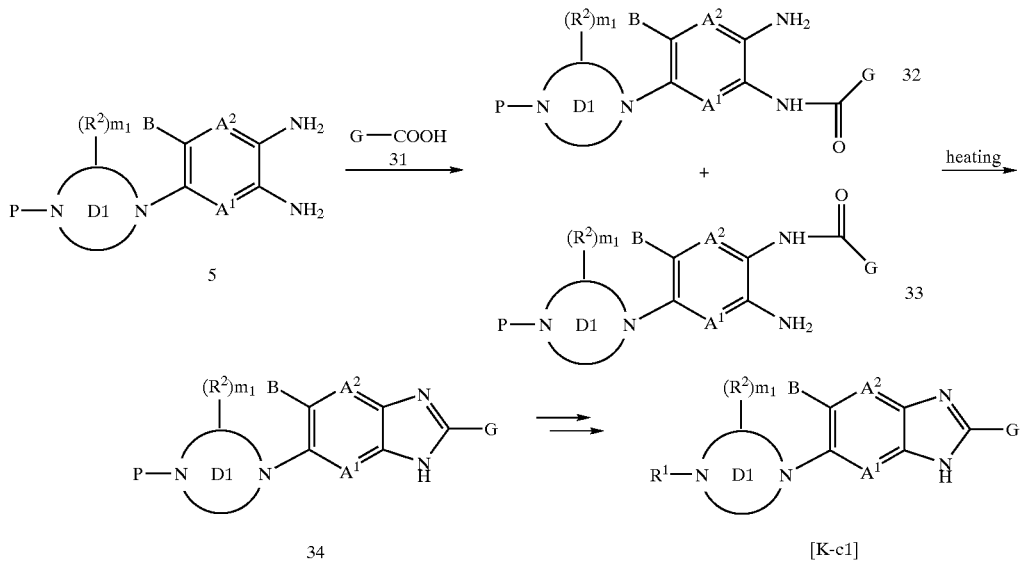

[in which $A^1$, $A^2$, B, G, $R^1$, $R^2$, m1, P and D1 ring are same to those as earlier defined].

Step 6-1: Reaction from Compound 5 to Compound 32 and/or Compound 33

Through amidation of compound 5 with a carboxylic acid 31, compound 32 and/or compound 33 (normally as their mixture) are obtained. For the amidation, hitherto known methods of activating the carboxylic acid 31 and subjecting it to the reaction can be used. For example, a method of converting the carboxylic acid 31 to an acid chloride with a chlorinating agent such as thionyl chloride, oxalyl chloride, phosphorus oxychloride or the like and putting it to the reaction; a method of using a condensing agent such as 1,3-dicyclohexylcarbodiimide, 1-ethyl-3-(3'-dimethylaminopropyl)carbodiimide or the like; a method of condensing with concurrent use of a condensing agent such as 1,3-dicyclohexylcarbodiimide, 1-ethyl-3-(3'-dimethylaminopropyl)carbodiimide or the like and N-hydroxybenzotriazole; a method to form an acid anhydride mixture using isobutyl chloroformate, methyl chloroformate or the like; or a method of converting it to an active ester such as p-nitrophenyl ester, N-hydroxysuccinimide ester or the like, can be adopted (hereinafter those compounds are collectively referred to as "activated carboxylic acid 31").

The amidation of this reaction can be conducted in a solvent. The solvent to be used is preferably optionally selected according to the amidation method, for example, from ether-type solvents such as dioxane, tetrahydrofuran, diethyl ether and the like; aromatic hydrocarbons such as benzene, toluene, xylene, chlorobenzene and the like; pyridine; ethyl acetate; N,N-dimethylformamide, dimethylsulfoxide; and hydrogenated hydrocarbons such as dichloroethane, chloroform, dichloromethane, carbon tetrachloride and the like.

This reaction can be accelerated by optional addition of an alkali metal carbonate such as lithium carbonate, sodium carbonate, potassium carbonate or the like; an alkali metal hydrogencarbonate such as sodium hydrogencarbonate, potassium hydrogencarbonate or the like; or an organic base such as triethylamine, diisopropylethylamine, tri-n-butylamine, 1,5-diazabicyclo[4.3.0]-5-nonene, 1,8-diazabicyclo[5.4.0]-7-undecene, pyridine, N,N-dimethylaminopyridine or the like.

As the use rates of compound 5 and carboxylic acid 31, 0.2–1 mole, preferably 0.4–0.6 mole, of carboxylic acid 31 or activated carboxylic acid 31 is used per mole of compound 5.

Through reaction of compound 5 with carboxylic acid 31 or activated carboxylic acid 31 in a reaction solvent at reaction temperatures ranging 0–60° C., preferably 0–30° C., for about 30 minutes–24 hours, preferably 30 minutes–15 hours, compound 32 and/or compound 33 are obtained.

The compounds 32 and 33 which are obtained by the amidtion reaction can be applied to the next reaction without separation from each other.

Step 6-2: Reaction from Compound 32 and/or Compound 33 to Compound 34

By heating compound 32 and/or compound 33 in the presence or absence of an acid (preferably in the presence of an acid), compound 34 is obtained.

A reaction solvent may be used for this reaction, useful solvent including ether-type solvents such as diethyl ether, tetrahydrofuran, 1,4-dioxane and the like, aromatic hydrocarbons such as benzene, toluene, xylene and the like; N,N'-dimethylformamide, dimethylsulfoxide; and halogen-containing solvents such as dichloroethane, chloroform, carbon tetrachloride and the like.

As the useful acid, conc. hydrochloric acid, acetic acid, trifluoroacetic acid and the like are exemplified. The use rate of such an acid is 10–500 wt parts, preferably 10–100 wt parts, per 100 wt parts of compound 32 and compound 33 as combined.

Heating is conducted at 50–150° C., preferably 80–100° C., and the reaction terminates normally in 2–50 hours.

It is also possible in the production process 6 to conduct the step 6-1 using compound 4 as the starting material to obtain compound 35.

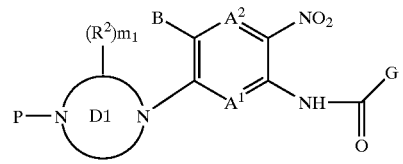

In this case the intended compound 34 can be obtained by hydrogenating and reducing the nitro group of compound 35 in the manner following the step 1-3 and successively conducting the step 6-2.

Thus obtained compound 34 can be converted to an object compound, by successively introducing the substituent $R^1$ thereinto, following the steps 1-6, 1-7 and 1-8.

Whereas, by conducting the reactions of Production process 6 using compound 12 or compound 22 in place of compound 5, a compound represented by a general formula [K-c2]

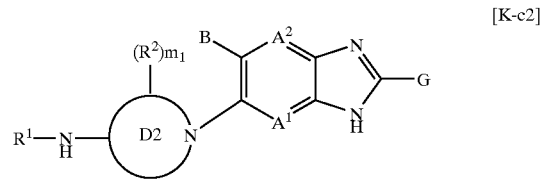

[K-c2]

[in which $A^1$, $A^2$, B, G, $R^1$, $R^2$, m1 and D3 ring are same to those as earlier defined], or a compound represented by the following formula

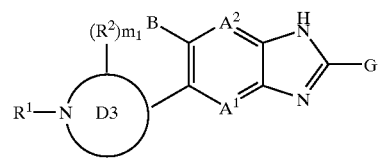

[in which $A^1$, $A^2$, B, G, $R^1$, $R^2$, m1 and D3 ring are same to those as earlier defined] can be obtained respectively.

Carboxylic acid 31 which is used in Production process 6 is a carboxylic acid in which a carboxyl group binds to the substituent G. Specifically, pivalic acid, cyclohexanecarboxylic acid, 4-tert-butylcyclohexanecarboxylic acid, 1-adamantanecarboxylic acid, 3-ethylpentanecarboxylic acid, 4-ethylhexanecarboxylic acid, 2-ethylbutanecarboxylic acid and the like can be exemplified as those on the market; and 2-(3-methoxy-1,3-dimethylbutoxy)acetic acid, 6-methoxy-4,6-dimethylheptanecarboxylic acid, 5-methoxy-5-methylhexanecarboxylic acid, 6-methoxy-6-methylheptanecarboxylic acid, 2-(1-ethylpropoxy)acetic acid, 2-(3-methoxy-3-methylbutoxy)acetic acid, 5-methoxy-3,5-dimethylhexanecarboxylic acid and the like can be exemplified as novel substances. As for those novel carboxylic acids 31 which are used in the present invention, their production methods are described in later-appearing Examples.

Production Process 7

The step 1-5 in Production process 1 may be replaced with the following method to prepare compound 7'.

Production Process 7

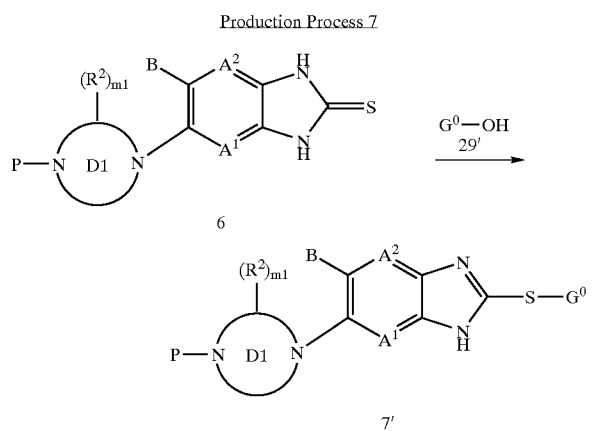

[in which $A^1$, $A^2$, B, $R^2$, m1, P and D1 ring are same to those as earlier defined: $G^0$ represents a group in which the substituent G is a primary carbon or a secondary carbon].

Step 7-1: Reaction from Compound 6 to Compound 7'

Through a comdensation reaction of compound 6 with compound 29' in a reaction solvent and in the presence of dialkyl azodicarboxylate and an organophosphorus compound such as triarylphosphine or trialkylphosphine or the like, compound 7' is obtained.

As dialkyl azodicarboxylate, dimethyl azodicarboxylate, diethyl azodicarboxylate, diisopropyl azodicarboxylate, di-t-butyl azodicarboxylate and the like are exemplified, and as triarylphosphine, triphenylphosphine, tritolylphosphine and the like can be exemplified. As trialkylphosphine, triethylphosphine, tributylphosphine, trioctylphosphine and the like are exemplified. In particular, the combination of diisopropyl azodicarboxylate or diethyl azodicarboxylate with triphenylphosphine are recommended.

As the molar ratio in the reaction of compound 6 with compound 29', 1–3 moles, preferably 1–1.5 moles, of compound 29' is used per mole of compound 6.

As the use rates of dialkyl azodicarboxylate and the organophosphorus compound such as triarylphosphine or trialkylphosphine, 1–3 moles, preferably 1–1.5 moles, of dialkyl azodicarboxylate, and 1–3 moles, preferably 1–1.5 moles, of the organophosphorus compound are used per mole of compound 6.

As the reaction solvent, halogenated carbons such as methylene chloride, chloroform, dichloroethane, carbon tetrachloride and the like; aliphatic hydrocarbons such as n-heptane, n-hexane and the like; aromatic hydrocarbons such as benzene, toluene, xylene and the like; ethers such as diethyl ether, tetrahydrofuran, 1,4-dioxane, ethylene glycol dimethyl ether and the like; esters such as methyl acetate, ethyl acetate and the like, and aprotic solvents such as N,N-dimethylformamide, dimethylsulfoxide and the like are exemplified.

As the reaction temperature, 0–100° C., preferably 0–50° C. are exemplified, and the reaction terminates normally in 2–24 hours.

Thus obtained compound 7' can be converted to a compound represented by a general formula [I-1'], by successively conducting the step 1-6 and step 1-7.

Compound 6', which is obtained by conducting Production process 1 using compound 2' in place of compound 2, can also provide the object product, after being subjected to the step 7-1. This production route is illustrated below.

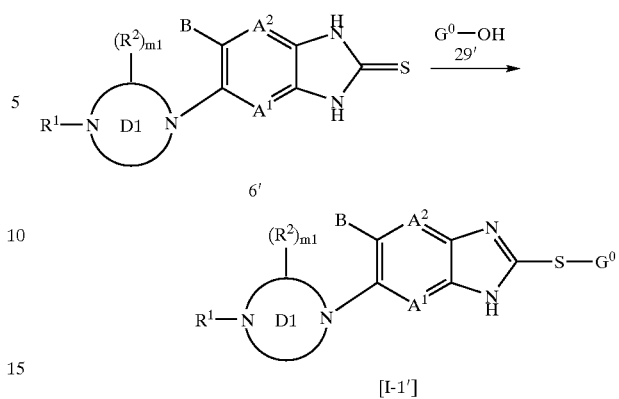

As the compound 29', those available in the market such as cyclohexyl methanol, 3-hydroxypentane, cyclopentanol, isopropanol, 3-methoxy-3-methyl-1-butanol, 5-methyl-1-hexanol, 1,3,3-trimethyl-1-butanol, 3-methoxy-1,3-dimethyl-1-butanol, 2-methoxy-2-methyl-1-propanol, 3-methoxy-1-butanol, tetrahydro-4H-pyran-4-ol, 3-methoxy-1-propanol, 3-azido-3-methyl-1-butanol, 3-hydroxy-2,3-dimethyl-1-butanol, 1-ethyl-3-hydroxy-3-methyl-1-butanol, 2-ethyl-2-hydroxy-1-butanol, tetrahydro-4H-pyran-4-ylmethanol, 3-tetrahydro-2H-pyran-4-yl-1-propanol, 2-(diisopropylamino)-1-ethanol, 2-(1-hydroxycyclohexyl)-1-ethanol, 2-(1-hydroxycyclopentyl)-1-ethanol, tetrahydro-3-furanylmethanol, 2,2-dimethyltetrahydro-4H-pyran-4-ol, 2-ethyl-3-hydroxy-3-methyl-1-butanol, 1,4-dioxaspiro[4,5]decan-8-ol, 1-methyl-3-hydroxypyrrolidine, 3-ethyl-3-hydroxy-1-pentanol, 1-(methoxymethyl)-1-propanol, 8-oxabicyclo[3.2.1]octan-3-ol, 4-[(ethoxycarbonyl)amino]cyclohexanol, methyl 3-hydroxy-tetrahydro-1(2H)-pyridinecarboxylate, 1,3-dimethoxy-2-propanol, 4-hydroxy-1-methylpiperidine, 1,3-diethoxy-2-propanol, ethyl 4-hydroxycyclohexanecarboxylate, ethyl 4-hydroxy-1-piperidinecarboxylate, isomannide, 3-hydroxy-1-methylpiperidine, methyl 3-hydroxy-1-pyrrolidinecarboxylate and 3-hydroxytetrahydrofuran are exemplified.

Production Example 8

Compound 7″ can also be prepared by the following method, instead of the step 1-5 in Production process 1.

Production Process 8

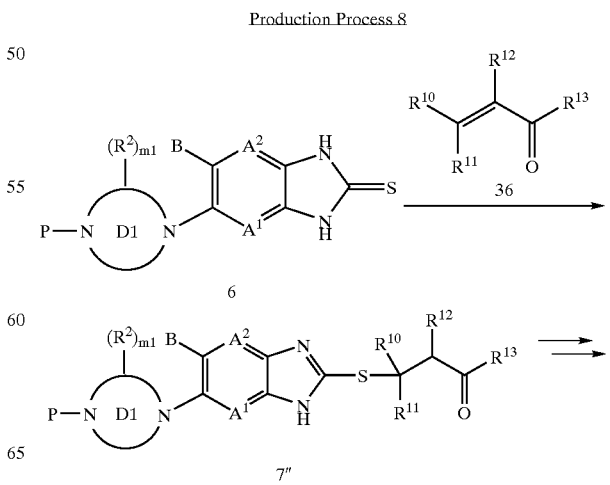

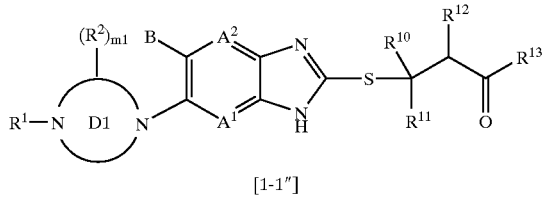

[1-1″]

in which $A^1$, $A^2$, B, $R^1$, $R^2$, m1, P and D1 ring are same to those as earlier defined; $R^{10}$ and $R^{11}$ are same or different and stand for hydrogen, methyl or ethyl; $R^{12}$ and $R^{13}$ are same or different and stand for hydrogen or $C_1$–$C_6$ lower alkyl; or $R^{10}$ and $R^{13}$ may together form a $C_5$–$C_6$ cycloalkane in combination with the carbon atoms to which they bind.

Compound 36 is converted to a compound of the formula G-1 in which x1=1, $R^{3a}$ and $R^{3b}$ are $R^{10}$ and $R^{11}$, respectively, $R^4$ is H, $R^5$ is $R^{12}$ and $R^6$ is an alkylcarbonyl (the alkyl group corresponding to $R^{13}$), by Michael addition to the sulfur atom of compound 6.

Step 8-1: Reaction from Compound 6 to Compound 7″

Through an addition reaction of compound 6 and compound 36 in a reaction solvent, in the presence of an acid catalyst, compound 7″ is obtained.

As the acid catalyst, aluminium chloride, Lewis acids such as BF3-OET$_2$ and the like and mineral acids such as hydrochloric acid, sulfuric acid, nitric acid and the like are exemplified, hydrochloric acid being preferred.

As the reaction solvent, halogenated carbons such as methylene chloride, chloroform, dichloroethane, carbon tetrachloride and the like; aliphatic hydrocarbons such as n-heptane, n-hexane and the like; aromatic hydrocarbons such as benzene, toluene, xylene and the like; alcohols such as methanol, ethanol, isopropyl alsohol, cyclohexanol and the like; ethers such as diethyl ether, tetrahydrofuran, 1,4-dioxane, ethylene glycol dimethyl ether and the like; and aprotic solvents such as N,N-dimethylformamide, dimethylsulfoxide and the like are exemplified.

As the use rates of compound 6 and compound 36, 1–3 moles, preferably 1–2 moles, of compound 36 is used per mole of compound 6.

As the use rate of the acid catalyst, 1–500 wt parts, preferably 1–200 wt parts of the acid catalyst is used per 100 wt parts of compound 6. As the reaction temperature, 0–100° C., preferably 0–30° C., are exemplified, and the reaction normally terminates in 2–24 hours.

Thus obtained compound 7″ can be converted to a compound represented by a general formula [I-1″], by successively going through the steps 1-6 and 1-7.

It is also possible to convert compound 7″ to its derivatives, by suitably reducing or alkylating its side chain substituent group.

By conducting the step 8-1 using compound 6′ as the starting material, which is obtained from Production process 1 using compound 2′, a compound represented by the general formula [I-1″] can be obtained. This production route is illustrated below.

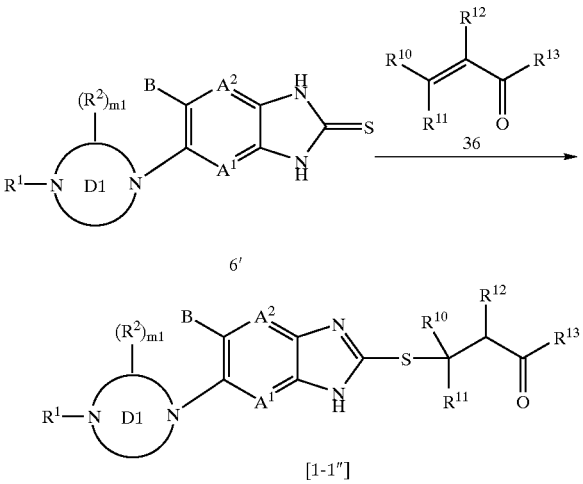

[1-1″]

As the compound 36 in Production process 8, as those available in the market, 3-methyl-2-cyclopenten-1-one, 3-methyl-2-cyclohexen-1-one, mesityl oxide, 3-methyl-2-butenal and the like are exemplified.

Production Process 9

Of those compounds 7, the compounds represented by a formula (X-1) in which G is quaternary carbon can be prepared by the following method.

Production Process 9

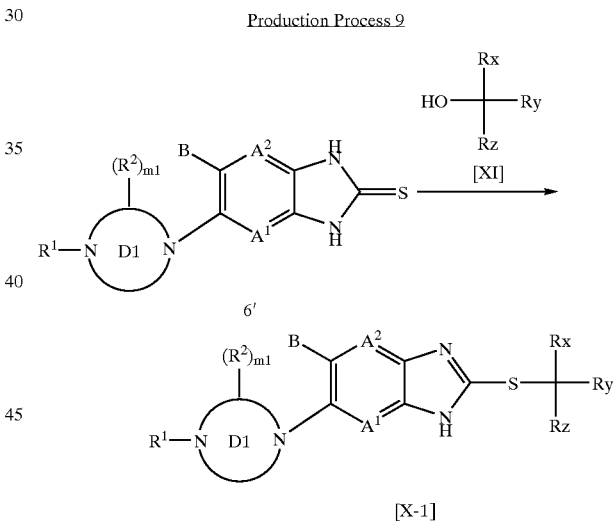

[X-1]

Step 9-1: Reaction from Compound 6′ to a Compound Represented by the General Formula [X-1]

Condensing compound 6′ with a compound represented by the general formula [XI] which is a tertiary alcohol in an acid solvent, a compound represented by the general formula [X-1] can be obtained. As the use rates of compound 6′ and the compound of the general formula [XI], 1–4 equivalents, preferably 1–2 equivalents, of the compound of the general formula [XI] per equivalent of compound 6 are exemplified. As the acid catalyst, trifluoroacetic acid, conc. hydrochloric acid, sulfuric acid, bistrifluoromethanesulfonimide and the like are exemplified, preferably trifluoroacetic acid and conc. hydrochloric acid being recommended. This reaction may be conducted in the presence of a reaction solvent such as methylene chloride, benzene, toluene, xylene or the like. As the reaction temperature, 10–100° C. are exemplified and preferably 10–50° C. are recommended.

As the reaction time, normally 1–100 hours are exemplified and preferably 1–24 hours are recommended. When this reaction is conducted using compound 6, 13 or 22 in place of compound 6', followed by Production process 1, 2 or 3, respectively, each corresponding compound of the general formula (X-1), (X-2) or (X-3) can be obtained.

As examples of the compounds of the general formula [XI] used in Production process 9, those on the market such as tert-butanol, tert-amyl alcohol, 1-methylcyclopentanol, 1-methylcyclohexanol and the like, and those known from literature such as 1-methylcyclobutanol, N-methoxycarbonyl-1-methylpiperidinol, N-ethoxycarbonyl-1-methylpiperidinol, 4-methoxycarbonylamino-1-methylcyclohexanol, 4-ethoxycarbonylamino-1-methylcyclohexanol and the like, are exemplified.

Production Process 10

Production process 10 is an effective production process where E in [D-3] in the general formula [I] is N(R) or O.

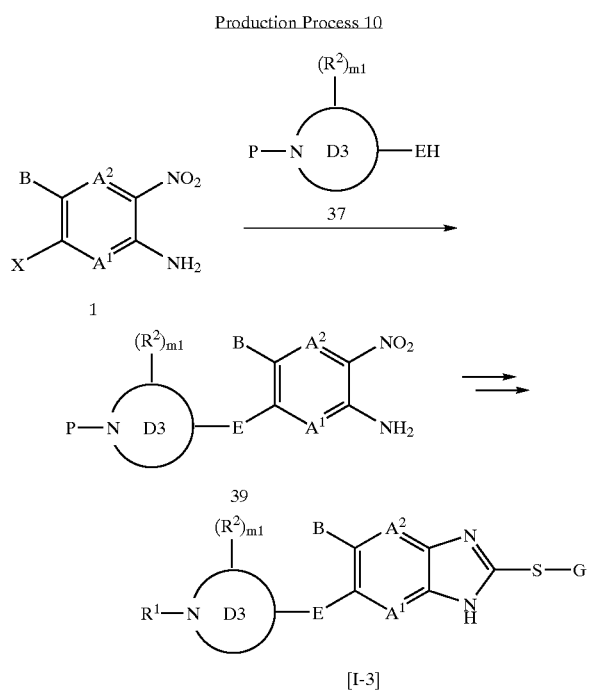

[I-3]

[in which $A^1$, $A^2$, B, G, X, P, $R^1$, $R^2$, m1 and D3 ring are same to those as earlier defined].

Step 10-1: Reaction from Compound 1 to Compound 39

Compound 1 and compound 37 are reacted following the step 1-1 to provide compound 39. Reaction conditions and molar ratio for the reaction as described in the step 1-1 are applicable. It is also possible to conduct the reactions of the step 1 using the compound 39, to lead it to a compound of the general formula [1-3].

Furthermore, by using compound 38 in place of compound 37

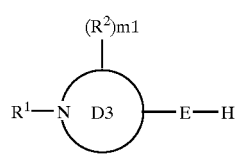

38 and conducting the reactions following the steps 1-1, 1-3, 1-4 and 1-5, a compound of the general formula [1-3] can be obtained.

As compound 37, 3-aminoazetidine, 3-minopyrrolidine, 3-aminopiperidine, 4-aminopiperidine, 3-aminohexamethyleneimine, 4-aminohexamethyleneimine, 3-aminoheptaethyleneimine, 4-aminoheptaethyleneimine and the like can be exemplified, and preferably 2-aminopyrrolidine, 3-aminopyrrolidine, 3-aminopiperidine and 4-aminopiperidine are recommended. These compounds as available in the market can be used.

Also as compound 38, those marketed can be used or it can be easily prepared from compound 37. That is, by protecting the free amino group in compound 37 with a protective group P', deprotecting protective group P, and subjecting the resulting amine to the reactions following the steps 1-7 and 1-8, the object compound can be prepared. Protective group P' is a protective group which can be deprotected by a mechanism differing from that for deprotection of protective group P. For example, when P is tert-butyloxycarbonyl group, benzyloxycarbonyl group is exemplified as P', where P is removable with trifluoroacetic acid or the like, P' is removed by catalytic reduction.

Those various intermediates in the syntheses (e.g., compounds 1 to 39) obtained through Production processes 1–10 or combinations thereof, or those compounds of the present invention can be given improved purity by purifying with known purification means. As the purification methods, column chromatography using an adsorbing resin such as silica gel or alumina, purification using ion-exchange resin, liquid chromatography, solvent extraction or recrystallization, reprecipitation and the like, and their combinations are exemplified.

Among the compounds of the present invention, there also exist the derivatives having asymmetric carbon atoms in the substituent G and/or substituent D. Such compounds may be used in the form of racemic mixture, or each of the isomers may be isolated by optical resolution by such means as chromatography with a column packed with an optically active filler.

The compounds of the present invention can be converted to pharmacologically acceptable salts by the means known per se. Conversely, conversion from salts to free compounds can also be easily conducted.

Pharmacological Activity of Compounds of the Present Invention

Utility of compounds of the invention as medicines is verified, for example, by the following pharmacological test examples.

Pharmacological Activity of Compounds of the Present Invention 1 (Nociceptin Receptor Binding Inhibition Assay)

cDNA which codes a human nociceptin receptor gene (accession No.X77130) was cloned into an expression vector pCR3 (Invitrogen) to prepare pCR3/ORL1. Next, pCR3/ORL1 was transfected in CHO cells using a transfectam (Nippongene) following the directions in the manual appended to the reagent to obtain a stable expression strain (CHO/ORL1 cells) having resistance against 1 mg/ml concentration G418. A membrane fraction (a precipitate fraction obtained by an hour's centrifuge at 100,000 G of the supernatant resulting from 15 minutes' certrifuge at 10,000 G) was prepared from this stable expression strain to carry out a receptor binding assay.

Eleven (11) μg of the membrane, 50 pM [$^{125}$I] Tyr$^{14}$-Nociceptin (Amersham Pharmacia Biotech) (specific activity 2000 Ci/mmol), 1 mg Wheatgerm agglutinin SPA beads (PVT based; Amersham Pharmacia Biotech) and a test compound were suspended in an NC buffer (50 mM Hepes, 10 mM sodium chloride, 1 mM magnesium chloride, 2.5 mM calcium chloride, 0.1% BSA, 0.025% bacitracin, pH 7.4) and incubated at 37° C. for 60 minutes, and then the radioactivity was determined with Top Count (Packard). The binding activity to the nociceptin receptor was expressed by the 50% inhibition concentration ($IC_{50}$ value) which was calculated from the inhibition activity to binding to ORL1 receptor of [$^{125}$I] Tyr$^{14}$-Nociceptin by the compounds of the present invention at various concentrations. The results were as shown in Table 1. From the results it can be understood that the compounds of the invention inhibit nociceptin action, with high affinity to the nociceptin receptor.

TABLE 1

Nociceptin receptor binding inhibition action

| Compound | $IC_{50}$ value (nM) |
| --- | --- |
| Example 1 | 2.1 |
| Example 26 | 1.3 |
| Example 89 | 6.5 |
| Example 101 | 9.2 |
| Example 102 | 3.5 |
| Example 142 | 0.95 |
| Referential Example 1 | 7.0 |
| Referential Example 13 | 430 |

Pharmacological Test Example 2 (Antagonism Against Nociceptin-elicited G Protein Activation)

CHO cells which stably expressed a nociceptin receptor ORL1 were used to investigate the action of tested compounds against nociceptin-elicited G protein activation. A membrane prepared from the CHO/ORL1 cell, 50 nM nociceptin, 200 pM GTPγ[$^{35}$S](NEN), 1.5 mg Wheatgerm agglutinin SPA beads (PVT based; Amersham Pharmacia Biotech) and each of the tested compounds were mixed in a GDP buffer (20 mM Hepes, 100 mM sodium chloride, 10 mM magnesium chloride, 1 mM EDTA, 5 μM GDP, pH 7.4) and incubated at 25° C. for 150 minutes, and then the radioactivity was determined. The antagonism against nociceptin-elicited G protein activation was shown by the 50% inhibition concentration ($IC_{50}$ value) which was calculated from GTP γ [$^{35}$S] binding inhibition activity of the compounds of the present invention at various concentrations. The results were as shown in Table 2. From the result it can be understood that the compounds of the invention have antagonism against nociceptin-elicited G protein activation via ORL1 receptor.

TABLE 2

Antagonism against nociceptin-elicited G protein activation

| Compound | $IC_{50}$ value (nM) |
| --- | --- |
| Example 1 | 9.1 |
| Example 26 | 5.3 |

TABLE 2-continued

Antagonism against nociceptin-elicited G protein activation

| Compound | $IC_{50}$ value (nM) |
| --- | --- |
| Example 89 | 6.8 |
| Example 101 | 8.0 |
| Example 142 | 0.57 |
| Referential Example 1 | 180 |
| Referential Example 13 | — |

The above indicates that the compounds of the invention act as nociceptin receptor antagonists.

Hence the compounds of the invention are useful as an analgesic against diseases accompanied with pain such as cancerous pain, postoperative pain, migraine, gout, chronic rheumatism, chronic pain and neuralgia, a reliever against tolerance to narcotic analgesic represented by morphine, a reliever against dependence on narcotic analgesic represented by morphine, an analgesic enhancer, an antiobestic, a drug for ameliorating brain function, prophylactic and treating agents for Alzheimer's disease, a prophylactic agent for dementia, an anti-dementia drug, a remedy for schizophrenia, a drug for treating neurodegenerative diseases represented by Parkinsonism and chorea, an antidepressant, a remedy for diabetes insipidus, a remedy for polyuria, or a remedy for hypotension.

Also by administering compounds of the invention to patients suffering from various diseases or symptoms associated with nociceptin receptors (e.g., obesity, Alzheimer's disease, dementia, schizophrenia, neurodegenerative diseases represented by Parkinsonism and chorea, depression, diabetes insipidus, polyuria or hypotension), these diseases or symptoms can be treated and also Alzheimer's disease and dementia can be prevented.

Furthermore, administration of compounds of the invention to said patients can serve as an analgesic method, remedial method against tolerance to narcotic analgesic, remedial method against dependence on narcotic analgesic, method for enhancing analgesic action and a method for ameliorating brain function.

Medical Preparations Containing Compounds of the Present Invention

The compounds of the present invention can be administered orally or parenterally and, as formulated into preparation forms suitable for such administration routes, can be used as an analgesic, a reliever against tolerance to narcotic analgesic represented by morphine, a reliever against dependence on narcotic analgesic represented by morphine, an analgesic enhancer, an antiobestic, a drug for ameliorating brain function, prophylactic and treating agents for Alzheimer's disease, a prophylactic agent for dementia, an anti-dementia drug, a remedy for schizophrenia, a drug for treating neurodegenerative diseases represented by Parkinsonism and chorea, an antidepressant, a remedy for diabetes insipidus, a remedy for polyuria, or a remedy for hypotension.

In clinically using the compounds of the present invention, pharmaceutically acceptable adjuvants are added to formulate medicinal compositions in accordance with individual forms of their administration. So formed preparations then can be administered. As the adjuvants, various additives customarily used in the field of medical preparations can be used, examples of which including gelatin, lactose, glucose, starch, corn starch, partial alpha-starch, crystalline cellulose, methyl cellulose, ethyl cellulose, hydroxypropyl cellulose, hydroxypropylmethyl cellulose, carboxymethyl cellulose, citric acid, trisodium citrate, sorbitol, sorbitan fatty acid ester, polysorbate, sucrose fatty acid ester, polyoxyethylene fatty acid ester, stearic acid, calcium stearate, magnesium stearate, light silicic anhydride, talc, titanium dioxide, magnesium aluminate methasilicate, calcium carbonate, anhydrous calcium phosphate, microcrystalline wax, white petrolatum, hydrous lanolin, vaseline, vegetable oil, hardened castor oil, cetyl alcohol, stearyl alcohol, benzyl alcohol, acacia, propylene glycol, polyvinyl alcohol, polyvinyl pyrrolidone, polyalkylene glycols such as polyethylene glycol or polypropylene glycol, cyclodextrin or hydroxypropyl cyclodextrin, ethanol and water.

As the forms of preparations formulated as pharmaceutical compositions, solid preparations such as tablets, capsules, granules, powders and suppositories; liquid preparations such as syrups, elixirs and injections; and the like can be named. These preparations may be formulated according to conventional techniques well-known in the field of pharmaceutics. Liquid preparations may be in a form which is dissolved or suspended in water or other suitable medium prior to use. In particular, injections may be in the form of a solution or suspension in physiological saline solution or a glucose solution, to which a buffer agent, a preservative or the like may be added.

These pharmaceutical compositions can cntain a compound or compounds of the present invention at the ratios of 0.1–99.5 wt %, preferably 1.0–60 wt %, to the total composition, and also 0.5–99.9 wt %, preferably 40–99.0 wt %, of pharmaceutically acceptable adjuvants.

Where the compounds of the present invention are used as an analgesic, a reliever against tolerance to narcotic analgesic represented by morphine, a reliever against dependence on narcotic analgesic represented by morphine, an analgesic enhancer, an antiobestic, a drug for ameliorating brain function, prophylactic and treating agents for Alzheimer's disease, a prophylactic agent for dementia, an antidementia drug, a remedy for schizophrenia, a drug for treating neurodegenerative diseases represented by Parkinsonism and chorea, an antidepressant, a remedy for diabetes insipidus, a remedy for polyuria, or a remedy for hypotension, their administration dosage or frequency differ depending on gender, age, body weight, degree of symptoms of individual patient and kind and extent of intended therapeutic effect. Whereas, so long as the dosage is of an amount sufficient for effectively expressing nociceptin receptor antagonism, it is subject to no specific limitation. Generally for oral administration, it is preferred to dispence 0.01–20 mg/kg per adult per day in 1—a few times; and for parenteral administration, 0.002–10 mg/kg, in 1—a few times.

Also in using the compounds of the present invention for pain-killing, relieving tolerance to narcotic analgesic, relieving dependence on narcotic analgesic, enhancing analgesic action or for ameliorating brain function; or for treating or preventing obesity, Alzheimer's disease, dementia, schizophrenia, neurodegenerative diseases represented by Parkinsonism and chorea, depression, diabetes insipidus, polyuria or hypotension, above pharmaceutical compositions can be utilized, their dosages being suitably determined referring to the above-described dosages of the compounds.

BEST MODES FOR CARRYING OUT THE INVENTION

Hereinafter the present invention is explained more specifically, referring to working Examples, it being understood that the invention is not limited thereto.

In the following, the mass spectra were measured by Fast Atom Bombardment (FAB) method using JMS SX-102A (Nihon Denshi), Atmospheric Pressure chemical Ionization (APcI) method using Quattro II (MicroMass) or Electrospray Ionization (ESI) method.

PRODUCTION EXAMPLE 1

Production of 5-(4-tert-butoxycarbonylpiperazin-1-yl)-6-chloro-1,3-dihydro-2H-benzimidazol-2-thione 1) 4-Chloro-2-nitro-5-(piperazin-1-yl)aniline Into a solution of 20.02 g of 4,5-dichloro-2-nitroaniline and 8.70 g of piperazine in 100 ml of cyclohexanol, 12.80 g of sodium carbonate was added and stirred at 150° C. for 14 hours. Cooling the reaction liquid to room temperature, water was added and the system was extracted with chloroform. The chloroform layer was dried on anhydrous magnesium sulfate and the solvent was distilled off. Thus obtained residue was washed with diisopropyl ether to provide 21.07 g of 4-chloro-2-nitro-5-(piperazin-1-yl) aniline as a yellow powder.

1HNMR(200 MHz, CDCl$_3$)δ:1.80(1H, brs),2.94–3.20 (8H, m), 6.14(2H, brs),6.20(1H, s),8.12(1H, s)

2) 5-(4-Tert-butoxycarbonylpiperazin-1-yl)-4-chloro-2-nitroaniline

In nitrogen atmosphere, 20.70 ml of di-tert-butyldicarbonate was added to a suspension of 21.00 g of the compound as obtained in 1) above in 500 ml of chloroform and stirred for 0.5 hour at room temperature. The reaction liquid was successively washed with water and saturated brine by the order stated, dried on anhydrous magnesium sulfate and the solvent was distilled off. Thus obtained residue was washed with diisopropyl ether to provide 28.00 g of 5-(4-tert-butoxycarbonylpiperazin-1-yl)-4-chloro-2-nitroaniline as a yellow powder.

1HNMR(200 MHz, CDCl$_3$)δ:1.48(9H, s),3.03–3.13(4H, m), 3.56–3.64(4H, m),6.14(2H, brs),6.21(1H, s),8.15(1H, s)

3) 2-Amino-5-(4-tert-butoxycarbonylpiperazin-1-yl)-4-chloroaniline

To a suspension of 27.86 g of the compound as obtained in 2) above, 20.90 g of ammonium chloride and 37.10 g of iron in 100 ml of tetrahydrofuran, 50 ml of methanol and 50 ml of water were added, and stirred at 100° C. for 2.7 hours. After cooling the reaction liquid to room temperature, saturated aqueous sodium hydrogencarbonate solution was added, and the insoluble matter was filtered off with Celite. The filtrate was extracted with ethyl acetate, and the ethyl acetate layer was washed with saturated brine and dried on anhydrous magnesium sulfate. Distilling the solvent off, 25.50 g of 2-amino-5-(4-tert-butoxycarbonylpiperazin-1-yl)-4-chloroalinine was obtained as a pale yellow, oily substance.

4) 5-(4-Tert-butoxycarbonylpiperazin-1-yl)-6-chloro-1,3-dihydro-2H-benzimidazol-2-thione To a solution obtained by dissolving 25.50 g of the compound as obtained in 3) above in 400 ml of ethanol, 195 ml of 1M aqueous sodium hydroxide solution and 71 ml of carbon disulfide were added and stirred at 80° C. for an hour. The reaction liquid was cooled to room temperature and water was added. Whereupon precipitated yellow solid was recoverd by filtration, and so obtained crystalline product was washed with water and hexane. Drying the same, 19.76 g of the title compound was obtained as a yellow solid.

1HNMR(300 MHz, CDCl$_3$)δ:1.49(9H, s),2.93–2.98(4H, m), 3.58–3.64(4H, m),6.90(1H, s),7.37(1H, s)

EXAMPLE 1

Production of 5-chloro-2-[(1-ethylpropyl)sulfanyl]-6-(piperazin-1-yl) benzimidazole dihydrochloride In nitrogen atmosphere, 2.21 g of potassium carbonate and 1.33 ml of 3-bromopentane were successively added to a solution of 3.94 g of the compound as obtained in Production Example 1 in 50 ml of dimethylformamide, followed by 17.5 hours' stirring at 80° C. The reaction liquid was cooled to room temperature, and to which water was added, followed by extraction with ethyl acetate. The ethyl acetate layer was washed with saturated brine, dried on anhydrous magnesium sulfate and the solvent was distilled off under reduced pressure. The residue was separated and purified on silica gel column chromatography [ethyl acetate/hexane=1/4], to provide 4.11 g of 2-{[5-chloro-6-(4-tert-butoxycarbonylpiperazin-1-yl)-1H-benzimidazol-2-yl]sulfanyl}-2-ethylpropane as a pale yellow solid. To 4.11 g of this compound 10% hydrogen chloride in methanol solution (20 ml) was added, and stirred for 14 hours at room temperature. Then adding diisopropyl ether, precipitated solid was recovered by filtration and dried to provide 3.71 g of the title compound as a white solid.

1HNMR(300 MHz, CD$_3$OD)δ:1.08(6H, t, J=7.4 Hz), 1.70–1.98(4H, m),3.26–3.50(8H, m),3.78–3.91(1H, m), 7.51(1H, s),7.81(1H, s)

ESI-MS Found:m/z 339.1[M+H]$^+$

EXAMPLE 2

Production of 2-[(1-ethylproyl)sulfanyl]-5-fluoro-6-(piperazin-1-yl)benzimidazole dihydrochloride Reactions were conducted following Example 1 except that 5-(4-tert-butoxycarbonylpiperazin-1-yl)-6-fluoro-1,3-dihydro-2H-benzimidazol-2-thione (which was prepared by the method as described in U.S. Pat. No. 6,051,570) was used in place of the 5-(4-tert-butoxycarbonyl-piperazin-1-yl)-6-chloro-1,3-dihydro-2H-benzimidazol-2-thione as obtained in Production Example 1, to provide the title compound as a colorless powder.

1HNMR(300 MHz, CD$_3$OD)δ:1.08(6H, t, J=7.5 Hz), 1.71–1.92(4H, m),3.36–3.42(8H, m),3.82–3.90(1H, m), 7.43(1H, d, J=7.0 Hz),7.54(1H, d, J=10.9 Hz)

ESI-MS Found:m/z 323.0[M+H]$^+$

EXAMPLE 3

Production of 2-[(cyclohexylmethyl)sulfanyl]-5-fluoro-6-(piperazin-1-yl)-benzimidazole Reaction similar to Example 2 were conducted using bromomethylcyclohexane in place of 3-bromopentane, to provide the title compound as a colorless amorphous substance.

1HNMR(300 MHz, CDCl$_3$)δ:1.15–1.75(11H, m), 1.82–1.92(2H, m), 3.01–3.15(8H, m),7.10(1H, d, J=7.8 Hz), 7.22(1H, d, J=11.7 Hz)

ESI-MS Found:m/z 349[M+H]$^+$

EXAMPLE 4

Production of 6-(1,4-diazabicyclo[3.2.1]octan-4-yl)-2-[(1-ethylpropyl)sulfanyl]-5-fluorobenzimidazole dihydrochloride Reactions were conducted following the steps of Production Example 1 except that 4,5-difluoro-2-nitroaniline was used in place of 4,5-dichloro-2-nitroaniline, 1,4-diazabicyclo[3.2.1]octane was used in place of piperazine and that the butyloxycarbonylation step 2) of Production Example 1 was not conducted, to provide 6-fluoro-5-(1,4-diazabicyclo[3.2.1]octan-4-yl)-1,3-dihydro-2H-benzimidazol-2-thione. Using this compound, the reactions were conducted similarly to Example 1 to provide the title compound as a colorless amorphous substance.

1HNMR(300 MHz, CD$_3$OD)δ:1.08(6H, t, J=7.3 Hz), 1.70–1.94(4H, m),2.20–2.31(2H, m),3.38–3.82(9H, m), 4.42–4.50(1H, m),7.35(1H, d, J=7.1 Hz),7.53(1H, d, J=11.2 Hz)

ESI-MS Found:m/z 349.2[M+H]$^+$

EXAMPLE 5

Production of 5-cyano-2-[(1-ethylpropyl)sulfanyl]-6-(piperazin-1-yl) benzimidazole dihydrochloride Reactions were conducted following the steps of Production Example 1 using 4-cyano-5-fluoro-2-nitroaniline (which was prepared by the method as described in *J. Med. Chem.*, 1994, 37, 467–475) in place of 4,5-dichloro-2-nitroaniline, to provide 5-(4-tert-butoxycarbonylpiperazin-1-yl)-6-cyano-1,3-dihydro-2H-benzimidazol2-thione. Conducting the reaction similar to Example 1 using this compound, the title compound was obtained as a colorless solid.

1HNMR(300 MHz, CD$_3$OD)δ:1.09(6H, t, J=7.4 Hz), 1.79–1.98(4H, m),3.47–3.51(8H, m),3.98–4.03(1H, m), 7.59(1H, s),8.10(1H, s)

ESI-MS Found:m/z 330.0[M+H]$^+$

EXAMPLE 6

Production of 5-acetyl-2-[(1-ethylpropyl)sulfanyl]-6-(piperazin-1-yl)-benzimidazole dihydrochloride Reactions were conducted following the steps of Production Example 1 using 4-acetyl-5-fluoro-2-nitroaniline (which was prepared by the method as described in *J. Med. Chem.* 1994, 37, 467–475) in place of 4,5-dichloro-2-nitroaniline, to provide 6-acetyl-5-(4-tert-butoxycarbonylpiperazin-1-yl)-1,3-dihydro-2H-benzimidazol-2-thione. Conducting the reactions similar to Example 1 using this compound, the title compound was obtained as a yellow powder.

1HNMR(200 MHz, CD$_3$OD)δ:1.09(6H, t, J=7.3 Hz), 1.67–2.04(4H, m),2.68(3H, s),3.28–3.37(4H, m), 3.37–3.47 (4H, m),7.59(1H, s),7.80(1H, s)

ESI-MS Found:m/z 347.1[M+H]$^+$

EXAMPLE 7

Production of 6-(4-aminopiperidin-1-yl)-5-chloro-2-[(1-ethylpropyl)-sulfanyl]-benzimidazole dihydrochloride Reactions were conducted following the steps of Production Example 1 except that 4-(tert-butoxycarbonylamino) piperidine was used in place of piperazine and that the butyloxycarbonylation step 2) of Production Example 1 was not conducted, to provide 6-chloro-5-(4-tert-butoxycarbonylaminopiperidin-1-yl)-1,3-dihydro-2H-benzimidazol-2-thione. Using this compound, the reactions were conducted by the method similar to Example 1, to provide the title compound as a white amorphous substance.

1HNMR(300 MHz, CD$_3$OD)δ:1.08(6H, t, J=7.3 Hz), 1.69–2.00(6H, m),2.07–2.23(2H, m),2.80–2.94(2H, m), 3.20–3.54(3H, m),3.78–3.90(1H, m),7.45(1H, s),7.78(1H, s)

ESI-MS Found:m/z 353.1[M+H]$^+$

EXAMPLE 8

Production of 5-chloro-6-[(3R,5S)-3,5-dimethylpiperazin-1-yl]-2-[(1-ethylpropyl)sulfan] benzimidazole dihydrochloride Reactions were conducted following the steps of Production Example 1 except that cis-2,6-dimethylpiperazine was used in place of piperazine and that the butyloxycarbonylation step 2) of Production Example 1 was not conducted, to provide 5-chloro-6-[(3R,5S)-3,5-dimethylpiperazin-1-yl]-1,3-dihydro-2H-benzimidazol-2-thione. Using this compound, the reactions were conducted by the method similar to Example 1, to provide the title compound as a colorless oily substance.

1HNMR(300 MHz, CDCl$_3$)δ:1.10(6H, t, J=7.4 Hz), 1.14 (6H, d, J=6.3 Hz),1.66–1.88(4H, m),2.34–2.41(2H, m), 3.22–3.28(4H, m),3.75–3.83(1H, m),7.20–7.80(2H, br)

ESI-MS Found:m/z 367.2[M+H]$^+$

EXAMPLE 9

Production of 6-(3-aminopyrrolidin-1-yl)-5-chloro-2-[(1-ethylpropyl)-sulfanyl] benzimidazole dihydrochloride Reactions were conducted following the steps of Production Example 1 except that 3-(tert-butoxycarbonylamino)pyrrolidine was used in place of piperazine and that the butyloxycarbonylation step 2) of Production Example 1 was not conducted, to provide 5-[3-(tert-butoxycarbonylamino)pyrrolidin-1-yl]-6-chloro-1,3-dihydro-2H-benzimidazol-2-thione. Using this compound, the reactions were conducted by the method similar to Example 1, to provide the title compound as a colorless powder.

1HNMR(300 MHz, CD$_3$OD)δ:1.07(6H, t, J=7.3 Hz), 1.72–1.93(4H, m),2.09–2.15(1H, m),2.48–2.56(1H, m), 3.34–3.40(1H, m),3.54–3.60(1H, m),3.65–3.74(2H, m), 3.90–3.96(1H, m),4.01–4.05(1H, m),7.42(1H, s),7.77(1H, s)

ESI-MS Found:m/z 339.0[M+H]$^+$

EXAMPLE 10

Production of 5-chloro-2-[(1-ethylpropyl)sulfanyl]-6-[(pyrrolidin-3-yl)-amino] benzimidazole 1) 5-[(1-Benzylpyrrolidin-3-yl)amino]-6-chloro-2-[(1-ethylpropyl)-sulfanyl] benzimidazole Reactions were conducted following the steps of Production Example 1 except that 1-benzyl-3-aminopyrrolidine was used in place of piperazine and that the butyloxycarbonylation step 2) of Production Example 1 was not conducted, to provide 5-(1-benzylpyrrolidin-3-yl)amino-6-chloro-1,3-dihydro-2H-benzimidazol-2-thione. Using this compound, the reactions were conducted by the method similar to Example 1, to provide 5-(1-benzylpyrrolidin-3-yl)amino-6-chloro-2-[(1-ethylpropyl)sulfanyl] benzimidazole.

2) 5-Chloro-2-[(1-ethylpropyl)sulfanyl]-6-[(pyrrrolidin-3-yl)amino]-benzimidazole In nitrogen atmosphere, to a solution of 111 mg of the compound as obtained in 1) above in 5 ml of dichloroethane, 0.50 ml of 1-chloroethyl chloroformate was added, followed by 2.5 hours' stirring at 100° C. After cooling the reaction liquid to room temperature, the solvent was distilled off under reduced pressure. To the residue 5 ml of methanol was added, and the resulting solution was stirred at 80° C. for an hour. After cooling the reaction liquid to room temperature, the solvent was distilled off under reduced pressure. Further a saturated aqueous sodium hydrogencarbonate solution was added to the residue, followed by extraction with chloroform. The chloroform layer was dried on anhydrous sodium sulfate. After distilling the solvent off under reduced pressure, the residue was separated and purified on preparative thin-layer chromatography [Kieselgel™ 60F$_{254}$, Art 5744 (Merck); chloroform/methanol=5/1] to provide 55 mg of the title compound as a colorless solid.

1HNMR(300 MHz, CDCl$_3$)δ:0.99(6H, t, J=7.4 Hz), 1.22–1.29(1H, m),1.67–1.80(4H, m),2.18–2.30(1H, m), 2.95–3.06(1H, m),3.19–3.25(1H, m),3.63–3.73(2H, m), 3.89–3.94(1H, m),4.24–4.28(1H, m),6.60(1H, s),7.47(1H, s)

ESI-MS Found:m/z 339.0[M+H]$^+$

EXAMPLE 11

Production of 5-chloro-6-(1,4-diazepan-1-yl)-2-[(1-ethylpropyl)-sulfanyl] benzimidazole dihydrochloride Reactions were conducted following the steps of Production Example 1 except that 1,4-diazepane was used in place of piperazine, to provide 5-(4-tert-butoxycarbonyl-1,4-diazepan-1-yl)-6-chloro-1,3-dihydro-2H-benzimidazol-2-thione. Using this compound, the reactions were conducted by the method similar to Example 1, to provide the title compound as a colorless solid.

1HNMR(300 MHz, CD$_3$OD)δ:1.00–1.12(6H, m), 1.68–1.97(4H, m),2.18–2.33(2H, m),3.30–3.42(2H, m), 2.32–3.60(6H, m),3.90–4.02(1H, m),7.62(1H, s),7.82(1H, s)

ESI-MS Found:m/z 353.2[M+H]$^+$

EXAMPLE 12

Production of 6-(3-aminopiperidin-1-yl)-5-chloro-2-[(1-ethylpropyl)-sulfanyl] benzimidazole dihydrochloride Reactions were conducted following the steps of Production Example 1 except that 3-aminopiperidine was used in place of piperazine, to provide 5-[3-(tert-butoxycarbonylamino)piperidin-1-yl]-6-chloro-1,3-dihydro-2H-benzimidazole-2-thione. Using this compound, the reactions were conducted by the method similar to Example 1, to provide the title compound as a colorless solid.

1HNMR(300 MHz, CD$_3$OD)δ:1.07(6H, t, J=7.4 Hz), 1.67–1.95(6H, m),1.95–2.14(2H, m),2.93–3.23(3H, m), 3.30–3.41(1H, m),3.48–3.60(1H, m),3.88(1H, quinted, J=6.3 Hz), 7.50(1H, s),7.79(1H, s)

ESI-MS Found:m/z 353.1[M+H]$^+$

EXAMPLE 13

Production of 5-chloro-6-[(1S,4S)-2,5-diazabicyclo[2.2.1]heptan-2-yl]-2-[(1-ethylpropoyl)sulfanyl] benzimidazole dihydrochloride Reactions were conducted following the steps of Production Example 1 except that (1S,4S)-2,5-diazabicyclo[2.2.1]heptane was used in plce of piperazine, to provide 5-chloro-6-[(1S,4S)-2,5-diazabicyclo[2.2.1]heptan-2-yl]-1,3-dihydro-2H-benzimidazol-2-thione. Using this compound, the reactions were conducted by the method similar to Example 1, to provide the title compound as a pale brown powder.

1HNMR(300 MHz, CD$_3$OD)δ:1.08(6H, t, J=7.3 Hz), 1.69–1.97(4H, m),2.09(1H, d, J=11.2 Hz),2.29(1H, d, J=11.2 Hz), 3.45(1H, dd, J=2.0, 11.8 Hz),3.65(2H, d, J=11.3 Hz), 3.80–3.91(2H, m),4.51(1H, s),4.62(1H, s),7.38(1H, s),7.74(1H, s)

ESI-MS Found:m/z 351.2[M+H]$^+$

EXAMPLE 14

Production of 5-chloro-2-[(1-ethylpropyl)sulfanyl]-6-[3,4,5,6tetrahydropyrrolo[3,4-C]pyrrol-2(1H)-yl] benzimidazole dihydrochloride Reactions were conducted following the steps of Production Example 1 except that 1,2,3,4,5,6-hexahydropyrrolo[3, 4-C]pyrrole (which was prepared by the method as described in *Heterocycles,* 1995, 41, 1291–1298) in place of piperazine, to provide 5-chloro-6-[3,4,5,6,-tetrahydropyrrolo[3,4-C]pyrrol-2(1H)-yl]-1,3-dihydro-2H-benzimidazol-2-thione. Using this compound, the reactions were conducted by the method similar to Example 1, to provide the title compound as a colorless amorphous substance.

1HNMR(300 MHz, CD$_3$OD)δ:1.08(6H, t, J=7.3 Hz), 1.70–1.96(4H, m),3.72–3.85(1H, m),4.19(4H, s),4.45(4H, s), 7.33(1H, s),7.70(1H, s)

ESI-MS Found:m/z 363.1[M+H]$^+$

PRODUCTION EXAMPLE 2

Production of 5-[4-(tert-butoxycarbonyl)-3-carboxypiperazin-1-yl ]-6-chloro-1,3-dihydro-2H-benzimidazol-2-thione 1) 5-(3-Carboxypiperazin-1-yl)-4-chloro-2-nitroaniline To a solution of 2.10 g of 4,5-dichloro-2-nitroaniline and 2.20 g of 2-piperazinecarboxylic acid in 20 ml of cyclohexanol, 4.80 g of sodium carbonate was added, followed by 14 hours' stirring at 150° C. After cooling the reaction liquid to room temperature, water was added and the system was washed with chloroform. The aqueous layer was purified with an ion-exchange resin (Diaion HP-20, Mitsubishi Kasei, eluent: methanol). Upon condensing the fraction containing the object product under reduced pressure, 2.20 g of the title compound was obtained.

2) 5-[4-(Tert-butoxycarbonyl)-3-carboxypiperazin-1-yl]-4-chloro-2-nitroaniline

To a suspension of 1.20 g of the compound as obtained in 1) above in 4.0 ml of tetrahydrofuran, 1.20 g of di-tert-butyldicarbonate and 18 ml of 1N aqueous sodium hydroxide solution was added, followed by 6 hours' stirring at room temperature. Water was added and the system was washed with chloroform. The aqueous layer was purified with an ion-exchange resin (Diaion HP-20, Mitsubishi Kasei, eluent:methanol). Upon condensing the fraction containing the object product under reduced pressure, 850 mg of the title compound was obtained.

3) 2-Amino-5-[4-(tert-butoxycarbonyl)-3-carboxypiperazin-1-yl]-4-chloroaniline

To a solution of 420 mg of the compound as obtained in 2) above in 50 ml ethanol-50 ml tetrahydrofuran- and 15 ml methanol, 10 mg of 10% palladium-on-carbon catalyst was added, followed by 12 hours' stirring at ambient temperature and pressure in hydrogen atmosphere. Filtering the reaction liquid with Celite, the solvent was distilled off under reduced pressure to provide 400 mg of the title compound.

4) 5-[4-(Tert-butoxycarbonyl)-3-carboxypiperazin-1-yl]-6-chloro-1,3-dihydro-2H-benzimidazole-2-thione To a solution of 300 mg of the compound as obtained in 3) above in 18 ml of ethanol, 3 ml of 1N aqueous sodium hydroxide solution and 1.5 ml of carbon disulfide were added, followed by 6 hours' stirring at 100° C. After cooling the reaction liquid to room temperature, 4 ml of 1N hydrochloric acid was added, followed by extraction with chloroform. The chloroform layer was dried on anhydrous magnesium sulfate, and the solvent was distilled off. The residue was separated and purified on silica gel column chromatography (chloroform/methanol=10/1) to provide 150 mg of the title compound.

EXAMPLE 15

Production of 6-(3-carboxypiperazin-1-yl)-5-chloro-2-[(1-ethylpropyl)-sulfanyl]benzimidazole dihydrochloride 1) 6-[4-(Tert-butoxycarbonyl)-3-(1-ethylpropoxy)carbonylpiperazin-1-yl]-5-chloro-2-[(1-ethylpropyl) sulfanyl] benzimidazol and 6-[4-(tert-butoxycarbonyl)-3-carboxypiperazin-1-yl]-5-chloro-2-[(1-ethylpropyl)-sulfanyl]benzimidazole To a solution of 39 mg of the compound as obtained in Production Example 2 in 4 ml of dimethylformamide, 30 mg of potassium carbonate and 0.014 ml of 3-bromopentane were successively added in nitrogen atmosphere, followed by 12 hours' stirring at room temperature. Water was added to the reaction liquid which then was extracted with ethyl acetate to be separated into an aqueous layer and ethyl acetate layer. The ethyl acetate layer was washed with saturated brine and dried on anhydrous sodium sulfate. After distilling the solvent off under reduced pressure, the residue was separated and purified on preparative thin-layer chromatography (Kieselgel™ 60F$_{254}$, Art. 5744 (Merck); hexane/ethyl acetate=1/1) to provide 17 mg of 6-[4-(tert-butoxycarbonyl)-3-(1-ethylpropoxy)carbonylpiperazin-1-yl]-5-chloro-2-[(1-ethylpropyl)sulfanyl]benzimidazole. To the aqueous layer, on the other hand, 15 ml of 0.1N hydrochloric acid was added, and the aqueous layer was extracted with ethyl acetate. So obtained ethyl acetate layer was washed with saturated brine and dried over anhydrous sodium sulfate. After distilling the solvent off under reduced pressure, the residue was separated and purified on preparative thin-layer chromatography (Kieselgel™ 60F$_{254}$, Art. 5744 (Merck); hexane/ethyl acetate=1/1) to provide 17 mg of 6-[4-(tert-butoxycarbonyl)-3-carboxypiperazin-1-yl]-5-chloro-2-[(1-ethylpropyl)-sulfanyl]benzimidazole.

2) 6-(3-Carboxypiperazin-1-yl)-5-chloro-2-[(1-ethylpropyl) sulfanyl]-benzimidazole dihydrochloride To 20 mg of 6-[4-(tert-butoxycarbonyl)-3-carboxypiperazin-1-yl]-5-chloro-2-[(1-ethylpropyl)-sulfanyl]benzimidzole as obtained in 1) above, 4N hydrogen chloride-in-dioxane solution (2 ml) was added, stirred for 2 hours at room temperature, and the solvent was distilled off under reduced pressure to provide 10 mg of the title compound as a colorless amorphous substance.

1HNMR(300 MHz, CD$_3$OD)δ:1.08(6H, t, J=7.4 Hz), 1.70–1.96(4H, m),3.18–3.50(4H, m),3.51–3.76(1H, m), 3.78–3.90(2H, m),4.38–4.48(1H, m),7.53(1H, s),7.81(1H, s)

ESI-MS Found:m/z 383.1[M+H]$^+$

EXAMPLE 16

Production of 5-chloro-2-[(1-ethylpropyl)sulfanyl]-6-[2-(methoxycarbonyl)-piperazin-1-yl] benzimidazole dihydrochloride To 20 mg of 6-[4-(tert-butoxycarbonyl)-3-carboxypiperazin1-yl ]-5-chloro-2-[(1-ethylpropyl)sulfanyl] benzimidazole as obtained in Example 15-1), 10% hydrogen chloride-in-methanol solution (2 ml) was added and stirred for 12 hours at 50° C. Distilling the solvent off under reduced pressure, 13 mg of the title compound was obtained as a colorless amorphous substance.

1HNMR(300 MHz, CD$_3$OD)δ:1.09(6H, t, J=7.3 Hz), 1.71–1.99(4H, m),3.22–3.50(4H, m),3.60–3.72(1H, m), 3.74–3.95(2H, m),3.88(3H, s),4.53(1H, dd, J=3.5,8.4 Hz), 7.58(1H, s),7.83(1H, s)

ESI-MS Found:m/z 397.1[M+H]$^+$

EXAMPLE 17

Production of 5-chloro-2-[(1-ethylpropyl)sulfanyl]-6-[3-(hydroxymethyl)-4-methylpiperazin-1-yl] benzimidazole dihydrochloride To a solution of 25 mg of 6-[4-(tert-butoxycarbonyl)-3-(1-ethylpropoxycarbonyl)piperazin-1-yl]-5-chloro-2-[(1- ethylpropyl)-sulfanyl]benzimidazole as obtained in Example 15-1) in 1 ml of tetrahydrofuran, 0.25 ml of 0.9M diisobutylaluminium hydride in hexane solution was added at −78° C., and stirred for an hour at room temperature. To the reaction liquid 250 mg of sodium sulfate decahydrate was added and the stirring was continued for further 4 hours at room temperature. The insoluble matter was separated by filtration, and the filtrate was concentrated under reduced pressure. The residue was separated and purified on preparative thin-layer chromatography (Kieselgel™ 60F$_{254}$, Art. 5744 (Merck); chloroform/methanol=10/1) to provide 5.6 mg 5-chloro-2-[(1-ethylpropyl)-sulfanyl]-6-[3-(hydroxymethyl)-4-methylpiperazin-1-yl]benzimidazole dihydrochloride as a colorless amorphous substance and 3.0 mg of 6-[4-(tert-butoxycarbonyl)-3-(hydroxymethyl) piperazin-1-yl]-5-chloro-2-[(1-ethylpropyl)sulfanyl] benzimidazole.

5-chloro-2-[(1-ethylpropyl)-sulfanyl]-6-[3-(hydroxymethyl)-4-methylpiperazin-1-yl]benzimidazole dihydrochloride 1HNMR(300 MHz, CD$_3$OD)δ:1.08(6H, t, J=7.4 Hz), 1.70–1.95(4H, m),3.05(3H, s),3.40–3.68(7H, m),3.72–3.89 (2H, m), 4.03–4.13(1H, m),7.50(1H, s),7.80(1H, s)

ESI-MS Found:m/z 383.2[M+H]$^+$

EXAMPLE 18

Production of 5-chloro-2-[(1-ethylpropyl)sufanyl]-6-[3-(hydroxymethyl)piperazin-1-yl] benzimidazole dihydrochloride To 3.0 mg of the other of the compounds as obtained in Example 17, 6-[4-(tert-butoxycarbonyl)-3-(hydroxymethyl) piperazin-1-yl]-5-chloro-2-[(1-ethylpropyl)sulfanyl] benzimidazole, 4N hydrogen chloride in dioxane solution (1 ml) was added, stirred for 12 hours at room temperature and the solvent was distilled off under reduced pressure to provide 3 mg of the title compound as a colorless amorphous substance.

1HNMR(300 MHz, CD$_3$OD)δ:1.08(6H, t, J=7.4 Hz), 1.70–1.95(4H, m),3.01–3.92(10H, m),7.47(1H, s),7.79(1H, s)

ESI-MS Found:m/z 369.2[M+H]$^+$

EXAMPLES 19–20

Production of 5-chloro-2-[(1-ethylpropyl)sulfanyl]-6-[(3R*)-3-methylpiperazin-1-yl]benzimidazole dihydrochloride and 5-chloro-2-[(1-ethylpropyl) sulfanyl]-6-[(3S*)-3-methylpiperazin-1-yl]-benzimidazole dihydrochloride 1) 5-Chloro-6-(3-methylpiperazin-1-yl)-1,3-dihydro-2H-benzimidazol-2-thione Reactions were conducted following the steps of Production Example 1 using 2-methylpiperazine in place of piperazine, the title compound was obtained.

2) 5-Chloro-2-[(1-ethylpropyl)sulfanyl]-6-[(3R*)-3-methylpiperazin-1-yl] benzimidazole dihydrochloride and 5-chloro-2-[(1-ethylpropyl)sulfanyl]-6-[(3S*)-3-methylpiperazin-1-yl ] benzimidazole dihydrochloride To a solution of 647 mg of the compound as obtained in 1) above in 15 ml of dimethylformamide, 355 mg of potassium carbonate and 0.30 ml of 3-bromopentane were successively added in nitrogen atmosphere, and stirred for an hour at 80° C. The reaction liquid was cooled to room temperature, water was added thereto and extracted with ethyl acetate. The ethyl acetate layer was washed with saturated brine, dried on anhydrous sodium sulfate, and the solvent was distilled off under reduced pressure. The residue was separated and purified on silica gel column chromatography (ethyl acetate/hexane=1/3) to provide 394 mg of 2-{[5-chloro-6-(4-tert-butoxycarbonyl-3-methylpiperazin-1-yl)-1H-benzimidazol-2-yl]-sulfanyl}-2-ethylpropane in the form of a racemic modification.

This racemic modification was optically resolved using an optically active column (Daicel, CHRALPAC AD Column; 0.1% diethylamine, hexane/isopropyl alcohol=19/1), to provide 186 mg of 2-{[5-chloro-6-(4-tert-butoxycarbonyl-3-methylpiperazin-1-yl)-1H-benzimidazol-2-yl]sulfanyl}-2-ethylpropane (3R*-configuration) from the earlier fraction and 189 mg of its (3S*-configuration) from the later fraction. (Because the two were unidentified, for convenience the former was recorded as 3R*-configuration and the other, as 3S*-configuration.) To each of the compounds 10% hydrogen chloride-in-methanol solution (2 ml) was added, stirred for 14 hours at room temperature and thereafter the solvent was distilled off to provide 168 mg of 5-chloro-2-[(1-ethylpropyl)sulfanyl]-6-[(3R*)-3-methylpiperazin-1-yl] benzimidazole dihydrochloride as a pale red powder, and 171 mg of 5-chloro-2-[(1-ethylpropyl)sulfanyl]-6-[(3S*)-3-methylpiperazin-1-yl]benzimidazole dihydrochloride, as a pale red powder.

(3R*)-configuration of the compound of Example 19

1HNMR(300 MHz, CD$_3$OD)δ:1.09(6H, t, J=7.3 Hz), 1.43 (3H, d, J=6.5 Hz),1.70–1.98(4H, m),2.94–3.08(1H, m), 3.11–3.25(1H, m),3.32–3.45(1H, m),3.45–3.69(4H, m), 3.81–3.92(1H, m),7.53(1H, s),7.81(1H, s)

ESI-MS Found:m/z 353.1[M+H]$^+$ (3S*)-configuration of the compound of Example 20

1HNMR(300 MHz, CD$_3$OD)δ:1.09(6H, t, J=7.3 Hz), 1.43 (3H, d, J=6.6 Hz),1.70–1.98(4H, m), 3.01(1H, dd, J=10.0, 12.9 Hz),3.12–3.26(1H, m), 3.32–3.44(1H, m),3.46–3.69 (4H, m),3.89(1H, quinted, J=6.4 Hz), 7.54(1H, s),7.81(1H, s)

ESI-MS Found:m/z 353.1[M+H]$^+$

PRODUCTION EXAMPLE 3

Production of 5-[1-(tert-butoxycarbonyl)piperidin-4-yl]]-6-chloro-1,3-dihydro-2H-benzimidazol-2-thione 1) Tert-butyl 4-(3-aminophenyl)-tetrahydro-1-(2H)-pyridinecarboxylate To a solution of 2.54 g of tert-butyl 1,2,3,6-tetrahydro-4-(3-nitrophenyl)pyridine-1-carboxylate (which was prepared by the method as described in *Synthesis*, 1991, 993–995) in 20 ml of methanol, 250 mg of 10% palladium-on-carbon catalyst was added, and stirred for an hour in hydrogen atmosphere at ambient temperature and pressure. After addition of 20 ml of tetrahydrofuran to the reaction liquid, the liquid was filtered with Celite. Distilling the solvent off under reduced pressure, 2.30 g of the title compound was obtained.

2) 3-(Piperidin-4-yl)aniline

To 2.30 g of the compound as obtained in 1) above, 10% hydrogen chloride-in-methanol solution (20 ml) was added, and stirred for 12 hours at room temperature. The solvent was distilled off under reduced tempereture. To the residue 1N aqueous sodium hydroxide solution (20 ml) was added, followed by extraction with chloroform. Drying the chloroform layer on anhydrous magnesium sulfate and distilling the solvent off, 1.40 g of the title compound was obtained.

3) N-[3-(1-acetylpiperidin-4-yl)phenyl]acetamide

To 1.40 g of the compound as obtained in 2) above, 2 ml of acetic anhydride and 40 ml of pyridine were added, and stirred for an hour at room temperature. The solvent was distilled off under reduced pressure. To the residue chloroform was added, followed by washing with 0.5N hydrochloric acid. The chloroform layer was dried on anhydrous magnesium sulfate, and the solvent was distilled off. The residue obtained was separated and purified on silica gel column chromatography (chloroform/methanol=10/1) to provide 1.96 g of the title compound.

4) N-[3-(1-acetylpiperidin-4-yl)-4-chlorophenyl]acetamide

To a solution of 1.93 g of the compound as obtained in 3) above in 12 ml of isopropyl alcohol, 1.48 g of N-chlorosuccinimide was added at 60° C., followed by 30 minutes' heating under reflux. Cooling the system to room temperature, the solvent was distilled off under reduced pressure. Chloroform was added to the residue which was then successively washed with saturated aqueous sodium hydrogencarbonate solution and saturated brine. The chloroform layer was dried on anhydrous magnesium sulfate, and the solvent was distilled off. The residue was separated and purified on silica gel chromatography (chloroform/methanol=10/1) to provide 1.45 g of the title compound.

5) N-[5-(1-acetylpiperidin-4-yl)-4-chloro-2-nitrophenyl]acetamide

To a solution of 1.45 g of the compound as obtained in 4) above in 15 ml of conc. sulfuric acid, 1.5 ml of fuming nitric acid was added at 0° C., followed by an hour's stirring at room temperature. Twenty (20) g of ice was added to the reaction solution which then was extracted with chloroform. The chloroform layer was washed with saturated brine, dried on anhydrous magnesium sulfate, and the solvent was distilled off to provide 1.65 g of the title compound.

6) 2-Nitro-4-chloro-5-(piperidin-4-yl)aniline dihydrochloride

To a solution of 1.65 g of the compound as obtained in 5) above in 7 ml of methanol, 7 ml of 2N hydrogen chloride-in-methanol solution was added, and heated for 12 hours under reflux. The reaction solution was cooled to room temperature, and the solvent was distilled off under reduced pressure to provide 1.60 g of the title compound.

7) 4-Chloro-2-nitro-5-[1-(tert-butoxycarbonyl)piperidin-4-yl]aniline

To a solution of 1.60 g of the compound as obtained in 6) above in 80 ml of chloroform-40 ml of methanol, 7 ml of triethylamine and 1.30 g of di-tert-butylcarbonate were successively added and stirred for 0.5 hour at room temperature. The reaction liquid was successively washed with water and saturated brine, dried on anhydrous magnesium sulfate and the solvent was distilled off. The residue was separated and purified on silica gel column chromatography (ethyl acetate/hexane=1/4) to provide 1.14 g of the title compound.

8) 5-[1-(Tert-butoxycarbonyl)piperidin-4-yl]-6-chloro-1,3-dihydro-2H-benzimidazol-2-thione In 10 ml of tetrahydrofuran, 610 mg of the compound as obtained in 7) above, 460 mg of ammonium chloride and 963 mg of iron were suspended, to which then 4 ml of methanol and 4 ml of water were added, followed by 2 hours' stirring at 100° C. Cooling the reaction liquid to room temperature, saturated aqueous sodium hydrogencarbonate solution was added to the liquid, and the insoluble matter was filtered off with Celite. The filtrate was extracted with ethyl acetate, and the ethyl acetate layer was washed with saturated brine, dried on anhydrous magnesium sulfate and the solvent was distilled off. The residue was dissolved in 20 ml of ethanol, and to the solution 4 ml of 1N aqueous sodium hydroxide solution and 2 ml of carbon disulfide were added, followed by an hour's stirring at 80° C. The reaction liquid was cooled to room temperature and water was added thereto. Thus obtained solution was extracted with chloroform. The chloroform layer was washed with saturated brine, dried on anhydrous magnesium sulfate, and the solvent was distilled off to provide 607 mg of the title compound.

EXAMPLE 21

Production of 5-chloro-2-[(1-ethylpropyl)sulfanyl]-6-(piperidin-4-yl)-benzimidazole dihydrochloride Reactions were conducted by the method similar to Example 1 using the compound as obtained in production Example 3, to provide the title compound as a white solid.

1HNMR(300 MHz, CD$_3$OD)δ:1.09(6H, t, J=7.3 Hz), 1.70–2.22(8H, m),3.15–3.40(2H, m),3.48–3.66(3H, m), 3.82–3.98(1H, m),7.71((1H, s),7.80(1H, s)

ESI-MS Found:m/z 338.1[M+H]$^+$

EXAMPLE 22

Production of 5-chloro-2-[(3-methoxy-1,3-dimethylbutyl)sulfanyl]-6-(piperidin-4-yl)benzimidazole dihydrochloride Reactions were conducted by the method similar to Example 21 except that 3-methoxy-1,3-dimethylbutyl methanesulfonate (which was prepared from 3-methoxy-1,3-dimethylbutanol and methanesulfonyl chloride by the known production method) was used in place of 3-bromopentane, to provide the title compound as a pale yellow, amorphous substance.

1HNMR(300 MHz, CD$_3$OD)δ:1.26(3H, s),1.28(3H, s), 1.53(3H, d, J=6.7 Hz),1.90–2.22(6H, m),3.15–3.32(2H, m), 3.22(3H, s),3.47–3.61(3H, m),4.10–4.25(1H, m), 7.66–7.72 (1H, m),7.80(1H, s)

ESI-MS Found:m/z 382.0[M+H]$^+$

EXAMPLE 23

Production of 5-chloro-2-[(1,3-dimethyl-3-hydroxybutyl)sulfanyl]-6-(piperidin-4-yl)benzimidazole Reactions were conducted by the method similar to Example 21 except that 1,3-dimethyl-3-hydroxybutyl methanesulfonate (which was prepared from 1,3-dimethyl-3-hydroxybutanol and methanesulfonyl chloride by the known production method) was used in place of 3-bromopentane, to provide the title compound as a pale yellow, oily substance.

1HNMR(300 MHz, CDCl$_3$)δ:1.27(3H, s),1.32(3H, s), 1.49(3H, d, J=7.0 Hz),1.60–1.80(2H, m),1.83–2.03(3H, m), 2.18–2.30(1H, m),2.83(2H, m),3.20–3.40(3H, m), 4.06–4.20(1H, m),7.39(1H, s),7.59(1H, s)

ESI-MS Found:m/z 368.0[M+H]$^+$

EXAMPLE 24

Production of 5-chloro-2-[(3-methoxy-3-methylbutyl)sulfanyl]-6-(piperazin-1-yl)benzimidazole dihydrochloride Reactions were conducted by the method similar to Example 1 except that 3-methoxy-3-methylbutyl methanesulfonate (which was prepared from 3-methyl-3-methoxybutanol and methanesulfonyl chloride by the known production method) was used in place of 3-bromopentane, to provide the title compound as a white solid.

1HNMR(300 MHz, CD₃OD)δ:1.25(6H, s),1.94–2.05(2H, m), 3.22(3H, s),3.28–3.56(10H, m),7.49(1H, s),7.78(1H, s)

ESI-MS Found:m/z 369.1[M+H]⁺

EXAMPLE 25

Production of 5-chloro-2-[(5-methylhexyl)sulfanyl]-6-(piperazin-1-yl)benzimidazole dihydrochloride Reactions were conducted by the method similar to Example 1 except that 5-methylhexyl methanesulfonate (which was prepared from 5-methylhexanol and methanesulfonyl chloride by the known production method) was used in place of 3-bromopentane, to provide the title compound as a white solid.

1HNMR(300 MHz, CD₃OD)δ:0.89(6H, d, J=6.6 Hz), 1.20–1.32(2H, m),1.44–1.62(3H, m),1.72–1.88(2H, m), 3.26–3.55(10H, m),7.49(1H, s),7.79(1H, s)

ESI-MS Found:m/z 367.1[M+H]⁺

EXAMPLE 26

Production of 5-chloro-6-(piperazin-1-yl)-2-[(1,3,3-trimethylbutyl)-sulfanyl]benzimidazole dihydrochloride Reactions were conducted by the method similar to Example 1 except that 1,3,3-trimethylbutyl methanesulfonate (which was prepared from 1,3,3-trimethylbutanol and methanesulfonyl chloride by the known production method) was used in place of 3-bromopentane, to provide the title compound as a white solid.

1HNMR(300 MHz, CD₃OD)δ:1.03(9H, s),1.51(3H, d, J=6.5 Hz), 1.68(2H, d, J=5.5 Hz),3.24–3.50(8H, m),3.99–4.12(1H, m), 7.51(1H, s),7.81(1H, s)

ESI-MS Found:m/z 367.1[M+H]⁺

EXAMPLE 27

Production of 5-chloro-2-[(cyclopentyl)sulfanyl]-6-(piperazin-1-yl)-benzimidazole dihydrochloride Reactions were conducted by the method similar to Example 1, except that cyclopentyl bromide was used in place of 3-bromopentane, to provide the title compound as a white solid.

1HNMR(300 MHz, CD₃OD)δ:1.68–1.99(6H, m), 2.22–2.40(2H, m),3.21–3.56(8H, m),4.16–4.30(1H, m), 7.50(1H, s),7.80(1H, s)

ESI-MS Found:m/z 337.1[M+H]⁺

EXAMPLE 28

Production of 5-chloro-2-[(3-methoxy-1,3-dimethylbutyl)sulfanyl]-6-(piperazin-1-yl) benzimidazole dihydrochloride Reactions were conducted by the method similar to Example 1 except that 3-methoxy-1,3-dimethylbutyl methanesulfonate (which was prepared from 3-methoxy-1,3-dimethylbutanol and methanesulfonyl chloride by the known production method) was used in place of 3-bromopentane, to provide the title compound as a pale yellow, oily substance.

1HNMR(200 MHz, CD₃OD)δ:1.28(3H, s),1.32(3H, s), 1.53(3H, d, J=6.6 Hz),2.01(2H, d, J=5.8 Hz),3.23(3H, s), 3.30–3.60(8H, m),4.15(1H, m),7.50(1H, s),7.81(1H, s)

ESI-MS Found:m/z 383.2[M+H]⁺

EXAMPLE 29

Production of 5-chloro-2-[(2-methoxy-2-methylpropyl)sulfanyl]-6-(piperazin-1-yl) benzimidazole dihydrochloride Reactions were conducted by the method similar to Example 1, except that 2-methoxy-2-methylpropyl methanesulfonate [which was prepared from 2-methoxy-2-methylpropanol (a compound described in *Kogyo Kagaku Zasshi*, 1968, 71, 1943–1944) and methanesulfonyl chloride by the known production method] was used in place of 3-bromopentane, to provide the title compound as a white solid.

1HNMR(200 MHz, CD₃OD)δ:1.37(6H, s),3.18(3H, s), 3.25–3.50(8H, m),3.60(2H, s),7.45(1H, s),7.77(1H, s)

ESI-MS Found:m/z 355.1[M+H]⁺

EXAMPLE 30

Production of 5-chloro-2-[(3-hydroxy-3-metylbutyl)sulfanyl]-6-(piperazin-1-yl)benzimidazole dihydrochloride Reactions were conducted by the method similar to Example 1 except that 3-hydroxy-3-methylbutyl 4-methylbenzenesulfonate (which compound was prepared from 3-hydroxy-3-methylbutanol and 4-methylbenzenesulfonyl chloride) was used in place of 3-bromopentane, to provide the title compound as a white solid.

1HNMR(200 MHz, CD₃OD)δ:1.28(6H, s),1.85–2.05(2H, m), 3.10–3.60(10H, m),7.48(1H, s),7.77(1H, s)

ESI-MS Found:m/z 355.1[M+H]⁺

EXAMPLE 31

Production of 2-[(3-butoxybutyl)sulfanyl]-5-chloro-6-(piperazin-1-yl)benzimidazole dihydrochloride Reactions were conducted by the method similar to Example 1 except that 3-methoxybutyl methanesulfonate (which was prepared by the known production method, from 3-methoxybutanol and methanesulfonyl chloride) was used in place of 3-bromopentane, to provide the title compound as a pale yellow, amorphous substance.

1HNMR(300 MHz, CD₃OD)δ:1.19(3H, d, J=6.0 Hz),1.94 (2H, m), 3.15–3.6(11H, m),3.32(3H, s),7.47(1H, s),7.77(1H, s)

ESI-MS Found:m/z 355.1[M+H]⁺

EXAMPLE 32

Production of 5-chloro-2-[(3-hydroxy-1,3-dimethylbutyl)sulfanyl]-6-(piperazin-1-yl) benzimidazole dihydrochloride Reactions were conducted by the method similar to Example 1 except that 1,3-dimethyl-3-hydroxybutyl methanesulfonate (which compound was prepared from 1,3-dimethyl-3-hydroxybutanol and methanesulfonyl chloride by the known method) in place of 3-bromopentane, to provide the title compound as a colorless oily substance.

1HNMR(300 MHz, CD₃OD)δ:1.31(3H, s),1.33(3H, s), 1.56(3H, d, J=6.6 Hz),1.90–2.15(2H, m),3.20–3.50(8H, m), 4.10–4.25(1H, m),7.51(1H, s),7.80(1H, s)

ESI-MS Found:m/z 369.1[M+H]⁺

EXAMPLE 33

Production of 5-chloro-6-(piperazin-1-yl)-2-[(tetrahydro-2H-pyran-4-yl)sulfanyl]benzimidazole dihydrochloride Reactions were conducted by the method similar to Example 1 except that tetrahydro-2H-pyran-4-yl methanesulfonate (which was prepared from tetrahydro-2H-pyran-4-ol and methanesulfonyl chloride by the known production method) was used in place of 3-bromopentane, to provide the title compound as a pale yellow solid.

1HNMR(200 MHz, CD$_3$OD)δ:1.60–2.20(4H, m), 3.00–3.70(10H, m),3.80–4.20(3H, m),7.53(1H, m),7.83(1H, m)

ESI-MS Found:m/z 353.1[M+H]$^+$

EXAMPLE 34

Production of 5-chloro-2-[(3-methoxypropyl)sulfanyl]-6-(piperazin-1-yl)benzimidazole dihydrochloride Reactions were conducted by the method similar to Example 1 except that 3-methoxypropyl methanesulfonate (which was prepared, from 3-methoxypropanol and methanesulfonyl chloride by the known production method) was used in place of 3-bromopentane, to provide the title compound as a white amorphous substance.

1HNMR(200 MHz, CD$_3$OD)δ:2.05(2H, m),3.00–3.70 (15H, m), 7.44(1H, s),7.76(1H, s)

ESI-MS Found:m/z 341.1[M+H]$^+$

EXAMPLE 35

Production of 5-chloro-2-[(3-hydroxy-2,3-dimethylbutyl)sulfanyl]-6-(piperazin-1-yl)benzimidazole dihydrochloride Reactions were conducted by the method similar to Example 1, except that 3-hydroxy-2,3-dimethylbutyl methanesulfonate [which was prepared from 3-hydroxy-2,3-dimethylbutanol (a compound described in *Acta. Chem. Scand.*, 1969, 23, 715–726) and methanesulfonyl chloride by the known method] was used in place of 3-bromopentane, to provide the title compound as a pale brown solid.

1HNMR(200 MHz, CD$_3$OD)δ:1.13(3H, d, J=6.8 Hz),1.22 (3H, s), 1.29(3H, s),1.93(1H, m),3.14(1H, dd, J=9.3,12.4 Hz), 3.25–3.5(8H, m),3.85(1H, dd, J=3.2,12.4 Hz),7.47(1H, s),7.77(1H, s)

ESI-MS Found:m/z 369.0[M+H]$^+$

EXAMPLE 36

Production of 5-chloro-2-[(3,3-dimethyl-2-oxobutyl)sulfanyl]-6-(piperazin-1-yl)benzimidazole dihydrochloride Reactions were conducted by the method similar to Example 1 except that 1-bromopinacolone was used in place of 3-bromopentane, to provide the title compound as a pale brown solid.

1HNMR(200 MHz, CD$_3$OD)δ:1.25(9H, s),3.25–3.50(8H, m), 4.80(2H, s),7.49(1H, s),7.78(1H, s)

ESI-MS Found:m/z 367.0[M+H]$^+$

EXAMPLE 37

Production of 5-chloro-2-{[1-(methoxycarbonyl)propyl]sulfanyl}-6-(piperazin-1-yl)benzimidazole dihydrochloride Reactions were conducted by the method similar to Example 1 except that methyl 2-bromobutyrate was used in place of 3-bromopentane, to provide the title compound as a colorless amorphous substance.

1HNMR(300 MHz, CD$_3$OD)δ:1.10(3H, t, J-7.4 Hz), 1.95–2.01(2H, m),3.32–3.50(8H, m),3.73(3H, s), 4.42(1H, t, J=6.9 Hz),7.51(1H, s),7.83(1H, s)

ESI-MS Found:m/z 369.0[M+H]$^+$

EXAMPLE 38

Production of 2-[(1-acetyl-2-oxopiropyl)sulfanyl]-5-chloro-6-(piperazin-1-yl)benzimidazole dihydrochloride Reactions were conducted by the method similar to Example 1 except that 3-chloro-2,4-pentanedione was used in place of 3-bromopentane, to provide the title compound as a colorless amorphous substance.

1HNMR(300 MHz, CD$_3$OD)δ:2.43(6H, s),3.32–3.49(8H, m), 4.85(1H, s),7.47(1H, s),7.76(1H, s)

ESI-MS Found:m/z 369.0[M+H]$^+$

EXAMPLE 39

Production of 5-chloro-2-[(2-ethyl-2-hydroxybutyl)sulfanyl]-6-(piperazin-1-yl)benzimidazole dihydrochloride Reactions were conducted by the method similar to Example 1 except that 2-ethyl-2-hydroxybutyl methanesulfonate (which was prepared from 2-ethyl-2-hydroxybutanol and methanesulfonyl chloride by the known production method) was used in place of 3-bromopentane, to provide the title compound as a pale yellow solid.

1HNMR(200 MHz, CD$_3$OD)δ:0.94(6H, t, J=7.5 Hz), 1.71 (4H, q.J=7.5 Hz),3.25–3.50(8H, m),3.56(2H, s), 7.49(1H, s),7.78(1H, s)

ESI-MS Found:m/z 369.1[M+H]$^+$

EXAMPLE 40

Production of 5-chloro-6-(piperazin-1-yl)-2-[(tetrahydro-2H-pyran-4-ylmethyl)sulfanyl] benzimidazole dihydrochloride Reactions were conducted by the method similar to Example 1, except that tetrahydro-2H-pyran-4-ylmethyl methanesulfonate [which was prepared from tetrahydro-2H-pyran-4-ylmethanol (a compound described in *J. Am. Chem. Soc.*, 1975, 97, 210–212) and methanesulfonyl chloride by the known method] was used in place of 3-bromopentane, to provide the title compound as a white solid.

1HNMR(300 MHz, CD$_3$OD)δ:1.25–1.50(2H, m), 1.76–2.08(3H, m),3.24–3.50(12H, m),3.89–4.00(2H, m), 7.46–7.54(1H, m),7.76–7.82(1H, m)

ESI-MS Found:m/z 367.1[M+H]$^+$

EXAMPLE 41

Production of 5-chloro-6-(piperazin-1-yl)-2-[(2-tetrahydro-2H-pyran-4-ylethyl)sulfanyl] benzimidazole dihydrochloride Reactions were conducted by the method similar to Example 1, except that 2-tetrahydro-2H-pyran-4-ylethyl methanesulfonate [which was prepared from 2-(tetrahydro-2H-pyran-4-yl)ethanol (Production Example A given later) and methanesulfonyl chloride by the known method] was used in place of 3-bromopentane, to provide the title compound as a white solid.

1HNMR(300 MHz, CD$_3$OD)δ:1.22–1.42(2H, m), 1.65–1.88(5H, m),3.26–3.60(12H, m),3.88–4.00(2H, m), 7.48–7.54(1H, m),7.81(1H, s)

ESI-MS Found:m/z 381.1[M+H]$^+$

PRODUCTION EXAMPLE A

Production method of 2-(tetrahydro-2H-pyran-4-yl)ethanol

To a solution of 4.00 ml of triethyl phosphonoacetate in tetrahydrofuran (20 ml), 800 mg of sodium hydride was added at 0° C. in nitrogen atmosphere, followed by 30 minutes' stirring at the same temperature. To said solution a solution of 1.00 g of tetrahydro-4H-pyran-4-one in tetrahydrofuran (2 ml) was added at 0° C., followed by an hour's stirring at room temperature. Ice (about 10 g) was added to the reaction solution, which then was extracted with ethyl acetate. The ethyl acetate layer was washed with saturated brine, dried with anhydrous sodium sulfate and the solvent was distilled off. The residue was separated and purified on silica gel column chromatography (ethyl acetate/hexane=10/1) to provide 1.61 g of ethyl 2-(tetrahydro-4H-pyran-4-ylidene)acetate. To a solution of 1.61 g of this compound in ethanol (20 ml), 240 mg of 10% palladium-on-carbon catalyst was added and stirred for an hour in hydrogen atmosphere (1 atm.). Filtering the catalyst off from the reaction solution, the filtrate was concentrated under reduced pressure. To a solution of so obtained residue in tetrahydrofuran (30 ml), 550 mg of lithium aluminum hydride was added at 0° C. in nitrogen atmosphere, followed by 30 minutes' stirring at the same temperature. Then 5 g of sodium sulfate decahydrate was added to the solution and stirred for 12 hours at room temperature. The insoluble matter was filtered off, and the filtrate was concentrated under reduced pressure to provide 1.20 g of the title compound.

EXAMPLE 42

Production of 5-chloro-6-(piperazin-1-yl)-2-{[3-(tetrahydro-2H-pyran-4-yl)propyl]sulfanyl}benzimidazole dihydrochloride Reactions were conducted by the method similar to Example 1, except that 3-(tetrahydro-2H-pyran-4-yl)propyl methanesulfonate [which was prepared from 3-(tetrahydro-2H-pyran-4-yl)propanol (Production Example B given later) and methanesulfonyl chloride by the known production method] was used in place of 3-bromopentane, to provide the title compound as a pale yellow amorphous substance.

1HNMR(300 MHz, CD$_3$OD)δ:1.14–1.35(2H, m), 1.40–1.70(5H, m),1.80–1.91(2H, m),3.26–3.55(12H, m), 3.84–3.94(2H, m),7.53(1H, s),7.80(1H, s)

ESI-MS Found:m/z 395.1[M+H]$^+$

PRODUCTION EXAMPLE B

Production method of 3-(tetrahydro-2H-pyran-4-yl)propanol

To a solution of 185 mg of 2-(tetrahydro-2H-pyran-4-yl)ethyl methanesulfonate, which was used in Example 41, in dimethylsulfoxide (2 ml), 90 mg of sodium cyanide was added in nitrogen atmosphere, followed by 2 hours' stirring at 80° C. Water was added to the reaction solution which then was extracted with ether. The ether layer was successively washed with water and saturated brine, dried on anhydrous sodium sulfate and the solvent was distilled off. To the residue 1 ml of conc. hydrochloric acid was added, followed by 12 hours' stirring at 100° C. The solution was cooled to room temperature, and the solvent was distilled off under reduced pressure. To the residue 2 ml of 10% hydrogen chloride-in-methanol solution was added, followed by 2 hours' stirring at 80° C. The solution was cooled to room temperature and the solvent was distilled off under reduced pressure. Saturated aqueous sodium hydrogencarbonate solution was added to the residue, which then was extracted with chloroform. The chloroform layer was dried on anhydrous sodium sulfate, and the solvent was distilled off. To a solution of so obtained residue in tetrahydrofuran (3 ml), 41 mg of lithium aluminum hydride was added at 0° C. in nitrogen atmosphere, followed by 30 minutes' stirring at the same temperature. To the solution 400 mg of sodium sulfate decahydrate was added and stirred for 1.5 hours at room temperature. The insoluble matter was filtered off, and the filtrate was concentrated under reduced pressure to provide 74 mg of the title compound.

EXAMPLE 43

Production of 5-chloro-2-{[2-(diisoproylamino)ethyl]sulfanyl}-6-(piperazin-1-yl)benzimidazole dihydrochloride Reactions were conducted by the method similar to Example 1 except that 2-(diisopropylamino)ethyl methanesulfonate (which was prepared from 2-(diisopropylamino)ethanol and methanesulfonyl chloride by the known production method) was used in place of 3-bromopentane, to provide the title compound as a pale brown, amorphous substance.

1HNMR(200 MHz, CD$_3$OD)δ:1.44(12H, brd), 3.20–3.50 (8H, m),3.63(2H, m),3.74–4.07(4H, m), 7.56(1H, s),7.84 (1H, s)

ESI-MS Found:m/z 396.2[M+H]$^+$

EXAMPLE 44

Production of 5-chloro-2-{[2-(1-hydroxycyclohexyl)ethyl]sulfanyl}-6-(piperazin-1-yl)benzimidazole dihydrochloride Reactions were conducted by the method similar to Example 1, except that 2-(1-hydroxycyclohexyl)ethyl methanesulfonate [which was prepared from 2-(1-hydroxycyclohexyl)ethanol (a compound described in J. Org. Chem., 1980, 45, 1828–1835) and methanesulfonyl chloride by the known production method] was used in place of 3-bromopentane, to provide the title compound as a white solid.

1HNMR(300 MHz, CD$_3$OD)δ:1.20–1.78(10H, m), 1.90–2.03(2H, m),3.26–3.60(10H, m),7.51(1H, s),7.79(1H, s)

ESI-MS Found:m/z 395.1[M+H]$^+$

EXAMPLE 45

Production of 5-chloro-2-{[2-(1-hydroxycyclopentyl)ethyl]sulfanyl}-6-(piperazin-1-yl)benzimidazol dihydrochloride Reactions were conducted by the method similar to Example 1, except that 2-(1-hydroxycyclopentyl)ethyl methanesulfonate [which was prepared from 2-(1-hydroxycyclopentyl)ethanol (a compound described in J. Org. Chem., 1980, 45, 1828–1835) and methanesulfonyl chloride by the known production method] was used in place of 3-bromopentane, to provide the title compound as a white solid.

1HNMR(300 MHz, CD$_3$OD)δ:1.52–1.90(8H, m), 2.02–2.13(2H, m),3.22–3.62(10H, m),7.50(1H, s),7.79(1H, s)

ESI-MS Found:m/z 381.1[M+H]$^+$

EXAMPLE 46

Production of 5-chloro-6-(piperazin-1-yl)-2-[(tetrahydro-3-furanylmethyl)sulfanyl]benzimidazole Reactions were conducted by the method similar to Example 1 except that tetrahydro-3-furanylmethyl methanesulfonate (which was prepared from tetrahydro-3-furanylmethanol and methanesulfonyl chloride by the known production method) was used in place of 3-bromopentane, to provide the title compound as a pale yellow, amorphous substance.

1HNMR(300 MHz, CD$_3$OD)δ:1.71–1.89(1H, m), 2.12–2.30(1H, m),2.58–2.73(1H, m),3.20–4.00(14H, m), 7.50(1H, s),7.79(1H, s)

ESI-MS Found:m/z 353.1[M+H]$^+$

EXAMPLE 47

Production of 5-chloro-2-[(2,2-dimethyltetrahydro-2H-pyran-4-yl)sulfanyl]-6-(piperazin-1-yl)benzimidazole Reactions were conducted by the method similar to Example 1 except that 2,2-dimethyltetrahydro-2H-pyran-4-yl methanesulfonate (which was prepared from 2,2-dimethyltetrahydro-2H-pyran-4-ol and methanesulfonyl chloride by the known production method) was used in place of 3-bromopentane, to provide the title compound as a pale yellow, amorphous substance.

1HNMR(300 MHz, CD$_3$OD)δ:1.24(3H, s),1.32(3H, s), 1.50–2.78(2H, m),1.98–2.11(2H, m),3.26–3.50(8H, m), 3.70–3.91(2H, m),4.20–4.37(1H, m),7.56(1H, s),7.85(1H, s)

ESI-MS Found:m/z 381.1[M+H]$^+$

EXAMPLE 48

Production of 5-chloro-2-[(2-ethyl-3-hydroxy-3-methylbutyl)sulfanyl]-6-(piperazin-1-yl)benzimidazole dihydrochloride Reactions were conducted by the method similar to Example 1, except that 2-ethyl-3-hydroxy-3-methylbutyl methanesulfonate [which was prepared from 2-ethyl-3-hydroxy-3-methylbutanol (a compound described in *Bull. Chem. Soc. Jpn.*, 1976, 49, 1041)and methanesulfonyl chloride by the known production method] was used in place of 3-bromopentane, to provide the title compound as a pale yellow, amorphous substance.

1HNMR(300 MHz, CD$_3$OD)δ:1.08(3H, t, J=7.4 Hz), 1.23 (3H, s),1.34(3H, s),1.35–1.50(1H, m),1.66–1.88(2H, m), 3.24–3.52(9H,m),3.76–3.87(1H, m),7.50(1H, s),7.77(1H, s)

ESI-MS Found:m/z 383.1[M+H]$^+$

EXAMPLE 49

Production of 5-chloro-2-[(1-methylpyrrolidin-3-yl)sulfanyl]-6-(piperazin-1-yl)benzimidazole dihydrochloride Reactions were conducted by the method similar to Example 1 except that 1-methylpyrrolidin-3-yl methanesulfonate (which was prepared from 1-methylpyrrolidin-3-ol and methanesulfonyl chloride by the known production method) was used in place of 3-bromopentane, to provide the title compound as a pale brown, oily substance.

1HNMR(300 MHz, CD$_3$OD)δ:2.10–3.10(2H, m),3.03 (3H, s), 3.20–3.50(8H, m),3.70–4.70(5H, m),7.59(1H, s),7.88(1H, s)

ESI-MS Found:m/z 352.1[M+H]$^+$

EXAMPLE 50

Production of 5-chloro-2-[(3-ethyl-3-hydroxypentyl)sulfanyl]-6-(pipierazin-1-yl)benimidazole dihydrochloride Reactions were conducted by the method similar to Example 1, except that 3-ethyl-3-hydroxypentyl methanesulfonate [which was prepared from 3-ethyl-3-hydroxypentanol (a compound described in *Synthesis*, 1981, 550–551) and methanesulfonyl chloride by the known production method] was used in place of 3-bromopentane, to provide the title compound as a white solid.

1HNMR(300 MHz, CD$_3$OD)δ:0.89(6H, t, J=7.5 Hz), 1.56 (4H, q, J=7.5 Hz),1.90(2H, t, J=8.0 Hz),3.20–3.60(9H, m), 7.49(1H, s),7.78(1H, s)

ESI-MS Found:m/z 383.1[M+H]$^+$

EXAMPEL 51

Production of 5-chloro-2-[((1R,3S)-3-hydroxy-1-methylbutyl)sulfanyl]-6-(piperazin-1-yl)benzimidazole dihydrochloride Reactions were conducted by the method similar to Example 1, except that (1S,3S)-3-[(tert-butyldimethylsilyl)oxy]-1-methylbutyl methanesulfonate [which was prepared from (2S,4S)-4-{[tert-butyldimethylsilyl]oxy}-2-pentanal (Production Example C given later) and methanesulfonyl chloride by the known production method] was used in place of 3-bromopentane, to provide the title compound as a pale yellow, amorphous substance.

1HNMR(300 MHz, CD$_3$OD)δ:1.22(3H, d, J=6.2 Hz), 1.53(3H, d, J=6.7 Hz),1.73–1.98(2H, m),3.26–3.50(8H, m), 3.89–4.18(2H, m),7.52(1H, s),7.82(1H, s)

ESI-MS Found:m/z 355.1[M+H]$^+$

PRODUCTION EXAMPLE C

Production method of (2S,4S)-4-[(tert-butyldimethylsilyl)oxy]-2-pentanal

To a solution of 1.07 g of (2R,4R)-2,4-pentanediol in tetrahydrofuran (20 ml), 500 mg of sodium hydride was added at 0° C. in nitrogen atmosphere and stirred for 2 hours at room temperature. To the solution 1.81 g of tert-butyldimethylsilyl chloride was added, and the stirring was continued for further 2 hours at the same temperature. The reaction solution was diluted with ether and successively washed with 2N aqueous sodium carbonate solution and saturated brine, dried on anhydrous sodium sulfate and the solvent was distilled off. The residue was separated and purified on silica gel column chromatography (ethyl acetate/hexane=1/10) to provide 1.93 g of the title compound.

EXAMPLE 52

Production of 5-chloro-2-[((1S,3S)-3-hydroxy-1-methylbutyl)sulfanyl]-6-(piperazin-1-yl)benzimidazole dihydrochloride Reactions were conducted by the method similar to Example 1, except that (1R,3S)-3-{[tert-butyldimethylsilyl]

oxy}-1-methylbutyl methanesulfonate [which was prepared from (2R,4S)-4-{[tert-butyldimethylsilyl]oxy}-2-pentanal (Production Example D given later) and methanesulfonyl chloride by the known production method] was used in place of 3-bromopentane, to provide the title compound as a pale yellow, amorphous substance.

1HNMR(300 MHz, CD$_3$OD)δ:1.25(3H, d, J=6.2 Hz), 1.56(3H, d, J=6.9 Hz),1.75–2.00(2H, m),3.22–3.50(8H, m), 3.92–4.22(2H, m),7.51(1H, s),7.80(1H, s)

ESI-MS Found:m/z 355.1[M+H]$^+$

PRODUCTION EXAMPLE D

Production method of (2R,4S)-4-[(tert-butyldimethylsilyl)oxy]-2-pentanal

To a solution of 446 mg of (2S,4S)-4-[(tert-butyldimethylsilyl)oxy]-2-pentanal of Production Example C, 0.15 ml of acetic acid and 640 mg of triphenylphosphine in tetrahydrofuran (4 ml), 0.55 ml of diisopropyl azodicarboxylate was added at 0° C. in nitrogen atmosphere, and stirred for 2 hours at room temperature. The solution was concentrated under reduced pressure, and the residue was purified on silica gel column chromatography (hexane/ethyl acetate=20/1) to provide 381 mg of (1S,3S)-3-[(tert-butylmethylsilyl)oxy]-1-methylbutylacetate. To a solution of 81 mg of this compound in methanol (2 ml), 64 mg of potassium carbonate was added and stirred for 6 hours at room temperature. Water was added to the solution which then was extracted with ether. The ether layer was dried on anhydrous magnesium sulfate, and concentrated under reduced pressure to provide 62 mg of the title compound.

EXAMPLE 53

Production of 5-chloro-2-[((1S,3R)-3-hydroxy-1-methylbutyl)sulfanyl]-6-(piperazin-1-yl) benzimidazole dihydrochloride Reactions were conducted by the method similar to Example 1, except that (1R,3R)-3-[(tert-butyldimethylsilyl) oxy]-1-methylbutyl methanesulfonate [which was prepared from (2R,4R)-4-[(tert-butyldimethylsilyl)oxy]-2-pentanal (Production Example E given later) and methanesulfonyl chloride by the known production method] was used in place of 3-bromopentane, to provide the title compound as a pale yellow, amorphous substance.

1HNMR(300 MHz, CD$_3$OD)δ:1.22(3H, d, J=6.2 Hz), 1.53(3H, d, J=6.7 Hz),1.73–1.98(2H, m),3.26–3.50(8H, m), 3.89–4.18(2H, m),7.52(1H, s),7.82(1H, s)

ESI-MS Found:m/z 355.1[M+H]$^+$

PRODUCTION EXAMPLE E

Production method of (2R,4R)-4-[(tert-butyldimethylsilyl)oxy]-2-pentanal

The title compound was obtained through the operations similar to those in Production Example C except that (2S, 4S)-2,4-pentanediol was used in place of (2R,4R)-2,4-pentanediol.

EXAMPLE 54

Production of 5-chloro-2-[((1R,3R)-3-hydroxy-1-methylbutyl)sulfanyl]-6-(piperazin-1-yl) benzimidazle dihydrochloride Reactions were conducted by the method similar to Example 1, except that (1S,3R)-3-[(tert-butyldimethylsilyl) oxy]-1-methylbutyl methanesulfonate [which was prepared from (2S,4R)-4-{[tert-butyldimethylsilyl]oxy}-2-pentanal (Production Example F given later) and methanesulfonyl chloride by the known production method] was used in place of 3-bromopentane, to provide the title compound as a pale yellow, amorphous substance.

1HNMR(300 MHz, CD$_3$OD)δ:1.25(3H, d, J=6.2 Hz), 1.56(3H, d, J=6.9 Hz),1.75–2.00(2H, m),3.22–3.50(8H, m), 3.92–4.22(2H, m),7.51(1H, s),7.80(1H, s)

ESI-MS Found:m/z 355.1[M+H]$^+$

PRODUCTION EXAMPLE F

Production method of (2S,4R)-4-[(tert-butyldimethylsilyl)oxy]-2-pentanal

The title compound was obtained through the operations similar to those in Production Example D except that (2R,4R)-4-[(tert-butyldimethylsilyl)oxy]-2-pentanal (the compound of Production Example E) was used in place of (2S,4S)-4-[(tert-butyldimethylsilyl)oxy]-2-pentanal.

EXAMPLE 55

Production of 5-chloro-2-[(1-ethyl-3-methyl-3-hydroxybutyl)sulfanyl]-6-(piperazin-1-yl) bezimidazole dihydrochloride Reactions were conducted by the method similar to Example 1, except that 1-ethyl-3-hydroxy-3-methylbutyl methanesulfonate [which was prepared from 1-ethyl-3-hydroxy-3-methylbutanol (a compound described in JP Hei 11 (1999)-199860A) and methanesulfonyl chloride by the known production method] was used in place of 3-bromopentane, to provide the title compound as a colorless amorphous substance.

1HNMR(300 MHz, CD$_3$OD)δ:1.11(3H, t, J=7.3 Hz), 1.31 (3H,S),1.32(3H, s),1.73–2.04(2H, m),2.05–2.10(2H, m), 3.30–3.48(8H, m),3.98–4.08(1H, m),7.46(1H, m),7.77(1H, m)

ESI-MS Found:m/z 383.1[M+H]$^+$

EXAMPLE 56

Production of 5-chloro-2-[(cyclohexylmethyl) sulfanyl]-6-(piperazin-1-yl)benzimidazole Reactions were conducted by the method similar to Example 1, except that bromomethylcyclohexane was used in place of 3-bromopentane, to provide the title compound as a colorless amorphous substance.

1HNMR(300 MHz, CDCl$_3$)δ:0.96–1.22(2H, m), 1.14–1.33(4H, m),1.57–1.78(4H, m),1.81–1.94(2H, m), 3.00–3.10(4H, m)3.10–3.16(4H, m),3.24(2H, d, J=6.6 Hz), 7.15–7.25(2H, m),7.54(1H, brs)

ESI-MS Found:m/z 365.2[M+H]$^+$

EXAMPLE 57

Production of 5-chloro-2-[(1-methylpiperidin-4-yl) sulfanyl]-6-(piperazin-1-yl)benzimidzole trihydrochloride To a solution of 45 mg of the compound as obtained in Production Example 1, 28 mg of N-methyl-4-hydroxypiperidine and 200 mg of triphenylphosphine in 2 ml of tetrahydrofuran, 0.15 ml of diisopropyl azodicarboxylate was added in nitrogen atmosphere, and stirred for 17.5 hours at room temperature. After distilling the solvent off under reduced pressure, the residue was separated and purified on silica gel chromatography (chloroform/methanol=10/1) to provide 25 mg of 6-(4-tert-butoxycarbonylpiperazin-1-yl)-5-chloro-2-[(1-methylpiperidin-4-yl)sulfanyl]benzimidazole. To 25 mg of this compound, 10% hydrogen chloride-in-methanol solution (2 ml) was added, stirred for 14 hours at room temperature, and the solvent was distilled off under reduced pressure. The residue was successively washed with chloroform and ethyl acetate, to provide 24 mg of the title compound as a colorless, amorphous substance.

1HNMR(300 MHz,DMSO-$d_6$)δ:1.58–1.78(1H, m), 1.82–2.08(2H, m),2.22–2.40(1H, m),2.61–2.81(4H, m), 2.89–3.50(12H, m),7.26(1H, s),7.60(1H, s),9.28(1H, brs), 9.35(1H, brs),10.77(1H, brs)

ESI-MS Found:m/z 366.1[M+H]$^+$

EXAMPLE 58

Production of 5-chloro-2-{[2-methoxy-(1-methoxymethyl)ethyl]-sulfanyl}-6-(piperazin-1-yl) benzimidazole dihydrochloride Reactions were conducted by the method similar to Example 57 except that 1,3-dimethoxy-2-propanol was used in place of N-methyl-4-hydroxypiperidine, to provide the title compound as a colorless amorphous substance.

1HNMR(300 MHz, CD$_3$OD)δ:3.34(6H, s),3.32–3.40(4H, m), 3.41–3.49(4H, m),3.74(1H, dd, J=6.4,10.1 Hz), 3.81 (2H, dd, J=4.5,10.1 Hz),4.10–4.19(1H, m),7.50(1H, s), 7.82 (1H, s)

ESI-MS Found:m/z 371.1[M+H]$^+$

EXAMPLE 59

Production of 5-chloro-6-(piperazin-1-yl)-2-[(tetrahydro-3-furanyl)sulfanyl]benzimidazole dihydrochloride Reactions were conducted by the method similar to Example 57 except that 3-hydroxytetrahydrofuran was used in place of N-methyl-4-hydroxypiperidine, to provide the title compound as a colorless amorphous substance.

1HNMR(300 MHz, CDCl$_3$)δ:1.96–2.10(1H, m), 2.42–2.58(1H, m),2.42–2.58(1H, m),2.91–3.15(8H, m), 3.83–3.92(2H, m),3.96–4.04(1H, m),4.20–4.28(1H, m), 4.32–4.45(1H, m),7.20–7.35(1H, brs),7.48–7.62(1H, brs)

ESI-MS Found:m/z 339.1[M+H]$^+$

EXAMPLE 60

Production of 5-chloro-2-{[2-ethoxy-1-(ethoxymethyl)ethyl]sulfanyl}-6-(piperazin-1-yl) benzimidazol dihydrochloride Reactions were conducted by the method similar to Example 57 except that 1,3-diethoxy-2-propanol was used in place of N-methyl-4-hydroxypiperidine, to provide the title compound as a colorless amorphous substance.

1HNMR(300 MHz, CD$_3$OD)δ:1.02(6H, t, J=7.0 Hz), 3.32–3.54(12H, m),3.78(2H, dd, J=6.6,10.2 Hz), 3.87(2H, dd, J=4.4,10.2 Hz),4.18–4.28(1H, m),7.54(1H, s), 7.82(1H, s)

ESI-MS Found:m/z 399.1[M+H]$^+$

EXAMPLE 61

Production of 5-chloro-2-{[4-(ethoxycarbonyl) cyclohexyl]sulfanyl}-6-(piperazin-1-yl)benzimidazol dihydrochloride Reactions were conducted by the method similar to Example 57 except that ethyl 4-hydroxycyclohexanecarboxylate was used in place of N-methyl-4-hydroxypiperidine, to provide the title compound as a colorless amorphous substance.

1HNMR(300 MHz, CD$_3$OD)δ:1.20–1.28(3H, m), 1.58–2.62(9H, m),3.32–3.40(4H, m),3.40–3.48(4H, m), 3.50–3.70(1H, m),4.04–4.18(2H, m),7.48(1H, s),7.80(1H,S)

ESI-MS Found:m/z 423.1[M+H]$^+$

EXAMPLE 62

Production of 5-chloro-2-{[1-(ethoxycarbonyl) piperidin-4-yl]sulfanyl}-6-(piperazin-1-yl) benzimidazole dihydrochloride Reactions were conducted by the method similar to Example 57 except that ethyl 4-hydroxy-1-piperidinecarboxylate was used in place of N-methyl-4-hydroxypiperidine, to provide the title compound as a colorless amorphous substance.

1HNMR(300 MHz, CD$_3$OD)δ:1.24(3H, t, J=7.1 Hz), 1.61–1.78(2H, m),2.09–2.20(2H, m),3.02–3.22(2H, m), 3.32–3.38(4H, m),3.41–3.49(4H, m),4.00–4.17(5H, m), 7.51(1H, s),7.83(1H, s)

ESI-MS Found:m/z 424.0[M+H]$^+$

EXAMPLE 63

Production of 5-chloro-2-[((1R,4R)-1,4-dihydroxyoctahydro-2-pentalenyl)sulfanyl]-6-(piperazin-1-yl)-benzimidazole dihydrochloride Reactions were conducted by the method similar to Example 57 except that isomannide was used in place of N-methyl-4-hydroxypiperidine, to provide the title compound as a colorless amorphous substance.

1HNMR(300 MHz, CD$_3$OD)δ:3.20–3.47(8H, m), 3.58–3.65(1H, m),3.83–3.92(1H, m),3.98–4.09(1H, m), 4.20–4.47(3H, m),4.55–4.62(1H, m),4.63–4.68(1H, m), 7.43(1H, s),7.74(1H, s)

ESI-MS Found:m/z 397.1[M+H]$^+$

EXAMPLE 64

Production of 5-chloro-2-[(1-methylpiperidin-3-yl) sulfanyl]-6-(piperazin-1-yl)benzimidazole dihydrochloride Reactions were conducted by the method similar to Example 57 except that 3-hydroxy-1-methylpiperidine was used in place of N-methyl-4-hydroxypiperidine, to provide the title compound as a pale brown, oily substance.

1HNMR(300 MHz, CD$_3$OD)δ:1.90–2.30(3H, m), 2.40–2.60(1H, m),3.07(3H, s),3.20–3.55(8H, m), 3.70–4.20 (5H, m),7.57(1H, s),7.83(1H, s)

ESI-MS Found:m/z 366.1[M+H]$^+$

EXAMPLES 65–66

Production of 5-chloro-2-[(2-dimethylamino-2-methylethyl)sulfanyl]-6-(piperazin-1-yl) benzimidazole trihydrochloride and 5-chloro-2-[(2-dimethylamino-1-methylethyl)sulfanyl]-6-(piperazin-1-yl)-benzimidazole trihydrochloride To a solution of 309 mg of 1-dimethylamino-2-propanol in 15 ml of chloroform, 0.50 ml of triethylamine and methanesulfonyl chloride were successively added in nitrogen atmosphere under cooling with ice, followed by 19 hours' stirring at room temperature. The reaction liquid was diluted with chloroform and washed successively with saturated aqueous sodium hydrogencarbonate solution and saturated brine, dried on anhydrous magnesium sulfate and the solvent was distilled off. To the residue as dissolved in 2 ml of dimethylformamide, 107 mg of the compound as obtained in Production Example 1, 60 mg of potassium carbonate and 70 mg of potassium iodide were added, and stirred for 18 hours at 80° C. The reaction liquid was diluted with ether, washed successively with water and saturated brine, dried on anhydrous magnesium sulfate and the solvent was distilled off. The residue was separated and purified on preparative thin-layer chromatography (Kieselgel™ 60F$_{254}$, Art.5744 (Merck); chloroform/methanol=10/1) to provide 52 mg of 6-[4-(tert-butoxycarbonyl)piperazin-1-yl]-5-chloro-2-[(2-dimethylamino-2-methylethyl)sulfanyl] benzimidazole and 15 mg of 6-[4-(tert-butoxycarbonyl) piperazin-1-yl]-5-chloro-2-[(2-dimethylamino-1-methylethyl)sulfanyl]benzimidazole.

To each of said two compounds, 4N hydrochloric acid-ethyl acetate solution was added and stirred for 14 hours at room temperature. The solvent was distilled off to provide 33 mg of the title compound, 5-chloro-2-[(2-dimethylamino-2-methylethyl)-sulfanyl]-6-(piperazin-1-yl)benzimidazole trihydrochloride as a pale yellow, oily substance and 12 mg of 5-chloro-2-[(2-dimethylamino-1-methylethyl)sulfanyl]-6-(piperazin-1-yl)benzimidazole trihydrochloride as a pale yellow, oily substance.

COMPOUND OF EXAMPLE 65

5-Chloro-2-[(2-dimethylamino-2-methylethyl) sulfanyl]-6-(piperazin-1-yl) benzimidazole trihydrochloride 1HNMR(200 MHz, CD$_3$OD)δ:1.50(3H, d.J=6.6 Hz), 2.93 (6H, s),3.20–3.50(8H, m),3.60(1H, m),3.90(2H, m), 7.50 (1H, s),7.78(1H, s)

ESI-MS Found:m/z 354.1[M+H]$^+$

COMPOUND OF EXAMPLE 66

5-Chloro-2-[(2-dimethylamino-1-methylethyl) sulfanyl]-6-(piperazin-1-yl) benzimidazole trihydrochloride 1HNMR(200 MHz, CD$_3$OD)δ:1.55(3H, d, J=7.0 Hz), 3.04(6H, s),3.20–3.50(8H, m),3.60(2H, m),4.25(1H, m), 7.50(1H, s),7.79(1H, s)

ESI-MS Found:m/z 354.1[M+H]$^+$

EXAMPLES 67–68

Production of 5-chloro-2-[(2-methyl-2-morpholinoethyl)sulfanyl]-6-(piperazin-1-yl) benzimidazole trihydrochloride and 5-chloro-2-[(1-methyl-2-morpholinoethyl)sulfanyl]-6-(piperazin-1-yl) benzimidazole trihydrochloride Reactions were conducted by the method similar to Example 65, except that N-(2-hydroxypropyl)morpholine was used in place of 1-dimethylamino-2-propanol, to provide 5-chloro-2-[(2-methyl-2-morpholinoethyl)sulfanyl]-6-(piperazin-1-yl)benzimidazole trihydrochloride as a pale brown, amorphous substance and 5-chloro-2-[(1-methyl-2-morpholinoethyl)sulfanyl]-6-(piperazin-1-yl)benzimidazole trihydrochloride as a pale brown, oily substance.

COMPOUND OF EXAMPLE 67

5-chloro-2-[(2-methyl-2-morpholinoethyl)sulfanyl]-6-(piperazin-1-yl)benzimidazole trihydrochloride 1HNMR(200 MHz, CD$_3$OD)δ:1.56(3H, d, J=6.6 Hz), 3.20–3.50(12H, m),3.64(1H, dd, J=9.4,13.6 Hz),3.83(1H, m), 4.03(4H, m),4.18(1H, dd, J=2.5,13.6 Hz),7.52(1H, s),7.82(1H, s)

ESI-MS Found:m/z 396.1[M+H]$^+$

COMPOUND OF EXAMPLE 68

5-chloro-2-[(1-methyl-2-morpholinoethyl)sulfanyl]-6-(piperazin-1-yl)-benzimidazole trihydrochloride 1HNMR(300 MHz, CD$_3$OD)δ:1.60(3H, d, J=6.9 Hz), 3.20–3.75(15H, m,),4.03(4H, t, J=4.6 Hz),7.53(1H, s), 7.84 (1H, s)

ESI-MS Found:m/z 396.1[M+H]$^+$

EXAMPLES 69~70

Production of 5-chloro-2-[(2-dimethylamino-2,2-dimethylethyl)-sulfanyl]-6-(piperazin-1-yl) benzimidazole trihydrochloride and 5-chloro-2-[(2-dimethylamino-1,1-dimethylethyl)sulfanyl]-6-(piperazin-1-yl) benzimidazole trihydrochloride Reactions were conducted by the method similar to Example 65, except that 2-dimethylamino-2-methyl-1-propanol was used in place of 1-dimethylamino-2-propanol, to provide the title compounds both as pale yellow, oily substances.

COMPOUND OF EXAMPLE 69

5-chloro-2-[(2-dimethylamino-2,2-dimethylethyl) sulfanyl]-6-(piperazin-1-yl) benzimidazole trihydrochloride 1HNMR(200 MHz, CD$_3$OD)δ:1.55(6H, s),2.96(6H, s), 3.30–3.50(8H, m),3.95(2H, s),7.51(1H, m),7.79(1H, m)

ESI-MS Found:m/z 368.1[M+H]$^+$

COMPOUND OF EXAMPLE 70

5-chloro-2-[(2-dimethylamino-1,1-dimethylethyl) sulfanyl]-6-(piperazin-1-yl)benzimidazole trihydrochloride 1HNMR(200 MHz, CD$_3$OD)δ:1.57(6H, s),3.13(6H, s), 3.20–3.50(8H, m),3.67(2H, s),7.47(1H, s),7.76(1H, s)

ESI-MS Found:m/z 368.1[M+H]$^+$

EXAMPLES 71~72

Production of 5-chloro-2-[(2,2-dimethyl-2-morpholinoethyl)sulfanyl]-6-(piperazin-1-yl) benzimidazole trihydrochloride and 5-chloro-2-[(1, 1-dimethyl-2-morpholinoethyl)sulfanyl]-6-(piperazin-1-yl)benzimidazole trihydrochloride Reactions were conducted by the method similar to Example 65, except that 2-methyl-1-morpholino-2-propanol was used in place of 1-dimethylamino-2-propanol, to provide the title compounds both as pale yellow, oily substances.

COMPOUND OF EXAMPLE 71

5-chloro-2-[(2,2-dimethyl-2-morpholinoethyl) sulfanyl]-6-(piperazin-1-yl)benzimidazole trihydrochloride 1HNMR(300 MHz, CD$_3$OD)δ:1.62(6H, s),3.25–3.50 (10H, m), 3.55–3.70(2H, m),3.90–4.20(2H, m),4.10(2H, s),7.59(1H, s), 7.81(1H, s)

ESI-MS Found:m/z 410.1[M+H]+

COMPOUND OF EXAMPLE 72

5-chloro-2-[(1,1-dimethyl-2-morpholinoethyl) sulfanyl]-6-(piperazin-1-yl)benzimidazole trihydrochloride ESI-MS Found:m/z 410.1[M+H]+

EXAMPLE 73

Production of 2-[(3-amino-3-methylbutyl)sulfanyl]-5-chloro-6-(piperazin-1-yl)benzimidazole trihydrochloride 1) 2-[(3-Azido-3-methylbutyl)sulfanyl]-5-chloro-6-(4-tert-butoxycarbonylpiperazin-1-yl)benzimidazole To a solution of 63 mg of the compound as obtained in Production Example 1 in 2 ml of dimethylformamide, 47 mg of potassium carbonate, 28 mg of potassium iodide and 39 mg of 3-azido-3-methylbutyl methanesulfonate [which compound was prepared from 3-azido-3-methylbutanol (*J. Org. Chem.*, 1986, 51, 4856–4861) and methanesulfonyl chloride by the known production process] were successively added in nitrogen atmosphere, and stirred for 17.5 hours at 80° C. The reaction liquid was cooled to room temperature, water was added thereto, and the reaction liquid was extracted with ethyl acetate. The ethyl acetate layer was washed with saturated brine and dried on anhydrous sodium sulfate. After distilling the solvent off under reduced pressure, the residue was separated and purified on silica gel column chromatography (ethyl acetate/hexane=1/3) to provide 70 mg of 2-[(3-azido-3-methylbutyl)sulfanyl]-5-chloro-6-[4-(tert-butoxycarbonyl)piperazin-1-yl]benzimidazole as a pale yellow, oily substance.

2) 2-[(3-Amino-3-methylbutyl)sulfanyl]-5-chloro-6-(piperazin-1-yl)benzimidazole trihydrochloride To a solution of 41 mg of the compound as obtained in 1) above in 2 ml of tetrahydrofuran, 12 mg of lithium aluminum hydride was added under cooling with ice, in nitrogen atmosphere, and stirred for 2 hours at 0° C. To the reaction liquid 120 mg of sodium sulfate decahydrate was added, followed by 14 hours' stirring at room temperature, and the insoluble matter was filtered off. The filtrate was concentrated under reduced pressure, and the residue was separated and purified by preparative thin-layer chromatography [Kieselgel™ 60F$_{254}$, Art. 5744 (Merck); chloroform/methanol=10/1] to provide 27 mg of 2-[(3-amino-3-methylbutyl)sulfanyl]-5-chloro-6-(4-tert-butoxycarbonylpiperazin-1-yl)benzimidazole as a colorless oily substance. To 27 mg of said compound 10% hydrogen chloride-in-methanol solution (1 ml) was added, stirred for 14 hours at room temperature, and the solvent was distilled off under reduced pressure to provide 25 mg of the title compound as a white solid.

1HNMR(300 MHz, CD$_3$OD)δ:1.44(6H, s),2.10–2.22(2H, m), 3.20–3.49(8H, m),3.49–3.70(2H, m).7.55(1H, s),7,82 (1H, s)

ESI-MS Found:m/z 354.3[M+H]+

PRODUCTION EXAMPLE 4

Production of 5-[4-(tert-butoxycarbonyl)piperazin-1-yl]-1,3-dihydro-2H-imidazo[4,5-b]pyridin-2-thione 1) 2-Amino-5-[4-(tert-butoxycarbonyl)piperazin-1-yl]-3-nitropyridine A suspension of 350 mg of 2-amino-6-chloro-3-nitropyridine, 744 mg of N-(tert-butoxycarbonyl)piperazine and 552 mg of potassium carbonate in 4 ml of N-methylpyrrolidone was stirred in nitrogen atmosphere for 15 minutes at 160° C. The suspension was cooled to room temperature, to which 10 ml of water was added. Whereupon formed solid was recovered by filtration, washed with hexane and dried to provide 323 mg of the title compound.

2) 2,3-Diamino-5-[4-(tert-butoxycarbonyl)piperazin-1-yl] pyridine

To a suspension of 323 mg of the compound as obtained in 1) above in 6 ml of ethanol, 30 mg of 10% palladium-on-carbon catalyst was added and stirred in hydrogen atmosphere for 15 hours, at ambient temperature and pressure. The reaction liquid was filtered with Celite, and the filtrate was distilled under reduced pressure to provide 300 mg of the title compound.

3) 5-[4-(Tert-butoxycarbonyl)piperazin-1-yl]-1,3-dihydro-2H-imidazo[4,5-b]pyridin-2-thione Three-hundred (300) mg of the compound as obtained in 2) above was dissolved in 20 ml of ethanol, and to the solution 4 ml of 1M aqueous sodium hydroxide solution and 2 ml of carbon disulfide were added, followed by 2 hours' stirring at 85° C. The reaction liquid was cooled to room temperature, to which then water was added. Whereupon precipitated yellow solid was separated by filtration, and the crystals so obtained were washed with water and hexane, and dried to provide 140 mg of the title compound as a yellow solid.

EXAMPLE 74

Production of 6-chloro-2-[(1-ethylpropyl)sulfanyl]-5-(piperazin-1-yl-imidazo[4,5-b]pyridine dihydrochloride 1) 5-[4-(Tert-butoxycarbonyl)piperazin-1-yl]-2-(1-ethylpropyl)sulfanyl-imidazo[4,5-b]pyridine To a solution of 140 mg of the compound as obtained in Production Example 4 in 2 ml of dimethylformamide, 83 mg of potassium carbonate and 0.07 ml of 3-bromopentane were successively added in nitrogen atmosphere, and stirred for 2 hours at 80° C. The reaction liquid was cooled to room temperature, to which water was added, followed by extraction with ethyl acetate. The ethyl acetate layer was washed with saturated brine and dried on anhydrous sodium sulfate. After distilling the solvent off under reduced pressure, the residue was separated and purified on silica gel column chromatography (ethyl acetate/hexane=1/3) to provide 150 mg of the title compound as a pale yellow solid.

2) 5-[4-(Tert-butoxycarbonyl)piperazin-1-yl]-6-chloro-2-[(1-ethylpropyl)sulfanyl]-imidazo[4,5-b]pyridine To a solution of 40 mg of the compound as obtained in 1) above in 2 ml of dichloroethane, 16 mg of N-chlorosuccinimide was added and heated under reflux for an hour at 85° C. Cooling the reaction liquid to room temperature, ethyl acetate was added thereto, followed by successive washing with saturated aqueous sodium hydrogencarbonate solution and saturated brine. The ethyl acetate layer was dried on anhydrous magnesium sulfate, and the solvent was distilled off. The residue was separated and purified on preparative thin-layer chromatography (Kieselgel™ 60F$_{254}$, Art. 5744 (Merck); hexane/ethyl acetate=3/1) to provide 45 mg of the title compound.

3) 6-Chloro-2-[(1-ethylpropyl)sulfanyl]-5-piperazin-1-yl-imidazo[4,5-b]pyridine dihydrochloride To 45 mg of the compound as obtained in 2) above, 10% hydrogen chloride-in-methanol solution (20 ml) was added and stirred for 3 hours at room temperature. The solvent was distilled off under reduced pressure to provide 35 mg of the title compound as a colorless amorphous substance.

1HNMR(300 MHz, CD$_3$OD)δ:0.96(6H, t, J=7.3 Hz), 1.60–1.85(4H, m),3.20–3.31(4H, m),3.32–3.41(4H, m), 3.81(1H, quinted, J=6.4 Hz),7.96(1H, s),9.08–9.22(1H, brs)

ESI-MS Found:m/z 340.0[M+H]$^+$

EXAMPLE 75

Production of 5-chloro-6-(4-ethylpiperazin-1-yl)-2-[(1-ethylpropyl)sulfanyl]benzimidazole dihydrochloride To a solution of 34 mg of the compound as obtained in Example 1 in 2 ml of methanol and 2 ml of tetrahydrofuran, 0.08 ml of acetaldehyde and 1 ml of advancedly formulated 0.3M methanol solution of sodium cyanoborohydride and zinc chloride (1:0.5 in molar ratio) were added at room temperature, and stirred for an hour at the same temperature. The reaction liquid was diluted with ethyl acetate, and the organic layer was successively washed with saturated sodium hydrogencarbonate solution and saturated brine, followed by drying on anhydrous sodium sulfate and distilling the solvent off under reduced pressure. The residue was separated and purified on preparative thin-layer chromatography (Kieselgel™ 60F$_{254}$, Art. 5744 (Merck); chloroform/methanol/aqueous ammonia=50/10/1) to provide 24 mg of 5-chloro-6-(4-ethylpiperazin-1-yl)-2-[(1-ethylpropyl)sulfanyl]benzimidazole. To 24 mg of this compound, 2 ml of 10% hydrogen chloride-in-methanol solution was added, stirred for 5 minutes at room temperature, and the solvent was distilled off under reduced pressure to provide 29 mg of the title compound as a white solid.

1HNMR(300 MHz, CD$_3$OD)δ:1.08(6H, t, J=7.4 Hz), 1.42 (3H, t, J=7.3 Hz),1.69–2.01(4H, m),3.14–3.44(6H, m), 3.54–3.89(5H, m),7.51(1H, s),7.80(1H, s)

ESI-MS Found:m/z 367.1[M+H]$^+$

EXAMPLE 76

Production of 5-chloro-2-[(1-ethylpropyl)sulfanyl]-6-(4-methylpiperazin-1-yl)benzimidazole Reactions were conducted by the method similar to Example 75, except that formaline was used in place of acetaldehyde, to provide the title compound as a white solid.

1HNMR(300 MHz, CDCl$_3$)δ:1.00(6H, t, J=7.4 Hz), 1.62–1.89(4H, m),2.44(3H, s),2.54–2.90(4H, m), 2.94–3.20 (4H, m),3.70–3.84(1H, m),7.00–7.80(2H, m)

ESI-MS Found:m/z 353.1[M+H]$^+$

EXAMPLE 77

Production of 5-chloro-2-[(1-ethylpropyl)sulfanyl]-6-(4-isopropylpiperazin-1-yl)benzimidazole dihydrochloride Reactions were conducted by the method similar to Example 75, except that acetone was used in place of acetaldehyde, to provide the title compound as a white solid.

1HNMR(300 MHz, CD$_3$OD)δ:1.09(6H, t, J=7.3 Hz), 1.46 (6H, d, J=6.7 Hz),1.71–2.00(4H, m),3.20–3.44(4H, m), 3.50–3.72(5H, m),3.80–3.93(1H, m),7.54(1H, s),7.82(1H, s)

ESI-MS Found:m/z 381.2[M+H]$^+$

EXAMPLE 78

Production of 5-chloro-6-[4-(cyclopropylmethyl) piperazin-1-yl]-2-[(1-ethylpropyl)sulfanyl] benzimidazole dihydrochloride Reactions were conducted by the method similar to Example 75, except that cyclopropanecarboxyaldehyde was used in place of acetaldehyde, to provide the title compound as a white solid.

1HNMR(300 MHz, CD$_3$OD)δ:0.40–0.60(2H, m), 0.72–0.85(2H, m),1.09(6H, t, J=7.4 Hz),1.10–1.34(1H, m), 1.69–2.00(4H, m),3.18(2H, d, J=7.5 Hz),3.20–3.43(4H, m), 3.50–3.64(2H, m),3.74–3.90(3H, m),7.53(1H, s),7.82(1H, s)

ESI-MS Found:m/z 393.2[M+H]$^+$

EXAMPLE 79

Production of 5-chloro-2-[(1-ethylpropyl)sulfanyl]-6-{4-[2-hydroxy-1-(hydroxymethyl)ethyl]piperazin-1-yl}benzimidazole dihydrochloride Reactions were conducted by the method similar to Example 75, except that dihydroxyacetone was used in place of acetaldehyde, to provide the title compound as a colorless amorphous substance.

1HNMR(300 MHz, CD$_3$OD)δ:1.08(6H, t, J=7.3 Hz), 1.70–1.98(4H, m),3.20–3.67(9H, m),3.70–4.63(4H, m), 4.08–4.20(1H, m),7.51(1H, s),7.81(1H, s)

ESI-MS Found:m/z 413.1[M+H]$^+$

EXAMPLE 80

Production of 5-chloro-2-[(1-ethylpropyl)sulfanyl]-6-[4-(1,3-thiazol-2-ylmethyl)piperazin-1-yl] benzimidazole Reactions were conducted by the method similar to Example 75, except that 2-formylthiazole was used in place of acetaldehyde, to provide the title compound as a yellow solid.

1HNMR(300 MHz, CDCl$_3$)δ:1.00(6H, t, J=7.3 Hz), 1.63–1.85(4H, m),2.75–2.84(4H, m),3.00–3.13(4H, m), 3.70–3.82(1H, m),3.98(2H, s),6.90–7.76(2H, m), 7.31(1H, d, J=3.3 Hz),7.75(1H, d, J=3.3 Hz),9.98–10.20(1H, m)

ESI-MS Found:m/z 436.1[M+H]$^+$

EXAMPLE 81

Production of 5-chloro-2-[(1-ethylpropyl)sulfanyl]-6-[(4-(1H)-imidazol-2-ylmethyl)piperazin-1-yl] benzimidazole trihydrochloride Reactions were conducted by the method similar to Example 75, except that 2-formylimidazole was used in place of acetaldehyde, to provide the title compound as a colorless solid.

1HNMR(300 MHz, CD$_3$OD)δ:1.08(6H, t, J=7.3 Hz), 1.70–1.98(4H, m),3.38–3.56(8H, m),3.79–3.90(1H, m), 4.74(2H, s),7.50(1H, s),7.74(2H, s),7.81(1H, s)

ESI-MS Found:m/z 419.1[M+H]$^+$

EXAMPLE 82

Production of 5-chloro-2-[(1-ethylpropyl)sulfanyl]-6-[(4-(1H)-midazol-5-ylmethyl)piperazin-1-yl] benzimidazole trihydrochloride Reactions were conducted by the method similar to Example 75, except that 4-formylimidazole was used in place of acetaldehyde, to provide the title compound as a colorless solid.

1HNMR(300 MHz, CD$_3$OD)δ:1.08(6H, t, J=7.3 Hz), 1.69–1.96(4H, m),3.37–3.66(8H, m),3.75–3.86(1H, m), 4.65(2H, s),7.49(1H, s),7.79(1H, s),7.95(1H, s),9.06(1H, s)

ESI-MS Found:m/z 419.1[M+H]$^+$

EXAMPLE 83

Production of 5-chloro-2-[(1-ethylpropyl)sulfanyl]-6-[(4-(1H)-pyrazol-3-ylmethyl)piperazine-1-yl]benzimidazole Reactions were conducted by the method similar to Example 75, except that 3-formylpyrazole was used in place of acetaldehyde, to provide the title compound as a colorless solid.

1HNMR(300 MHz, CDCl$_3$)δ:0.96(6H, t, J=7.3 Hz), 1.60–1.83(4H, m),2.61–2.76(4H, m),2.84–3.03(4H, m), 3.70(2H, s),3.68–3.81(1H, m),6.24(1H, d, J=1.7 Hz), 6.63–7.74(2H, m),7.55(1H, d, J=1.7 Hz),11.40(1H, brs)

ESI-MS Found:m/z 419.1[M+H]$^+$

EXAMPLE 84

Production of 5-chloro-6-[4-(2,6-dimethoxybenzyl)piperazin-1-yl]-2-[(1-ethylpropyl)sulfanyl]benzimidazole Reactions were conducted by the method similar to Example 75, except that 2,6-dimethoxybenzaldehyde was used in place of acetaldehyde, to provide the title compound as a colorless solid.

1HNMR(300 MHz, CDCl$_3$)δ:0.97(6H, t, J=7.3 Hz), 1.61–1.83(4H, m),2.79–2.92(4H, m),2.96–3.09(4H, m), 3.73(6H, s),3.68–3.83(1H, m),3.88(2H, s),6.54(2H, d, J=8.4 Hz), 7.21(1H, t, J=8.4 Hz),6.74–7.66(2H, m)

ESI-MS Found:m/z 489.1[M+H]$^+$

EXAMPLE 85

Production of 5-chloro-6-(4-ethylpiperazin-1-yl)-2-[(3-methoxy-1,3-dimethylbutyl)sulfanyl]benzimidazole dihydrochloride Reactions were conducted by the method similar to Example 75, except that the compound of Example 28 was used in place of the compound of Example 1, to provide the title compound as a colorless oily substance.

1HNMR(200 MHz, CD$_3$OD)δ:1.25(3H, s),1.27(3H, s), 1.42(3H, t, J=7.3 Hz),1.51(3H, d, J=6.8 Hz),1.98(2H, d, J=5.8 Hz), 3.21(3H, s),3.10–3.45(6H, m),3.50–3.80(4H, m),4.10(1H, m), 7.47(1H, s),7.76(1H, s)

ESI-MS Found:m/z 411.1[M+H]$^+$

EXAMPLE 86

Production of 5-chloro-6-(1-ethylpiperizin-4-yl)-2-[(1-ethylpropyl)sulfanyl]benzimidazole dihydrochloride Reactions were conducted by the method similar to Example 75, except that the compound of Example 21 was used in place of the compound of Example 1, to provide the title compound as a white solid.

1HNMR(300 MHz, CD$_3$OD)δ:1.08(6H, t, J=7.4 Hz), 1.42 (3H, t, J=7.3 Hz),1.70–2.00(4H, m),2.00–2.30(4H, m), 3.10–3.35(5H, m),3.44–3.61(1H, m),3.65–3.80(2H, m), 7.67(1H, s),7.78(1H, s)

ESI-MS Found:m/z 366.3[M+H]$^+$

EXAMPLE 87

Production of 5-chloro-6-(4-ethyl-1,4-diazepan-1-yl)-2-[(1-ethylpropyl)sulfanyl]benzimidazole Reactions were conducted by the method similar to Example 75, except that the compound of Example 11 was used in place of the compound of Example 1, to provide the title compound as a colorless oily substance.

1HNMR(300 MHz, CDCl$_3$)δ:0.98(6H, t, J=7.3 Hz), 1.13 (3H, t, J=7.1 Hz),1.62–1.85(4H, m),1.95–2.06(2H, m), 2.70 (2H, q, J=7.1 Hz),2.88–2.98(4H, m),3.18–3.32(4H, m), 3.73–3.83(1H, m),7.22(1H, brs),7.51(1H, brs)

ESI-MS Found:m/z 381.1[M+H]$^+$

EXAMPLE 88

Production of 5-chloro-2-[(1-ethylpropyl)sulfanyl]-6-(4-methyl-1,4-diazepan-1-yl)benzimidazole Reactions were conducted by the method similar to Example 76, except that the compound of Example 11 was used in place of the compound of Example 1, to provide the title compound as a colorless solid.

1HNMR(300 MHz, CDCl$_3$)δ:0.99(6H, t, J=7.3 Hz), 1.63–1.86(4H, m),2.02–2.13(2H, m),2.55(3H, s), 2.92–3.03 (4H, m),3.18–3.26(2H, m),3.29–3.36(2H, m), 3.74–3.84 (1H, m),7.22(1H, brs),7.52(1H, brs)

ESI-MS Found:m/z 367.1[M+H]$^+$

EXAMPLE 89

Production of 5-chloro-2-[(1-ethylpropyl)sulfanyl]-6-[4-(2-hydroxyethyl)piperazin-1-yl]benzimidazole dihydrochloride To 244 mg of the compound as obtained in Example 1, saturated aqueous sodium hydrogencarbonate solution (5 ml) was added, and the aqueous solution was extracted with chloroform. The chloroform layer was dried on anhydrous magnesium sulfate and the solvent was distilled off under reduced pressure. Thus obtained residue was dissolved in methanol (4 ml)-tetrahydrofuran (4 ml) solution, to which 0.15 ml of tert-butyldimethylsilyloxyacetaldehyde and 3 ml of an advancedly prepared 0.3M sodium cyanoborohydride and zinc chloride (1:0.5 in molar ratio) in methanol solution were added at room temperature, followed by 1.5 hours' stirring at the same temperature. The reaction liquid was diluted with ethyl acetate, and the organic layer was successively washed with saturated aqueous sodium hydrogencarbonate solution and saturated brine, dried on anhydrous sodium sulfate and the solvent was distilled off under reduced pressure. To the residue 10% hydrogen chloride-in-methanol solution (25 ml) was added. After stirring the solution for 2 hours at room temperature, the solvent was distilled off under reduced pressure. Saturated aqueous sodium hydrogencarbonate solution was added to the residue, which then was extracted with ethyl acetate. The ethyl acetate layer was dried on anhydrous magnesium sulfate, and the solvent was distilled off under reduced pressure. The residue was separated and purified on silica gel column chromatography (chloroform/methanol=8/1) to provide 5-chloro-2-[(1-ethylpropyl)sulfanyl]-6-[4-(2-hydroxyethyl)piperazin-1-yl]benzimidazole as a colorless oily substance. To said product 1 ml of 4N hydrochloric acid-ethyl acetate was added to dissolve the former, and the solvent was distilled off under reduced pressure. Upon drying, 167 mg of the title compound was obtained as a brown amorphous substance.

1HNMR(300 MHz, CD$_3$OD)δ:1.09(6H, t, J=7.4 Hz), 1.70–2.01(4H, m),3.20–3.50(6H, m),3.50–3.68(2H, m), 3.70–4.04(5H, m),7.56(1H, s),7.82(1H, s)

ESI-MS Found:m/z 383.1[M+H]$^+$

EXAMPLE 90

Production of 5-chloro-2-[(1-ethylpropyl)sulfanyl]-6-[1-(2-hydroxyethyl)piperidin-4-yl]benzimidazole dihydrochloride Reactions were conducted by the method similar to Example 89, except that the compound of Example 21 was used in place of the compound of Example 1, to provide the title compound as a pale yellow, amorphous substance.

1HNMR(300 MHz, CD$_3$OD)δ:1.09(6H, t, J=7.3 Hz), 1.72–2.00(4H, m),2.00–2.30(4H, m),3.20–3.40(3H, m), 3.44–3.65(2H, m),3.75–4.00(5H, m),7.70(1H, s),7.80(1H, s)

ESI-MS Found:m/z 382.1[M+H]$^+$

EXAMPLE 91

Production of 5-chloro-6-[4-(2-hydroxyethyl) piperazin-1-yl]-2-[(3-methoxy-1,3-dimethylbutyl) sulfanyl]benzimidazole dihydrochloride Reactions were conducted by the method similar to Example 89, except that the compound of Example 28 was used in place of the compound of Example 1, to provide the title compound as a colorless oily substance.

1HNMR(200 MHz, CD$_3$OD)δ:1.25(3H, s),1.27(3H, s), 1.51(3H, d, J=6.6 Hz),1.99(2H, d, J=6.0 Hz),3.21(3H, s), 3.3–3.85(10H, m),3.95(2H, m),4.11(1H, m),7.49(1H, s),7.78(1H, s)

ESI-MS Found:m/z 427.1[M+H]$^+$

EXAMPLE 92

Production of 5-chloro-6-[4-(2-hydroxyethyl) piperazin-1-yl]-2-[(3-methoxy-1,3-dimethylbutyl) sulfanyl]benzimidazole dihydrochloride Reactions were conducted by the method similar to Example 89, except that the compound of Example 22 was used in place of the compound of Example 1, to provide the title compound as a pale yellow, amorphous substance.

1HNMR(300 MHz, CD$_3$OD)δ:1.26(3H, s),1.29(3H, s), 1.54(3H, d, J=6.6 Hz),2.02(2H, d, J=6.0 Hz),2.12–2.26(4H, m), 3.20–3.35(4H, m),3.22(3H, s),3.49–3.64(1H, m),3.75–3.86(2H, m), 3.89–4.00(2H, m),4.14–4.25(1H, m),7.71(1H, s),7.81(1H, s)

ESI-MS Found:m/z 426.0[M+H]$^+$

EXAMPLE 93

Production of 6-chloro-2-[(1-ethylpropyl)sulfanyl]- 5-[4-(2-hydroxyethyl)piperazin-1-yl]-imidazo[4,5-b] pyridine dihydrochloride Reactions were conducted by the method similar to Example 89, except that the compound of Example 74 was used in place of the compound of Example 1, to provide the title compound as a colorless amorphous substance.

1HNMR(300 MHz, CD$_3$OD)δ:1.08(6H, t, J=7.3 Hz), 1.70–1.99(4H, m),3.31–3.49(6H, m),3.69–3.89(3H, m), 3.91–4.10(4H, m),8.15(1H, s)

ESI-MS Found:m/z 384.0[M+H]$^+$

EXAMPLE 94

Production of 5-chloro-2-[(1-ethyl-3-methyl-3- hydroxybutyl)sulfanyl]-6-[4-(2-hydroxyethyl) piperazin-1-yl]benzimidazole dihydrochloride Reactions were conducted by the method similar to Example 89, except that the compound of Example 55 was used in place of the compound of Example 1, to provide the title compound as a colorless amorphous substance.

1HNMR(300 MHz, CDCl$_3$)δ:1.09(3H, t, J=7.3 Hz),1.32 (3H, m), 1.34(3H, s),1.50–1.95(2H, m),1.97(1H, dd, J=5.2, 6.2 Hz), 2.19(1H, dd, J=4.4,5.2 Hz),2.64(2H, t, J=5.3 Hz), 2.68–2.78(4H, m), 2.90–3.10(4H, m),3.68(2H, t, J=5.3 Hz), 3.78–3.89(1H, m), 6.90–7.70(2H, m)

ESI-MS Found:m/z 427.1[M+H]$^+$

EXAMPLE 95

Production of 5-chloro-6-[4-(2-hydroxyethyl) piperazin-1-yl]-2-[(tetrahydro-2H-pyran-4-yl) sulfanyl]benzimidazole dihydrochloride Reactions were conducted by the method similar to Example 89, except that the compound of Example 33 was used in place of the compound of Example 1, to provide the title compound as a pale yellow, amorphous substance.

1HNMR(300 MHz, CD$_3$OD)δ:1.73–1.90(2H, m), 2.04–2.16(2H, m),3.20–3.50(6H, m),3.50–3.65(4H, m), 3.70–3.82(2H, m),3.90–4.20(5H, m),7.50–7.60(1H, m),7.84 (1H, s)

ESI-MS Found:m/z 397.1[M+H]$^+$

EXAMPLE 96

Production of 5-chloro-6-[4-(2-hydroxyethyl) piperazin-1-yl]-2-[(tetrahydro-2H-pyran-4-ylmethyl) sulfanyl]benzimidazole dihydrochloride Reactions were conducted by the method similar to Example 89, except that the compound of Example 40 was used in place of the compound of Example 1, to provide the title compound as a white solid.

1HNMR(300 MHz, CD$_3$OD)δ:1.25–1.50(2H, m), 1.78–2.07(3H, m), 3.20–3.50(10H, m),3.50–3.65(2H, m), 3.68–3.80(2H, m), 3.90–4.00(4H, m),7.54(1H, s),7.81(1H, s)

ESI-MS Found:m/z 411.1[M+H]$^+$

EXAMPLE 97

Production of 5-chloro-2-[(2-dimethylamino-1,1- dimethylethyl)sulfanyl]-6-[4-(2-hydroxyethyl) piperazin-1-yl]benzimidazole trihydrochloride Reactions were conducted by the method similar to Example 89, except that the compound of Example 70 was used in place of the compound of Example 1, to provide the title compound as a colorless oily substance.

1HNMR(300 MHz, CD$_3$OD)δ:1.65(6H, s),3.12(6H, s), 3.20–3.50(8H, m),3.50–3.80(4H, m),3.96(2H, m),7.64(1H, m), 7.94(1H, m)

ESI-MS Found:m/z 412.1[M+H]$^+$

EXAMPLE 98

Production of 5-chloro-2-[(1-ethylpropyl)sulfanyl]- 6-[4-(2-hydroxyethyl)-1,4-diazepan-1-yl] benzimidazole Reactions were conducted by the method similar to Example 89, except that the compound of Example 11 was used in place of the compound of Example 1, to provide the title compound as a colorless solid.

1HNMR(300 MHz, CDCl$_3$)δ:1.02(6H, t, J=7.4 Hz), 1.65–1.86(4H, m),1.97–2.07(2H, m),2.79(2H, t, J=5.3 Hz), 2.92–3.00(4H, m),3.22–3.29(4H, m),3.64(2H, t, J=5.3 Hz), 3.72–3.82(1H, m),6.88–7.80(2H, m)

ESI-MS Found:m/z 397.1[M+H]$^+$

EXAMPLE 99

Production of 5-chloro-6-[4-(2-hydroxyethyl) piperazin-1-yl]-2-[((1R,3S)-3-hydroxy-1- methylbutyl)sulfanyl]benzimidazole dihydrochloride Reactions were conducted in the manner same to Example 89, except that the compound of Example 51 was used in place of the compound of Example 1, to provide the title compound as a pale yellow, oily substance.

1HNMR(300 MHz, CD$_3$OD)δ:1.22(3H, d, J=6.2 Hz), 1.53(3H, d, J=6.7 Hz),1.75–1.98(2H, m),3.20–3.66(8H, m), 3.70–3.82(2H, m),3.90–4.18(4H, m),7.54(1H, s),7.83(1H, s)

ESI-MS Found:m/z 399.1[M+H]$^+$

EXAMPLE 100

Production of 5-chloro-6-[(1R,4S)-5-(2-hydroxyethyl)-2,5-diazabicyclo[2.2.1]heptan-2-yl]-2-[(1-ethylpropyl)sulfanyl]-benzimidazole dihydrochloride Reactions were conducted by the method similar to Example 89, except that the compound of Example 13 was used in place of the compound of Example 1, to provide the title compound as a pale brown powder.

1HNMR(300 MHz, CD$_3$OD)δ:1.08(6H, t, J=7.3 Hz), 1.68–1.97(4H, m),2.23–2.45(2H, m),3.30–3.39(1H, m), 3.41–3.53(2H, m),3.77–4.11(6H, m),4.53–4.68(2H, m), 7.35–7.40(1H, m),7.73–7.78(1H, m)

ESI-MS Found:m/z 395.1[M+H]$^+$

EXAMPLE 101

Production of 5-chloro-2-[(1,1-dimethyl-2-morpholinoethyl)sulfanyl]-6-[4-(2-hydroxyethyl) piperazin-1-yl]benzimidazole trihydrochloride Reactions were conducted by the method similar to Example 89, except that 5-chloro-2-[(1,1-dimethyl-2-morpholinoethyl)sulfanyl]-6-(piperazin-1-yl)bezimidazole trihydrochloride of Example 72 was used in place of the compound of Example 1, to provide the title compound as a colorless oily substance.

1HNMR(300 MHz, CD$_3$OD)δ:1.63(3H, s),1.64(3H, s), 3.15–3.80(12H, m),3.34(2H, s),3.90–4.00(2H, m), 4.00–4.20(4H, m),7.40–7.55(1H, m),7.75–7.85(1H, m)

ESI-MS Found:m/z 454.1[M+H]$^+$

EXAMPLE 102

Production of 5-chloro-2-[(cyclohexylmethyl) sulfanyl]-6-[4-(cyclopropylmethyl)piperazin-1-yl] benzimidazole Reactions were conducted by the method similar to Example 75, except that the compound of Example 56 was used in place of the compound of Example 1 and cyclopropanecarboxyaldehyde was used in place of acetaldehyde, to provide the title compound as a colorless amorphous substance.

1HNMR(300 MHz, CDCl$_3$)δ:0.12–0.19(2H, m), 0.56(2H, d, J=8.1 Hz),0.85–1.30(8H, m),1.55–1.94(4H, m), 2.39(2H, brs),2.80(4H, brs),3.08(4H, brs),3.23(2H, d, J=6.9 Hz), 6.95–7.70(3H, m)

ESI-MS Found:m/z 419.2[M+H]$^+$

EXAMPLE 103

Production of 5-chloro-2-[(1-ethylpropyl)sulfanyl]-6-[4-(3-hydroxypropyl)piperazin-1-yl]benzimidazole Reactions were conducted by the method similar to Example 89, except that 3-tert-butyldimethylsilyloxypropionaldehyde (which was prepared by the method as described in *J. Org. Chem.*, 1984, 49, 2301–2309) was used in place of tert-butyldimethylsilyloxyacetaldehyde, to provide the title compound as a colorless solid.

1HNMR(300 MHz, CDCl$_3$)δ:1.00(6H, t, J=7.4 Hz), 1.62–1.88(6H, m),2.64–2.85(6H, m),2.88–3.12(4H, m), 3.73–3.83(1H, m),3.87–3.97(2H, m),6.88(1H, brs),7.56(1H, brs)

ESI-MS Found:m/z 397.0[M+H]$^+$

EXAMPLE 104

Production 6-[4-(2-aminoethyl)piperazin-1-yl]-5-chloro-2-[(1-ethylpropyl)sulfanyl]benzimidazole trihydrochloride To a solution of 516 mg of the compound as obtained in Example 89 in 6 ml of tetrahydrofuran, 0.35 ml of triethylamine and 0.12 ml of methanesulfonyl chloride were added by the order stated, in nitrogen atmosphere at room temperature, and stirred for 2 hours at room temperature. Saturated aqueous sodium hydrogencarbonate solution was added to the reaction liquid which then was extracted with chloroform. The chloroform layer was washed with saturated brine and dried on anhydrous sodium sulfate. After distilling the solvent off under reduced pressure, the residue was dissolved in 6 ml of dimethylformamide, to which 411 mg of sodium azide was added. This suspension was stirred for 15.5 hours at 80° C. in nitrogen atmosphere. The reaction liquid was cooled to room temperature, diluted with water and extracted with ethyl acetate. The ethyl acetate layer was washed with saturated brine and dried on anhydrous sodium sulfate. After distilling the solvent off under reduced pressure, the residue was separated and purified on silica gel column chromatography (ethyl acetate/hexane=1/1) to provide 368 mg of 6-[1-(3-azidopropyl)piperidin-4-yl]-5-chloro-2-[(1-ethylpropyl)sulfanyl]benzimidazole. To a solution of 344 mg of this compound in 4 ml of tetrahydrofuran, 321 mg of triphenylphosphine and 0.4 ml of water were added, and stirred for 13 hours at room temperature. Then 15 ml of 10% hydrogen chloride-in-methanol solution was added to the solution, followed by washing with ethyl acetate. The aqueous layer was concentrated under reduced pressure to provide 427 mg of the title compound as a colorless solid.

1HNMR(300 MHz, CD$_3$OD)δ:1.08(6H, t, J=7 Hz), 1.70–1.99(4H, m),3.32–3.92(13H, m),7.52(1H, s),7.81(1H, s)

ESI-MS Found:m/z 382.1[M+H]$^+$

EXAMPLE 105

Production of 6-{4-[2-(acetamido)ethyl]piperazin-1-yl}-5-chloro-2-[(1-ethylpropyl)sulfanyl] benzimidazole To a solution of 50 mg of the compound as obtained in Example 104 in 2 ml of chloroform, 0.028 ml of triethylamine and 0.09 ml of acetyl chloride were added in nitrogen atmosphere by the order stated, and stirred for 1.5 hours at room temperature. Saturated aqueous carbonic acid solution was added to the solution which then was extracted with chloroform. The chloroform layer was washed with saturated brine and dried on anhydrous sodium sulfate. After distilling the solvent off under reduced pressure, 2 ml of methanol was added to the residue and so formed solution was stirred for 2 hours at 90° C. The solvent was distilled off under reduced pressure, and the residue was separated and purified on preparative thin-layer chromatography (Kieselgel™ 60F$_{254}$, Art.5744 (Merck); chloroform/methanol=9/1) to provide 22 mg of the title compound as a colorless solid.

1HNMR(300 MHz, CDCl$_3$)δ:1.01(6H, t, J=7.3 Hz), 1.64–1.87(4H, m),2.03(3H, s),2.59(2H, t, J=5.9 Hz), 2.63–2.75(4H, m),2.96–3.12(4H, m),3.37–3.47(2H, m), 3.73–3.84(1H, m),6.12–6.27(1H, m),6.90–7.76(2H, m), 9.96–10.39(1H, m)

ESI-MS Found:m/z 424.1[M+H]$^+$

EXAMPLE 106

Production of 6-{4-[2-(methanesulfonylamino)ethyl]piperazin-1-yl}-5-chloro-2-[(1-ethylpropyl)sulfanyl]benzimidazole To a solution of 50 mg of the compound as obtained in Example 104 in 2 ml of chloroform, 0.029 ml of triethylamine and 0.10 ml of methanesulfonyl chloride were added in nitrogen atmosphere by the order stated, and stirred for 3 hours at room temperature. To the solution then saturated aqueous carbonic acid solution was added, followed by extraction with chloroform. The chloroform layer was washed with saturated brine and dried on anhydrous sodium sulfate. After distilling the solvent off under reduced pressure, 2 ml of methanol was added to the residue. So formed solution was stirred for 2 hours at 90° C. After distilling the solvent off under reduced pressure, the residue was separated and purified on preparative thin-layer chromatography (Kieselgel™ 60F$_{254}$, Art.5744 (Merck); chloroform/methanol=9/1) to provide 21 mg of the title compound as a colorless solid.

1HNMR(300 MHz, CDCl$_3$)δ:1.02(6H, t, J=7.4 Hz), 1.65–1.92(4H, m),2.60–2.79(6H, m),3.01(3H, s),2.94–3.08 (4H, m), 3.26(2H, t, J=5.8 Hz),3.71–3.83(1H, m),4.80–5.30 (1H, m), 6.84–7.76(2H, m),9.21–9.85(1H, m)

ESI-MS Found:m/z 460.1[M+H]$^+$

EXAMPLE 107

Production of 6-{4-[2-(aminocarbonylamino)ethyl]piperazin-1-yl}-5-chloro-2-[(1-ethylpropyl)sulfanyl]benzimidazole To a solution of 50 mg of the compound as obtained in Example 104 in 5 ml of tetrahydrofuran, a solution of 84 mg of potassium cyanate in 5 ml of water was added, and stirred for 8 hours at room temperature. The solution was extracted with chloroform. The chloroform layer was washed with saturated brine and dried on anhydrous sodium sulfate. The solvent was distilled off under a reduced pressure and the residue was separated and purified on preparative thin-layer chromatography (Kieselgel™ 60F$_{254}$, Art.5744 (Merck); chloroform/methanol=4/1) to provide 22 mg of the title compound as a colorless solid.

1HNMR(300 MHz, CD$_3$OD)δ:1.02(6H, t, J=7.4 Hz), 1.59–1.82(4H, m),2.58(2H, t, J=6.6 Hz),2.66–2.80(4H, m), 3.00–3.12(4H, m),3.26–3.34(2H, m),3.56–3.66(1H, m), 7.21(1H, brs),7.49(1H, brs)

ESI-MS Found:m/z 425.1[M+H]$^+$

EXAMPLE 108

Production of 6-[4-(3-aminopropyl)piperazin-1-yl]-5-chloro-2-[(1-ethylpropyl)sulfanyl]benzimidazole Reactions were conducted by the method similar to that of Example 104 except that the compound of Example 103 was used in place of the compound of Example 89, to provide the title compound as a colorless solid.

1HNMR(300 MHz, CD$_3$OD)δ:1.08(6H, t, J=7 Hz), 1.70–1.97(4H, m),2.18–2.31(2H, m),3.05–3.15(2H, m), 3.32–3.46(6H, m),3.53–3.63(2H, m),3.71–3.88(3H, m), 7.51(1H, s),7.80(1H, s)

ESI-MS Found:m/z 396.0[M+H]$^+$

EXAMPLE 109

Production of 6-{4-[3-(methanesulfonylamino)propyl]piperazin-1-yl}-5-chloro-2-[(1-ethylpropyl)sulfanyl]benzimidazole Reactions were conducted by the method similar to that of Example 106 except that the compound of Example 108 was used in place of the compound of Example 104, to provide the title compound as a colorless solid.

1HNMR(300 MHz, CDCl$_3$)δ:1.00(6H, t, J=7 Hz), 1.62–1.88(6H, m),2.55–2.76(6H, m),2.80–3.10(7H, m), 3.22–3.33(2H, m),3.70–3.82(1H, m),6.64–7.73(2H, m)

ESI-MS Found:m/z 474.1[M+H]$^+$

EXAMPLE 110

Production 6-{4-[3-(aminocarbonylamino)propyl]piperazin-1-yl}-5-chloro-2-[(1-ethylpropyl)sulfanyl]benzimidazole Reactions were conducted by the method similar to that of Example 107 except that the compound of Example 108 was used in place of the compound of Example 104, to provide the title compound as a colorless solid.

1HNMR(300 MHz, CD$_3$OD)δ:0.94–1.07(6H, m), 1.57–1.85(6H, m),2.45–2.58(2H, m),2.62–2.80(4H, m), 2.98–3.22(6H, m),3.50–3.67(1H, m),7.12–7.26(1H, brs), 7.40–7.52(1H, brs)

ESI-MS Found:m/z 439.1[M+H]$^+$

EXAMPLE 111

Production 5-chloro-6-[4-(2,2-dimethyl-2-hydroxyethyl)piperazin-1-yl]-2-[(1-ethylpropyl)sulfanyl]benzimidazole dihydrochloride 1) 5-Chloro-6-{4-[(methoxycarbonyl)methyl]piperazin-1-yl}-2-[(1-ethylpropyl)sulfanyl]benzimidazole To a solution of 82 mg of the compound of Example 1 in 2 ml of tetrahydrofuran, 0.14 ml of triethylamine and 0.017 ml of methyl bromoacetate were added by the order stated, and stirred for 3 hours at room temperature. Water was added to the solution which then was extracted with ethyl acetate. The ethyl acetate layer was washed with saturated brine and dried on anhydrous sodium sulfate. After distilling the solvent off under reduced pressure, the residue was separated and purified on silica gel column chromatography (chloroform/methanol=20/1) to provide 80 mg of the title compound.

2) 5-Chloro-6-[4-(2,2-dimethyl-2-hydroxyethyl)piperazin-1-yl)]-2-[(1-ethylpropyl)sulfanyl]benzimidazole dihydrochloride To a solution of 70 mg of the compound as obtained in 1) above in 2 ml of tetrahydrofuran, 0.6 ml of 3M methyl magnesium bromide-tetrahydrofuran solution was added under cooling with ice, followed by an hour's stirring at room temperature. To the solution saturated aqueous sodium hydrogencarbonate solution was added, followed by extraction with chloroform. The chloroform layer was washed with saturated brine and dried on anhydrous sodium sulfate.

After distilling the solvent off under reduced pressure, the residue was separated and purified on preparative thin-layer chromatography (Kieselgel™ 60F$_{254}$, Art.5744 (Merck); chloroform/methanol/aqueous ammonia=10/1/0.1) to provide 30 mg of the title compound as a colorless amorphous substance.

1HNMR(300 MHz, CD$_3$OD)δ:1.08(6H, t, J=7.3 Hz), 1.40 (6H, s),1.70–1.95(4H, m),3.29–3.57(8H, m), 3.75–3.90(3H, m),7.50(1H, s),7.80(1H, s)

ESI-MS Found:m/z 411.2[M+H]$^+$

PRODUCTION EXAMPLE 5

Production of 6-chloro-5-[4-(2-hydroxyethyl) piperazin-1-yl]-1,3-dihydro-2H-benzimidazol-2-thione 1) 4-Chloro-2-nitro-5-[4-(2-hydroxyethyl)piperazin-1-yl] aniline To a solution of 4.14 g of 4,5-dichloro-2-nitroaniline and 2.73 g of 1-piperazine ethanol in 20 ml of cyclohexanol, 2.65 g of sodium carbonate was added, and stirred for 14 hours at 150° C. After cooling the reaction liquid to room temperature, water was added thereto, followed by extraction with chloroform. The chloroform layer was dried on anhydrous magnesium sulfate and the solvent was distilled off. The residue was separated and purified on silica gel column chromatography (chloroform/methanol=10/1) to provide 5.31 g of the title compound.

2) 2-Amino-4-chloro-5-[4-(2-hydroxyethyl)piperazin-1-yl] aniline

To a solution of 444 mg of the compound as obtained in 1) above in 10 ml of methanol and 5 ml of chloroform, 120 mg of 10% palladium-on-carbon catalyst was added, and stirred for 14 hours in hydrogen atmosphere, at ambient temperature and pressure. The reaction liquid was filtered with Celite, and the solvent was distilled off under reduced pressure to provide 400 mg of the title compound.

3) 6-Chloro-5-[4-(2-hydroxyethyl)piperazin-1-yl]-1,3-dihydro-2H-benzimidazol-2-thione To a solution of 400 mg of the compound as obtained in 2) above in 10 ml of methanol, 2 ml of 1M aqueous sodium hydroxide solution and 2 ml of carbon disulfide were added, and stirred for 18 hours at 50° C. The reaction liquid was cooled to room temperature and then water was added. The pH of the solution was adjusted to 7 with 1N hydrochloric acid, and the solution was extracted with ethyl acetate. The ethyl acetate layer was washed with saturated brine and dried on anhydrous sodium sulfate. The solvent was distilled off under reduced pressure to provide 296 mg of the title compound.

EXAMPLE 112

Production of 5-chloro-6-[4-(2-hydroxyethyl) piperazin-1-yl]-2-[(1-methylethyl)sulfanyl] benzimidazole dihydrochloride To a solution of 31 mg of the compound as obtained in Production Example 5 in 1 ml of dimethylformamide, 14 mg of potassium carbonate and 0.010 ml of 2-bromopropane were added, in nitrogen atmosphere by the order stated, and stirred for 3 hours at 80° C. After cooling the reaction liquid to room temperature, water was added thereto, followed by extraction with chloroform. The chloroform layer was washed with saturated brine and dried on anhydrous sodium sulfate. After distilling the solvent off under reduced pressure, the residue was separated and purified on preparative thin-layer chromatography (Kieselgel™ 60F$_{254}$, Art. 5744 (Merck); chloroform/methanol/aqueous ammonia=5/1/0.1) to provide 5-chloro-6-[4-(2-hydroxyethyl)piperazin-1-yl]-2-[(1-methylethyl)sulfanyl]benzimidazole. To this compound 10% hydrogen chloride-in-methanol solution (2 ml) was added, stirred for 5 minutes at room temperature and the solvent was distilled off under reduced pressure to provide 34 mg of the title compound as a colorless amorphous substance.

1HNMR(300 MHz, CD$_3$OD)δ:1.49–1.53(6H, m), 3.25–3.50(5H, m),3.55–3.65(3H, m),3.75–3.83(2H, m), 3.94–3.99(2H, m),4.03–4.16(1H, m),7.50–7.55(1H, m), 7.80–7.83(1H, m)

ESI-MS Found:m/z 355.1[M+H]$^+$

EXAMPLE 113

Production of 5-chloro-2-{[(1,4-cis)-4-(ethoxycarbonylamino)-cyclohexyl]sulfanyl}-6-[4-(2-hydroxyethyl)piperazin-1-yl]-benzimidazole dihydrochloride Reactions were conducted by the method similar to Example 112, except that (1,4-trans)-4-[(ethoxycarbonyl) amino]cyclohexyl methanesulfonate [which compound was prepared from (1,4-trans)-4-[(ethoxycarbonyl)amino] cyclohexanol (see Production Example G given later) and methanesulfonyl chloride by the known production method] was used in place of 3-bromopropane, to provide the title compound as a pale yellow, amorphous substance.

1HNMR(300 MHz, CD$_3$OD)δ:1.22(3H, t, J=7.1 Hz), 1.67–2.14(8H, m),3.19–3.50(6H, m),3.50–3.67(3H, m), 3.70–3.82(2H, m),3.90–4.20(5H, m),7.50(1H, s),7.79(1H, s)

ESI-MS Found:m/z 482.1[M+H]$^+$

PRODUCTION EXAMPLE G

Production Process of (1,4-trans)-4-[(ethoxycarbonyl)amino]-cyclohexanol

To a solution of 740 mg of trans-4-aminocyclohexanol and 1.3 ml of triethylamine in tetrahydrofuran (8 ml)-dimethylformamide (4 ml)-methanol (4 ml), 0.65 ml of ethyl chloroformate was added at room temperature, and stirred for an hour at the same temperature. The solution was concentrated under reduced pressure and chloroform was added to the residue, followed by successive washing with water and with saturated brine and concentration under reduced pressure. The residue was solidified with hexane-ethyl acetate to provide 581 mg of the title compound.

EXAMPLE 114

Production of 5-chloro-6-[4-(2-hydroxyethyl) piperazin-1-yl]-2-[(1-methoxymethylpropyl) sulfanyl]benzimidazole dihydrochloride Reactions were conducted by the method similar to Example 112, except that 1-(methoxymethyl)propyl methanesulfonate (which was prepared from 1-(methoxymethyl) propanol and methanesulfonyl chloride by the known production method) was used in place of 3-bromopropane, to provide the title compound as a colorless amorphous substance.

1HNMR(300 MHz, CD$_3$OD)δ:1.14(3H, t, J=7.4 Hz), 1.68–2.02(2H, m),3.28(3H, s),3.22–3.50(6H, m), 3.54–3.67 (3H, m),3.72–3.83(3H, m),3.92–4.04(3H, m), 7.56(1H, s),7.83(1H, s)

ESI-MS Found:m/z 399.1[M+H]$^+$

EXAMPLE 115

Production of 2-{[1-(tert-butylaminocarbonyl) propyl]sulfanyl}-5-chloro-6-[4-(2-hydroxyethyl) piperazin-1-yl]benzimidazole dihydrochloride Reactions were conducted by the method similar to Example 112, except that 2-bromo-N-(tert-butyl) butanamide (which was prepared by the method as described in *J. Chromatogr.*, 1985, 318, 235–246) was used in place of 3-bromopropane, to provide the title compound as a colorless amorphous substance.

1HNMR(300 MHz, CD$_3$OD)δ:1.05(3H, t, J=7.3 Hz),1.33 (9H, s), 1.85–2.10(2H, m),3.20–3.50(6H, m),3.54–3.63(2H, m), 3.72–3.80(2H, m),3.91–3.99(2H, m),4.04–4.12(1H, m), 7.57(1H, s),7.86(1H, s)

ESI-MS Found:m/z 454.1[M+H]$^+$

EXAMPLE 116

Production of 5-chloro-6-[4-(2-hydroxyethyl) piperazin-1-yl]-2-{[1-(morphoholinocarbonyl) propyl]sulfanyl}benzimidazole dihydrochloride Reactions were conducted by the method similar to Example 112, except that 2-bromo-1-morpholino-1-butanone (which was prepared by the method as described in U.S. Pat. No. 5,013,837) was used in place of 3-bromopropane, to provide the title compound as a colorless amorphous substance.

1HNMR(300 MHz, CD$_3$OD)δ:1.05(3H, t, J=7.4 Hz), 1.92–2.11(2H, m),3.20–3.50(6H, m),3.52–3.80(12H, m), 3.90–3.99(2H, m),4.94(1H, t, J=6.6 Hz),7.52(1H, s),7.82 (1H, s)

ESI-MS Found:m/z 468.1[M+H]$^+$

EXAMPLE 117

Production of 5-chloro-6-[4-(2-hydroxyethyl) piperazin-1-yl]-2-{[1-(methoxycarbonyl)pyrrolidin-3-yl]sulfanyl}benzimidazole dihydrochloride Reactions were conducted by the method similar to Example 112, except that 1-(methoxycarbonyl)pyrrolidin-3-yl methanesulfonate [which compound was prepared from 1-methoxycarbonyl-3-pyrrolidinol (*J. Am. Chem. Soc.*, 1982, 104, 6697–6703) and methanesulfonyl chloride by the known production method] was used in place of 3-bromopropane, to provide the title compound as a colorless oily substance.

1HNMR(300 MHz, CD$_3$OD)δ:2.15(1H, m),2.55(1H, m), 3.20–3.50(6H, m),3.50–3.65(4H, m),3.68(3H, s),3.70–3.82 (2H, m), 3.82–4.00(4H, m),4.50(1H, m),7.53(1H, s),7.82 (1H, s)

ESI-MS Found:m/z 440.1[M+H]$^+$

EXAMPLES 118–119

Production of 5-chloro-6-[4-(2-hydroxyethyl) piperazin-1-yl]-2-{[(endo and exo)-8-oxabicyclo [3.2.1]octan-3-yl]sulfanyl}benzimidazole Using 8-oxabicyclo[3.2.1]octan-3-yl methanesulfonate which was a mixture of endo-form and exo-form [which compound was prepared from 8-oxabicyclo[3.2.1]octan-3-ol, a mixture of endo- and exo-forms (see Production Example H given later) and methanesulfonyl chloride by the known production method] in place of 3-bromopropane, a mixture of 5-chloro-6-[4-(tert-butoxycarbonyl)piperazin-1-yl]-2-[((endo and exo)-8-oxabicyclo[3.2.1]octane-3-yl)-sulfanyl]benzimidazole was prepared following Example 1 but without de butyloxycarbonylation. This mixture was separated and purified on preparative thin-layer chromatography (Kieselgel™ 60F$_{254}$, Art. 5744 (Merck); hexane/ethyl acetate=1/1) to provide the title compounds. (Because the two were unidentified, for convenience one was recorded as the endo-form and the other, as the exo-form.) Each of the compounds was de butyloxycarbonylated following Example 1, and then subjected to reductive amination following Example 89, to provide the title compounds.

5-chloro-6-[4-(2-hydroxyethyl)piperazin-1-yl]-2-(((endo)-8-oxabicyclo[3.2.1]octan-3-yl]sulfanyl) benzimidazole dihydrochloride.

1HNMR(300 MHz, CD$_3$OD)δ:1.70–2.10(8H, m), 3.20–3.50(6H, m),3.50–3.67(2H, m),3.70–3.84(2H, m), 3.90–4.04(2H, m),4.17–4.50(3H, m),7.55(1H, s),7.83(1H, s)

ESI-MS Found:m/z 423.1[M+H]$^+$ 5-chloro-6-[4-(2-hydroxyethyl)piperazin-1-yl]-2-[((exo)-8-oxabicyclo[3.2.1]octan-3-yl)sulfanyl]benzimidazole dihydrochloride.

1HNMR(300 MHz, CD$_3$OD)δ:1.70–2.30(6H, m), 2.40–2.70(2H, m),3.00–3.69(8H, m),3.69–3.88(2H, m), 3.88–4.10(2H, m),4.30–4.60(3H, m),7.51(1H, s),7.81(1H, s)

ESI-MS Found:m/z 423.1[M+H]$^+$

PRODUCTION EXAMPLE H

Production Method of 8-oxabicyclo[3.2.1]octan-3-ol Which is a Mixture of Endo- and Exo-forms To a solution of 71 mg of 8-oxabicyclo[3.2.1]octan-3-one (which was prepared by the method as described in *Bull. Chem. Soc. Jpn.*, 1978, 51, 2745–2746) in tetrahydrofuran (2 ml), 32 mg of lithium aluminium hydride was added in nitrogen atmosphere at 0° C., and stirred for 30 minutes at the same temperature. To the solution 300 mg of sodium sulfate decahydrate was added, followed by 15 hours' stirring at room temperature. The insoluble matter was removed by filtration, and the filtrate was concentrated under reduced pressure to provide 72 mg of the title compound.

EXAMPLE 120

Production of 5-chloro-2-{(1,4-trans)-4-[(ethoxycarbonylamino)-cyclohexyl]sulfanyl}-6-[4-(2-hydroxyethyl)piperazin-1-yl]-benzimidazole dihydrochloride Reactions were conducted by the method similar to Example 112, except that (1,4-cis)-4-[(ethoxycarbonyl) amino]cyclohexyl methanesulfonate [which compound was prepared from (1,4-cis)-4-[(ethoxycarbonyl)amino] cyclohexanol (see Production Example I given later) and methanesulfonyl chloride by the known production method] was used in place of 3-bromopropane, to provide the title compound as a pale yellow, amorphous substance.

1HNMR(300 MHz, CD$_3$OD)δ:1.21(3H, t, J=7.2 Hz), 1.34–1.78(4H, m),1.90–2.28(4H, m),3.15–3.50(7H, m), 3.50–3.70(2H, m),3.70–3.90(3H, m),3.90–4.13(4H, m), 7.53(1H, s),7.82(1H, s)

ESI-MS Found:m/z 482.1[M+H]$^+$

PRODUCTION EXAMPLE I

Production of (1,4-cis)-4-[(ethoxycarbonyl)amino]cyclohexanol

To a solution of 800 mg of (1,4-trans)-4-[(ethoxycarbonyl)amino]cyclohexanol described in Example 113, 1.07 g of 4-nitrobenzoic acid and 1.68 g of triphenylphosphine in tetrahydrofuran (20 ml), 1.30 ml of diisopropyl azodicarboxylate was added in nitrogen atmosphere at 0° C., and stirred for 30 minutes at room temperature. The solution was concentrated under reduced pressure. To a solution of the obtained residue in ethanol (10 ml), 640 mg of potassium carbonate was added, and stirred for 12 hours at room temperature. Water was added to the solution which then was extracted with chloroform. The chloroform layer was dried on anhydrous magnesium sulfate and concentrated under reduced pressure. The residue was separated and purified on silica gel column chromatography (hexane/ethyl acetate=1/1) to provide 183 mg of the title compound.

EXAMPLE 121

Production of 5-chloro-6-[4-(2-hydroxyethyl)piperazin-1-yl]-2-{[1-(methoxycarbonyl)piperidin-3-yl]sulfanyl}benzimidazole dihydrochloride Reactions were conducted by the method similar to Example 112, except that 1-(methoxycarbonyl)piperidin-3-yl methanesulfonate [which compound was prepared from 1-methoxycarbonyl-3-piperidinol (a compound described in *Acta. Chem. Scand. Ser. B*, 1981, B35, 289–294) and methanesulfonyl chloride by the known production method] was used in place of 3-bromopropane, to provide the title compound as a colorless oily substance.

1HNMR(300 MHz, CD$_3$OD)δ:1.65(1H, m),1.85(2H, m), 2.25(1H, m),2.90–4.20(20H, m),7.54(1H, s),7.84(1H, s)

ESI-MS Found:m/z 454.1[M+H]$^+$

EXAMPLE 122

Production of 2-{[1-(allyloxycarbonyl)piperidin-4-yl]sulfanyl}-5-chloro-6-[4-(2-hydroxyethyl)piperidin-1-yl]benzimidazole dihydrochloride Reactions were conducted by the method similar to Example 112, except that 1-[(allyloxy)carbonyl]piperidin-4-yl methanesulfonate [which compound was prepared from 1-[(allyloxy)carbonyl]-4-piperidinol (a compound described in *J. Med. Chem.*, 1998, 41, 4983–4994) and methanesulfonyl chloride by the known production method] was used in place of 3-bromopropane, to provide the title compound as a pale red amorphous substance.

1HNMR(300 MHz, CD$_3$OD)δ:1.60–1.75(2H, m), 2.08–2.19(2H, m),3.09–3.45(7H, m),3.50–3.60(3H, m), 3.74(2H, brd, J=11.7 Hz),3.93(2H, t, J=5.1 Hz),4.00–4.15 (3H, m), 4.53(2H, dt, J=1.4,5.5 Hz),5.16(1H, dd, J=1.4,10.5 Hz), 5.25(1H, dd, J=1.4,17.2 Hz),5.83–5.96(1H, m),7.54 (1H, s), 7.81(1H, s)

ESI-MS Found:m/z 480.1 [M+H]$^+$

EXAMPLE 123

Production of 5-chloro-6-[4-(2-hydroxyethyl)piperazin-1-yl]-2-{[1-(methoxycarbonyl)piperidin-4-yl]sulfanyl}benzimidazole dihydrochloride Reactions were conducted by the method similar to Example 112, except that 1-(methoxycarbonyl)piperidin-4-yl methanesulfonate [which compound was prepared from 1-methoxycarbonyl-4-piperidinol (a compoud described in *J. Am. Chem. Soc.*, 1980, 102, 4438–4447) and methanesulfonyl chloride by the known production method] was used in place of 3-bromopropane, to provide the title compound as a pale red oily substance.

1HNMR(300 MHz, CD$_3$OD)δ:1.60–1.80(2H, m), 2.05–2.20(2H, m),3.00–3.50(8H, m),3.50–3.80(4H, m), 3.68(3H, s),3.80–4.12(5H, m),7.53(1H, s),7.82(1H, s)

ESI-MS Found:m/z 454.1[M+H]$^+$

EXAMPLE 124

Production of 5-chloro-2-{[1-(methylsulfonyl)piperidin-4-yl]sulfanyl}-6-[4-(2-hydroxyethyl)piperazin-1-yl]benzimidazole dihydrochloride Reactions were conducted by the method similar to Example 112, except that 1-(methylsulfonyl)piperidin-4-yl methanesulfonate [which compound was prepared from 1-(methylsulfonyl)-4-piperidinol (EP471236A1) and methanesulfonyl chloride by the known production method] was used in place of 3-bromopropane, to provide the title compound as a pale brown solid.

1HNMR(300 MHz, CD$_3$OD)δ:1.75–1.95(2H, m), 2.15–2.30(2H, m),2.87(3H, s),2.95–3.1(2H, m), 3.20–3.50 (6H, m),3.50–3.65(2H, m),3.65–3.80(4H, m), 3.90–4.05 (3H, m),7.53(1H, s),7.83(1H, s)

ESI-MS Found:m/z 474.1[M+H]$^+$

EXAMPLE 125

Production of 2-[(1-acetylpiperidin-4-yl)sulfanyl]-5-chloro-6-[4-(2-hydroxyethyl)piperazin-1-yl]benzimidazole dihydrochloride Reactions were conducted by the method similar to Example 112, except that 1-acetylpiperidin-4-yl methanesulfonate [which compound was prepared from 1-acetyl-4-piperidinol (a compound described in *J. Med. Chem.*, 1998, 41, 4983–4994) and methanesulfonyl chloride by the known production method] was used in place of 3-bromopropane, to provide the title compound as a pale brown oily substance.

1HNMR(300 MHz, CD$_3$OD)δ:1.50–1.90(2H, m), 1.90–2.30(2H, m),2.11(3H, s),2.90–3.50(8H, m), 3.50–3.65 (2H, m),3.65–3.85(2H, m),3.85–4.05(3H, m), 4.05–4.25 (1H, m),4.30–4.45(1H, m),7.57(1H, s),7.86(1H, s)

ESI-MS Found:m/z 438.1[M+H]$^+$

EXAMPLE 126

Production of 5-chloro-2-{[1-(ethoxycarbonyl)piperidin-4-yl]sulfanyl}-6-[4-(2-hydroxyethyl)piperazin-1-yl]benzimidazole dihydrochloride Reactions were conducted by the method similar to Example 112, except that 1-(ethoxycarbonyl)piperidin-4-yl methanesulfonate [which was prepared from 1-ethoxycarbonyl-4-piperidinol (a compound described in U.S. Pat. No. 4,695,575) and methanesulfonyl chloride by the known production method] was used in place of 3-bromopropane, to provide the title compound as a pale red oily substance.

1HNMR(300 MHz, CD$_3$OD)δ:1.23(3H, t, J=7.2 Hz), 1.60–1.80(2H, m),2.05–2.20(2H, m),3.05–3.50(8H, m), 3.50–3.65(2H, m),3.65–3.85(2H, m),3.90–4.15(5H, m), 4.11(2H, q, J=7.2 Hz),7.54(1H, s),7.83(1H, s)

ESI-MS Found:m/z 468.1[M+H]$^+$

EXAMPLE 127

Production of 5-chloro-2-[(1,1-dimethylpropyl) sulfanyl]-6-[4-(2-hydroxyethyl)piperazin-1-yl] benzimidazole dihydrochloride A mixture of a 12 ml of tert-amyl alcohol, 0.15 ml of diisopropylcarbodiimide and 1 mg of copper chloride (I) was stirred for 3 days at room temperature in nitrogen atmosphere. To the formed suspension a solution of 20 mg of the compound as obtained in Production Example 5 in 3 ml of tetrahydrofuran was added, followed by 6 hours' stirring at room temperature. To the reaction liquid 2 ml of 0.5N hydrochloric acid was added, followed by washing with ethyl acetate. To the aqueous layer 2 ml of 1N aqueous sodium hydroxide solution was added, and the layer was extracted with chloroform. The chloroform layer was dried on anhydrous sodium sulfate. After distilling the solvent off under reduced pressure, the residue was separated and purified on preparative thin-layer chromatography (Kieselgel™ 60F$_{254}$, Art. 5744 (Merck); chloroform/methanol/aqueous ammonia=5/1/0.1) to provide 5-chloro-2-[(1,1-dimethylpropyl)sulfanyl]-6-[4-(2-hydroxyethyl) piperazin-1-yl]-benzimidazole. To this compound 10% hydrogen chloride-in-methanol solution (2 ml) was added, stirred for 5 minutes at room temperature, and the solvent was distilled off under reduced pressure to provide 5 mg of the title compound as a colorless amorphous substance.

1HNMR(300 MHz, CD$_3$OD)δ:1.10(3H, t, J=7.4 Hz),1.47 (6H, s), 1.78(2H, q, J=7.4 Hz),3.25–3.50(6H, m),3.62(2H, brd, J=12.6 Hz), 3.78(2H, brd, J=12.6 Hz),3.96(2H, t, J=5.1 Hz),7.59(1H, s), 7.92(1H, s)

ESI-MS Found:m/z 383.1 [M+H]$^+$

EXAMPLE 128

Production of 5-chloro-2-[(1,1-dimethylethyl) sulfanyl]-6-[4-(2-hydroxyethyl)piperazin-1-yl] benzimidazole dihydrochloride Reactions were conducted by the method similar to Example 127 except that tert-butyl alcohol was used in place of tert-amyl alcohol, to provide the title compound as a colorless amorphous substance.

1HNMR(300 MHz, CD$_3$OD)δ:1.53(9H, s),3.14–3.54(7H, m), 3.56–3.66(1H, m),3.70–3.84(2H, m),3.92–4.00(2H, m),7.60(1H, s), 7.92 (1H, s)

ESI-MS Found:m/z 369.1[M+H]$^+$

PRODUCTION EXAMPLE 6

Production of 6-chloro-5-(4-benzylpiperazin-1-yl)-1,3-dihydro-2H-benzimidazol-2-thione 1) 4-Chloro-2-nitro-5-(4-benzylpiperazin-1-yl)aniline The title compound was obtained by the method similar to Production Example 5-1), except that N-benzylpiperazin was used in place of 1-piperazine-ethanol.

2) 2-Amino-4-chloro-5-(4-benzylpiperazin-1-yl)aniline

The title compound was obtained by the method similar to Production Example 5-2), using the compound as obtained in 1) above.

3) 6-Chloro-5-(4-benzylpiperazin-1-yl)-1,3-dihydro-2H-benzimidazol-2-thione

The title compound was obtained by the method similar to Production Example 5-3), using the compound as obtained in 2) above.

EXAMPLE 129

Production of 6-(4-benzylpiperazin-1-yl)-5-chloro-2-[(1,4-dioxaspiro-[4,5]decan-8-yl)sulfanyl] benzimidazole Reactions were conducted by the method similar to Example 112 except that the compound as obtained in Production Example 6 was used in place of that as obtained in Production Example 5, and that 1,4-dioxaspiro[4,5]decan-8-yl methanesulfonate [which compound was prepared from 1,4-dioxaspiro[4,5]decan-8-ol and methanesulfonyl chloride by the known production method] was used in place of 3-bromopropane, to provide the title compound as a pale yellow, amorphous substance.

1HNMR(300 MHz, CDCl$_3$)δ:1.50–1.78(2H, m),1.78–1.96(4H, m), 2.12–2.26(2H, m),2.66–2.76(4H, brs),3.00–3.15(4H, brs), 3.61(2H, d, J=4.0 Hz),3.95(4H, s),7.00(0.5H, s),7.25–7.43(6H, m), 7.69(0.5H, s),8.98–9.04(1H, m)

ESI-MS Found:m/z 499.1 [M+H]$^+$

EXAMPLE 130

Production of 6-(4-benzylpiperazin-1-yl)-5-chloro-2-[(4-oxocyclohexyl)sulfanyl]benzimidazole dihydrochloride To a solution of 10 mg of the compound as obtained in Example 129 in 1 ml of tetrahydrofuran, 0.3 ml of 1N hydrochloric acid was added and stirred for 3 hours at 50° C. The solution was concentrated under reduced pressure. The residue was separated and purified on preparative thin-layer chromatography (Kieselgel™ 60F$_{254}$, Art. 5744 (Merck); chloroform/methanol/aqueous ammonia=5/1/0.1) to provide 6-(4-benzylpiperazin-1-yl)-5-chloro-2-[(4-oxocyclohexyl)sulfanyl]benzimidazole. To this compound 10% hydrogen chloride-in-methanol solution (2 ml) was added, stirred for 5 minutes at room temperature, and the solvent was distilled off under reduced pressure to provide 7 mg of the title compound as a colorless amorphous substance.

1HNMR(300 MHz, CDCl$_3$)δ:2.00–2.17(2H, m), 2.38–2.60(6H, m),2.79(4H, brs),3.10(4H, brs), 3.71(2H, s),4.25–4.34(1H, m),7.00–7.65(7H, m)

ESI-MS Found:m/z 455.1[M+H]$^+$

EXAMPLE 131

Production of 5-chloro-6-[4-(2-hydroxyethyl) piperazin-1-yl]-2-[(4-oxocyclohexyl)sulfanyl] benzimidazole dihydrochloride To a solution of 191 mg of the compound as obtained in Example 130 in 4 ml of chloroform, 0.10 ml of 1-chloroethyl chloroformate was added in nitrogen atmosphere and stirred for 3 days at room temperature. To the solution 5 ml of methanol was added, and stirred for 3 hours at 80° C. After cooling the reaction liquid to room temperature, the solvent was distilled off under reduced pressure. The residue was dissolved in methanol (2 ml)-tetrahydrofuran (2 ml) solution, to which 0.16 ml of tert-butyldimethylsilyloxyacetaldehyde and 2 ml of advancedly prepared 0.3M methanol solution of sodium cyanoborohydride and zinc chloride (1:0.5, molar ratio) were added at room temperature, followed by an hour's stirring at the same temperature. The reaction liquid was diluted with ethyl acetate, and the organic layer was washed successively with saturated sodium hydrogencarbonate solution and saturated brine, and dried on anhydrous sodium sulfate. After distilling the solvent off under reduced pressure, 10% hydrogen chloride-in-methanol solution (25 ml) was added to the residue, stirred for 2 hours at room temperature, and the solvent was distilled off under reduced pressure. Saturated aqueous sodium hydrogen carbonate solution was added to the residue, which then was extracted with ethyl acetate. The ethyl acetate layer was dried on anhydrous magnesium sulfate and the solvent was distilled off under reduced pressure. The residue was separated and purified on preparative thin-layer chromatography (Kieselgel™ 60F$_{254}$, Art. 5744 (Merck); chloroform/methanol/aqueous ammonia=5/1/0.1) to provide 5-chloro-6-[4-(2-hydroxyethyl)piperazin-1-yl]-2-[(4-oxocyclohexyl)sulfanyl]benzimidazole. To this compound 10% hydrogen chloride-in-methanol solution (2 ml) was added, stirred for 5 minutes at room temperature and the solvent was distilled off under reduced pressure to provide 50 mg of the title compound as a colorless amorphous substance.

1HNMR(300 MHz, CDCl$_3$)δ:2.00–2.20(2H, m),2.40–2.60(6H, m), 2.69(2H, t, J=5.3 Hz),2.79(4H, brs), 3.08(4H, brs), 3.72(2H, t, J=5.3 Hz),4.25–4.35(1H, m),7.00–7.30(1H, m), 7.40–7.65(1H, m)

ESI-MS Found:m/z 409.1 [M+H]$^+$

EXAMPLE 132

Production of 5-chloro-2-[(4-hydroxycyclohexyl) sulfanyl]-6-[4-(2-hydroxyethyl)piperazin-1-yl] benzimidazole dihydrochloride To a solution of 46 mg of the compound as obtained in Example 131 in 1 ml of methanol, 4 mg of sodium borohydride was added and stirred for 15 minutes at room temperature. Saturated sodium hydrogencarbonate solution was added to the reaction liquid, which then was extracted with chloroform. The chloroform layer was dried on anhydrous sodium sulfate and the solvent was distilled off under reduced pressure. The residue was separated and purified on preparative thin-layer chromatography (Kieselgel™ 60F$_{254}$, Art. 5744 (Merck); chloroform/methanol/aqueous ammonia=10/1/0.1) to provide 5-chloro-2-[(4-hydroxycyclohexyl)sulfanyl]-6-[4-(2-hydroxyethyl) piperazin-1-yl]benzimidazole. To this compound 10% hydrogen chloride-in-methanol solution (2 ml) was added, stirred for 5 minutes at room temperature and the solvent was distilled off under reduced pressure to provide 21 mg of the title compound as a pale yellow amorphous substance.

1HNMR(300 MHz, CD$_3$OD)δ:1.40–1.70(3H, m), 1.74–1.83(1H, m),1.94–2.09(3H, m),2.16–2.26(1H, m), 3.20–3.40(8H, m),3.40–3.65(2H, m),3.73–3.83(2H, m), 3.92–3.97(2H, m),7.47(1H, s),7.77(1H, s)

ESI-MS Found:m/z 411.2 [M+H]$^+$

EXAMPLES 133–134

Production of 5-chloro-6-[4-(2-hydroxyethyl) piperazin-1-yl]-2-[((1,4-cis*)-4-hydroxy-4-methylcyclohexyl)sulfanyl]benzimidazole dihydrochloride and 5-chloro-6-[4-(2-hydroxyethyl) piperazin-1-yl]-2-[((1,4-trans*)-4-hydroxy-4-methylcyclohexyl)sulfanyl]benzimidazole dihydrochloride To a solution of 46 mg of the compound as obtained in Example 131 in 1 ml of tetrahydrofuran, 0.6 ml of 1.14M methyl lithium-ether solution was added under cooling with ice, followed by 30 minutes' stirring at the same temperature. Saturated sodium hydrogencarbonate solution was added to the reaction liquid which then was extracted with chloroform. The chloroform layer was dried on anhydrous sodium sulfate and the solvent was distilled off under reduced pressure. The residue was separated and purified on preparative thin-layer chromatography (Kieselgel™ 60F$_{254}$, Art.5744 (Merck); chloroform/methanol/aqueous ammonia=10/1/0.1.) From the low polarity fraction 5-chloro-6-[4-(2-hydroxyethyl)piperazin-1-yl]-2-[((1,4-cis*)-4-hydroxy-4-methylcyclohexyl)sulfanyl]benzimidazole was obtained, and from the high polarity fraction, (1,4-trans*)-form of the same compound was obtained. (Because the two were unidentified, for convenience one of them was recorded as cis-form and the other, as trans-form.)

To each of the compounds 10% hydrogen chloride-in-methanol solution (2 ml) was added, stirred for 5 minutes at room temperature, and the solvent was distilled off under reduced pressure to provide 5 mg each of the respective compounds as pale yellow amorphous substances.

COMPOUND OF EXAMPLE 133

(1,4-cis*)-form

1HNMR(300 MHz, CD$_3$OD)δ:0.80–1.40(3H, m), 1.58–1.69(1H, m),1.72–1.83(1H, m),1.90–2.10(3H, m), 3.23–3.50(7H, m),3.51–3.66(2H, m),3.73–3.85(2H, m), 3.95(2H, t, J=5.2 Hz),7.51(1H, s),7.81(1H, s)

ESI-MS Found:m/z 425.1[M+H]$^+$

COMPOUND OF EXAMPLE 134

(1,4-trans*)-form

1HNMR(300 MHz, CD$_3$OD)δ:1.10–1.30(2H, m), 1.55–1.79(5H, m),2.09–2.29(1H, m),3.20–3.45(7H, m), 3.52–3.60(2H, m),3.70–3.76(2H, m),3.92(2H, t, J=5.2 Hz), 7.48(1H, s),7.78(1H, s)

ESI-MS Found:m/z 425.1[M+H]$^+$

EXAMPLE 135

Production of 6-(4-benzylpiperazin-1-yl)-5-chloro-2-[(1,1-dimethyl-3-oxobutyl)sulfanyl]benzimidazol To a solution of 300 mg of the compound as obtained in Production Example 6 in 12 ml of 10% hydrogen chloride-in-methanol, 0.19 ml of mesityl oxide was added and stirred for 7 hours at room temperature. The solution was concentrated under reduced pressure, and to the residue saturated sodium hydrogencarbonate solution was added, followed by extraction with chloroform. The chloroform layer was dried on anhydrous sodium sulfate, and the solvent was distilled off under reduced pressure. The residue was separated and purified on silica gel column chromatography (chloroform/methanol=100/2) to provide 268 mg of the title compound.

EXAMPLE 136

Production of 5-chloro-6-[4-(2-hydroxyethyl) piperazin-1-yl]-2-[(1,1,3-trimethyl-3-hydroxybutyl) sulfanyl]benzimidazole dihydrochloride 1) 6-(4-Benzylpiperazin-1-yl)-5-chloro-2-[(1,1,3-trimethyl-3-hydroxybutyl)sulfanyl]benzimidazole A solution of 187 mg of the compound as obtained in Example 135 in 1 ml of tetrahydrofuran was dropwisely added into 1.44 ml of 1.14M methyl lithium-ether solution under cooling with ice and stirred for 15 minutes at the same temperature. The reaction liquid was diluted with ether and washed successively with water and saturated brine. The ether layer was dried on anhydrous sodium sulfate and the solvent was distilled off under reduced pressure. The residue was separated and purified on silica gel column chromatography (hexane/ethyl acetate=1/2) to provide 154 mg of the title compound.

2) 5-Chloro-6-[4-(2-hydroxyethyl)piperazin-1-yl]-2-[(1,1,3-trimethyl-3-hydroxybutyl)sulfanyl]benzimidazole dihydrochloride Reactions were conducted by the method similar to Example 131 using the compound as obtained in 1) above, to provide the title compound as a colorless amorphous substance.

1HNMR(300 MHz, CDCl$_3$)δ:1.42(6H, s),1.46(6H, s), 1.92(2H, s),2.66–2.74(2H, m),2.76–2.88(4H, m),3.00–3.17 (4H, m), 3.69–3.77(2H, m),7.10–7.75(2H, m)

ESI-MS Found:m/z 427.1[M+H]$^+$

EXAMPLE 137

Production of 2-[(3-acetoxy-1,1-dimethylbutyl) sulfanyl]-5-chloro-6-(piperazin-1-yl)benzimidazole To a solution of 67 mg of the compound as obtained in Example 135 in methanol (1 ml)-chloroform (1 ml), 6 mg of sodium borohydride was added under cooling with ice, and stirred for 30 miutes at the same temperature. Water was added to the solution which then was extracted with ethyl acetate. The ethyl acetate layer was washed with saturated brine, dried on anhydrous sodium sulfate and the solvent was distilled off under reduced pressure. To the residue 0.5 ml of acetic anhydride and 0.5 ml of pyridine were added and stirred for 14 hours at room temperature. The solution was concentrated under reduced pressure. The residue was dissolved in 4 ml of chloroform in nitrogen atmosphere, to which 0.03 ml of 1-chloroethyl chloroformate was added, followed by 3 days' stirring at room temperature. To the solution 2 ml of methanol was added and stirred for 3 hours at 80° C. The reaction liquid was cooled to room temperature and the solvent was distilled off under reduced pressure. The residue was separated and purified on preparative thin-layer chromatography (Kieselgel™ 60F$_{254}$, Art. 5744 (Merck); chloroform/methanol/aqueous ammonia=10/1/0.1) to provide 11 mg of the title compound as a pale yellow amorphous substance.

1HNMR(300 MHz, CDCl$_3$)δ:1.28(3H, d, J=6.3 Hz),1.38 (3H, s), 1.48(3H, s),1.90(1H, dd, J=3.9,15.0 Hz),2.05(3H, s), 2.07(1H, dd, J=7.6,15.0 Hz),3.02–3.10(4H, m),3.10–3.20 (4H, m), 5.28–5.39(1H, m),7.29(1H, s),7.67(1H, s)

ESI-MS Found:m/z 411.1[M+H]$^+$

EXAMPLE 138

Production of 5-chloro-2-[(3-hydroxy-1,1-dimethylbutyl)sulfanyl]-6-[4-(2-hydroxyethyl) piperazin-1-yl]benzimidazole dihydrochloride Reactions were conducted by the method similar to Example 89 using the compound as obtained in Example 137, to provide the title compound as a colorless amorphous substance.

1HNMR(300 MHz, CDCl$_3$)δ:1.30(3H, d, J=6.3 Hz),1.39 (6H, s), 1.65(1H, dd, J=1.6,15.2 Hz),1.96(1H, dd, J=8.1,15.2 Hz), 2.69(2H, t, J=5.3 Hz),2.78(4H, brs),3.06(4H, brs), 3.72(2H, t, J=5.3 Hz),4.29–4.40(1H, m),7.20(1H, brs),7.65 (1H, brs)

ESI-MS Found:m/z 413.2[M+H]$^+$

EXAMPLE 139

Production of 5-chloro-2-{[1,1-dimethyl-2-(piperidin-1-yl)ethyl]-sulfanyl}-6-[4-(2-hydroxyethyl)piperazin-1-yl]benzimidazole trihydrochloride 1) 5-Chloro-2-{[1,1-dimethyl-2-(piperidin-1-yl)ethyl] sulfanyl}-6-[4-(tert-butoxycarbony)piperazin-1-yl] benzimidazole 20 mg and 5-chloro-2-{[2,2-dimethyl-2-(piperidin-1-yl)ethyl]sulfanyl}-6-[4-(tert-butoxycarbonyl) piperazin-1-yl]benzimidazole A mixed solution of 0.15 ml of isobutylene oxide, 0.18 ml of piperidine and 0.04 ml of methanol was stirred for 6.5 hours at 65° C. in nitrogen atmosphere. The solution was concentrated under reduced pressure. The residue was dissolved in 1 ml of chloroform, and to the solution 0.16 ml of methanesulfonyl chloride and 0.28 ml of triethylamine were added, followed by 15 hours' stirring at 40° C. The reaction solution was diluted with chloroform, washed with saturated aqueous sodium hydrogencarbonate solution, dried on anhydrous sodium sulfate and the solvent was distilled off under reduced pressure. The residue was dissolved in 2 ml of dimethylformamide in nitrogen atmosphere, to which 45 mg of potassium carbonate and 80 mg of the compound of Production Example 1 were added by the order stated, followed by 13 hours' stirring at 80° C. The reaction liquid was cooled to room temperature, water was added thereto, and the liquid was extracted with ethyl acetate. The ethyl acetate layer was washed with saturated brine and dried on anhydrous sodium sulfate. After distilling the solvent off under reduced pressure, the residue was separated and purified on preparative thin-layer chromatography (Kieselgel™ 60F$_{254}$, Art. 5744 (Merck); chloroform/methanol/diethylamine=30/1/0.1) to provide 20 mg of 5-chloro-2-{[1,1-dimethyl-2-(piperidin-1-yl)ethyl] sulfanyl}-6-[4-(tert-butoxcarbonyl)piperazine-1-yl] benzimidazole and 30 mg of 5-chloro-2-{[2,2-dimethyl-2-(piperidin-1-yl)ethyl]sulfanyl}-6-[4-(tert-butoxycarbonyl) piperazin-1-yl]benzimidazole.

2) 5-Chloro-2-{[1,1-dimethyl-2-(piperidin-1-yl)ethyl] sulfanyl}-6-[4-(2-hydroxyethyl)piperazin-1-yl)] benzimidazole trihydrochloride To 20 mg of 5-chloro-2-{[1,1-dimethyl-2-(piperidin-1-yl) ethyl]sulfanyl}-6-[4-(tert-butoxycarbonyl)piperazin-1-yl]-benzimidazole as obtained in 1) above, 8 ml of 10% hydrogen chloride-in-methanol solution was added and stirred for 12 hours at room temperature. The solution was concentrated under reduced pressure and whereby obtained 5-chloro-2-{[1,1-dimethyl-2-(piperidin-1-yl)ethyl] sulfanyl}-6-(piperazin-1-yl)benzimidazole was used in the reactions following the method of Example 89, to provide the title compound as a colorless oily substance.

1HNMR(300 MHz, CD$_3$OD)δ:1.85–2.15(6H, m), 3.10–3.80(16H, m),3.95(2H, m),7.43(1H, s),7.74(1H, s)

ESI-MS Found:m/z 452.2[M+H]$^+$

EXAMPLE 140

Production of 5-chloro-2-{[1,1-dimethyl-2-(pyrrolidin-1-yl)ethyl]-sulfanyl}-6-[4-(2-hydroxyethyl)piperazin-1-yl]benzimidazole trihydrochloride 1) 5-Chloro-2-{[1,1-dimethyl-2-(pyrrolidin-1-yl)ethyl] sulfanyl}-6-[4-(tert-butoxycarbonyl)piperazin-1-yl] benzimidazole Reactions were conducted following the method of Example 139-1) except that pyrrolidine was used in place of piperidine, to provide the title compound.

2) 5-Chloro-2-{[1,1-dimethyl-2-(pyrrolidin-1-yl)ethyl] sulfanyl}-6-[4-(2-hydroxyethyl)piperazin-1-yl] benzimidazole trihydrochloride Reactions were conducted by the method similar to Example 139-2) using the compound as obtained in 1) above, to provide the title compound as a colorless oily substance.

1HNMR(300 MHz, CD$_3$OD)δ:1.61(6H, s),2.10–2.30(4H, m), 3.20–3.50(8H, m),3.50–3.65(2H, m),3.70–3.85(2H, m),3.76(2H, s), 3.85–4.00(4H, m),7.51(1H, s),7.91(1H, s)

ESI-MS Found:m/z 438.2[M+H]$^+$

EXAMPLE 141

Production 5-chloro-6-[4-(2-hydroxyethyl)piperazin-1-yl]-2-[(1-methylcyclobutyl)sulfanyl]benzimidazole dihydrochloride To a solution of 313 mg of the compound as obtained in Production Example 5 in 5 ml of trifluoroacetic acid, 172 mg of 1-methylcyclobutanol was added, followed by 3 days' stirring at room temperature. The reaction liquid was concentrated under reduced pressure, and to the residue saturated aqueous sodium hydrogencarbonate solution was added, followed by extraction with chloroform. The chloroform layer was dried on anhydrous sodium sulfate and the solvent was distilled off. The residue was separated and purified on silica gel column chromatography (chloroform/methanol=10/1) to provide 273 mg of 5-chloro-6-[4-(2-hydroxyethyl)piperazin-1-yl]-2-[(1-methycyclobutyl)sufanyl]benzimidazole as a colorless solid. To a solution of 273 mg of this compound in 3 ml of methanol, 3N-hydrogen chloride-in-methanol solution was added and the solvent was distilled off under reduced pressure. The residue was washed with ether and 277 mg of the title compound was obtained as a colorless solid.

1HNMR(400 MHz, CD$_3$OD)δ:1.69(3H, s),2.04–2.22(2H, m), 2.29–2.36(2H, m),2.35–2.52(2H, m),3.28–3.48(6H, m), 3.60(2H, d, J=12.4 Hz),3.78(2H, d, J=11.6 Hz), 3.97(2H, t, J=5.2 Hz),7.61(1H, s),7.90(1H, s)

ESI-MS Found:m/z 381.1[M+H]$^+$

EXAMPLE 142

Production of 5-chloro-7-fluoro-6-[4-(2-hydroxyethyl)piperazin-1-yl]-2-[(1-methylcyclopentyl)sulfanyl]benzimidazole 1) 4-Chloro-6-fluoro-2-nitro-5-[4-(2-hydroxyethyl)piperazin-1-yl]-aniline To a solution of 6.79 g of 4-chloro-2,3-difluoro-6-nitroaniline (which was synthesized following WO9856761 or WO9835977) and 4.70 g of 1-piperazine ethanol in 30 ml of dimethylsulfoxide, 9.23 g of potassium carbonate was added, followed by an hour's stirring at 50° C. After cooling the reaction liquid to room temperature, water was added thereto, followed by extraction with chloroform. The chloroform layer was dried on anhydrous magnesium sulfate, the solvent was distilled off and 6.98 g of the title compound in crude form was obtained as a yellow oily substance.

2) 6-Chloro-4-fluoro-5-[4-(2-hydroxyethyl)piperazin-1-yl]-1,3-dihydro-2H-benzimidazol-2-thione Reactions were conducted following the method similar to Production Example 5-2) and 3) except that the compound as obtained in 1) above was used in place of the compound of Production Example 5-1), to provide the title compound as a colorless solid.

3) 5-Chloro-7-fluoro-6-[4-(2-hydroxyethyl)piperazin-1-yl]-2-[(1-methylcyclopentyl)sulfanyl]benzimidazole Reactions were conducted following the method similar to Example 141 except that the compound as obtained in 2) above was used in place of the compound of Production Example 5 and 1-methylcyclopentanol was used in place of 1-methylcyclobutanol, to provide the title compound as a colorless solid, without converting it to hydrochloride.

1HNMR(300 MHz, CD$_3$OD)δ:1.53(3H, s),1.65–2.03(8H, m), 3.20–3.70(10H, m),3.93(2H, t, J=5.3 Hz),6.70(2H, s),7.43(1H, s)

ESI-MS Found:m/z 413.2[M+H]$^+$

EXAMPLE 143

Production of 5-cyano-2-[(1,1-dimethylethyl)sulfanyl]-7-fluoro-6-[(4-(2-fluoroethyl)-(2R*)-2-methylpiperazin-1-yl)benzimidazole and 5-cyano-2-[(1,1-dimethylethyl)sulfanyl]-7-fluoro-6-[(4-(2-fluoroethyl)-(2S*)-2-methylpiperazin-1-yl)benzimidazole 1) 5-(4-Tert-butoxycarbonyl-2-methylpiperazin-1-yl)-4-cyano-2-nitroaniline To a solution of 8.00 g of 4-cyano-3-fluoro-6-nitroaniline (which was synthesized following *J. Med. Chem.* 1994, 37, 467) and 17.60 g of 1-tert-butoxycarbonyl-3-methylpiperazine in 25 ml of dimethylsulfoxide, 23 ml of diisopropylethylamine was added and stirred for 3 hours at 140° C. and 12 hours at room temperature. 1N aqueous sodium hydroxide solution was added to the reaction liquid which then was extracted with chloroform. The chloroform layer was dried on anhydrous magnesium sulfate and the solvent was distilled off. The residue was washed with chloroform-methanol, to provide 12.2 g of the title compound as a pale yellow solid.

2) 5-(2-Methylpiperazin-1-yl)-4-cyano-6-fluoro-2-nitroaniline

To a solution of 860 mg of the compound as obtained in 1) above in 10 ml of dichloroethane, 300 mg of sodium hydrogencarbonate and 1.13 g of 1-fluoro-2,6-dichloropyridinium triflate were added at room temperature and stirred for 30 minutes at 55° C. and 30 minutes at 75° C. To the reaction liquid which was cooled to room temperature, saturated aqueous sodium hydrogencarbonate solution was added, followed by extraction with chloroform-methanol (5/1). The extract was washed with saturated brine, dried on anhydrous magnesium sulfate and the solvent was distilled off. The residue was separated and purified on silica gel column chromatography (chloroform/methanol=6/1) to provide 520 mg of the title compound as a white solid.

3) 4-Cyano-6-fluoro-5-[4-(2-fluoroethyl)-2-methylpiperazin-1-yl]]-2-nitroaniline To a solution of 233 mg of the compound as obtained in 2) above in 10 ml of dimethylformamide, 0.15 ml of 1-bromo-2-fluoroethane, 256 mg of potassium carbonate and 54 mg of potassium iodide were added and stirred at room temperature. After 3 hours, further 0.05 ml of 1-bromo-2-fluoroethane was added, followed by 5 hours' stirring at 80° C. After cooling the reaction solution to room temperature water was added thereto, followed by extraction with ethyl acetate. The extract was dried on anhydrous sodium sulfate and distilled. The residue was separated and purified on silica gel column chromatography (chloroform/methanol=40/1) to provide 150 mg of the title compound as a pale yellow, oily substance.

4) 6-Cyano-4-fluoro-5-[4-(2-fluoroethyl)-2-methylpiperazin-1-yl]-1,3-dihydro-2H-benzimidazol-2-thione Reactions were conducted following the method similar to Production Example 5-2) and 3) except that the compound as obtained in 3) above was used in place of the compound of Production Example 5-1), to provide the title compound as a pale orange, oily substance.

5) 5-Cyano-2-[(1,1-dimethylethyl)sulfanyl]-7-fluoro-6-[(4-(2-fluoroethyl)-(2R*)-2-methylpiperazin-1-yl)benzimidazole and 5-cyano-2-[(1,1-dimethylethyl)

sulfanyl]-7-fluoro-6-[(4-(2-fluoroethyl)-(2S*)-2-methylpiperazin-1-yl)benzimidazole Reactions were conducted following the method similar to Example 141 except that the compound as obtained in 4) above was used in place of the compound of Production Example 5 and tert-butanol was used in place of 1-methylcyclobutanol, to provide racemic modification of the title compounds as a pale yellow solid, without conversion to the corresponding hydrochloride. This racemic modification was optically resolved with an optically active column (Daicel Chemical Ind., Ltd., CHIRALCEL OJ Column; 0.1% diethylamine, hexane/isopropyl alcohol=9/1). From the earlier fraction 5-cyano-2-[(1,1-dimethylethyl)sulfanyl]-7-fluoro-6-[(4-(2-fluoroethyl)-2-methylpiperazin-1-yl)benzimidazole (2R*-configuration) was obtained and from the later fraction the corresponding (2S*-configuration) was obtained, each as a pale yellow solid. (Because the two were unidentified, for convenience one of them was recorded as 2R*-configuration and the other, as 2S*-configuration.)

1HNMR(300 MHz, CDCl$_3$)δ:0.91(3H, d, J=6.26 Hz),1.58 (9H, s), 2.12–2.23(1H, m),2.51–2.62(1H, m),2.78(2H, dt, J=4.90,28.35 Hz), 2.89–3.00(2H, m),3.05–3.15(1H, m),3.33–3.47(1H, m), 3.54–3.68(1H, m),4.62(2H, dt, J=4.91,47.72 Hz),7.50–7.78(1H, br s)

ESI-MS Found:m/z 394.3[M+H]$^+$

EXAMPLE 144

Production of 5-chloro-2-[(1,1-dimethylethyl)sulfanyl]-6-[1-(2-methoxyethyl)pyrrolidin-(3R*)-3-yl](methyl)aminobenzimidazole and 5-chloro-2-[(1,1-dimethylethyl)sulfanyl]-6-[1-(2-methoxyethyl)-pyrrolidin-(3S*)-3-yl](methyl)aminobenzimidazole 1) 1-(2-Methoxyethyl)-3-(N-tert-butoxycarbonyl-N-methylamino)-prrolidine To a solution of 5 g of 3-(N-tert-butoxycarbonyl-N-methylamino)pyrrolidine in 20 ml of dimethylformamide, 2.5 ml of 2-chloroethyl methyl ether and 3 g of potassium carbonate were added, and stirred for 15 hours at 80° C. After cooling the reaction solution to room temperature, water was added thereto, followed by extraction with ethyl acetate. The extract was washed with saturated brine, dried on anhydrous sodium sulfate and distilled. The residue was separated and purified on silica gel column chromatography (chloroform/methanol=4/1) to provide 4.38 g of the title compound as a yellow oily substance.

2) 1-(2-Methoxyethyl)-3-(N-methylamino)pyrrolidine dihydrochloride

To a solution of 4.38 g of the compound as obtained in 1) above in 20 ml of methanol, 20 ml of 3N-hydrogen chloride-in-methanol solution was added, and stirred for 1.5 hours at 90° C. The reaction solution was cooled to room temperature and concentrated to provide 3.0 g of crude title compound as a yellow oily substance.

3) 5-[1-(2-Methoxyethyl)pyrrolidin-3-yl](methyl)amino-4-chloro-2-nitroaniline

The reaction was conducted by the method similar to Example 143-1) except that 4-chloro-5-fluoro-2-nitroaniline (which was prepared in Production Example 7 given later) was used in place of the 4-cyano-3-fluoro-6-nitroaniline of Example 143-1), and the compound as obtained in 2) above was used in place of 1-tert-butoxycarbonyl-3-methylpiperazine, to provide the title compound as a yellow oily substance.

4) 6-Chloro-5-[1-(2-methoxyethyl)pyrrolidin-3-yl](methyl)amino-1,3-dihydro-2H-benzimidazol-2-thione Reactions were conducted by the method similar to Production Example 5-2) and 3) except that the compound as obtained in 3) above was used in place of the compound of Production Example 5-1), to provide the title compound as a reddish brown oily substance.

5) 5-Chloro-2-[(1,1-dimethylethyl)sulfanyl]-6-[1-(2-methoxyethyl)-pyrrolidin-(3R*)-3-yl](methyl)aminobenzimidazole and 5-chloro-2-[(1,1-dimethylethyl)sulfanyl]-6-[1-(2-methoxyethyl)pyrrolidin-(3S*)-3-yl](methyl)aminobenzimidazole The reaction similar to Example 143-5) was conducted except that the compound as obtained in 4) above was used in place of the compound of Example 143-4), to provide the title compounds each as a pale yellow oily substance.

1HNMR(300 MHz, CDCl$_3$)δ:1.50(9H, s),1.76–1.89(1H, m), 1.96–2.10(1H, m),2.47–2.91(8H, m),2.95–3.05(1H, m),3.34(3H, s), 3.51(2H, t, J=5.60 Hz),3.85–3.98(1H, m),7.10–7.81(2H, brd)

ESI-MS Found:m/z 397.2[M+H]$^+$

PRODUCTION EXAMPLE 7

Production of 4-chloro-5-fluoro-2-nitroaniline 1) 4-Chloro-3-fluoroaniline

To a solution of 96 ml of 3-fluoroaniline in 1000 ml of dichloromethane, 147 g of N-chlorosuccinimide was added at 0° C. and stirred for 12 hours at room temperature. Water was added to the reaction solution which then was extracted with chloroform. The extract was washed with saturated brine, dried on anhydrous sodium sulfate and distilled. The residue was separated and purified on silica gel column chromatography (hexane/ethyl acetate=5/1) to provide 21 g of the title compound as a yellow solid.

2) 4-Chloro-5-fluoro-2-nitroaniline

To 250 ml of trifluoroacetic anhydride, 21 g of the compound as obtained in 2) above and 15 g of potassium nitrate were successively added at 0° C., followed by 12 hours' stirring at room temperature. Ice water was added to the reaction solution which then was extracted with ethyl acetate. The extract was washed with saturated brine, dried on anhydrous sodium sulfate and distilled. To the solution formed by dissolving the residue in 400 ml of methanol, 200 ml of 7% aqueous potassium carbonate solution was added and stirred for 30 minutes at room temperature. Recovering the whereby formed yellow solid by filtration, 26.5 g of the title compound was obtained.

EXAMPLE 145

5-Cyano-2-[(1,1-dimethylpropyl)sulfanyl]-6-(1-ethylpyrrolidin-3-yl)-oxybenzimidazole 1) 5-(1-Ethylpyrrolidin-3-yl)oxy-4-cyano-2-nitroaniline To 183 mg of 4-cyano-3-fluoro-6-nitroaniline (which was synthesized following J. Med. Chem. 1994, 37, 467) and 201 mg of 1-ethyl-3-pyrrolidinol, 0.5 ml of diisopropylethylamine was added and stirred for 3 hours at 140° C. The reaction liquid was cooled to room temperature, and concentrated after addition of chloroform-methanol (1/1). The residue was separated and purified on preparative thin-layer chromatography [Kieselgel™ 60F$_{254}$, Art.5744 (Merck); chloroform/methanol=4/1] to provide 114 mg of the title compound as a yellow solid.

2) 6-Cyano-5-(1-ethylpyrrolidin-3-yl)oxy-1,3-dihydro-2H-benzimidazol-2-thione

Reactions were conducted by the method similar to Production Example 5-2) and 3) except that the compound as obtained in 1) above was used in place of the compound of Production Example 5-1), to provide the title compound as a pale brown solid.

3) 5-Cyano-2-[(1,1-dimethylpropyl)sulfanyl]-6-(1-ethylpyrrolidin-(3R*)-3-yl)oxybenzimidazole and 5-cyano-2-[(1,1-dimethylpropyl)sulfanyl]-6-(1-ethylpyrrolidin-(3S*)-3-yl)oxybenzimidazole Reactions were conducted following the method similar to Example 141 except that the compound as obtained in 2) above was used in place of the compound of Production Example 5 and tert-amyl alcohol was used in place of 1-methylcyclobutanol, to provide racemic modification of the title compounds as a white solid, without conversion to the corresponding hydrochloride. This racemic modification was optically resolved with an optically active column (Daicel Chemical Ind., Ltd., CHIRAL PAK AD Column; 0.1% diethylamine, hexane/isopropyl alcohol=9/1). From the earlier fraction 5-cyano-2-[(1,1-dimethylpropyl)sulfanyl]-6-(1-ethylpyrrolidin-(3R*)-3-yl)oxybenzimidazole was obtained and from the later fraction the corresponding (3S*-cnfiguration) was obtained, each as a white solid. (Because the two were unidentified, for convenience one of them was recorded as 3R*-configuration and the other, as 3S*-configuration.)

1HNMR(300 MHz, CDCl$_3$)δ:1.00(3H, t, J=7.3 Hz), 1.15 (3H, t, J=7.2 Hz),1.46(6H, s),1.80(2H, q, J=7.3 Hz), 2.09–2.37(2H, m),2.62(2H, q, J=7.2 Hz),2.73–2.85(3H, m), 3.18–3.28(1H, m),4.85–4.93(1H, m),6.90–7.03(1H, br), 7.71–7.82(1H, br)

ESI-MS Found:m/z 359.2[M+H]$^+$

EXAMPLE 146

6-[(4-Ethyl-(2R*)-2-methylpiperazin-1-yl)-2-[(1,1-dimethylethyl)-sulfanyl]-5-methylbenzimidazole and 6-[(4-ethyl-(3R*)-2-methylpiperazin-1-yl)-2-[(1,1-dimethylethyl)sulfanyl]-5-methylbenzimidazole 1) 5-Fluoro-4-methyl-2-nitroaniline A reaction was conducted by the method similar to Production Example 7-2) except that 3-fluoro-4-methylaniline was used in place of 4-chloro-3-fluoroaniline, to provide the title compound as an orange-yellow solid.

2) 5-(4-Ethyl-2-methylpiperazin-1-yl)-4-methyl-2-nitroaniline

A reaction was conducted by the method similar to Example 143-1) except that the compound of 1) above was used in place of 4-cyano-3-fluoro-6-nitroaniline and 1-ethyl-3-methylpiperazine was used in place of 1-tert-butoxycarbonyl-3-methylpiperazine, to provide the title compound as an orange-yellow solid.

3) 6-Methyl-5-(4-ethyl-2-methylpiperazin-1-yl)-1,3-dihydro-2H-benzimidazol-2-thione Reactions were conducted by the method similar to Production Example 5-2) and 3) except that the compound as obtained in 2) above was used in place of the compound of Production Example 5-1), to provide the title compound as a brown solid.

4) 6-[(4-Ethyl-(2R*)-2-methylpiperazin-1-yl)-2-[(1,1-dimethylethyl)-sulfanyl]-5-methylbenzimidazole and 6-[(4-ethyl-(3R*)-2-methylpiperazin-1-yl)-2-[(1,1-dimethylethyl)sulfanyl]-5-methylbenzimidazole Reactions were conducted following the method similar to Example 141 except that the compound as obtained in 3) above was used in place of the compound of Production Example 5 and tert-butyl alcohol was used in place of 1-methylcyclobutanol, to provide racemic modification of the title compounds as a white solid, without conversion to the corresponding hydrochloride. This racemic modification was optically resolved with an optically active column (Daicel Chemical Ind., Ltd., CHIRAL PAK OD Column; 0.1% diethylamine, hexane/isopropyl alcohol=19/1). From the earlier fraction 6-[(4-ethyl-(2R*)-2-methylpiperazin-1-yl)-2-[(1,1-dimethylethyl)sulfanyl]-5-methylbenzimidazole was obtained and from the later fraction the corresponding (2S*-configuration) was obtained, each as a white solid. (Because the two were unidentified, for convenience one of them was recorded as 2R*-configuration and the other, as 2S*-configuration.)

1HNMR(400 MHz, CDCl$_3$)δ:0.82(3H, d, J=6.0 Hz), 1.15 (3H, t, J=7.6 Hz),1.48(9H, s),1.70–2.08(1H, m), 2.22–2.58 (6H, m),2.72–3.02(4H, m),3.19–3.32(1H, m), 7.14–7.30 (1H, m),7.52–7.64(1H, m)

ESI-MS Found:m/z 347.2[M+H]$^+$

EXAMPLE 147

6-[(4-Ethyl-(2R*)-2-methylpiperazin-1-yl)-2-[(1,1-dimethylpropyl)sulfanyl]-5-trifluoromethylbenzimidazole and 6-[(4-ethyl-(2S*)-2-methylpiperazin-1-yl]-2-[(1,1-dimethylpropyl)sulfanyl]-5-trifluoromethylbenzimidazole 1) 5-Fluoro-2-nitro-4-trifluoromethylaniline A reaction was conducted by the method similar to Production Example 7-2) except that 3-fluoro-4-trifluoromethylaniline was used in place of 4-chloro-3-fluoroaniline, to provide the title compound as an orange-yellow solid.

2) 5-(4-Ethyl-2-methylpiperazin-1-yl)-2-nitro-4-trifluoromethylaniline

A reaction was conducted by the method similar to Example 143-1) except that the compound of 1) above was used in place of 4-cyano-3-fluoro-6-nitroaniline (which was synthesized following J. Med. Chem., 1994, 37, 467) and 1-ethyl-3-methylpiperazine was used in place of 1-tert-butoxycarbonyl-3-methylpiperazine, to provide the title compound as an orange-yellow solid.

3) 5-(4-Ethyl-2-methylpiperazin-1-yl)-6-trifluoromethyl-1,3-dihydro-2H-benzimidazol-2-thione Reactions were conducted by the method similar to Production Example 5-2) and 3) except that the compound as obtained in 2) above was used in place of the compound of Production Example 5-1), to provide the title compound as a brown solid.

4) 6-[(4-Ethyl-(2R*)-2-methylpiperazin-1-yl)-2-[(1,1-dimethylproyl)sulfanyl]-5-trifluoromethylbenzimidazole and 6-[(4-ethyl-(2S*)-2-methylpiperazin-1-yl]-2-[(1,1-dimethylpropyl)sulfanyl]-5-trifluoromethylbenzimidazole Reactions were conducted following the method similar to Example 141 except that the compound as obtained in 3) above was used in place of the compound of Production Example 5 and tert-amyl alcohol was used in place of 1-methylcyclobutanol, to provide racemic modification of the title compounds as a white solid, without conversion to the corresponding hydrochloride. This racemic modification was optically resolved with an optically active column (Daicel Chemical Ind., Ltd., CHIRAL PAK AD Column; 0.1% diethylamine, hexane/isopropyl alcohol=19/1). From the earlier fraction 6-[(4-ethyl-(2R*)-2-methylpiperazin-1-yl]-2-[(1,1-dimethylpropyl)sulfanyl]-5-trifluoromethylbenzimidazole was obtained and from the later fraction the corresponding (2S*-configuration) was obtained, each as a white solid. (Because the two were unidentified, for convenience one of them was recorded as 2R*-configuration and the other, as 2S*-configuration.)

1HNMR(400 MHz, CDCl$_3$)δ:0.78(3H, d, J=6.0 Hz), 1.02 (3H, t, J=7.6 Hz),1.15(3H, t, J=6.8 Hz),1.47(6H, s), 1.75–1.90(2H, m),1.95–2.06(1H, m),2.24–2.40(1H, m), 2.42–2.60(2H, m),2.80–3.02(4H, m),3.19–3.30(1H, m), 7.26–8.18(2H, m)

ESI-MS Found:m/z 415.2[M+H]$^+$

PRODUCTION EXAMPLE 8

Production of 2-chloro-5-chloro-6-[4-(tert-butoxycarbonyl)piperazin-1-yl]-1-(tetrahydropyran-2-yl)benzimidazole 1) 2-Amino-5-chloro-6-[4-(tert-butoxycarbonyl)piperazin-1-yl]-benzimidazole A solution of 350 mg of 2-amino-5-[4-(tert-butoxycarbonyl)piperazin-1-yl]-4-chloroaniline as obtained in production Example 1-3) in 2 ml of methanol was added dropwisely into a solution of 123 mg of cyarogen bromide in 0.22 ml of acetonitrile-2 ml of water, at room temperature. The reaction liquid was stirred for 1.5 hours at room temperature, to which 10 ml of saturated aqueous sodium hydrogencarbonate solution was added, followed by extraction with ethyl acetate. The ethyl acetate layer was washed with saturated brine and dried on anhydrous sodium sulfate. The solvent was distilled off to provide 372 mg of the title compound.

2) 2-Chloro-5-chloro-6-[4-(tert-butoxycarbonyl)piperazin-1-yl]-benzimidazole

To a solution of 0.17 ml of tert-butyl nitrite in 3 ml of acetone, 134 mg of copper (II) chloride was added and stirred for 30 minutes at room temperature. To said solution 170 mg of the compound as obtained in 1) above was gradually added, followed by 30 minutes' heating under reflux. The reaction liquid was cooled to room temperature, diluted with ethyl acetate, washed successively with water, saturated aqueous sodium hydrogencarbonate solution and saturated brine, and dried on anhydrous sodium sulfate. After distilling the solvent off under reduced pressure, the residue was separated and purified on silica gel column chromatography (ethyl acetate/hexane=1/3) to provide 372 mg of the title compound.

3) 2-Chloro-5-chloro-6-[4-(tert-butoxycarbonyl)piperazin-1-yl]-1-(tetrahydropyran-2-yl)benzimidazole To a solution of 52 mg of the compound as obtained in 3) above in 3 ml of tetrahydrofuran, 10 mg of camphorsulfonic acid and 0.1 ml of 3,4-dihydro-2H-pyran were added in nitrogen atmosphere at room temperature and stirred for 15 hours at 50° C. Saturated aqueous sodium hydrogencarbonate solution was added to the solution which then was extracted with ethyl acetate. The ethyl acetate layer was washed with saturated brine, dried on anhydrous sodium sulfate and the solvent was distilled off under reduced pressure. The residue was separated and purified on preparative thin-layer chromatography (Kieselgel™ 60F$_{254}$, Art.5744 (Merck); ethyl acetate/hexane=1/2) to provide 46 mg of the title compound.

REFERENTIAL EXAMPLE 1

Production of 5-chloro-2-[(2-ethylbutyl)oxy]-6-(piperazin-1-yl)benzimidazole dihydrochloride 1) 5-Chloro-2-[(2-ethylbutyl)oxy]-6-[4-(tert-butoxycarbonyl)piperazin-1-yl]-1-(tetrahydropyran-2-yl]benzimidazole To a solution of 17 mg of 2-ethylbutanol in 1 ml of dimethylformamide, 11 mg of sodium hydride was added in nitrogen atmosphere at room temperature and stirred for 15 minutes at the same temperature. To said solution a solution of 27 mg of the compound as obtained in Production Example 8 in 2 ml of dimethylformamide was added and stirred for 16 hours at 80° C. The reaction solution was cooled to room temperature, water was added thereto and extracted with ethyl acetate. The ethyl acetate layer was washed with saturated brine, dried on anhydrous sodium sulfate and the solvent was distilled off under reduced pressure. The residue was separated and purified on preparative thin-layer chromtography [Kieselgel™ 60F$_{254}$, Art.5744 (Merck); ethyl acetate/hexane=1/2] to provide 19 mg of the title compound.

2) 5-Chloro-2-[(2-ethylbutyl)oxy]-6-(piperazin-1-yl) benzimidazole dihydrochloride To 19 mg of the compound as obtained in 1) above, 10% hydrogen chloride-in-methanol solution (2 ml) was added, stirred for 14 hours at room temperature, and the solvent was distilled off under reduced pressure. The residue was separated and purified on preparative thin-layer chromatography [Kieselgel™ 60F$_{254}$, Art.5744 (Merck); chloroform/methanol/aqueous ammonia=50/10/1] to provide 12 mg of the title compound as a white solid.

1HNMR(300 MHz, CD$_3$OD)δ:0.98(6H, t, J=7.4 Hz), 1.45–1.65(4H, m),1.71–1.84(1H, m),3.20–3.50(8H, m), 4.48(2H, d, J=5.7 Hz),7.29(1H, s),7.50(1H, s)

ESI-MS Found:m/z 337.2[M+H]$^+$

REFERENTIAL EXAMPLE 2

Production of 5-chloro-2-(1-ethylpropyl)-6-(piperazin-1-yl)-benzimidazole dihydrochloride To a solution of 171 mg of the 2-amino-5-[4-(tert-butoxycarbonyl)piperazin-1-yl]-4-chloroaniline as obtained in Production Example 1-3) and 30 mg of 2-ethylbutanecarboxylic acid in 3 ml of chloroform, 75 mg of 1-ethyl-3-(3'-dimethylaminopropyl)arbodiimide hydrochloride and 119 mg of N-hydroxybenzotriazole monohydrate were added in nitrogen atmosphere, followed by 15 hours' stirring at room temperature. Saturated aqueous sodium hydrogencarbonate solution was added to the solution which then was extracted with ethyl acetate. The ethyl acetate layer was washed with saturated brine, dried on anhydrous sodium sulfate and the solvent was distilled off under reduced pressure. The residue was separated and purified on silica gel column chromatography (ethyl acetate/hexane=1/3) to provide 26 mg of a mixture of 5-[4-(tert-butoxycarbonyl)piperazin-1-yl]-4-chloro-2-[(2-ethylbutanoyl)amino]aniline and 4-[4-(tert-butoxycarbonyl) piperazin-1-yl]-5-chloro-2-[(2-ethylbutanoyl)amino] aniline. The solution of 26 mg of said mixture in 2 ml of trifluoroacetic acid was stirred for 2 days at 70° C., which then was concentrated under reduced pressure and the residue was separated and purified on preparative thin-layer chromatography [Kieselgel™ 60F$_{254}$, Art. 5744 (Merck); chloroform/methanol/aqueous ammonia=50/10/1] to provide 37 mg of the title compound as a pale yellow oily substance.

1HNMR(300 MHz, CD$_3$OD)δ:0.92(6H, dd, J=7.5,8.4 Hz), 1.81–2.08(4H, m),3.04–3.18(1H, m),3.30–3.50(8H, m), 7.58(1H, s),7.88(1H.s)

ESI-MS Found:m/z 307.1[M+H]$^+$

REFERENTIAL EXAMPLE 3

Production of 5-chloro-2-(2-ethylbutyl)-6-(piperazin-1-yl)benzimidazole dihydrochloride Reactions were conducted by the method similar to Referential Example 2, except that 3-ethylpentanecarboxylic acid was used in place of 2-ethylbutanecarboxylic acid, to provide the title compound as a white solid.

1HNMR(300 MHz, CD$_3$OD)δ:0.94(6H, t, J=7.6 Hz), 1.22–1.56(4H, m),1.85–2.04(1H, m),3.09(2H, d, J=7.1 Hz), 3.20–3.52(8H, m),7.58(1H, s),7.86(1H.s)

ESI-MS Found:m/z 321.2[M+H]$^+$

REFERENTIAL EXAMPLE 4

Production of 5-chloro-2-(3-ethylpentyl)-6-(piperazin-1-yl)benzimidazole dihydrochloride Reactions were conducted by the method similar to Referential Example 2, except that 4-ethylhexanecarboxylic acid (which was prepared by the method as described in *J. Pract. Chem.*, 1975, 317, 273–283) was used in place of 2-ethylbutanecarboxylic acid, to provide the title compound as a pale yellow amorphous substance.

1HNMR(300 MHz, CD$_3$OD)δ:0.93(6H, t, J=7.2 Hz), 1.22–1.55(5H, m),1.80–1.98(2H, m),3.05–3.24(2H, m), 3.24–3.56(8H, m),7.57(1H, s),7.86(1H.s)

ESI-MS Found:m/z 335.2[M+H]$^+$

REFERENTIAL EXAMPLE 5

Production of 5-chloro-2-(4-methoxy-4-methylpentyl)-6-(piperazin-1-yl)benzimidazole dihydrochloride Reactions were conducted by the method similar to Referential Example 2, except that 5-methoxy-5-methylhexanecarboxylic acid (Production Example 14 given later) was used in place of 2-ethylbutanecarboxylic acid, to provide the title compound as a pale brown solid.

1HNMR(200 MHz, CD$_3$OD)δ:1.18(6H, s),1.52–2.30(4H, m), 3.11–3.26(2H, m),3.16(3H, s),3.32–3.50(8H, m),7.58 (1H, s), 7.88(1H, s)

ESI-MS Found:m/z 351.1[M+H]$^+$

PRODUCTION EXAMPLE 9

Production of 2-(1-ethylpropoxy)acetic acid

To a solution of 198 mg of 3-pentanol in tetrahydrofuran (4 ml), 180 mg of sodium hydride was added in nitrogen atmosphere at 0° C., and stirred for an hour at room temperature. To the solution 261 mg of sodium chloroacetate was added, followed by 2 hours' stirring at 100° C. The reaction solution was cooled to room temperature, diluted with water, acidified with 1N hydrochloric acid and extracted with chloroform. The chloroform layer was dried on anhydrous magnesium sulfate. The solvent was distilled off under reduced pressure to provide 103 mg of the title compound.

PRODUCTION EXAMPLE 10

Production of 2-(3-methoxy-3-methylbutoxy)acetic acid

Reactions were conducted by the method similar to Production Example 9 except that 3-methoxy-3-methylbutanol was used in place of 3-pentanol, to provide the title compound.

PRODUCTION EXAMPLE 11

Production of 2-(3-methoxy-1,3-dimethylbutoxy) acetic acid

Reactions were conducted by the method similar to Production Example 9 except that 3-methoxy-1,3-dimethylbutanol was used in place of 3-pentanol, to provide the title compound.

PRODUCTION EXAMPLE 12

Production of 5-methoxy-3,5-dimethylhexanecarboxylic acid

To a solution of 1.83 ml of triethyl phosphonoacetate in tetrahydrofuran (15 ml), 340 mg of sodium hydride was added in nitrogen atmosphere at 0° C. and stirred for 30 minutes at the same temperature. To said solution a solution of 1.00 g of 4-methoxy-4-methyl-2-pentanone in tetrahydrofuran (5 ml) was added at 0° C., followed by 15 hours' stirring at room temperature. The reaction solution was diluted with ether, washed successively with water and saturated brine, dried on anhydrous sodium sulfate and the solvent was distilled off. So obtained residue was diisolved in methanol (10 ml), and to which solution 60 mg of 10% palladium-on-carbon catalyst was added, followed by 2 hours' stirring in hydrogen atmosphere (1 atm.). The catalyst was removed from the reaction solution and the filtrate was concentrated under reduced pressure. To a solution of the residue in methanol (4 ml), 2N sodium hydroxide was added and stirred for 2 hours at room temperature. The solution was acidified with 1N hydrochloric acid and extracted with ethyl acetate. The ethyl acetate layer was dried on anhydrous sodium sulfate. Thereafter distilling the solvent off, 223 mg of the title compound was obtained.

PRODUCTION EXAMPLE 13

Production of 6-methoxy-4,6-dimethylheptanecarboxylic acid

To a solution of 3.95 g of methoxymethyltriphenylphosphonium chloride in tetrahydrofuran (15 ml), 6.3 ml of 1.6N n-butyl lithium-hexane solution was added in nitrogen atmosphere at 0° C., followed by an hour's stirring at the same temperature. To said solution a solution of 1.00 g of 4-methoxy-4-methyl-2-pentanone in tetrahydrofuran (5 ml) was added at 0° C. and stirred for an hour at room temperature. The reaction solution was diluted with ether, washed successively with water and saturated brine, dried on anhydrous sodium sulfate and the solvent was distilled off, to provide 4-methoxy-2,4-dimethyl-pentanal*). A reaction by the method similar to Production Example 12 was conducted except that this compound was used in place of 4-methoxy-4-methyl-2-pentanone, to provide the title compound.

PRODUCTION EXAMPLE 14

Production of 5-methoxy-5-methylhexanecarboxylic acid

Reactions were conducted by the method similar to Production Example 12 except that 3-methoxy-3-methylbutanal (which was prepared by the method described in JP-Hei8 (1996)-176054A) was used in place of 4-methoxy-4-methyl-2-pentanone, to provide the title compound.

PRODUCTION EXAMPLE 15

Production of 6-methoxy-6-methylheptanecarboxylic acid

Reactions were conducted by the method similar to Production Example 12 except that 4-methoxy-4-methylpentanal (which was prepared by the method described in U.S. Pat. No. 4,891,447) was used in place of 4-methoxy-4-methyl-2-pentanone, to provide the title compound.

REFERENTIAL EXAMPLE 6

Production of 5-chloro-2-(5-methoxy-5-methylhexyl)-6-(piperazin-1-yl) benzimidazole dihydrochloride A reaction was conducted by the method similar to Referential Example 2 except that 6-methoxy-6-methylheptanecarboxylic acid (Production Example 15) was used in place of 2-ethylbutanecarboxylic acid, to provide the title compound as a red solid.

1HNMR(200 MHz, $CD_3OD$)δ:1.15(6H, s),1.40–1.63(4H, m), 1.79–2.00(2H, m),3.13–3.23(2H, m),3.16(3H, s),3.32–3.49(8H, m), 7.57(1H, s),7.87(1H, s)

ESI-MS Found:m/z 365.2[M+H]$^+$

REFERENTIAL EXAMPLE 7

Production of 5-chloro-2-(5-methoxy-3,5-dimethylhexyl)-6-(piperazin-1-yl)benzimidazole dihydrochloride A reaction was conducted by the method similar to Referential Example 2 except that 6-methoxy-4,6-dimethylheptanecarboxylic acid (Production Example 13) was used in place of 2-ethylbutanecarboxylic acid, to provide the title compound as a purple solid.

1HNMR(200 MHz, $CD_3OD$)δ:1.07(3H, d, J=6.2 Hz),1.16 (6H, s), 1.37–2.06(5H, m)3.13–3.24(2H, m),3.15(3H, s),3.32–3.49(8H, m), 7.57(1H, s),7.86(1H, s)

ESI-MS Found:m/z 379.2[M+H]$^+$

REFERENTIAL EXAMPLE 8

Production of 5-chloro-2-(4-methoxy-2,4-dimethylpentyl)-6-(piperazin-1-yl)benzimidazole dihydrochloride A reaction was conducted by the method similar to Referential Example 2 except that 5-methoxy-3,5-dimethylhexanecarboxylic acid (Production Example 12) was used in place of 2-ethylbutanecarboxylic acid, to provide the title compound as a light brown solid.

1HNMR(300 MHz, $CD_3OD$)δ:1.03(3H, d, J=6.7 Hz),1.18 (3H, s), 1.22(3H, s),1.50–1.65(2H, m),2.27–2.46(1H, m),2.92–3.01(1H, m), 3.30–3.41(5H, m),3.41–3.48(4H, m),7.58(1H, s),7.88(1H, s)

ESI-MS Found:m/z 365.3[M+H]$^+$

REFERENTIAL EXAMPLE 9

Production of 5-chloro-2-[(1-ethylpropoxy)methyl]-6-(piperazin-1-yl)benzimidazole dihydrochloride A reaction was conducted by the method similar to Referential Example 2 except that 2-(1-ethylpropoxy)acetic acid (Production Example 9) was used in place of 2-ethylbutanecarboxylic acid, to provide the title compound as a pale brown solid.

1HNMR(200 MHz, $CD_3OD$)δ:0.96(6H, t, J=7.5 Hz), 1.57–1.75(4H, m),3.31–3.56(9H, m),5.02(2H, s),7.62(1H, s), 7.91(1H, s)

ESI-MS Found:m/z 337.1[M+H]$^+$

REFERETIAL EXAMPLE 10

Production of 5-chloro-2-[(3-methoxy-3-methylbutoxy)methyl]-6-(piperazin-1-yl) benzimidazole dihydrochloride A reaction was conducted by the method similar to Referential Example 2 except that 2-(3-methoxy-3-methylbutoxy)acetic acid (Production Example 10) was used in place of 2-ethylbutanecarboxylic acid, to provide the title compound as a pale brown solid.

1HNMR(200 MHz, $CD_3OD$)δ:1.21(6H, s),1.95(2H, t, J=7.3 Hz), 3.20(3H, s),3.33–3.50(8H, m),3.80(2H, t, J=7.3 Hz),5.02(2H, s), 7.62(1H, s),7.91(1H, s)

ESI-MS Found:m/z 367.2[M+H]$^+$

REFERENTIAL EXAMPLE 11

Production of 5-chloro-2-[(3-methoxy-1,3-dimethylbutoxy)methyl]-6-(piperazin-1-yl) benzimidazole dihydrochloride A reaction was conducted by the method similar to Referential Example 2 except that 2-(3-methoxy-1,3-dimethylbutoxy)acetic acid (Production Example 11) was used in place of 2-ethylbutanecarboxylic acid, to provide the title compound as a pale brown solid.

1HNMR(200 MHz, $CD_3OD$)δ:1.23(3H, s),1.24(3H, s), 1.31(3H, d, J=6.2 Hz),1.60–1.73(1H, m),1.93–2.07(1H, m), 3.22(3H, s),3.33–3.50(8H, m),3.86–4.04(1H, m),4.95–5.15 (2H, m), 7.61(1H, s),7.91(1H, s)

ESI-MS Found:m/z 381.2[M+H]$^+$

REFERENTIAL EXAMPLE 12

Production of 5-chloro-2-[(1-ethylpropyl)amino]-6-(piperazin-1-yl)benzimidazole dihydrochloride To a solution of 64 mg of thiocarbonyldiimidazole and imidazole in acetonitrile (3 ml), 21 mg of (1-ethylpropyl)amine was added dropwise in nitrogen atmosphere at 0° C., followed by 3 hours' stirring at the same temperature. To the solution then a solution of 150 mg of 2-amino-5-[4-(tert-butoxycarbonyl)piperazin-1-yl]-4-chloroaniline as obtained in Production Example 1-3) in acetonitrile (2 ml) was added, followed by 3 hours' stirring at 50° C. and 2 days' stirring at room temperature. Thus obtained reaction solution was concentrated under reduced pressure. The residue was separated and purified on silica gel column chromatography (hexane/ethyl acetate=2/1) to provide 60 mg of a mixture of N-[2-amino-5-chloro-4-(4-(tert-butoxycarbonyl)piperazin-1-yl)phenyl]-N'-(1-ethylpropyl)-thiourea and N-[2-amino-4-chloro-5-(4-(tert-butoxycarbonyl)-piperazin-1-yl)phenyl]-N'-(1-ethylpropyl)-thiourea.

A suspension of 60 mg of the above mixture, 70 mg of mercury oxide and 2 mg of sulfur in ethanol (3 ml) was stirred for 4 hours at 80° C. Then the insoluble matter was removed by filtration and the filtrate was concentrated under reduced pressure. The residue was separated and purified on preparative thin-layer chromatography (Kieselgel™ 60F$_{254}$, Art.5744 (Merck); chloroform/methanol/aqueous ammonia=10/1/0.1) to provide 19 mg of 5-chloro-2-[(1-ethylpropyl)amino]-6-[4-(tert-butoxycarbonyl)piperazin-1-yl]benzimidazole. To 19 mg of this compound 1 ml of 10% hydrogen chloride-in-methanol solution was added and stirred for 12 hours at room temperature. The same solution was concentrated under reduced pressure to provide 19 mg of the title compound as a white solid.

1HNMR(300 MHz, $CD_3OD$)δ:0.80(6H, t, J=7.4 Hz), 1.32–1.64(4H, m),3.00–3.36(9H, m),6.40(1H, s),7.04(1H, s), 7.24(1H, s)

ESI-MS Found:m/z 322.2[M+H]$^+$

REFERENTIAL EXAMPLE 13

Production of 5-chloro-2-[(1-ethylbutyl)amino]-6-(piperazin-1-yl)-benzimidazole dihydrochloride Reactions were conducted by the method similar to Referential Example 12 except that 1-(ethylbutyl)amine was used in place of 1-(ethylpropylamine, to provide the title compound as a colorless oily substance.

1HNMR(300 MHz, CD$_3$OD)δ:0.96(6H, t, J=7.4 Hz), 1.40–1.53(4H, m),1.53–1.71(1H, m), 3.22–3.46(10H, m),7.27(1H, s),7.45(1H, s)

ESI-MS Found:m/z 336.2[M+H]$^+$

FORMULATION EXAMPLE 1

Twenty (20.0) g of the compound of Example 1, 417.0 g of lactose, 80.0 g of crystalline cellulose and 80.0 g of partial alpha starch were mixed with a V-shaped mixer, and further 3.0 g of magnesium stearate was added and mixed. The powdery mixture was tabletted by a conventional method to provide 3000 tablets having a diameter of 7.0 mm and a weight of 150 mg per tablet.

| Ingredients per tablet | |
|---|---|
| Compound of Example 1 | 5.0 mg |
| Lactose | 104.25 mg |
| Crystalline cellulose | 20.0 mg |
| Partial alpha starch | 20.0 mg |
| Magnesium stearate | 0.75 mg |

FORMULATION EXAMPLE 2

In 172.5 g of purified water, 10.8 g of Hydroxypropyl-cellulose 2910 and 2.1 g of Polyethylene glycol 6000 were dissolved and in which 2.1 g of titanium dioxide was dispersed to provide a coating liquid. The coating liquid was spray-coated onto 2500 tablets of Formulation Example 1 which were separately prepared, with HICOATER MINI, to provide film-coated tablets weighting 155 mg.

| Ingredients per tablet | |
|---|---|
| Tablet of Formulation Example 1 | 150 mg |
| Hydroxypropylcellulose 2910 | 3.6 mg |
| Polyethylene glycol 6000 | 0.7 mg |
| Titanium dioxide | 0.7 mg |

Industrial Applicability

Compounds of the present invention inhibit actions of nociceptin as they exhibit high affinity to nociceptin receptor, and hence are useful as an analgesic against diseases accompanied with pain such as cancerous pain, postoperative pain, migraine, gout, chronic rheumatism, chronic pain and neuralgia; a reliever against tolerance to narcotic analgesic represented by morphine, a reliever against dependence on narcotic analgesic represented by morphine, an analgesic enhancer, an antiobestic, a drug for ameliorating brain function, a prophylactic for Alzheimer's disease, a drug for treating Alzheimer's disease, a prophylactic for dementia, an anti-dementia drug, a remedy for schizophrenia, a drug for treating regressive neurodegenerative diseases represented by Parkinsonism and chorea, an antidepressant, a remedy for diabetes insipidus, a remedy for polyuria or a remedy for hypotension.

What is claimed is:

1. Benzimidazole derivatives represented by the following formula I or pharmaceutically acceptable salts thereof:

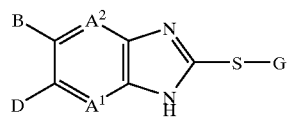

in which $A^1$ and $A^2$ are methine groups or $A^1$ is fluorinated methine group and $A^2$ is methine group;

B represents a member selected from the group consisting of halogen, cyano, lower alkylcarbonyl, lower alkylsulfonyl, mono-lower alkylsulfamoyl, di-lower alkylsulfamoyl, optionally fluorine-substituted lower alkyl and optionally fluorine-substituted lower alkyloxy;

D is an aliphatic, nitrogen-containing heterocyclic group which is selected from the group consisting of those of a formula D-1, formula D-2 and formula D-3

in which $R^1$ represents hydrogen atom or lower alkyl, and said lower alkyl may be substituted with a substituent selected from a group consisting of halogen, hydroxyl, amino, lower alkyloxy, lower alkylsulfonylamino, aminocarbonylamino, mono-lower alkylcarbamoyl, acetamido, lower cycloalkyl, aromatic heterocyclic group and aromatic carbocyc lie group;

$R^2$ binds to an optional carbon atom or atoms on the aliphatic, nitrogen-containing heterocyclic ring, and represents carboxyl, lower alkyloxycarbonyl, carbamoyl, mono-lower alkylcarbamoyl, di-lower alkylcarbamoyl or lower alkyl, said lower alkyl being optionally substituted with a substituent selected from a group consisting of halogen, hydroxyl, optionally fluorine-substituted lower alkyloxy, lower alkylcarbonyl, carboxyl, lower alkyl, lower alkyloxycarbonyl, carbamoyl, mono-lower alkylcarbamoyl and di-lower alkylcarbamoyl, or two $R^2$'s together form an oxo group;

m1 stands for 0 or an integer of 1–2, and where m1=2, two $R^2$'s, which may be same or different, bind to same or different optional carbon atom(s) on the aliphatic nitrogen-containing heterocyclic ring;

E stands for a single bond, NR or O, R standing for hydrogen atom, methyl or ethyl;

stands for a 5–10 membered mono- or di-cyclic aliphatic, nitrogen-containing heterocyclic group which has two nitrogen atoms;

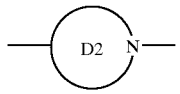

stands for a 3–10 membered mono- or di-cyclic aliphatic, nitrogen-containing heterocyclic group which has one nitrogen atom;

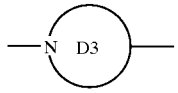

stands for a 3–10 membered mono- or di-cyclic aliphatic, nitrogen-containing heterocyclic group which has one nitrogen atom;

G is a $C_3$–$C_{20}$ aliphatic group represented by a formula G-1

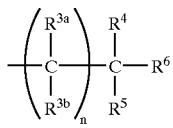

G-1 in which $R^{3a}$ and $R^{3b}$ are same or different and stand for hydrogen atom, methyl or ethyl, $R^4$ stands for hydrogen atom or optionally substituted lower alkyl, and $R^5$ and $R^6$ are same or different and have the same meaning as $R^4$, or $R^5$ and $R^6$ together form an aliphatic cyclic group, in combination with the carbon atom to which they bind, and n is 0 or an integer of 1–4.

2. Benzimidazole derivatives represented by formula I-1 or their pharmaceutically acceptable salts:

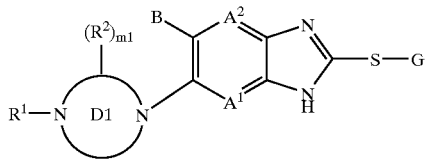

I-1 in which $A^1$ and $A^2$ are methine groups or $A^1$ is fluorinated methine group and $A^2$ is methine group;

B represents a member selected from the group consisting of halogen, cyano, lower alkylcarbonyl, lower alkylsulfonyl, mono-lower alkylsulfamoyl, di-lower alkylsulfamoyl, optionally fluorine-substituted lower alkyl and optionally fluorine-substituted lower alkyloxy;

G is a $C_3$–$C_{20}$ aliphatic group represented by a formula G-1

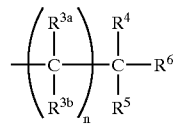

[G-1]

in which $R^{3a}$ and $R^{3b}$ are same or different and stand for hydrogen atom, methyl or ethyl, $R^4$ stands for hydrogen atom or optionally substituted lower alkyl, and $R^5$ and $R^6$ are same or different and have the same meaning as $R^4$, or $R^5$ and $R^6$ together form an aliphatic cyclic group, in combination with the carbon atom to which they bind, and n is 0 or an integer of 1–4.

$R^1$ represents hydrogen atom or lower alkyl, and said lower alkyl may be substituted with a substituent selected from the group consisting of halogen, hydroxyl, amino, lower alkyloxy, lower alkylsulfonylamino, aminocarbonylamino, mono-lower alkylcarbamoyl, acetamido, lower cycloalkyl, aromatic heterocyclic group and aromatic carbocyclic group;

$R^2$ binds to an optional carbon atom or atoms on the aliphatic, nitrogen-containing heterocyclic ring, and represents carboxyl, lower alkyloxycarbonyl, carbamoyl, mono-lower alkylcarbamoyl, di-lower alkylcarbamoyl or lower alkyl, said lower alkyl being optionally substituted with a substituent selected from a group consisting of halogen, hydroxyl, optionally fluorine-substituted lower alkyloxy, lower alkylcarbonyl, carboxyl, lower alkyl, lower alkyloxycarbonyl, carbamoyl, mono-lower alkylcarbamoyl and di-lower alkylcarbamoyl, or two $R^2$'s together form an oxo group;

m1 stands for 0 or an integer of 1–2, and where m1=2, two $R^2$'s, which may be same or different, bind to same or different optional carbon atom(s) on the aliphatic nitrogen-containing heterocyclic ring; and

stands for a 5–10 membered mono- or di-cyclic aliphatic, nitrogen-containing heterocyclic group which has two nitrogen atoms.

3. Compounds which are described in claim 1 or 2, wherein B is fluorine atom, chlorine atom, cyano group or methyl group.

4. Compounds which are described in claim 1 or 2, wherein optionally substituted lower alkyl groups represented by $R^4$ are lower alkyl groups optionally having substituents selected from the following group α: halogen, hydroxyl, amino, mono-lower alkylamino, di-lower alkylamino, optionally fluorine-substituted lower alkyloxy, lower alkyloxycarbonyl, (lower alkyloxycarbonyl)amino, (lower alkyloxycarbonyl)lower alkylamino, carboxyl, lower alkylcarbonyl, lower alkylcarbonyloxy, (lower alkylcarbonyl)amino, (lower alkylcarbonyl)lower alkylamino, carbamoyl, mono-lower alkylcarbamoyl, di-lower alkylcarbamoyl, carbanioylamino, mono-lower alkylcarbamoylamino, di-lower alkylcarbamoylamino, (mono-lower alkylcarbamoyl)lower alkylaniino, (di-lower alkylcarbamoyl)lower alkylamino, carbamoyloxy, mono-lower alkylcarbamoyloxy, di-lower alkylcarbamoyloxy, lower alkylsulfonyl, lower alkylsulfonylamino, sulfamoyl, mono-lower alkylsulfamoyl, di-lower alkylsulfamoyl, sulfamoylamino, (mono-lower alkylsulfamoyl)amino, (di-lower alkylsulfamoyl)amino, (mono-lower alkylsulfamoyl) lower alkylamino and (di-lower alkylsulfamoyl) lower alkylamino.

5. Compounds which are described in claim 1 or 2, wherein D is a member selected from the group consisting of piperazin-1-yl, 4-methylpiperazin-1-yl, 4-ethylpiperazin-1-yl, 4-isopropylpiperazin-1-yl, 4-(cyclopropylmethyl) piperazin-1-yl, 4-(2-fluoroethyl)piperazin-1-yl, 4-(2-methoxyethyl)piperazin-1-yl, 4-ethyl-2-methylpiperazin-1-yl, 4-(2-fluoroethyl)-2-methylpiperazin-1-yl, 4-(2-methoxyethyl)-2-methylpiperazin-1-yl, 4-(2-hydroxyethyl)-2-methylpiperazin-1-yl, 4-(2-hydroxyethyl)piperazin-1-yl, 4-2-(acetamido)ethyljpiperazin-1-yl, 4-(2,6-dimethoxybenzyl)piperazin-1-yl, 2,5-diazabicyclo[2.2.1] heptan-2-yl, 5-(2-hydroxyethyl)-2,5-diazabicyclo[2.2.1]heptan-2-yl, 1,4-diazepan-1-yl, 4-(2-hydroxyethyl)-1,4-diazepan-1-yl, 1-ethylpyrrolidin-3-yl, 1-(2-methoxyethyl) pyrrolidin-3-yl, [1-(2-methoxyethyl)pyrrolidin-3-yl](methyl)amino and 1-(2-methoxyethyl)pyrrolidin-3-yl]oxy.

6. Compounds which are described in claim 1, or 2, wherein G is a member selected from the group consisting of 2-methoxy-1-(methoxymethyl)ethyl, 2-ethoxy-1-(ethoxymethyl)ethyl, 2-dimethylamino-1,1-dimethylethyl, 2-dimethylamino-1-methylethyl, 2-(acetamido)ethyl, 2-hydroxy-1-(hydroxymethyl)ethyl, 1-(methoxycarbonyl) propyl, 1-ethyipropyl, tert-butyl, 1,1-dimethylpropyl, 1,1-dimethylbutyl, 1,3,3-trimethylbutyl, 3-methoxy-1,3-dimethylbutyl, 3-hydroxy-1,3-dimethylbutyl, 1-ethyl-3-methyl-3-hydroxybutyl, 3-acetoxy-1,1-dimethylbutyl, 3-hydroxy-1,1-dimethylbutyl, cyclobutyl, 1-methylcyclobutyl, cyclopentyl, 1-methylcyclopentyl, cyclohexyl, 1-methylcyclohexyl, 4-(methoxycarbonyl) cyclohexyl, 4-oxocyclohexyl, 4-(ethoxycarbonylamino) cyclohexyl, 4-methoxycarbonylamino-1-methylcyclohexyl, 4-ethoxycarbonylamino-1-methylcyclohexyl, 4-hydroxycyclohexyl, 4-hydroxy-4-methylcyclohexyl, 4-(ethoxycarbonylamino)cyclohexyl, 1-methylpiperidin-4-yl, 1-(methoxycarbonyl)piperidin-4-yl, 1-(ethoxycarbonyl) piperidin-4-yl, 1-methoxycarbonyl-4-methylpiperidin-4-yl, 1-ethoxycarbonyl-4-methylpiperidin-4-yl, 1-methylpyrrolidin-3-yl, 1-methylpiperidin-3-yl, 1-(methoxycarbonyl)pyrrolidin-3-yl, 1-(methoxycarbonyl) piperidin-3-yl, 1-(allyloxycarbonyl)piperidin-4-yl, 1-(ethylsulfonyl)piperidin-4-yl, 1-acetylpiperidin-4-yl, tetrahydrofiiran-3-yl, tetrahydro-2H-pyran-4-yl, 4-methyl-tetrahydro-2H-pyran-4-yl, 4-ethyl-tetrahydro-2H-pyran-4-yl, 1,4-dihydroxyoctahydro-2-pentalenyl, 1,4-dioxaspiro[4,5]decan-8-yl, 8-oxabicyclo[3.2.1]octan-3-yl and 8-oxabicyclo[3.2.1]octan-3-yl.

7. Benzimidazole derivatives represented by the following formula I or pharmaceutically acceptable salts thereof:

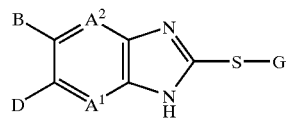

I in which $A^1$ and $A^2$ are methine groups or $A^1$ is fluorinated methine group and $A^2$ is methine group;

B represents a member selected from the group consisting of halogen, cyano, lower alkylcarbonyl, lower alkylsulfonyl, mono-lower alkylsulfamoyl, di-lower alkylsulfamoyl, optionally fluorine-substituted lower alkyl and optionally fluorine-substituted lower alkyloxy;

D is an aliphatic, nitrogen-containing heterocyclic group which is selected from the group consisting of those of a formula D-1, formula D-2 and formula D-3

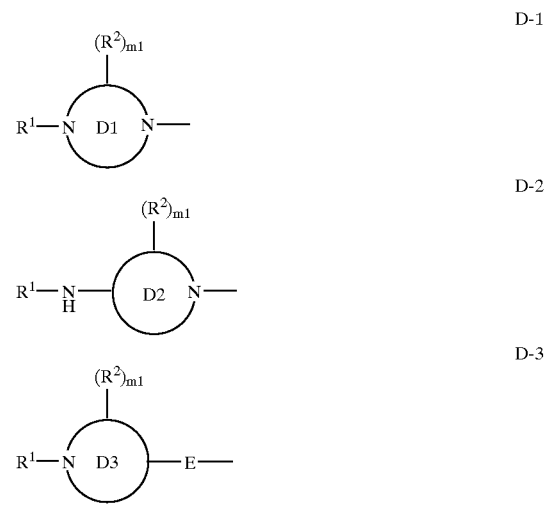

in which $R^1$ represents hydrogen atom or lower alkyl, and said lower alkyl may be substituted with a substituent selected from the group consisting of halogen, hydroxyl, amino, lower alkyloxy, lower alkylsulfonylamino, aminocarbonylamino, mono-lower alkylcarbamoyl, acetamido, lower cycloalkyl, aromatic heterocyclic group and aromatic carbocyclic group;

$R^2$ binds to an optional carbon atom or atoms on the aliphatic, nitrogen-containing heterocyclic ring, and represents carboxyl, lower alkyloxycarbonyl, carbamoyl, mono-lower alkylcarbamoyl, di-lower alkylcarbamoyl or lower alkyl, said lower alkyl being optionally substituted with a substituent selected from a group consisting of halogen, hydroxyl, optionally fluorine-substituted lower alkyloxy, lower alkylcarbonyl, carboxyl, lower alkyl, lower alkyloxycarbonyl, carbamoyl, mono-lower alkylcarbamoyl and di-lower alkylcarbamoyl, or two $R^2$'s together form an oxo group;

m1 stands for 0 or an integer of 1–2, and where m1=2, two $R^2$'s, which may be same or different, bind to same or different optional carbon atom(s) on the aliphatic nitrogen-containing heterocyclic ring;

E stands for a single bond, NR or O, R standing for hydrogen atom, methyl or ethyl;

stands for a 5–10 membered mono- or di-cyclic aliphatic, nitrogen-containing heterocyclic group which has two nitrogen atoms;

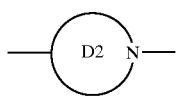

stands for a 3–10 membered mono- or di-cyclic aliphatic, nitrogen-containing heterocyclic group which has one nitrogen atom;

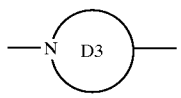

stands for a 3–10 membered mono- or di-cyclic aliphatic, nitrogen-containing heterocyclic group which has one nitrogen atom;

G is a $C_3$–$C_{20}$ aliphatic group represented by a formula G-2,

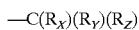                                        G-2 in which $R_X$ stands for lower alkyl which may have a substituent selected from the group α, $R_Y$ and $R_Z$ are same or different, and stand for lower alkyl which may have a substituent selected from the group α wherein α is a member selected from the group consisting of halogen, hydroxyl, amino, mono-lower alkylamino, di-lower alkylamino, optionally fluorine-substituted lower alkyloxy, lower alkyloxycarbonyl, (lower alkyloxycarbonyl)amino, (lower alkyloxycarbonyl)lower alkylamino, carboxyl, lower alkylcarbonyl, lower alkylcarbonyloxy, (lower alkylcarbonyl)amino, (lower alkylcarbonyl)lower alkylamino, carbamoyl, mono-lower alkylcarbamoyl, di-lower alkylcarbamoyl, carbamoylamino, mono-lower alkylcarbamoylamino, di-lower alkylcarbamoylamino, (mono-lower alkylcarbamoyl) lower alkylamino, (di-lower alkylcarbamoyl)lower alkylamino, carbamoyloxy, mono-lower alkylcarbamoyloxy, di-lower alkylcarbamoyloxy, lower alkylsulfonyl, lower alkylsulfonylamino, sulfamoyl, mono-lower alkylsulfamoyl, di-lower alkylsulfamoyl, sulfamoylamino, (mono-lower alkylsulfamoyl)amino, (di-lower alkylsulfamoyl) amino, (mono-lower alkylsulfamoyl)lower alkylamino and (di-lower alkylsulfamoyl) lower alkylamino, or $R_Y$ and $R_Z$ together form a 3–10 membered aliphatic carbocyclic ring together with the carbon atom to which they bind.

8. Compounds which are described in claim 7, in which G is a member selected from the group consisting of 1-methylcyclobutyl, 1-methylcyclopentyl, 1-methylcyclohexyl, tert-butyl, 1,1-dimethylpropyl, 1,1-dimethylbutyl, 3-methyltetrahydrofbran-3-yl and 4-methyltetrahydro-2H-pyran-4-yl.

9. Compounds which are described in claim 1, in which the benzimidazole derivatives represented by the formula I are 5-chloro-6-[4-(2-hydroxyethyl)piperazin-1-yl]-2-[1-(methylcyclobutyl)sulfanyl]benzimidazole, 5-chloro-7-fluoro-6-[4-(2-hydroxyethyl)piperazin-1-yl]-2-[(1-methylcyclopentyl)sulfanyl]benzimidazole, 6-[4-ethyl-2-methylpiperazin-1-yl]-2-[(1,1-dimethylethyl)-sulfanyl]-5-methylbenzimidazole, 5-chloro-2-[(1-ethylpropyl)sulfanyl]-6-[1-(2-hydroxyethyl)-piperidin-4-yl]benzimidazole, 5-chloro-6-[1,4-diazabicyclo[3.2.1]octan-4-yl]-2-[(1,1-dimethylpropyl)sulfanyl]benzimidazole, 5-chloro-2-[4-[(ethoxycarbonyl)amino]-1-methylcyclohexyl]-sulfanyl]-6-[4-(2-fluoroethyl) piperazin-1-yl]benzimidazole, 5-chloro-2-[(1,1-dimethylpropyl)sulfanyl]-6-[4-(2-hydroxyethyl)piperazin-1-yl]benzimidazole, 5-cyano-2-[(1,1-dimethylethyl)sulfanyl]-7-fluoro-6-[4-(2-fluoroethyl)-2-methylpiperazin-1-yl]benzimidazole, or 5-chloro-2-[(1-ethylpropyl)sulfanyl]-6-[5-(2-hydroxyethyl)-2,5-diazabicyclo[2.2.1]hept-2-yl] benzimidazole.

10. A pharmaceutical composition comprising a nociceptin receptor-antagonistically effective amount of a compound of formula I as set forth in claim 1 or pharmaceutically acceptable salts thereof, and at least one pharmaceutically acceptable adjuvant.

11. A method for producing a compound represented by the formula I-1.

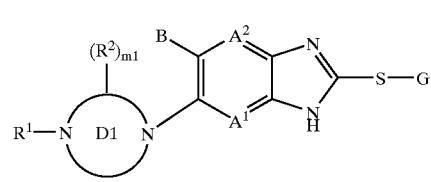                                        I-1 in which $A^1$ and $A^2$ are methine groups or $A^1$ is fluorinated methine group and $A^2$ is methine group;

B represents a member selected from the group consisting of halogen, cyano, lower alkylcarbonyl, lower alkylsulfonyl, mono-lower alkylsulfamoyl, di-lower alkylsulfamoyl, optionally fluorine-substituted lower alkyl and optionally fluorine-substituted lower alkyloxy;

G is a $C_3$–$C_{20}$ aliphatic group represented by a formula G-1

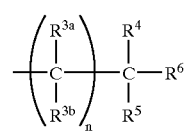                                        G-1 in which $R^{3a}$ and $R^{3b}$ are same or different and stand for hydrogen atom, methyl or ethyl, $R^4$ stands for hydrogen atom or optionally substituted lower alkyl, and $R^5$ and $R^6$ are same or different and have the same meaning as $R^4$, or $R^5$ and $R^6$ together form an aliphatic cyclic group, in combination with the carbon atom to which they bind, and n is 0 or an integer of 1–4;

$R^1$ represents hydrogen atom or lower alkyl, and said lower alkyl may be substituted with a substituent selected from the group consisting of halogen, hydroxyl, amino, lower alkyloxy, lower alkylsulfonylamino, aminocarbonylamino, mono-lower alkylcarbamoyl, acetamido, lower cycloalkyl, aromatic heterocyclic group and aromatic carbocyclic group;

$R^2$ binds to an optional carbon atom or atoms on the aliphatic, nitrogen-containing heterocyclic ring, and represents carboxyl, lower alkyloxycarbonyl, carbamoyl, mono-lower alkylcarbamoyl, di-lower alkylcarbamoyl or lower alkyl, said lower alkyl being optionally substituted with a substituent selected from a group consisting of halogen, hydroxyl, optionally fluorine-substituted lower alkyloxy, lower alkylcarbonyl, carboxyl, lower alkyl, lower alkyloxycarbonyl, carbamoyl, mono-lower alkylcarbamoyl and di-lower alkylcarbanioyl, or two $R^2$'s together form an oxo group;

m1 stands for 0 or an integer of 1–2, and where m1=2, two $R^2$'s, which may be same or different, bind to same or different optional carbon atom(s) on the aliphatic nitrogen-containing heterocyclic ring; and

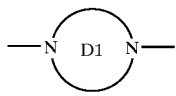

stands for a 5–10 membered mono- or di-cyclic aliphatic, nitrogen-containing heterocyclic group which has two nitrogen atoms;

which comprises 1) a step of reacting a compound represented by formula II

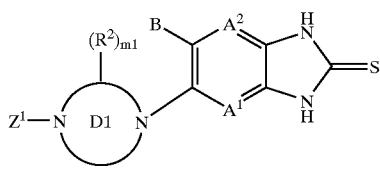

II in which $Z^1$ stands for $R^1$ or P, P stands for an amino-protective group, and $A^1$, $A^2$, B, $R^1$, $R^2$, m1 and

are same as above defined,
with a compound of a formula III

G-L  III in which G is same as above defined, and L stands for a leaving group selected from the group consisting of halogen, lower alkylsulfonyloxy, arylsulfonyloxy, imidazolinyl and 0-isourea,
in a reaction solvent and in the presence or absence of a basic compound, to obtain a compound represented by formula IV

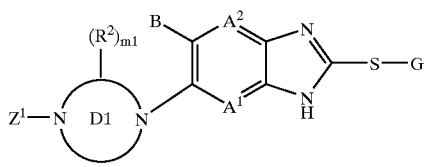

IV in which $A^1$, $A^2$, B, G, $R^2$, $Z^1$, m1 and

are same as above defined, 2) a step of eliminating the protective group P in the compound represented by the formula IV, where $Z^1$ is P, and 3) optionaLly, a step of condensing the compound obtained in above step 2) with a compound represented by a formula V $R^{1a}$—CHO  V in which $R^{1a}$ stands for a group of $R^1$ from whose α-position side methylene group is removed, in a reaction solvent, and in the presence of a reducing agent.

12. A method for producing a compound represented by a formula I-2

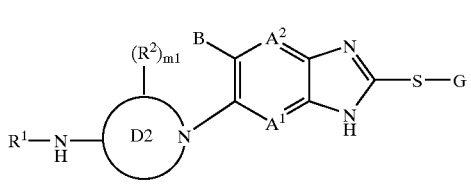

I-2 in which $A^1$ and $A^2$ are methine groups or $A^1$ is fluorinated methine group and $A^2$ is methine group;

B represents a member selected from the group consisting of halogen, cyano, lower alkylcarbonyl, lower alkylsulfonyl, mono-lower alkylsulfamoyl, di-lower alkylsul famoyl, optionally fluorine-substituted lower alkyl and optionally fluorine-substituted lower alkyloxy;

G is a $C_3$–$C_{20}$ aliphatic group represented by formula G-1

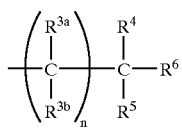

G-1

$R^{3a}$ and $R^{3b}$ are same or different and stand for hydrogen atom, methyl or ethyl, $R^4$ stands for hydrogen atom or optionally substituted lower alkyl, and $R^5$ and $R^6$ are same or different and have the same meaning as $R^4$, or $R^5$ and $R^6$ together form an aliphatic cyclic group, in combination with the carbon atom to which they bind, and n is 0 or an integer of 1–4;

$R^1$ represents hydrogen atom or lower alkyl, and said lower alkyl may be substituted with a substituent selected from a group consisting of halogen, hydroxyl, amino, lower alkyloxy, lower alkylsulfonylamino, aminocarbonylamino, mono-lower alkylcarbamoyl, acetamido, lower cycloalkyl, aromatic heterocyclic group and aromatic carbocyclic group;

$R^2$ binds to an optional carbon atom or atoms on the aliphatic, nitrogen-containing heterocyclic ring, and represents carboxyl, lower alkyloxycarbonyl, carbamoyl, mono-lower alkylcarbamoyl, di-lower alkylcarbamoyl or lower alkyl, said lower alkyl being optionally substituted with a substituent selected from a group consisting of halogen, hydroxyl, optionally fluorine-substituted lower alkyloxy, lower alkylcarbonyl, carboxyl, lower alkyl, lower alkyloxycarbonyl, carbamoyl, mono-lower alkylcarbamoyl and di-lower alkylcarbamoyl, or two $R^2$'s together form an oxo group;

m1 stands for 0 or an integer of 1–2, and where m1=2, two $R^2$'s, which may be same or different, bind to same or different optional carbon atom(s) on the aliphatic nitrogen-containing heterocyclic ring; and

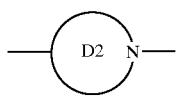

stands for a 3–10 membered mono- or di-cyclic aliphatic, nitrogen-containing heterocyclic group which has one nitrogen atom;

which comprises 1) a step for reacting a compound represented by formula VI

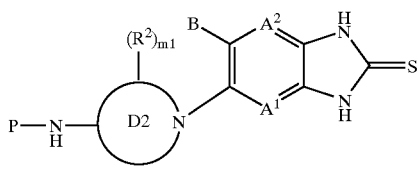

in which $A^1$, $A^2$, B, $R^2$, m1, P and

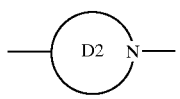

are as defined above, and P is an amino protective group, with a compound represented by the formula III

G-L    III in which G is as defined above and L stands for a leaving group selected from the group consisting of halogen, lower alkylsulfonyloxy, imidazolinyl and 0-isourea, in a reaction solvent and in the presence or absence of a basic compound,
to obtain a compound represented by formula VII

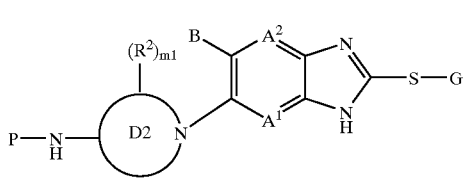

in which $A^1$, $A^2$, B, G, $R^2$, m1, P, and

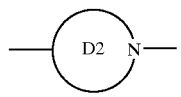

are same as those above defined, 2) a step for eliminating the protective group P in the compound of the formula VII which is obtained in the above step 1), and 3) optionally, a step of condensing the compound obtained in above step 2) with a compound represented by the formula V $R^{1a}$—CHO    V in which $R^{1a}$ stands for a group $R^1$ from whose α-position side methylene group is removed in a reaction solvent, and in the presence of a reducing agent.

13. A method for producing a compound represented by formula X-1

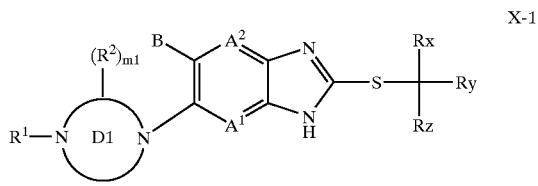

in which $A^1$ and $A^2$ are methine groups of $A^1$ is fluorinated methine group and $A^2$ is methine group;

B represents a member selected from the group consisting of halogen, cyano, lower alkylcarbonyl, lower alkylsulfonyl, mono-lower alkylsulfamoyl, di-lower alkylsulfamoyl, optionally fluorine-substituted lower alkyl and optionally fluorine-substituted lower alkyloxy;

in which $R^1$ represents hydrogen atom or lower alkyl, and said lower alkyl may be substituted with a substituent selected from a group consisting of halogen, hydroxyl, amino, lower alkyloxy, lower alkylsulfonylamino, aminocarbonylamino, mono-lower alkylcarbamoyl, acetamido, lower cycloalkyl, aromatic heterocyclic group and aromatic carbocyclic group;

$R^2$ binds to an optional carbon atom or atoms on the aliphatic, nitrogen-containing heterocyclic ring, and represents carboxyl, lower alkyloxycarbonyl, carbamoyl, mono-lower alkylcarbamoyl, di-lower alkylcarbamoyl or lower alkyl, said lower alkyl being optionally substituted with a substituent selected from a group consisting of halogen, hydroxyl, optionally fluorine-substituted lower alkyloxy, lower alkylcarbonyl, carboxyl, lower alkyl, lower alkyloxycarbonyl, carbamoyl, mono-lower alkylcarbamoyl and di-lower alkylcarbamoyl, or two $R^2$'s together form an oxo group;

m1 stands for 0 or an integer of 1–2, and where m1=2, two $R^2$'s, which may be same or different, bind to same or different optional carbon atom(s) on the aliphatic nitrogen-containing heterocyclic ring;

stands for a 5–10 membered mono- or di-cyclic aliphatic, nitrogen-containing heterocyclic group which has two nitrogen atoms;

and wherein $R_X$ stands for lower alkyl which may have a substituent selected from the group α, $R_Y$ and $R_Z$ are same or different, and stand for lower alkyl which may have a substituent selected from the group α, wherein α is a member selected from the group consisting of halogen, hydroxyl, amino, mono-lower alkylamino, di-lower alkylamino, optionally fluorine-substituted lower alkyloxy, lower alkyloxycarbonyl, (lower alkyloxycarbonyl)amino, (lower alkyloxycarbonyl) lower alkylamino, carboxyl, lower alkylcarbonyl, lower alkylcarbonyloxy, (lower alkylcarbonyl)amino, (lower alkylcarbonyl)lower alkylamino, carbamoyl, mono-lower alkylcarbamoyl, di-lower alkylcarbanioyl, carbamoylamino, mono-lower alkylcarbamoylamino, di-lower alkylcarbamoylamino, (mono-lower alkylcarbamoyl)lower alkylamino, (di-lower alkylcarbamoyl)lower alkylamino, carbamoyloxy, mono-lower alkylcarbamoyloxy, di-lower alkylcarbamoyloxy, lower alkylsulfonyl, lower alkylsulfonylamino, sulfamoyl, mono-lower alkylsulfamoyl, di-lower alkylsulfamoyl, sulfamoylamino, (mono-lower alkylsulfamoyl)amino, (di-lower alkylsulfamoyl)amino, (mono-lower alkylsulfamoyl)lower alkylamino and (di-lower alkylsulfamoyl) lower alkylamino, or $R_Y$ and $R_Z$ together form a 3–to membered aliphatic carbocyclic ring together with the carbon atom to which they bind, which comprises a step of reacting a compound represented by a formula 6′

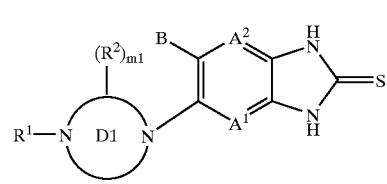

6′ in which $A^1$, $A^2$, B, $R^2$, m1 and

are same as above defined with a compound represented by formula XI $$R_X\text{—}C(R_Y)(R_Z)\text{—}OH \qquad\qquad XI$$

in which $R_X$, $R_Y$ and $R_Z$ are same as above defined, in the presence of an acid catalyst.

* * * * *